United States Patent
Testolin et al.

(10) Patent No.: US 11,034,648 B2
(45) Date of Patent: Jun. 15, 2021

(54) CYSTOBACTAMIDE DERIVATIVES

(71) Applicant: HELMHOLTZ-ZENTRUM FÜR INFEKTIONSFORSCHUNG GMBH, Braunschweig (DE)

(72) Inventors: Giambattista Testolin, Braunschweig (DE); Mark Brönstrup, Braunschweig (DE); Hans-Peter Prochnow, Braunschweig (DE); Jennifer Herrmann, Braunschweig (DE); Rolf Müller, Braunschweig (DE); Charlotte Grandclaudon, Braunschweig (DE); Tim Mollner, Braunschweig (DE); Antje Ritter, Braunschweig (DE)

(73) Assignees: HELMHOLTZ-ZENTRUM FÜR, Braunschweig (DE); INFEKTIONSFORSCHUNG GMBH, Braunschweig (DE)

( * ) Notice: Subject to any disclaimer, the term of this patent is extended or adjusted under 35 U.S.C. 154(b) by 0 days.

(21) Appl. No.: 16/641,101

(22) PCT Filed: Aug. 23, 2018

(86) PCT No.: PCT/EP2018/072817
§ 371 (c)(1),
(2) Date: Feb. 21, 2020

(87) PCT Pub. No.: WO2019/038405
PCT Pub. Date: Feb. 28, 2019

(65) Prior Publication Data
US 2020/0190020 A1 Jun. 18, 2020

(30) Foreign Application Priority Data
Aug. 23, 2017 (EP) ..................... 17187536

(51) Int. Cl.
C07D 333/38 (2006.01)
C07D 213/85 (2006.01)
A61P 31/04 (2006.01)
C07C 237/40 (2006.01)
C07C 255/60 (2006.01)

(52) U.S. Cl.
CPC ............ *C07C 237/40* (2013.01); *A61P 31/04* (2018.01); *C07C 255/60* (2013.01); *C07D 213/85* (2013.01); *C07D 333/38* (2013.01)

(58) Field of Classification Search
CPC ...... C07D 333/38; C07D 213/85; A61P 31/04
USPC ....................................................... 514/344
See application file for complete search history.

(56) References Cited

U.S. PATENT DOCUMENTS

2016/0145304 A1* 5/2016 Baumann ............... C12N 15/52
514/2.4
2017/0204052 A1 7/2017 Kim et al.

FOREIGN PATENT DOCUMENTS

EP 1867331 A1 12/2007
WO 2014/125075 A1 8/2014
WO 2015003816 A2 1/2015
WO 2016082934 A1 6/2016

OTHER PUBLICATIONS

Kretz, Julian, et al. "Total synthesis of albicidin: a lead structure from Xanthomonas albilineans for potent antibacterial gyrase inhibitors." Angewandte Chemie International Edition 54.6 (2015): 1969-1973 (5 pages).
Grätz, Stefan, et al. "Synthesis and antimicrobial activity of albicidin derivatives with variations of the central cyanoalanine building block." ChemMedChem 11.14 (2016): 1499-1502 (4 pages).
Kerwat, Dennis, et al. "Synthesis of Albicidin derivatives: assessing the role of N?terminal acylation on the antibacterial activity." ChemMedChem 11.17 (2016): 1899-1903 (5 pages).
Kim, Yu Jin, et al. "Isolation of coralmycins A and B, potent anti-gram negative compounds from the myxobacteria Corallococcus coralloides M23." Journal of natural products 79.9 (2016): 2223-2228 (6 pages).
Petras, Daniel, et al. "The O-carbamoyl-transferase alb15 is responsible for the modification of albicidin." ACS chemical biology 11.5 (2016): 1198-1204 (7 pages).
Von Eckardstein, Leonard, et al. "Total synthesis and biological assessment of novel albicidins discovered by mass spectrometric networking." Chemistry—A European Journal 23.61 (2017): 15316-15321 (6 pages).

(Continued)

*Primary Examiner* — Niloofar Rahmani
(74) *Attorney, Agent, or Firm* — Mintz Levin Cohn Ferris Glovsky and Popeo, P.C.; Peter F. Corless

(57) ABSTRACT

The present invention relates to novel derivatives of cystobactamides of formula (Ib) and the use thereof for the treatment or prophylaxis of bacterial infections.

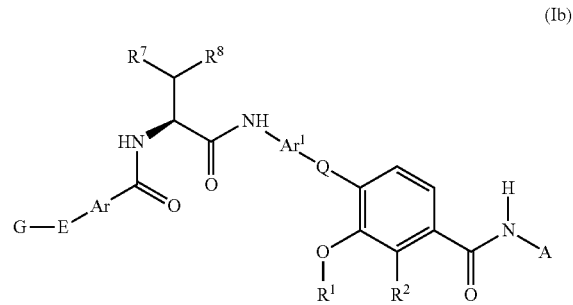

(Ib)

19 Claims, No Drawings

(56) References Cited

OTHER PUBLICATIONS

Lakemeyer, Markus, et al. "Thinking Outside the Box-Novel Antibacterials to Tackle the Resistance Crisis." Angewandte Chemie International Edition 57.44 (2018): 14440-14475 (38 pages).
International Search Report in counterpart International Application PCT/EP2018/072817 (9 pages).
Written Opinion in counterpart International Application PCT/EP2018/072817 (14 pages).
Baumann, Sascha, et al. "Cystobactamids: myxobacterial topoisomerase inhibitors exhibiting potent antibacterial activity." Angewandte Chemie International Edition 53.52 (2014): 14605-14609 (6 pages).
Hüttel, Stephan, et al. "Discovery and Total Synthesis of Natural Cystobactamid Derivatives with Superior Activity against Gramâ€? Negative Pathogens." Angewandte Chemie International Edition 56.41 (2017): 12760-12764.
Kovacic, Peter, and Ratnasamy Somanathan. "Nitroaromatic compounds: Environmental toxicity, carcinogenicity, mutagenicity, therapy and mechanism." Journal of Applied Toxicology 34.8 (2014): 810-824.
Moreno, Maria, et al. "Synthesis and Biological Evaluation of Cystobactamid 507: A Bacterial Topoisomerase Inhibitor from *Cystobacter* sp." Synlett 26.09 (2015): 1175-1178.
Brown, Matthew F., et al. "Pyridone-conjugated monobactam antibiotics with gram-negative activity." Journal of medicinal chemistry 56.13 (2013): 5541-5552.
Tichenor, Mark S., David B. Kastrinsky, and Dale L. Boger. "Total synthesis, structure revision, and absolute configuration of (+)-yatakemycin." Journal of the American Chemical Society 126.27 (2004): 8396-8398 (3 pages).
Kishimoto, Shinji, et al. "Total Synthesis and Antimicrobial Activity of Chlorocatechelin A." The Journal of organic chemistry 80.12 (2015): 6076-6082 (7 pages).
Kobayashi, Yoshiro, et al. "Studies on Organic Fluorine Compounds. XLII. Synthesis and Reactions of Phenyltrifluoromethylacetylenes." Chemical and pharmaceutical bulletin 32.11 (1984): 4402-4409 (8 pages).
Sau, Samaresh Chandra, et al. "An Abnormal Nâ€?Heterocyclic Carbeneâ€"Copper (I) Complex in Click Chemistry." Advanced Synthesis & Catalysis 355.14â€?15 (2013): 2982-2991 (10 pages).
Han, Hong Sik, et al. "Stereoselective photoredox-catalyzed chlorotrifluoromethylation of alkynes: Synthesis of tetrasubstituted alkenes." Organic letters 19.8 (2017): 1962-1965 (4 pages).
Busseron, Eric, et al. "Synthesis and recognition studies with a ditopic, photoswitchable deep cavitand." Chemical Communications 49.42 (2013): 4842-4844 (3 pages).
Rasmussen, Lars Kyhn, Brant C. Boren, and Valery V. Fokin. "Ruthenium-catalyzed cycloaddition of aryl azides and alkynes." Organic Letters 9.26 (2007): 5337-5339 (3 pages).
Majireck, Max M., and Steven M. Weinreb. "A study of the scope and regioselectivity of the ruthenium-catalyzed [3+2]-cycloaddition of azides with internal alkynes." The Journal of organic chemistry 71.22 (2006): 8680-8683 (4 pages).
Xiao, Zuâ€?Feng, et al. "Zinc Iodideâ€?Mediated Direct Synthesis of 2, 3â€?Dihydroisoxazoles from Alkynes and Nitrones." Advanced Synthesis & Catalysis 358.11 (2016): 1859-1863 (5 pages).
Cawkill, Eric, and Nigel G. Clark. "The reaction between cyanide ion and nitrones; a novel imidazole synthesis." Journal of the Chemical Society, Perkin Transactions 1 (1980): 244-248 (5 pages).
Soldaini, Gianluca, Francesca Cardona, and Andrea Goti. "Catalytic oxidation of imines based on methyltrioxorhenium/urea hydrogen peroxide: A mild and easy chemo- and regioselective entry to nitrones." Organic letters 9.3 (2007): 473-476 (4 pages).
Gella, Carolina, et al. "A metal-free general procedure for oxidation of secondary amines to nitrones." The Journal of organic chemistry 74.16 (2009): 6365-6367 (3 pages).
Floresta, Giuseppe, et al. "I$^3$-Cyclodextrin as a catalyst for the synthesis of 2-methyl-3, 5-diarylisoxazolidines in water." The Journal of organic chemistry 82.9 (2017): 4631-4639.
Cheng, Bichu, Rolf Müller, and Dirk Trauner. "Total Syntheses of Cystobactamids and Structural Confirmation of Cystobactamid 919â€?2." Angewandte Chemie 129.41 (2017): 12929-12933.

\* cited by examiner

CYSTOBACTAMIDE DERIVATIVES

CROSS-REFERENCES TO RELATED APPLICATIONS

This application is a 35 U.S.C. § 371 U.S. national entry of International Application No. PCT/EP2018/072817, having an International filing date of Aug. 23, 2018 which claims under 35 U.S.C. § 119 the benefit of European Patent Application 17187536.2 filed on Aug. 23, 2017. The entire contents of these applications are incorporated herein by reference in their entirety.

The present invention relates to novel derivatives of cystobactamides and the use thereof for the treatment or prophylaxis of bacterial infections.

Cystobactamides are novel natural products that have been isolated from myxobacterium *Cystobacter velatus* (MCy8071; internal name: *Cystobacter ferrugineus*). Cystobactamides exhibit a good antibiotic activity, especially against selected Gram-negative bacteria, such as *E. coli*, *P. aeruginosa*, and *A. baumannii*, as well as a broad-spectrum activity against Gram-positive bacteria. Cystobactamides have been described in WO 2015/003816, WO2016/082934, Angew. Chem. Int. Ed. 2014, 53, 14605-14609 (doi: 10.1002/anie. 201409964), Angew. Chem. Int. Ed. 2017, 56 (doi:10.1002/anie.201705913), and in Synlett 2015, 26(09), 1175-1178 (doi: 10.1055/s-0034-1380509).

Albicidin is a natural product produced by *Xanthomonas albilineans* possessing antibacterial activity. Albicidin and derivatives thereof are described in WO 2014/125075.

The present invention provides compounds of formula (Ib):

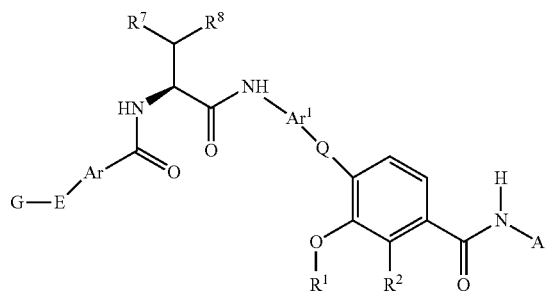

wherein
$R^1$ is a hydrogen atom or a group of formula —$C_{1-6}$ alkyl;
$R^2$ is a hydrogen atom, an OH group or a group of formula —O—$C_{1-6}$ alkyl; A is an alkynyl, a cycloalkyl, heterocycloalkyl, alkylcycloalkyl, heteroalkylcycloalkyl, aryl, heteroaryl, aralkyl or heteroaralkyl group, all of which may optionally be substituted;
Q is a group of formula —C(=O)—NH—, wherein the NH-group is bound to the phenyl group carrying $R^2$, or an optionally substituted heteroaryl group containing 5 ring atoms selected from O, S, N and C, or an optionally substituted heterocycloalkyl group containing 5 ring atoms selected from O, S, N and C, or a group of formula —CO-heteroaryl wherein the heteroaryl group is optionally substituted and contains 5 ring atoms selected from O, S, N and C;
Ar is a phenylene group or a naphthylene group or a heteroarylene group containing 5 or 6 to 10 ring atoms selected from O, S, N and C or a $C_{3-7}$ cycloalkyl group or a heterocycloalkyl group containing from 3 to 7 ring atoms selected from C, O, S and N or a $C_{2-4}$ alkynyl group; all of which groups may optionally be substituted;

$Ar^1$ is a phenylene group or a naphthylene group or a heteroarylene group containing 5 or 6 to 10 ring atoms selected from O, S, N and C or a $C_{3-7}$ cycloalkyl group or a heterocycloalkyl group containing from 3 to 7 ring atoms selected from C, O, S and N or a $C_{2-4}$ alkynyl group; all of which groups may optionally be substituted;

E is a bond or a group of formula —C≡C— or a heteroarylene group containing 5 ring atoms selected from O, S, N and C (preferably from C and N) or a group of formula -L-C(=O)—NH—*, —C(=O)—NH—$(CH_2)_m$—*, —$SO_2$—NH—$(CH_2)_m$—*, -L-$SO_2$—NH—* or —N=N—, wherein * denotes the point of attachment to group Ar and wherein L is a bond or a —NH—, a $C_{1-6}$ alkylene, a $C_{2-6}$ alkenylene or a heteroalkylene group containing from 1 to 6 carbon atoms and 1, 2 or 3 heteroatoms selected from O, S and N, and wherein m is an integer of from 1 to 4;

G is a phenyl group or a heteroaryl group containing 5 or 6 to 10 ring atoms selected from O, S, N and C or a heterocycloalkyl group containing 5 or 6 ring atoms selected from O, S, N and C; all of which groups may be unsubstituted or substituted by 1, 2, 3, 4 or 5 groups $R^6$;

the groups $R^6$ are independently from each other selected from a halogen atom, $NO_2$, $N_3$, OH, $NH_2$, SH, CN or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; or two groups $R^6$ are linked together via an alkylene, alkenylene or heteroalkylene group, all of which may optionally be substituted;

$R^7$ is a hydrogen atom, an OH group, a $NH_2$ group, a $C_{1-6}$ alkyl group, an —O—$C_{1-6}$ alkyl group or an —O—C(=O)—$C_{1-6}$ alkyl group; and $R^8$ is an OH group, a SH group, a CN group, a $C_{1-6}$ alkyl group, a —O—$C_{1-6}$ alkyl group, a —S—$C_{1-6}$ alkyl group, a phenyl group, a 4-hydroxyphenyl group or a heteroaryl group containing 5 or 6 ring atoms selected from O, S, N and C or a group of formula —C(=O)—N($R^9$)—$R^{10}$; or $R^7$ and $R^8$ together with the carbon atom to which they are bound are part of an optionally substituted $C_{3-7}$ cycloalkyl group or an optionally substituted heterocycloalkyl group containing 3, 4, 5, 6 or 7 ring atoms selected from O, S, N and C;

$R^9$ is a hydrogen atom or a $C_{1-6}$ alkyl group; and $R^{10}$ is a hydrogen atom, a $C_{1-6}$ alkyl group or a $C_{3-7}$ cycloalkyl group; or $R^9$ and $R^{10}$ together with the nitrogen atom to which they are bound are part of an optionally substituted heterocycloalkyl group containing 3, 4, 5, 6 or 7 ring atoms selected from O, S, N and C;

or a pharmaceutically acceptable salt, solvate or hydrate or a pharmaceutically acceptable formulation thereof.

Preferably, $Ar^1$ is an optionally substituted phenylene group; further preferably an optionally substituted 1,4-phenylene group.

Moreover preferably, $Ar^1$ is unsubstituted.

According to a preferred embodiment, the present invention provides compounds of formula (I):

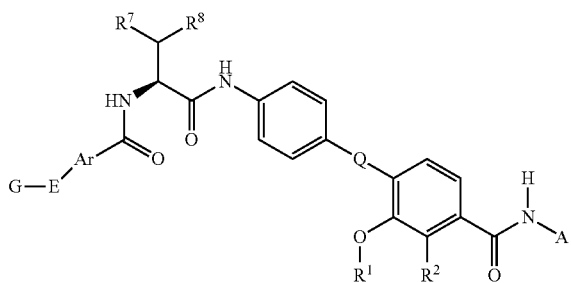

(I)

wherein $R^1$ is a hydrogen atom or a group of formula —$C_{1-6}$ alkyl;

$R^2$ is a hydrogen atom, an OH group or a group of formula —O—$C_{1-6}$ alkyl;

A is an alkynyl, a cycloalkyl, heterocycloalkyl, alkylcycloalkyl, heteroalkylcycloalkyl, aryl, heteroaryl, aralkyl or heteroaralkyl group, all of which may optionally be substituted;

Q is a group of formula —C(=O)—NH—, wherein the NH-group is bound to the phenyl group carrying $R^2$, or an optionally substituted heteroaryl group containing 5 ring atoms selected from O, S, N and C, or an optionally substituted heterocycloalkyl group containing 5 ring atoms selected from O, S, N and C, or a group of formula —CO-heteroaryl wherein the heteroaryl group is optionally substituted and contains 5 ring atoms selected from O, S, N and C;

Ar is a phenylene group or a heteroarylene group containing 5 or 6 ring atoms selected from O, S, N and C or a $C_{3-7}$ cycloalkyl group or a heterocycloalkyl group containing from 3 to 7 ring atoms selected from C, O, S and N or a $C_{2-4}$ alkynyl group; all of which groups may optionally be substituted;

E is a bond or a group of formula —C≡C— or a heteroarylene group containing 5 ring atoms selected from O, S, N and C (preferably from C and N) or a group of formula -L-C(=O)—NH—*, —C(=O)—NH—$(CH_2)_m$—*, —$SO_2$—NH—$(CH_2)_m$—*, -L-$SO_2$—NH—* or —N=N—, wherein * denotes the point of attachment to group Ar and wherein L is a bond or a —NH—, a $C_{1-6}$ alkylene, a $C_{2-6}$ alkenylene or a heteroalkylene group containing from 1 to 6 carbon atoms and 1, 2 or 3 heteroatoms selected from O, S and N, and wherein m is an integer of from 1 to 4;

G is a phenyl group or a heteroaryl group containing 5 or 6 ring atoms selected from O, S, N and C or a heterocycloalkyl group containing 5 or 6 ring atoms selected from O, S, N and C; all of which groups may be unsubstituted or substituted by 1, 2, 3, 4 or 5 groups $R^6$;

the groups $R^6$ are independently from each other selected from a halogen atom, $NO_2$, $N_3$, OH, $NH_2$, SH, CN or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; or two groups $R^6$ are linked together via an alkylene, alkenylene or heteroalkylene group, all of which may optionally be substituted;

$R^7$ is a hydrogen atom, an OH group, a $NH_2$ group, a $C_{1-6}$ alkyl group, an —O—$C_{1-6}$ alkyl group or an —O—C(=O)—$C_{1-6}$ alkyl group; and $R^8$ is an OH group, a SH group, a CN group, a $C_{1-6}$ alkyl group, a —O—$C_{1-6}$ alkyl group, a —S—$C_{1-6}$ alkyl group, a phenyl group, a 4-hydroxyphenyl group or a group of formula —C(=O)—N($R^9$)—$R^{10}$; or $R^7$ and $R^8$ together with the carbon atom to which they are bound are part of an optionally substituted $C_{3-7}$ cycloalkyl group or an optionally substituted heterocycloalkyl group containing 3, 4, 5, 6 or 7 ring atoms selected from O, S, N and C;

$R^9$ is a hydrogen atom or a $C_{1-6}$ alkyl group; and $R^{10}$ is a hydrogen atom, a $C_{1-6}$ alkyl group or a $C_{3-7}$ cycloalkyl group; or $R^9$ and $R^{10}$ together with the nitrogen atom to which they are bound are part of an optionally substituted heterocycloalkyl group containing 3, 4, 5, 6 or 7 ring atoms selected from O, S, N and C;

or a pharmaceutically acceptable salt, solvate or hydrate or a pharmaceutically acceptable formulation thereof.

Preferably, E is a group of formula -L-C(=O)—NH—*, —C(=O)—NH—$(CH_2)_m$—*, —$SO_2$—NH—$(CH_2)_m$—*, -L-$SO_2$—NH—* or —N=N—, wherein * denotes the point of attachment to group Ar and wherein L is a bond or a —NH—, a $C_{1-6}$ alkylene, a $C_{2-6}$ alkenylene or a heteroalkylene group containing from 1 to 6 carbon atoms and 1, 2 or 3 heteroatoms selected from O, S and N, and wherein m is an integer of from 1 to 4.

According to a further preferred embodiment, the present invention provides compounds of formula (I) wherein $R^1$ is a hydrogen atom or a group of formula —$C_{1-6}$ alkyl;

$R^2$ is a hydrogen atom, an OH group or a group of formula —O—$C_{1-6}$ alkyl;

A is an alkynyl, a cycloalkyl, heterocycloalkyl, alkylcycloalkyl, heteroalkylcycloalkyl, aryl, heteroaryl, aralkyl or heteroaralkyl group, all of which may optionally be substituted;

Q is a group of formula —C(=O)—NH—, wherein the NH-group is bound to the phenyl group carrying $R^2$, or an optionally substituted heteroaryl group containing 5 ring atoms selected from O, S, N and C, or an optionally substituted heterocycloalkyl group containing 5 ring atoms selected from O, S, N and C;

Ar is a phenylene group or a heteroarylene group containing 5 or 6 ring atoms selected from O, S, N and C; all of which groups may optionally be substituted;

E is a group of formula -L-C(=O)—NH—*, —C(=O)—NH—$(CH_2)_m$—*, —$SO_2$—NH—$(CH_2)_m$—*, -L-$SO_2$—NH—* or —N=N—, wherein * denotes the point of attachment to group Ar and wherein L is a bond or a —NH—, a $C_{1-6}$ alkylene, a $C_{2-6}$ alkenylene or a heteroalkylene group containing from 1 to 6 carbon atoms and 1, 2 or 3 heteroatoms selected from O, S and N, and wherein m is an integer of from 1 to 4;

G is a phenyl group or a heteroaryl group containing 5 or 6 ring atoms selected from O, S, N and C or a heterocycloalkyl group containing 5 or 6 ring atoms selected from O, S, N and C; all of which groups may be unsubstituted or substituted by 1, 2, 3, 4 or 5 groups $R^6$;

the groups $R^6$ are independently from each other selected from a halogen atom, $NO_2$, $N_3$, OH, $NH_2$, SH, CN or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; or two groups $R^6$ are linked together via an alkylene, alkenylene or heteroalkylene group, all of which may optionally be substituted;

$R^7$ is a hydrogen atom, an OH group, a $NH_2$ group, a $C_{1-6}$ alkyl group, an —O—$C_{1-6}$ alkyl group or an —O—C(=O)—$C_{1-6}$ alkyl group; and $R^8$ is an OH group, a SH group, a CN group, a $C_{1-6}$ alkyl group, a —O—$C_{1-6}$ alkyl group, a —S—$C_{1-6}$ alkyl group, a phenyl group, a 4-hydroxyphenyl group or a group of formula —C(=O)—N($R^9$)—$R^{10}$; or $R^7$ and $R^8$ together with the carbon atom to which they are bound are part of an optionally substituted $C_{3-7}$ cycloalkyl group or an optionally substituted heterocycloalkyl group containing 3, 4, 5, 6 or 7 ring atoms selected from O, S, N and C;

$R^9$ is a hydrogen atom or a $C_{1-6}$ alkyl group; and $R^{10}$ is a hydrogen atom, a $C_{1-6}$ alkyl group or a $C_{3-7}$ cycloalkyl group; or $R^9$ and $R^{10}$ together with the nitrogen atom to which they are bound are part of an optionally substituted heterocycloalkyl group containing 3, 4, 5, 6 or 7 ring atoms selected from O, S, N and C;

or a pharmaceutically acceptable salt, solvate or hydrate or a pharmaceutically acceptable formulation thereof.

Preferably, Q is a group of formula —C(=O)—NH—, wherein the NH-group is bound to the phenyl group carrying $R^2$.

Further preferably, Q is an optionally substituted heteroaryl group containing 5 ring atoms selected from O, S, N and C.

Moreover preferably, Q is selected from the following groups:

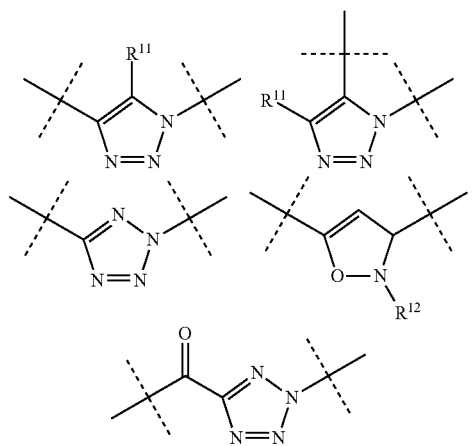

wherein $R^{11}$ is a hydrogen atom or an alkyl group (such as $CH_3$ or $CF_3$) or an aryl group and $R^{12}$ is a hydrogen atom or an alkyl group (such as $CH_3$ or $CF_3$) or an aryl group. Preferably, the nitrogen atom of these preferred groups Q is bound to the phenyl group carrying $R^2$.

Especially preferably, $R^{11}$ is a hydrogen atom.

According to a preferred embodiment, the present invention provides compounds of formula (Ia):

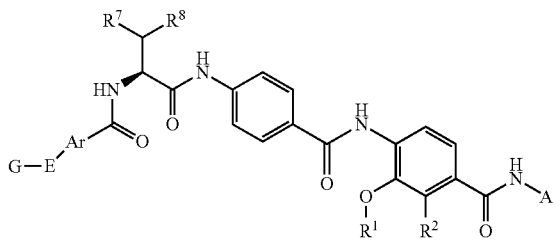

(Ia)

wherein $R^1$ is a hydrogen atom or a group of formula —$C_{1-6}$ alkyl;

$R^2$ is a hydrogen atom, an OH group or a group of formula —O—$C_{1-6}$ alkyl;

A is an alkynyl, a cycloalkyl, heterocycloalkyl, alkylcycloalkyl, heteroalkylcycloalkyl, aryl, heteroaryl, aralkyl or heteroaralkyl group, all of which may optionally be substituted;

Ar is a phenylene group or a heteroarylene group containing 5 or 6 ring atoms selected from O, S, N and C; all of which groups may optionally be substituted;

E is a group of formula -L-C(=O)—NH—*, —C(=O)—NH—(CH$_2$)$_m$—*, —SO$_2$—NH—(CH$_2$)$_m$—*, -L-SO$_2$—NH—* or —N=N—, wherein * denotes the point of attachment to group Ar and wherein L is a bond or a —NH—, a $C_{1-6}$ alkylene, a $C_{2-6}$ alkenylene or a heteroalkylene group containing from 1 to 6 carbon atoms and 1, 2 or 3 heteroatoms selected from O, S and N, and wherein m is an integer of from 1 to 4;

G is a phenyl group or a heteroaryl group containing 5 or 6 ring atoms selected from O, S, N and C; all of which groups may be unsubstituted or substituted by 1, 2, 3, 4 or 5 groups $R^6$;

the groups $R^6$ are independently from each other selected from a halogen atom, $NO_2$, $N_3$, OH, $NH_2$, SH, CN or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; or two groups $R^6$ are linked together via an alkylene, alkenylene or heteroalkylene group, all of which may optionally be substituted;

$R^7$ is a hydrogen atom, an OH group, a $NH_2$ group, a $C_{1-6}$ alkyl group, an —O—$C_{1-6}$ alkyl group or an —O—C(=O)—$C_{1-6}$ alkyl group; and $R^8$ is an OH group, a SH group, a CN group, a $C_{1-6}$ alkyl group, a —O—$C_{1-6}$ alkyl group, a —S—$C_{1-6}$ alkyl group, a phenyl group, a 4-hydroxyphenyl group or a group of formula —C(=O)—N($R^9$)—$R^{10}$; or $R^7$ and $R^8$ together with the carbon atom to which they are bound are part of an optionally substituted $C_{3-7}$ cycloalkyl group or an optionally substituted heterocycloalkyl group containing 3, 4, 5, 6 or 7 ring atoms selected from O, S, N and C;

$R^9$ is a hydrogen atom or a $C_{1-6}$ alkyl group; and $R^{10}$ is a hydrogen atom, a $C_{1-6}$ alkyl group or a $C_{3-7}$ cycloalkyl group; or $R^9$ and $R^{10}$ together with the nitrogen atom to which they are bound are part of an optionally substituted heterocycloalkyl group containing 3, 4, 5, 6 or 7 ring atoms selected from O, S, N and C;

or a pharmaceutically acceptable salt, solvate or hydrate or a pharmaceutically acceptable formulation thereof.

Preferably, Ar is a phenylene group or a pyridylene group, both of which may be substituted.

Further preferably, Ar is an unsubstituted phenylene group or an unsubstituted pyridylene group.

Especially preferably, Ar is an unsubstituted phenylene group; especially preferably an unsubstituted 1,4 phenylene group.

Moreover preferably, Ar is a cyclohexylene group or a group of formula —CH$_2$—C≡C— or —C≡C—CH$_2$—.

Further preferably, $R^7$ is a hydrogen atom.

Moreover preferably, $R^7$ is an —OMe group.

Further preferably, $R^7$ is an —O—$C_{1-6}$ alkyl group.

Moreover preferably, $R^7$ is an —O—C(=O)—$C_{1-6}$ alkyl group.

Further Preferably, $R^8$ is a group of formula —C(=O)—NH$_2$.

Moreover preferably, $R^8$ is a CN group.

Further Preferably, $R^8$ is a CN group and $R^7$ is an —OMe group.

Moreover Preferably, $R^8$ is a heteroaryl group containing 5 ring atoms selected from C and N.

Further preferably, $R^7$ and $R^8$ together with the carbon atom to which they are bound are part of a heterocycloalkyl group containing 5 ring atoms selected from O, N and C which may be substituted by an =O group.

Especially preferably, $R^7$ is a hydrogen atom and $R^8$ is a group of formula —$CONH_2$.

Moreover preferably, if $R^7$ is an —OMe group, G is substituted by a —CN group.

Especially preferably, $R^7$ is an —OMe group and $R^8$ is a group of formula —$CONH_2$ and G is substituted by a —CN group.

Preferably, the present invention provides compounds of formula (II):

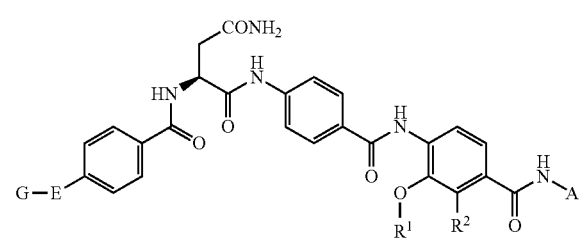

(II)

wherein $R^1$, $R^2$, A, E and G are as defined above, or a pharmaceutically acceptable salt, solvate or hydrate or a pharmaceutically acceptable formulation thereof.

Preferably, $R^1$ is a $C_{1-4}$ alkyl group.

Further preferably, $R^1$ is a group of formula —$CH(CH_3)_2$ or —$CH_2CH(CH_3)_2$; especially preferably a group of formula —$CH(CH_3)_2$.

Further preferably, $R^2$ is a hydrogen atom or an OH group; especially preferably an OH group.

Moreover preferably, A is an optionally substituted phenyl group; an optionally substituted heteroaryl group containing 5 or 6 ring atoms selected from O, S, N and C; an optionally substituted cycloalkyl group containing from 3 to 7 ring atoms; or an optionally substituted heterocycloalkyl group containing from 3 to 7 ring atoms selected from O, S, N and C; or an optionally substituted acetylenyl group (e.g. a group of formula —C≡C—COOH).

Further preferably, A is a group of formula —$CH_2$-A' or NH-A', wherein A' is an optionally substituted phenyl group; an optionally substituted heteroaryl group containing 5 or 6 ring atoms selected from O, S, N and C; an optionally substituted cycloalkyl group containing from 3 to 7 ring atoms; or an optionally substituted heterocycloalkyl group containing from 3 to 7 ring atoms selected from O, S, N and C; or an optionally substituted acetylenyl group (e.g. a group of formula —C≡C—COOH).

Especially preferably, A is an optionally substituted phenyl group.

Preferably, A is substituted by 1, 2 or 3 substituents which are independently selected from a halogen atom, COOH, $SO_2NH_2$, OH, —$B(OH)_2$, $CH_2COOH$, —O—$C_{1-6}$ alkyl, $SO_3H$ and $C_{1-6}$ alkyl or a group of the following formula:

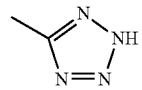

Moreover preferably, A is a group of the following formula:

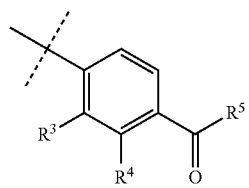

wherein $R^3$ is a hydrogen atom, a halogen atom, an OH group, a $C_{1-6}$ alkyl group or a group of formula —O—$C_{1-6}$ alkyl; $R^4$ is a hydrogen atom, a halogen atom, an OH group, a $C_{1-6}$ alkyl group or a group of formula —O—$C_{1-6}$ alkyl; and $R^5$ is an OH group or a $NH_2$ group; especially preferably, $R^3$ is a hydrogen atom or a group of formula —O—$C_{1-4}$ alkyl (especially a group of formula —O—CH$(CH_3)_2$), $R^4$ is a hydrogen atom or an OH group and $R^5$ is an OH group.

Further preferably, A is selected from the following groups:

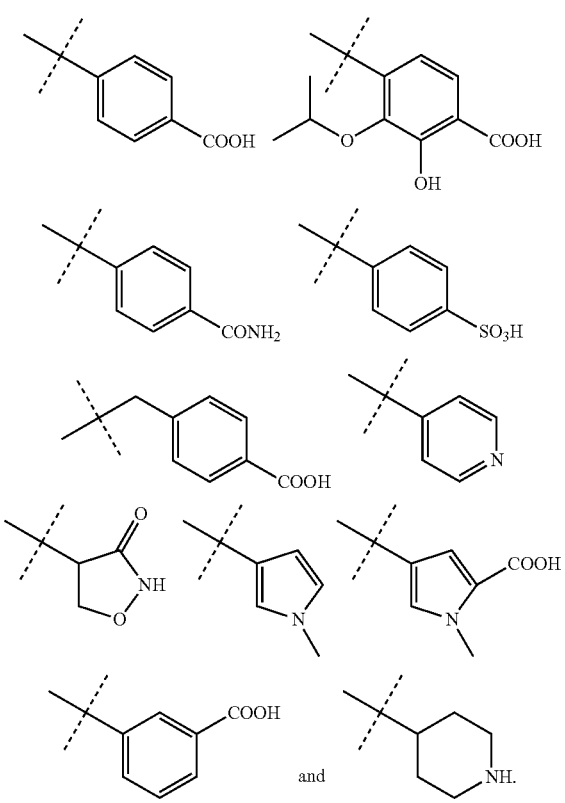

and

Moreover preferably, A is selected from the following groups:

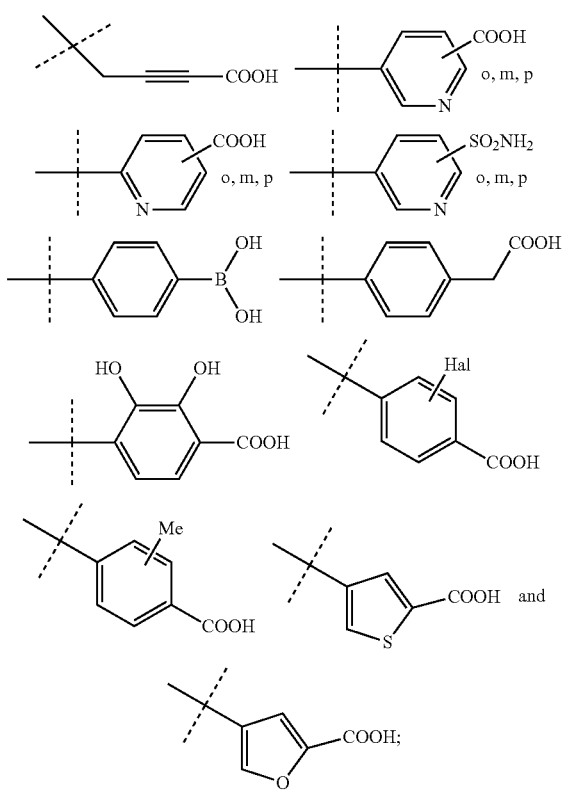

Wherein Hal is a halogen atom.

Further preferably, A is selected from the following groups:

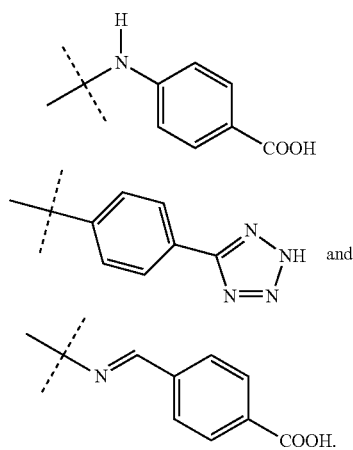

Especially preferably, A is selected from the following groups:

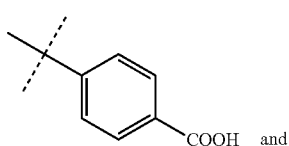

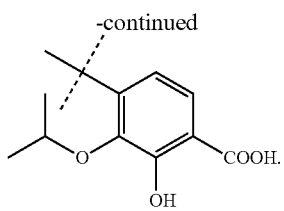

Moreover preferably, E is selected from the following groups: —C(=O)—NH—*, —CH=C(CH$_3$)—C(=O)—NH—*, —O—CH(CH$_3$)—C(=O)—NH—*, —S—CH(CH$_3$)—C(=O)—NH—*, —CH$_2$—C(=O)—NH—*, —CH$_2$—CH$_2$—C(=O)—NH—*, —C(=O)—NH—CH$_2$—*, —C(=O)—NH—CH$_2$—CH$_2$—*, —SO$_2$—NH—* or —N=N—, wherein * denotes the point of attachment to group Ar; especially preferably, E is selected from —C(=O)—NH—* or —CH=C(CH$_3$)—C(=O)—NH—*.

Especially preferably, E is a group of formula: —C(=O)—NH—*, wherein * denotes the point of attachment to group Ar.

Further preferably, G is an optionally substituted phenyl group or an optionally substituted heteroaryl group containing 5 or 6 ring atoms selected from C, N, O and S.

Moreover preferably, G is a phenyl group which is unsubstituted or substituted by 1, 2 or 3 groups $R^6$.

Especially preferably, G is substituted by a —CN group. The presence of a CN group at group G has the advantage of broadening of the spectrum coverage against relevant pathogenic bacteria such as *P. aeruginosa* DSM-46316, *K. pneumoniae* DSM-30104 and *E. aerogenes* DSM-30053, and of significantly increasing the potency against relevant pathogenic bacteria such as *E. faecalis* ATCC-29212, *S. epidermidis* DSM-28765, *S. pneumoniae* DSM-20566, fluoroquinolone resistant *E. coli* WT-3 [gyrA(S83L,D87G)] and *E. coli* WT-III [marRΔ74 bp], *S. aureus*. Moreover, nitro groups are prone to metabolic instability from which potential toxicity problems might arise whereas a cyano group is less likely to give these issues. (see e.g.: Nitroaromatic compounds: Environmental toxicity, carcinogenicity, mutagenicity, therapy and mechanism, Peter Kovacica* and Ratnasamy Somanathana, J. Appl. Toxicol. 2014; 34: 810-824).

Further preferably, the groups $R^6$ are independently selected from —F, —Cl, —Br, —NO$_2$, —OH, —O—C$_{1-6}$ alkyl (especially —OMe or —O—CH(CH$_3$)$_2$), —NH$_2$, —CN, -Me, —N$_3$, —CF$_3$, NHAc, —NHMe, —NMe$_2$, —NHCONH$_2$ and —SO$_2$Me; or wherein two groups $R^6$ together form a group of the formula —CH$_2$—O—C(=O)—, —NH—N=N— or —CH=CH—CH=N—.

Moreover preferably, G is a group of the following formula:

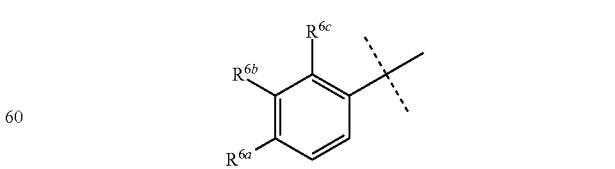

wherein $R^{6a}$ is —H, —NO$_2$, —F, —NHAc, —N$_3$, —NMe$_2$, —CN, —OH, —NH$_2$, —CF$_3$, —NHCONH$_2$ or —SO$_2$Me; $R^{6b}$ is —H, —NO$_2$, —OMe, —Cl, —Br, —NH$_2$, —O—CH(CH$_3$)$_2$, —F or -Me; and $R^{6c}$ is —H, —F, —NO$_2$, —NH$_2$—

OH or -Me; or wherein $R^{6c}$ is —H and $R^{6a}$ and $R^b$ together form a group of the formula —CH$_2$—O—C(=O)—.

Especially preferably, $R^{6a}$ is CN.

More preferably, $R^{6a}$ is CN and $R^{6b}$ and $R^{6c}$ are both hydrogen atoms.

Further preferably, $R^{6a}$ is a NO$_2$ group.

More preferably, $R^{6a}$ is NO$_2$ and $R^{6b}$ and $R^{6c}$ are both hydrogen atoms.

Further preferably, G-E together are selected from the following groups:

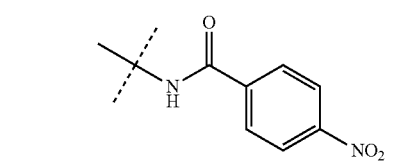

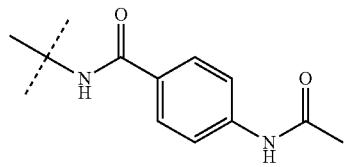

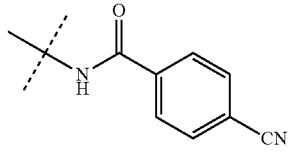

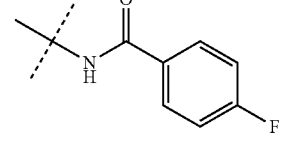

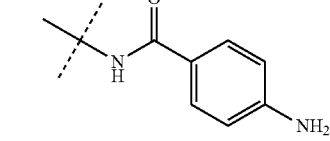

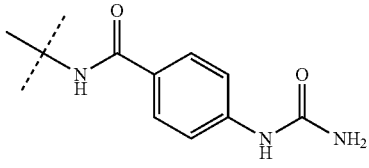

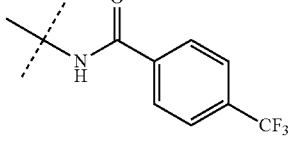

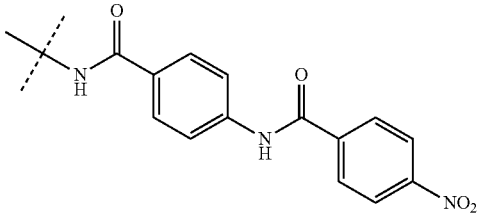

-continued

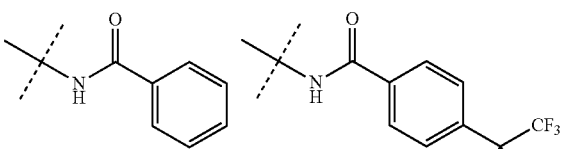

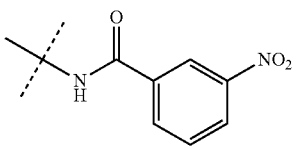

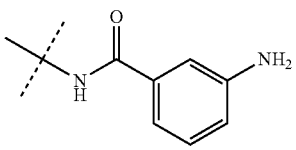

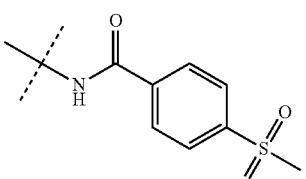

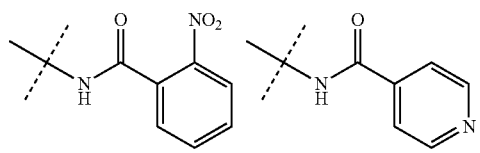

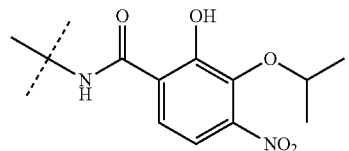

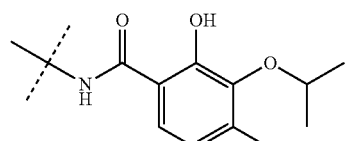

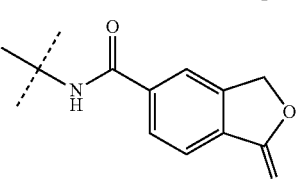

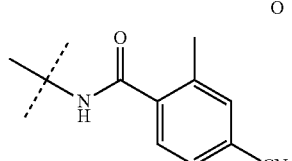

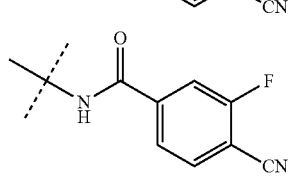

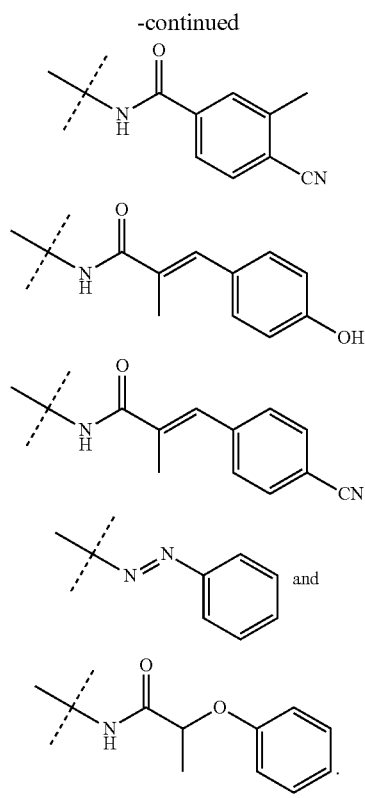
Moreover preferably. G-E together are selected from the following groups:
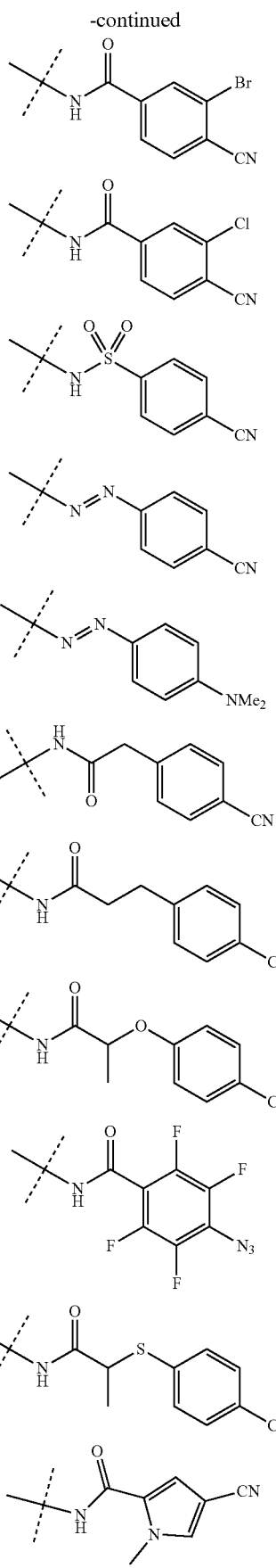

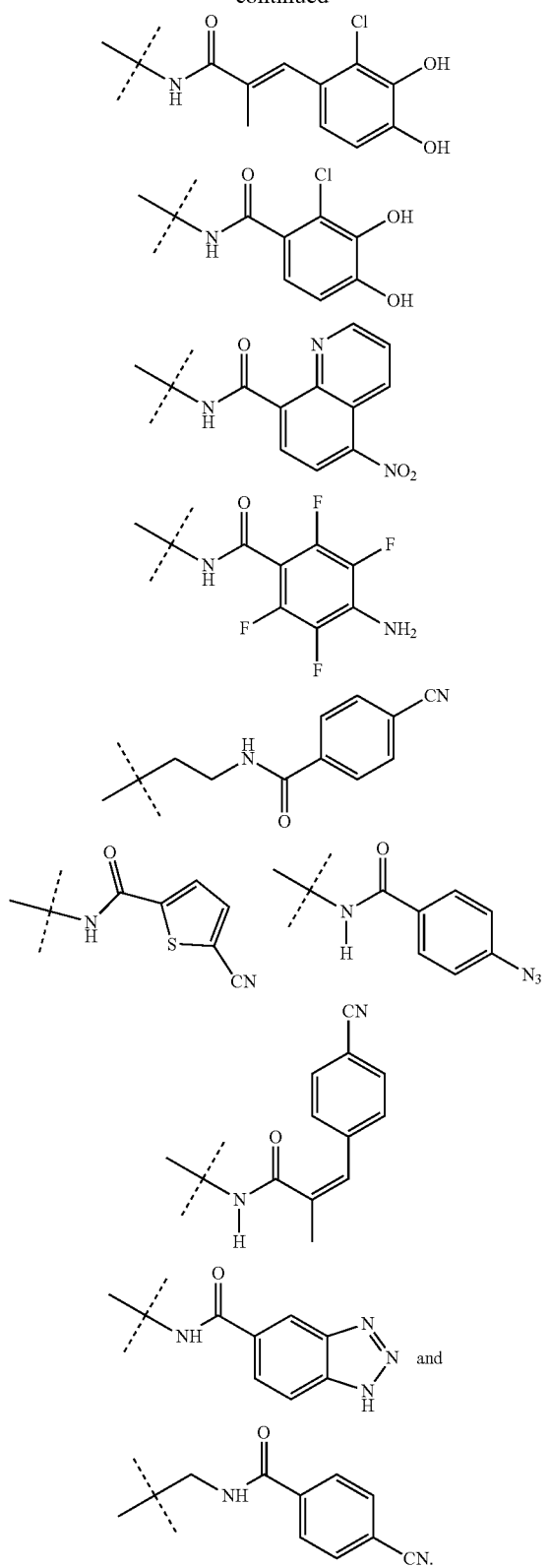
Especially preferably, G-E are selected from the following groups:
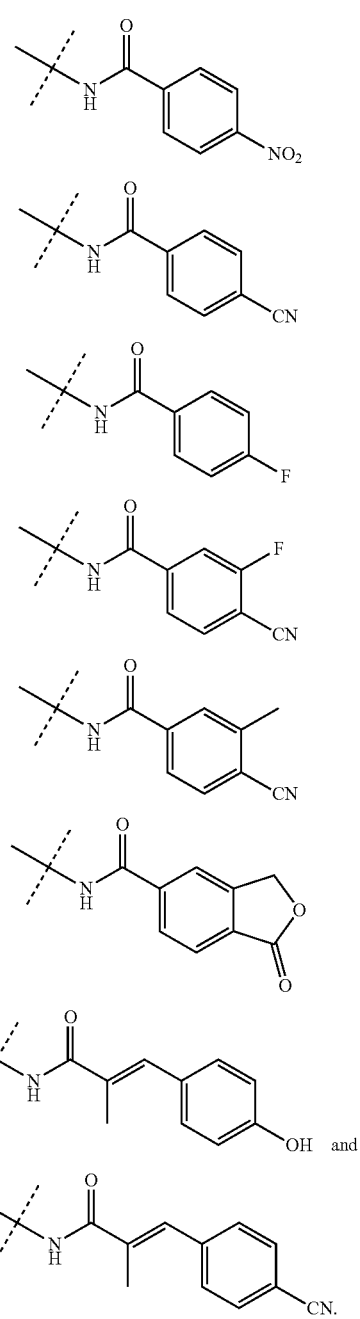
Moreover, especially preferably, G-E are selected from the following groups:
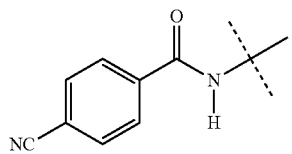

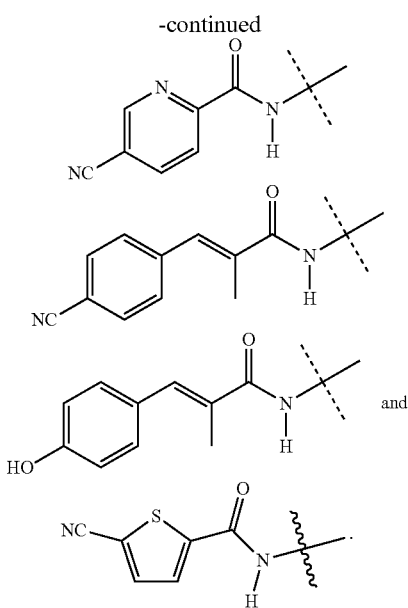

Further preferred are compounds of formula (III):

$R^1$ is a hydrogen atom or a group of formula —$C_{1-6}$ alkyl;
$R^2$ is a hydrogen atom, an OH group or a group of formula —O—$C_{1-6}$ alkyl;
$R^3$ is a hydrogen atom, an OH group or a group of formula —O—$C_{1-6}$ alkyl;
$R^4$ is a hydrogen atom, an OH group or a group of formula —O—$C_{1-6}$ alkyl;
$R^5$ is an OH group or a $NH_2$ group;
the groups $R^6$ are independently from each other selected from —F, —$NO_2$, —OH, —O—$C_{1-6}$ alkyl (especially —O—CH(CH$_3$)$_2$), —NH$_2$, —CN, —Me, —CF$_3$, NHAc, —NHCONH$_2$ and —SO$_2$Me; or
wherein two groups $R^6$ together form a group of the formula —CH$_2$—O—C(=O)—.
also, 1, 2 or 3; and
L is a bond or a —NH—, a $C_{1-6}$ alkylene, a $C_{2-6}$ alkenylene or a heteroalkylene group containing from 1 to 6 carbon atoms and 1, 2 or 3 heteroatoms selected from O, S and N;
or a pharmaceutically acceptable salt, solvate or hydrate or a pharmaceutically acceptable formulation thereof.

Further preferably, L is a bond or a group of formula —CH=C(CH$_3$)—, —O—CH(CH$_3$)—, —S—C(CH$_3$)—, —CH$_2$— or —CH$_2$—CH$_2$—.

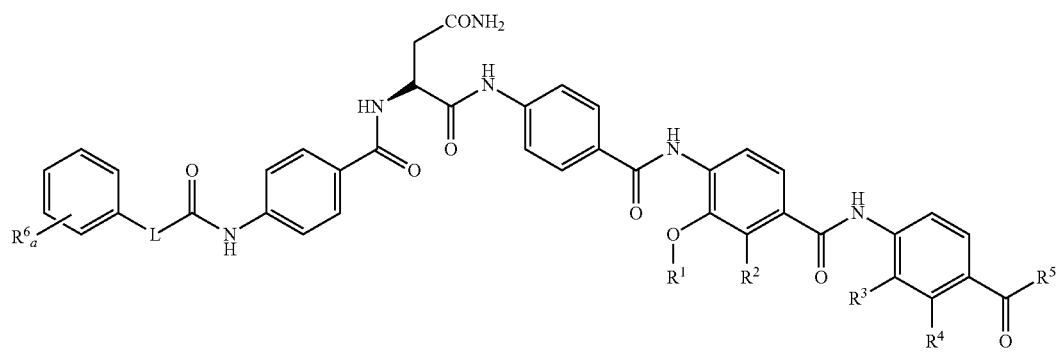

wherein $R^1$, $R^2$, $R^3$, $R^4$, $R^5$, $R^6$ and L are as defined above and a is 0, 1, 2, 3, 4 or 5, or a pharmaceutically acceptable salt, solvate or hydrate or a pharmaceutically acceptable formulation thereof.

Especially preferred are compounds of formula (III) wherein

Especially preferably, L is a bond or a group of formula —CH=C(CH$_3$)—.

Further preferably, L is a bond.

Moreover preferably, one of $R^6$, if present, is in para position to group L.

Further preferred are compounds of formula (IV):

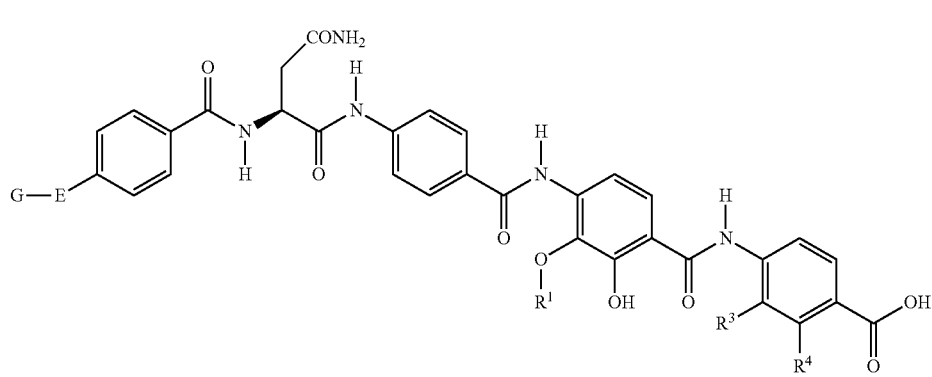

wherein
R¹ is a $C_{1-4}$ alkyl group (preferably a group of formula $CH(CH_3)_2$);
R³ is hydrogen or a —O—$C_{1-4}$ alkyl group (preferably hydrogen or a group of formula —O—$CH(CH_3)_2$);
R⁴ is hydrogen or an OH group; and
G and E are defined as above;
or a pharmaceutically acceptable salt, solvate or hydrate or a pharmaceutically acceptable formulation thereof.

Moreover preferred are compounds of formula (V):

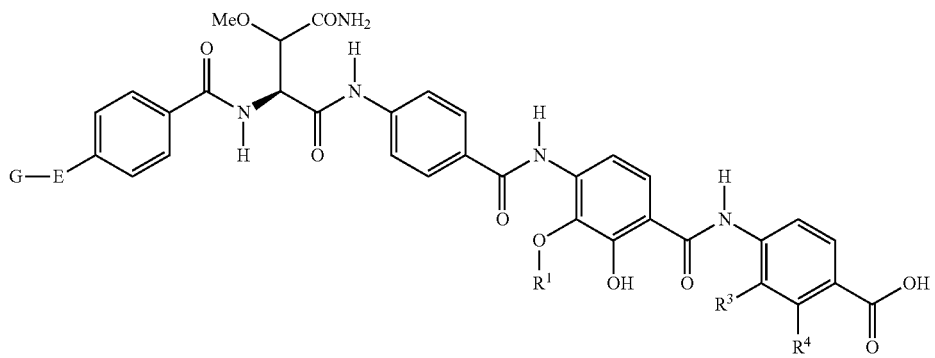

(V)

wherein
R¹ is a $C_{1-4}$ alkyl group (preferably a group of formula $CH(CH_3)_2$);
R³ is hydrogen or a —O—$C_{1-4}$ alkyl group (preferably hydrogen or a group of formula —O—$CH(CH_3)_2$);
R⁴ is hydrogen or an OH group; and
G and E are defined as above;
or a pharmaceutically acceptable salt, solvate or hydrate or a pharmaceutically acceptable formulation thereof.

Especially preferred are compounds of formula (IV) or (V), wherein R³ and R⁴ are both hydrogen or wherein R³ is a group of formula —O—$CH(CH_3)_2$ and R⁴ is an OH group.

The most preferred compounds of the present invention are the compounds disclosed in the examples or a pharmaceutically acceptable salt, solvate or hydrate or a pharmaceutically acceptable formulation thereof.

The expression alkyl refers to a saturated, straight-chain or branched hydrocarbon group that contains from 1 to 20 carbon atoms, preferably from 1 to 15 carbon atoms, especially from 1 to 10 (e.g. 1, 2, 3 or 4) carbon atoms, for example a methyl, ethyl, propyl, iso-propyl, n-butyl, iso-butyl, sec-butyl, tert-butyl, n-pentyl, iso-pentyl, n-hexyl, 2,2-dimethylbutyl or n-octyl group.

The expression $C_{1-6}$ alkyl refers to a saturated, straight-chain or branched hydrocarbon group that contains from 1 to 6 carbon atoms. The expression $C_{1-4}$ alkyl refers to a saturated, straight-chain or branched hydrocarbon group that contains from 1 to 4 carbon atoms. Examples are a methyl (Me), $CF_3$, ethyl, propyl, iso-propyl, n-butyl, iso-butyl, sec-butyl or tert-butyl group.

The expressions alkenyl and alkynyl refer to at least partially unsaturated, straight-chain or branched hydrocarbon groups that contain from 2 to 20 carbon atoms, preferably from 2 to 15 carbon atoms, especially from 2 to 10 (e.g. 2, 3 or 4) carbon atoms, for example an ethenyl (vinyl), propenyl (allyl), iso-propenyl, butenyl, ethinyl, propinyl, butinyl, acetylenyl, propargyl, isoprenyl or hex-2-enyl group. Preferably, alkenyl groups have one or two (especially preferably one) double bond(s), and alkynyl groups have one or two (especially preferably one) triple bond(s).

Furthermore, the terms alkyl, alkenyl and alkynyl refer to groups in which one or more hydrogen atoms have been replaced by a halogen atom (preferably F or Cl) such as, for example, a 2,2,2-trichloroethyl or a trifluoromethyl group.

The expression heteroalkyl refers to an alkyl, alkenyl or alkynyl group in which one or more (preferably 1 to 8; especially preferably 1, 2, 3 or 4) carbon atoms have been replaced by an oxygen, nitrogen, phosphorus, boron, selenium, silicon or sulfur atom (preferably by an oxygen, sulfur or nitrogen atom) or by a SO or a $SO_2$ group. The expression heteroalkyl furthermore refers to a carboxylic acid or to a group derived from a carboxylic acid, such as, for example, acyl, acylalkyl, alkoxycarbonyl, acyloxy, acyloxyalkyl, carboxyalkylamide or alkoxycarbonyloxy.

Preferably, a heteroalkyl group contains from 1 to 12 carbon atoms and from 1 to 8 heteroatoms selected from oxygen, nitrogen and sulphur (especially oxygen and nitrogen). Especially preferably, a heteroalkyl group contains from 1 to 6 (e.g. 1, 2, 3 or 4) carbon atoms and 1, 2, 3 or 4 (especially 1, 2 or 3) heteroatoms selected from oxygen, nitrogen and sulphur (especially oxygen and nitrogen). The term $C_1$-$C_6$ heteroalkyl refers to a heteroalkyl group containing from 1 to 6 carbon atoms and 1, 2 or 3 heteroatoms selected from O, S and/or N (especially O and/or N). The term $C_1$-$C_4$ heteroalkyl refers to a heteroalkyl group containing from 1 to 4 carbon atoms and 1, 2 or 3 heteroatoms selected from O, S and/or N (especially O and/or N). Furthermore, the term heteroalkyl refers to groups in which one or more hydrogen atoms have been replaced by a halogen atom (preferably F or Cl).

Especially preferably, the expression heteroalkyl refers to an alkyl group as defined above (straight-chain or branched) in which one or more (preferably 1 to 6; especially preferably 1, 2, 3 or 4) carbon atoms have been replaced by an oxygen, sulfur or nitrogen atom; this group preferably contains from 1 to 6 (e.g. 1, 2, 3 or 4) carbon atoms and 1, 2, 3 or 4 (especially 1, 2 or 3) heteroatoms selected from oxygen, nitrogen and sulphur (especially oxygen and nitrogen); this group may preferably be substituted by one or more (preferably 1 to 6; especially preferably 1, 2, 3 or 4) fluorine, chlorine, bromine or iodine atoms or OH, =O, SH, =S, $NH_2$, =NH, $N_3$, CN or $NO_2$ groups.

Examples of heteroalkyl groups are groups of formulae:
$R^a$—O—$Y^a$—, $R^a$—S—$Y^a$—, $R^a$—SO—$Y^a$—, $R^a$—$SO_2$—$Y^a$—, $R^a$—N($R^b$)—$Y^a$—, $R^a$—CO—$Y^a$—, $R^a$—O—CO—$Y^a$—, $R^a$—CO—O—$Y^a$—, $R^a$—CO—N($R^b$) —$Y^a$—, $R^a$—N($R^b$)—CO—$Y^a$—, $R^a$—O—CO—N ($R^b$)—$Y^a$—, $R^a$—N($R^b$)—CO—O—$Y^a$—, $R^a$—N($R^b$)—CO—N($R^c$)—$Y^a$—, $R^a$—O—CO—O—$Y^a$—, $R^a$—N($R^b$)—C(=N$R^d$)—N($R^c$)—$Y^a$—, $R^a$—CS—$Y^a$—, $R^a$—O—CS—$Y^a$—, $R^a$—CS—O—$Y^a$—, $R^a$—CS—N($R^b$)—$Y^a$—, $R^a$—N($R^b$)—CS—$Y^a$—, $R^a$—O—CS—N($R^b$)—$Y^a$—, $R^a$—N($R^b$)—CS—O—$Y^a$—, $R^a$—N($R^b$)—CS—N($R^c$)—$Y^a$—, $R^a$—O—CS—O—$Y^a$—, $R^a$—S—CO—$Y^a$—, $R^a$—CO—S—$Y^a$—, $R^a$—S—CO—N($R^b$)—$Y^a$—, $R^a$—N($R^b$)—CO—S—$Y^a$—, $R^a$—S—CO—O—$Y^a$—, $R^a$—O—CO—S—$Y^a$—, $R^a$—S—CO—S—$Y^a$—, $R^a$—S—CS—$Y^a$—, $R^a$—CS—S—$Y^a$—, $R^a$—S—CS—N($R^b$)—$Y^a$—, $R^a$—N($R^b$)—CS—S—$Y^a$—, $R^a$—S—CS—O—$Y^a$—, $R^a$—O—CS—S—$Y^a$—, wherein $R^a$ being a hydrogen atom, a $C_1$-$C_6$ alkyl, a $C_2$-$C_6$ alkenyl or a $C_2$-$C_6$ alkynyl group; $R^b$ being a hydrogen atom, a $C_1$-$C_6$ alkyl, a $C_2$-$C_6$ alkenyl or a $C_2$-$C_6$ alkynyl group; R being a hydrogen atom, a $C_1$-$C_6$ alkyl, a $C_2$-$C_6$ alkenyl or a $C_2$-$C_6$ alkynyl group; $R^d$ being a hydrogen atom, a $C_1$-$C_6$ alkyl, a $C_2$-$C_6$ alkenyl or a $C_2$-$C_6$ alkynyl group and $Y^a$ being a bond, a $C_1$-$C_6$ alkylene, a $C_2$-$C_6$ alkenylene or a $C_2$-$C_6$ alkynylene group, wherein each heteroalkyl group contains at least one carbon atom and one or more hydrogen atoms may be replaced by fluorine or chlorine atoms.

Specific examples of heteroalkyl groups are methoxy, trifluoromethoxy, ethoxy, n-propyloxy, isopropyloxy, butoxy, tert-butyloxy, methoxymethyl, ethoxymethyl, —CH$_2$CH$_2$OH, —CH$_2$OH, —SO$_2$Me, —COOH, —NHCONH$_2$, —NHAc, methoxyethyl, 1-methoxyethyl, 1-ethoxyethyl, 2-methoxyethyl or 2-ethoxyethyl, methylamino, ethylamino, propylamino, isopropylamino, dimethylamino, diethylamino, isopropylethylamino, methylamino methyl, ethylamino methyl, diisopropylamino ethyl, methylthio, ethylthio, isopropylthio, enol ether, dimethylamino methyl, dimethylamino ethyl, acetyl, propionyl, butyryloxy, acetyloxy, methoxycarbonyl, ethoxycarbonyl, propionyloxy, acetylamino or propionylamino, carboxymethyl, carboxyethyl or carboxypropyl, N-ethyl-N-methylcarbamoyl or N-methylcarbamoyl. Further examples of heteroalkyl groups are nitrile (—CN), isonitrile, cyanate, thiocyanate, isocyanate, isothiocyanate and alkylnitrile groups.

The expression alkylene group refers to a divalent alkyl group; the expression alkenylene group refers to a divalent alkenyl group (e.g. a group of formula —CH=C(CH$_3$)—); and the expression heteroalkylene group refers to a divalent heteroalkyl group (e.g. a group of formula —O—CH(CH$_3$)— or —CO—O—CH$_2$—).

The expression cycloalkyl refers to a saturated or partially unsaturated (for example, a cycloalkenyl group) cyclic group that contains one or more rings (preferably 1 or 2), and contains from 3 to 14 ring carbon atoms, preferably from 3 to 10 (especially 3, 4, 5, 6 or 7) ring carbon atoms. The expression cycloalkyl refers furthermore to groups in which one or more hydrogen atoms have been replaced by fluorine, chlorine, bromine or iodine atoms or by OH, =O, SH, =S, NH$_2$, =NH, N$_3$ or NO$_2$ groups, thus, for example, cyclic ketones such as, for example, cyclohexanone, 2-cyclohexenone or cyclopentanone. Further specific examples of cycloalkyl groups are a cyclopropyl, cyclobutyl, cyclopentyl, spiro[4,5]decanyl, norbornyl, cyclohexyl, cyclopentenyl, cyclohexadienyl, decalinyl, bicyclo[4.3.0]nonyl, tetraline, cyclopentylcyclohexyl, fluorocyclohexyl or cyclohex-2-enyl group.

The expression heterocycloalkyl refers to a cycloalkyl group as defined above in which one or more (preferably 1, 2 or 3) ring carbon atoms have been replaced by an oxygen, nitrogen, silicon, selenium, phosphorus or sulfur atom (preferably by an oxygen, sulfur or nitrogen atom) or a SO group or a SO$_2$ group. A heterocycloalkyl group has preferably 1 or 2 ring(s) containing from 3 to 10 (especially 3, 4, 5, 6 or 7) ring atoms (preferably selected from C, O, N and S). The expression heterocycloalkyl refers furthermore to groups that are substituted by fluorine, chlorine, bromine or iodine atoms or by OH, =O, SH, =S, NH$_2$, =NH, N$_3$ or NO$_2$ groups. Examples are a piperidyl, prolinyl, imidazolidinyl, piperazinyl, morpholinyl, urotro-pinyl, pyrrolidinyl, tetrahydrothiophenyl, tetrahydropyranyl, tetrahydrofuryl or 2-pyrazolinyl group and also lactames, lactones, cyclic imides and cyclic anhydrides.

The expression alkylcycloalkyl refers to groups that contain both cycloalkyl and also alkyl, alkenyl or alkynyl groups in accordance with the above definitions, for example alkylcycloalkyl, cycloalkylalkyl, alkylcycloalkenyl, alkenylcycloalkyl and alkynylcycloalkyl groups. An alkylcycloalkyl group preferably contains a cycloalkyl group that contains one or two rings having from 3 to 10 (especially 3, 4, 5, 6 or 7) ring carbon atoms, and one or two alkyl, alkenyl or alkynyl groups (especially alkyl groups) having 1 or 2 to 6 carbon atoms.

The expression heteroalkylcycloalkyl refers to alkylcycloalkyl groups as defined above in which one or more (preferably 1, 2 or 3) carbon atoms have been replaced by an oxygen, nitrogen, silicon, selenium, phosphorus or sulfur atom (preferably by an oxygen, sulfur or nitrogen atom) or a SO group or a SO$_2$ group. A heteroalkylcycloalkyl group preferably contains 1 or 2 rings having from 3 to 10 (especially 3, 4, 5, 6 or 7) ring atoms, and one or two alkyl, alkenyl, alkynyl or heteroalkyl groups (especially alkyl or heteroalkyl groups) having from 1 or 2 to 6 carbon atoms. Examples of such groups are alkylheterocycloalkyl, alkylheterocycloalkenyl, alkenylheterocycloalkyl, alkynylheterocycloalkyl, heteroalkylcycloalkyl, heteroalkylheterocycloalkyl and heteroalkylheterocycloalkenyl, the cyclic groups being saturated or mono-, di- or tri-unsaturated.

The expression aryl refers to an aromatic group that contains one or more rings containing from 6 to 14 ring carbon atoms, preferably from 6 to 10 (especially 6) ring carbon atoms. The expression aryl refers furthermore to groups that are substituted by fluorine, chlorine, bromine or iodine atoms or by OH, SH, NH$_2$, N$_3$ or NO$_2$ groups. Examples are the phenyl, naphthyl, biphenyl, 2-fluorophenyl, anilinyl, 3-nitrophenyl or 4-hydroxyphenyl group.

The expression heteroaryl refers to an aromatic group that contains one or more rings containing from 5 to 14 ring atoms, preferably from 5 to 10 (especially 5 or 6 or 9 or 10) ring atoms, comprising one or more (preferably 1, 2, 3 or 4) oxygen, nitrogen, phosphorus or sulfur ring atoms (preferably O, S or N). The expression heteroaryl refers furthermore to groups that are substituted by fluorine, chlorine, bromine or iodine atoms or by OH, SH, N$_3$, NH$_2$ or NO$_2$ groups. Examples are pyridyl (e.g. 4-pyridyl), imidazolyl (e.g. 2-imidazolyl), phenylpyrrolyl (e.g. 3-phenylpyrrolyl), thiazolyl, isothiazolyl, 1,2,3-triazolyl, 1,2,4-triazolyl, oxadiazolyl, thiadiazolyl, indolyl, indazolyl, tetrazolyl, pyrazinyl, pyrimidinyl, pyridazinyl, 4-hydroxypyridyl (4-pyridonyl), 3,4-hydroxypyridyl (3,4-pyridonyl), oxazolyl, isoxazolyl, triazolyl, tetrazolyl, isoxazolyl, indazolyl, indolyl, benzimidazolyl, benzoxazolyl, benz-isoxazolyl, benzthiazolyl, pyridazinyl, quinolinyl, isoquinolinyl, pyrrolyl, purinyl, carbazolyl, acridinyl, pyrimidyl, 2,3'-bifuryl, pyrazolyl (e.g. 3-pyrazolyl) and isoquinolinyl groups.

The expression aralkyl refers to groups containing both aryl and also alkyl, alkenyl, alkynyl and/or cycloalkyl groups in accordance with the above definitions, such as, for example, arylalkyl, arylalkenyl, arylalkynyl, arylcycloalkyl, arylcycloalkenyl, alkylarylcycloalkyl and alkylarylcycloalkenyl groups. Specific examples of aralkyls are toluene, xylene, mesitylene, styrene, benzyl chloride, o-fluorotoluene, 1H-indene, tetraline, dihydronaphthalene, indanone, phenylcyclopentyl, cumene, cyclohexylphenyl, fluorene and indane. An aralkyl group preferably contains one or two aromatic ring systems (especially 1 or 2 rings), each containing from 6 to 10 carbon atoms and one or two alkyl, alkenyl and/or alkynyl groups containing from 1 or 2 to 6 carbon atoms and/or a cycloalkyl group containing 5 or 6 ring carbon atoms.

The expression heteroaralkyl refers to groups containing both aryl and/or heteroaryl groups and also alkyl, alkenyl, alkynyl and/or heteroalkyl and/or cycloalkyl and/or heterocycloalkyl groups in accordance with the above definitions. A heteroaralkyl group preferably contains one or two aromatic ring systems (especially 1 or 2 rings), each containing from 5 or 6 to 9 or 10 ring atoms (preferably selected from C, N, O and S) and one or two alkyl, alkenyl and/or alkynyl groups containing 1 or 2 to 6 carbon atoms and/or one or two heteroalkyl groups containing 1 to 6 carbon atoms and 1, 2 or 3 heteroatoms selected from O, S and N and/or one or two cycloalkyl groups each containing 5 or 6 ring carbon atoms and/or one or two heterocycloalkyl groups, each containing 5 or 6 ring atoms comprising 1, 2, 3 or 4 oxygen, sulfur or nitrogen atoms.

Examples are arylheteroalkyl, arylheterocycloalkyl, arylheterocycloalkenyl, arylalkyl-heterocycloalkyl, arylalkenyl-heterocycloalkyl, arylalkynylheterocycloalkyl, arylalkylhetero-cycloalkenyl, heteroarylalkyl, heteroarylalkenyl, heteroarylalkynyl, heteroarylheteroalkyl, heteroarylcycloalkyl, heteroarylcycloalkenyl, heteroarylheterocycloalkyl, hetero-arylheterocycloalkenyl, heteroarylalkylcycloalkyl, heteroarylalkylheterocycloalkenyl, hetero-arylheteroalkylcycloalkyl, heteroarylheteroalkylcycloalkenyl and heteroarylheteroalkylhetero-cycloalkyl groups, the cyclic groups being saturated or mono-, di- or tri-unsaturated. Specific examples are a tetrahydroisoquinolinyl, benzoyl, phthalidyl, 2- or 3-ethylindolyl, 4-methyl-pyridino, 2-, 3- or 4-methoxyphenyl, 4-ethoxyphenyl, 2-, 3- or 4-carboxyphenylalkyl group.

As already stated above, the expressions cycloalkyl, heterocycloalkyl, alkylcycloalkyl, heteroalkylcycloalkyl, aryl, heteroaryl, aralkyl and heteroaralkyl also refer to groups that are substituted by fluorine, chlorine, bromine or iodine atoms or by OH, =O, SH, =S, NH$_2$, =NH, N$_3$ or NO$_2$ groups.

The expression "optionally substituted" especially refers to groups that are optionally substituted by fluorine, chlorine, bromine or iodine atoms or by OH, =O, SH, =S, NH$_2$, =NH, —SO$_3$H, —SO$_2$NH$_2$, —COOH, —CONH$_2$, —CN, —NHCONH$_2$, N$_3$ or NO$_2$ groups. This expression refers furthermore especially to groups that may be substituted by one, two, three or more (preferably unsubstituted) C$_1$-C$_{10}$ alkyl, C$_2$-C$_{10}$ alkenyl, C$_2$-C$_{10}$ alkynyl, C$_1$-C$_{10}$ heteroalkyl, C$_3$-C$_{18}$ cycloalkyl, C$_2$-C$_{17}$ heterocycloalkyl, C$_4$-C$_{20}$ alkylcycloalkyl, C$_2$-C$_{19}$ heteroalkylcycloalkyl, C$_6$-C$_{18}$ aryl, C$_1$-C$_{17}$ heteroaryl, C$_7$-C$_{20}$ aralkyl or C$_2$-C$_{19}$ heteroaralkyl groups. This expression refers furthermore especially to groups that may be substituted by one, two, three or more (preferably unsubstituted) C$_1$-C$_6$ alkyl, C$_2$-C$_6$ alkenyl, C$_2$-C$_6$ alkynyl, C$_1$-C$_6$ heteroalkyl, C$_3$-C$_{10}$ cycloalkyl, C$_2$-C$_9$ heterocycloalkyl, C$_7$-C$_{12}$ alkylcycloalkyl, C$_2$-C$_{11}$ heteroalkylcycloalkyl, C$_6$-C$_{10}$ aryl, C$_1$-C$_9$ heteroaryl, C$_7$-C$_{12}$ aralkyl or C$_2$-C$_{11}$ heteroaralkyl groups.

Preferred substituents are: halogen atoms (e.g. F, Cl, Br), groups of formula —OH, —O—C$_{1-6}$ alkyl (e.g. —OMe, —OEt, —O-nPr, —O-iPr, —O-nBu, —O-iBu or —O-tBu), —NH$_2$, —NHC$_{1-6}$ alkyl, —N(C$_{1-6}$ alkyl)$_2$, —COOH, —SO$_3$H, =O, —SO$_2$NH$_2$, —CONH$_2$, —CN, —C$_{1-6}$ alkyl (e.g. —Me, -Et, -nPr, -iPr, -nBu, -iBu, -tBu or —CF$_3$), —SH, —S—C$_{1-6}$ alkyl, NHAc, —NO$_2$, —C≡CH, —NHCONH$_2$, —SO$_2$Me, cyclopropyl and a group of the following formulas:

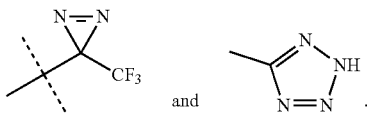

and

The term halogen refers to F, Cl, Br or I.

According to a preferred embodiment, all alkyl, alkenyl, alkynyl, heteroalkyl, aryl, heteroaryl, cycloalkyl, heterocycloalkyl, alkylcycloalkyl, heteroalkylcycloalkyl, aralkyl and heteroaralkyl groups described herein may independently of each other optionally be substituted.

When an aryl, heteroaryl, cycloalkyl, alkylcycloalkyl, heteroalkylcycloalkyl, heterocycloalkyl, aralkyl or heteroaralkyl group contains more than one ring, these rings may be bonded to each other via a single or double bond or these rings may be annulated.

Owing to their substitution, the compounds of the present invention may contain one or more centers of chirality. The present invention therefore includes both all pure enantiomers and all pure diastereoisomers and also mixtures thereof in any mixing ratio. The present invention moreover also includes all cis/trans-isomers of the compounds of the present invention and also mixtures thereof. The present invention moreover includes all tautomeric forms of the compounds of the present invention.

The present invention further provides pharmaceutical compositions comprising one or more compounds described herein or a pharmaceutically acceptable salt, solvate or hydrate thereof, optionally in combination with one or more carrier substances and/or one or more adjuvants.

The present invention furthermore provides compounds or pharmaceutical compositions as described herein for use in the treatment and/or prophylaxis of bacterial infections, especially caused by *E. coli, P. aeruginosa, A. baumannii*, other Gram-negative bacteria, and Gram-positive bacteria.

Moreover preferably, the present invention provides compounds for use in the treatment and/or prophylaxis of bacterial infections, especially caused by *Pseudomonas aeruginosa* and other Gram-negative bacteria.

Further preferably, the present invention provides compounds for use in the treatment and/or prophylaxis of bacterial infections caused by *K. pneumoniae*.

Moreover preferably, the present invention provides compounds for use in the treatment and/or prophylaxis of bacterial infections, especially caused by *S. aureus, S. epidermidis* and *E. faecalis*.

It is a further object of the present invention to provide a compound as described herein or a pharmaceutical composition as defined herein for the preparation of a medicament for the treatment and/or prophylaxis of bacterial infections, especially caused by selected Gram-negative bacteria and Gram-positive bacteria.

Examples of pharmacologically acceptable salts of sufficiently basic compounds are salts of physiologically acceptable mineral acids like hydrochloric, hydrobromic, sulfuric and phosphoric acid; or salts of organic acids like methanesulfonic, p-toluenesulfonic, lactic, acetic, trifluoroacetic, citric, succinic, fumaric, maleic and salicylic acid. Further, a sufficiently acidic compound may form alkali or earth alkali metal salts, for example sodium, potassium, lithium, calcium or magnesium salts; ammonium salts; or organic base salts, for example methylamine, dimethylamine, trimethylamine, triethylamine, ethylenediamine, ethanolamine, choline hydroxide, meglumin, piperidine, morpholine, tris-(2-hydroxyethyl)amine, lysine or arginine salts; all of which are also further examples of salts of the compounds described herein. Preferred pharmacologically acceptable salts are ammonium salts.

The compounds described herein may be solvated, especially hydrated. The hydratization/hydration may occur during the process of production or as a consequence of the hygroscopic nature of the initially water free compounds. The solvates and/or hydrates may e.g. be present in solid or liquid form.

The therapeutic use of the compounds described herein, their pharmacologically acceptable salts, solvates and hydrates, respectively, as well as formulations and pharmaceutical compositions also lie within the scope of the present invention.

The pharmaceutical compositions according to the present invention comprise at least one compound described herein and, optionally, one or more carrier substances and/or adjuvants.

As mentioned above, therapeutically useful agents that contain compounds described herein, their solvates, salts or formulations are also comprised in the scope of the present invention. In general, the compounds described herein will be administered by using the known and acceptable modes known in the art, either alone or in combination with any other therapeutic agent.

For oral administration such therapeutically useful agents can be administered by one of the following routes: oral, e.g. as tablets, dragees, coated tablets, pills, semisolids, soft or hard capsules, for example soft and hard gelatine capsules, aqueous or oily solutions, emulsions, suspensions or syrups, parenteral including intravenous, intramuscular and subcutaneous injection, e.g. as an injectable solution or suspension, rectal as suppositories, by inhalation or insufflation, e.g. as a powder formulation, as microcrystals or as a spray (e.g. liquid aerosol), transdermal, for example via an transdermal delivery system (TDS) such as a plaster containing the active ingredient or intranasal. For the production of such tablets, pills, semisolids, coated tablets, dragees and hard, e.g. gelatine, capsules the therapeutically useful product may be mixed with pharmaceutically inert, inorganic or organic excipients as are e.g. lactose, sucrose, glucose, gelatine, malt, silica gel, starch or derivatives thereof, talc, stearinic acid or their salts, dried skim milk, and the like. For the production of soft capsules one may use excipients as are e.g. vegetable, petroleum, animal or synthetic oils, wax, fat, and polyols. For the production of liquid solutions, emulsions or suspensions or syrups one may use as excipients e.g. water, alcohols, aqueous saline, aqueous dextrose, polyols, glycerin, lipids, phospholipids, cyclodextrins, vegetable, petroleum, animal or synthetic oils. Especially preferred are lipids and more preferred are phospholipids (preferred of natural origin; especially preferred with a particle size between 300 to 350 nm) preferred in phosphate buffered saline (pH=7 to 8, preferred 7.4). For suppositories one may use excipients as are e.g. vegetable, petroleum, animal or synthetic oils, wax, fat and polyols. For aerosol formulations one may use compressed gases suitable for this purpose, as are e.g. oxygen, nitrogen and carbon dioxide. The pharmaceutically useful agents may also contain additives for conservation, stabilization, e.g. UV stabilizers, emulsifiers, sweetener, aromatizers, salts to change the osmotic pressure, buffers, coating additives and antioxidants.

In general, in the case of oral or parenteral administration to adult humans weighing approximately 80 kg, a daily dosage of about 1 mg to about 10,000 mg, preferably from about 5 mg to about 1,000 mg, should be appropriate, although the upper limit may be exceeded when indicated. The daily dosage can be administered as a single dose or in divided doses, or for parenteral administration, it may be given as continuous infusion or subcutaneous injection.

EXAMPLES

1. General

All commercial chemicals and solvents were reagent grade and were used without further purification. Reaction progress was monitored by TLC on pre-coated silica gel 60 F254 plates (Merck) and visualization was accomplished with UV light (254 nm) and with potassium permanganate staining solution (Dissolve 1.5 g of $KMnO_4$, 10 g $K_2CO_3$, and 1.25 mL 10% NaOH in 200 mL water) and LCMS with the following instruments: LC (Agilent technologies 1260 Infinity II) coupled to MS (Agilent technologies 6130 quadrupole LC/MS) using an Agilent poroshell 120 SB-C18 2.7 m 2.1×30 mm column and LCMS (API150EX, Applied Biosystems) using a YMC Pack J'sphere H80, 33×2.1 mm JH 085040302 QC column. LCMS analyses, analytical data were recorded with LC (Agilent technologies 1200 series) coupled to amaZon SL using a Gemini-NX 3u C18 110A 50×2.0 mm column. $^1H$ and $^{13}C$ NMR spectra were recorded on Bruker AVANCE III 500 and 700 spectrometers. Chemical shifts are reported as δ values in parts per million (ppm) and referenced to residual solvent peak as internal reference ($CDCl_3$, DMSO-d6); J values were given in Hz. When peak multiplicities are given the following abbreviations are used: s, singlet; d, doublet; t, triplet; q, quartet; hept, heptet; m, multiplet; br, broadened signal. ReverelisX2 flash chromatography system was used for purification of the compounds (GraceResolv cartridges), alternatively, silica gel 60M MACHEREY-NAGEL (0.040-0.063 mm; 230-400 mesh) was used for column chromatography. Preparative reversed phase (RP) HPLC was carried out using a Thermo Scientific Dionex (UltiMate 3000 HPLC system) with a Phenomenex Luna C18(2) (250 mm×21.2 mm) column. For microwave assisted reaction, Biotage® Initiator+ was used. Purity and identity of the compounds were assayed by means of TLC (Merck F-254 silica gel), LCMS (API150EX, Applied Biosystems), HRMS (maxis HD, Bruker), IR and NMR analyses.

Solvents and chemicals abbreviation:
Pet. Et.=petrolether
EA=ethyl acetate
DCM=dichloromethane
THF=tetrahydrofuran
DMSO=dimethyl sulfoxide
TEA=trimethylamine
DiPEA=diisopropylethylamin
$CH_3CN$=acetonitrile
TFA=Trifluoroacetic acid
EDC=N-(3-Dimethylaminopropyl)-N'-ethylcarbodiimide hydrochloride
DCC=Dicyclohexylcarbodiimid
HBTU=2-(1H-benzotriazol-1-yl)-1,1,3,3-tetramethyluronium hexafluorophosphate
HOAt=1-Hydroxy-7-azabenzotriazole
BTC=Bis(trichloromethyl) carbonate Tips=Triisopropylsilane
AcOH=acetic acid

1.1 Marfey Assay

Sample (5 μmol) treated with HCl 6N at 110° C. for 6 h. Sample dried via Freeze-drying, residue treated with NaHCO₃ saturated solution (100 μL) and a solution 1% of Marfey reagent (FDAA) in acetone (200 μL). Reaction stirred at 40° C. for 1 h and quenched with HCl 1 N (100 μL). Sample analyzed by LCMS. (column, Gemini-NX 3u C18 110 Å 50.0×2.0 mm) Results are given in % of the two diasteroisomers formed upon derivatization. The method itself, presumably during the hydrolysis step, entails partial racemization, which was quantified in around 5%.

2. Synthesis 1
2.1 Retrosynthetic Disconnection fragmets

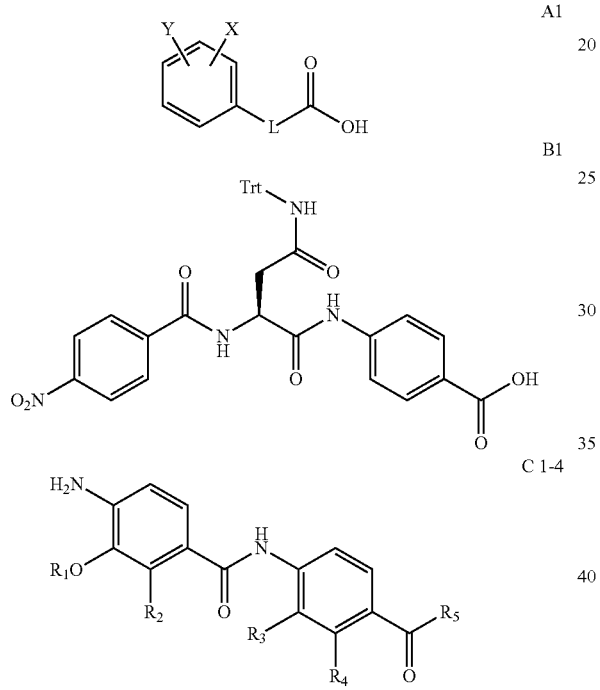

In the above formula A1, groups X and Y independently represent H or $R^6$.

2.2 Building Blocks Synthesis
a. Fragments A1
Carboxylic Acids Synthesized:

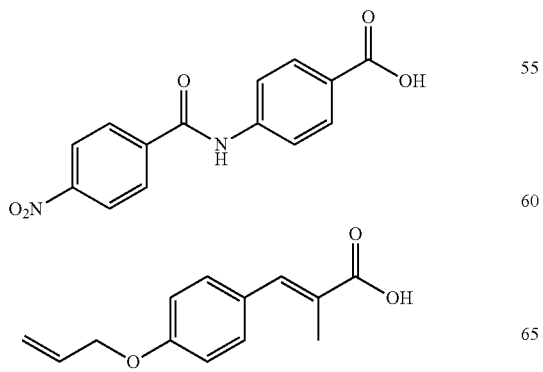

-continued

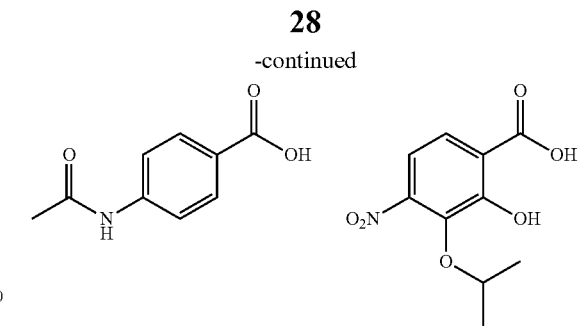

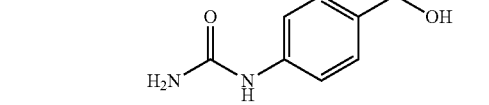

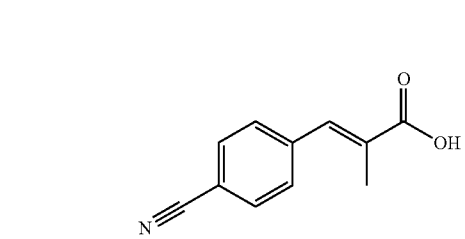

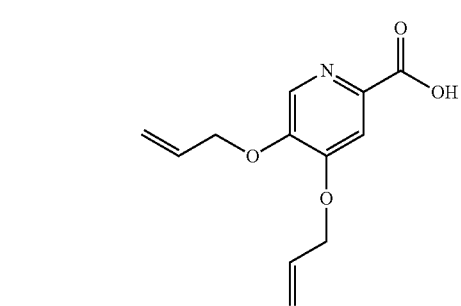

Syntheses:

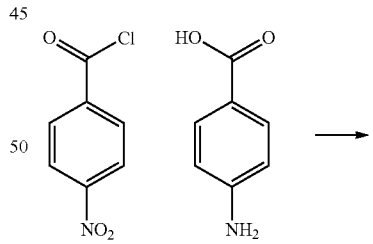

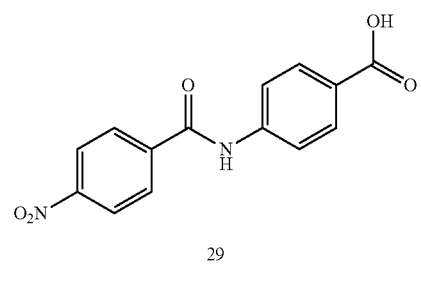

4-(4-nitrobenzamido)benzoic acid

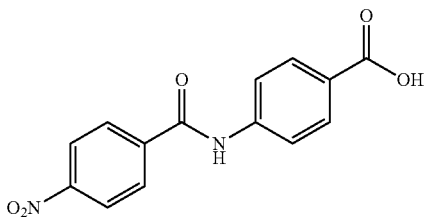 [SMILES: O=C(O)c1ccc(NC(=O)c2ccc([N+](=O)[O-])cc2)cc1]

4-Aminobenzoic acid (800 mg; 5.84 mmol) was dissolved in THF (4.0 mL) and NaHCO$_3$ saturated solution (4.0 mL), to it 4-nitrobenzoyl chloride (1.08 g; 5.84 mmol) was added at 0° C. Reaction stirred for 2 hours, precipitate collected by filtration, washed with water and THF, dried under high vacuum to give 1.30 g of a solid (4.55 mmol; y=77%).

$^1$H NMR (500 MHz, DMSO) δ 12.80 (br, 1H), 10.83 (s, 1H), 8.43-8.35 (m, 2H), 8.25-8.14 (m, 2H), 7.99-7.94 (m, 2H), 7.94-7.90 (m, 2H).

$^{13}$C NMR (126 MHz, DMSO) δ 166.9, 164.3, 149.3, 142.8, 140.3, 130.3, 129.4, 126.0, 123.6, 119.7.

HRMS (ESI) calculated for C14H9N2O5 (M−H) 285.0517, found 285.0536.

(E)-3-(4-(allyloxy)phenyl)-2-methylacrylic acid

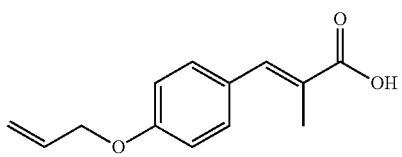

See: Angew. Chem. Int. Ed. 2014, 53, 1-6

$^1$H NMR (700 MHz, DMSO) δ 12.35 (br, 1H), 7.54 (d, J=1.1 Hz, 1H), 7.46-7.42 (m, 2H), 7.03-6.99 (m, 2H), 6.05 (ddt, J=17.3, 10.5, 5.2 Hz, 1H), 5.40 (dq, J=17.3, 1.7 Hz, 1H), 5.27 (dq, J=10.5, 1.5 Hz, 1H), 4.61 (dt, J=5.3, 1.5 Hz, 2H), 2.03 (d, J=1.5 Hz, 3H). $^{13}$C NMR (176 MHz, DMSO) δ 169.6, 158.3, 137.4, 133.5, 131.4, 128.1, 126.2, 117.6, 114.7, 68.2, 13.9.

HRMS (ESI) calculated for C13H13O3 (M−H) 217.0870, found 217.0873.

4-acetamidobenzoic acid

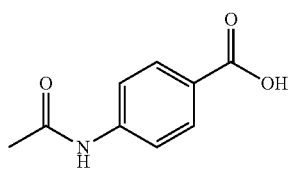

See: J. Org. Chem. 2013, 78, 11765-11771.

$^1$H NMR (500 MHz, DMSO) δ 12.67 (br, 1H), 10.23 (s, 1H), 7.90-7.84 (m, 2H), 7.68 (d, J=8.7 Hz, 2H), 2.08 (s, 3H).

$^{13}$C NMR (126 MHz, DMSO) δ 168.8, 166.9, 143.3, 130.4, 124.9, 118.1, 24.1.

HRMS (ESI) calculated for C9H8NO3 (M−H) 178.0510, found 178.0510.

2-(allyloxy)-3-isopropoxy-4-nitrobenzoic acid

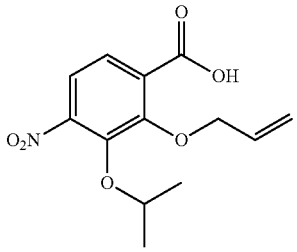 [SMILES: C=CCOc1c(C(=O)O)ccc([N+](=O)[O-])c1OC(C)C]

See synthesis of building bock C1 (section 2.2c).

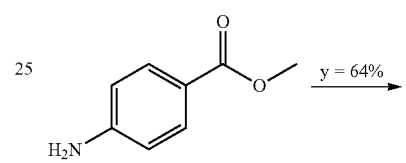

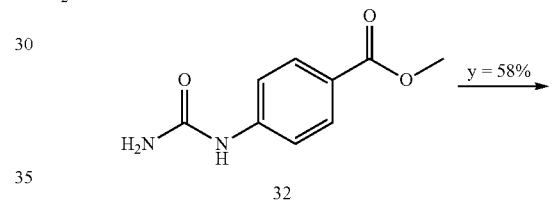

32

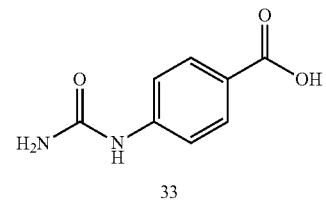

33

Methyl 4-ureidobenzoate

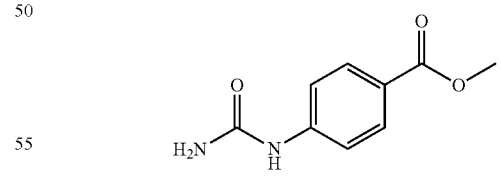

A solution of methyl 4-aminobenzoate (500 mg; 3.31 mmol) and DiPEA (0.86 mL; 4.97 mmol) in DCM (10 mL) was added dropwise at 0° C. to a solution of BTC (328 mg; 1.10 mmol) in DCM (20 mL). Reaction stirred at 0° C. for 2 h. Solvent reduced under vacuum, residue dissolved in 5 mL of DCM and added to a cooled solution of NH$_4$OH conc. The mixture was stirred for 2 hours, the solid was collected by filtration, washed with water and twice with Et$_2$O, dried under high vacuum to give 410 mg of a white powder (2.11 mmol; y=64%).

¹H NMR (500 MHz, DMSO) δ 8.98 (s, 1H), 7.87-7.79 (m, 2H), 7.57-7.48 (m, 2H), 6.05 (s, 2H), 3.79 (s, 3H).

¹³C NMR (126 MHz, DMSO) δ 166.0, 155.6, 145.3, 130.3, 121.6, 116.8, 51.7.

HRMS (ESI) calculated for C9H11N2O3 (M+H) 195.0764, found 195.0766.

4-ureidobenzoic acid

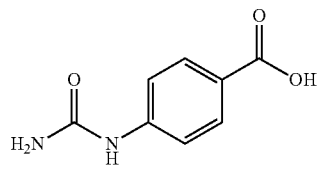 [SMILES: NC(=O)Nc1ccc(C(=O)O)cc1]

Methyl 4-ureidobenzoate (150 mg; 0.77 mmol) was suspended in THF (4 mL) and water (2 mL). A solution of LiOH (185 mg; 7.7 mmol) in water (2 mL) was added to the suspension at 0° C. Reaction stirred overnight, pH adjusted to 1, the precipitate was collected by filtration washed with water and three times with Et₂O, dried at high vacuum to give 80 mg of a white powder (0.44 mmol; y=58%).

¹H NMR (500 MHz, DMSO) δ 12.50 (br, 1H), 8.90 (s, 1H), 7.84-7.77 (m, 2H), 7.54-7.45 (m, 2H), 6.02 (s, 1H).

¹³C NMR (126 MHz, DMSO) δ 167.1, 155.6, 144.9, 130.4, 122.9, 116.7.

HRMS (ESI) calculated for C8H7N2O3 (M−H) 179.0462, found 179.0470.

ethyl (E)-3-(4-cyanophenyl)-2-methylacrylate

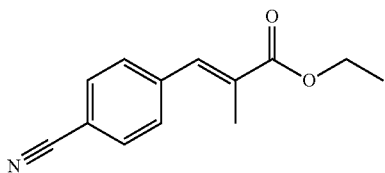 [SMILES: CCOC(=O)/C(C)=C/c1ccc(C#N)cc1]

4-hydroxybenzaldehyd (500 mg; 3.82 mmol) was dissolved in DCM (3.0 mL) at rt, ethyl-2-(triphenylphosphoranylidene) propionate (1.06 g; 2.94 mmol) was added. The mixture was stirred overnight at 37° C. then concentrated under reduced pressure. The crude was purified on silica gel with a gradient 1-50% EA in Pet. Et. to give 570 mg of white solid (2.65 mmol; y=90%).

¹H NMR (500 MHz, CDCl₃) δ 7.70-7.66 (m, 2H), 7.64 (s, 1H), 7.47 (d, J=8.2 Hz, 2H), 4.29 (q, J=7.1 Hz, 2H), 2.10 (d, J=1.5 Hz, 3H), 1.35 (t, J=7.1 Hz, 3H).

¹³C NMR (126 MHz, CDCl₃) δ 167.9, 140.6, 136.4, 132.1, 131.8, 130.0, 118.6, 111.7, 61.3, 14.3, 14.2.

HRMS (ESI) calculated for C13H14NO2 (M+H) 216.1019, found 216.1014.

(E)-3-(4-cyanophenyl)-2-methylacrylic acid (35)

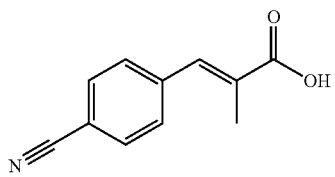

Ethyl (E)-3-(4-cyanophenyl)-2-methylacrylate (150 mg; 0.67 mmol) was dissolved in THF (3.35 mL) and water (1.68 mL), solution cooled to 0 C and a mixture of LiOH (167 mg; 6.98 mmol) in water (1.68 mL) added to it. Reaction stirred at 0 C for 10 min. then to r.t. overnight. Reaction quenched adjusting pH to 1, then diluted with EA (20 mL) and HCl 1 N (20 mL), organic solvent washed with brine and dried over sodium sulphate. Solvent reduce under vacuum to afford 125 mg of a white solid (0.67 mmol; y=q.).

¹H NMR (500 MHz, DMSO) δ 7.91-7.87 (m, 2H), 7.65 (d, J=8.2 Hz, 2H), 7.61 (s, 1H), 2.02 (d, J=1.5 Hz, 3H). ¹³C NMR (126 MHz, DMSO) δ 168.9, 140.4, 135.8, 132.3, 130.3, 127.6, 118.7, 110.6, 14.0.

HRMS (ESI) calculated for C11H10NO2 (M+H) 188.0706, found 188.0709.

4,5-bis(allyloxy)picolinic acid

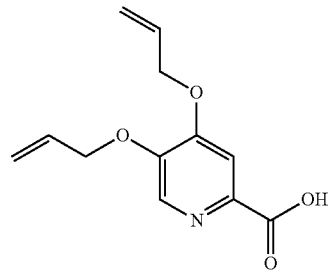 [SMILES: C=CCOc1cnc(C(=O)O)cc1OCC=C]

Synthesized following modified experimental procedures reported in "WO 2010070523 and *J. Med. Chem.*, 2013, 56 (13), pp 5541-5552". Allyl Bromide was used instead of benzyl bromide.

¹H NMR (500 MHz, MeOD) δ 8.16 (s, 1H), 7.82 (s, 1H), 6.11 (m, 2H), 5.54-5.44 (m, 2H), 5.36 (m, 2H), 4.86 (dt, J=5.3, 1.5 Hz, 2H), 4.77 (dt, J=5.3, 1.5 Hz, 2H).

¹³C NMR (126 MHz, MeOD) δ 165.4, 159.9, 149.2, 144.4, 133.6, 132.9, 131.0, 119.5, 119.2, 110.5, 72.0, 71.5.

HRMS (ESI) calculated for C12H14NO4 (M+H) 236.0917, found 236.0922.

b. Fragments B1
Synthesis:

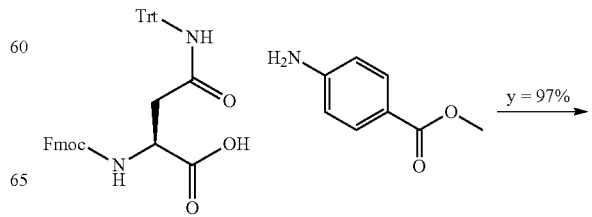

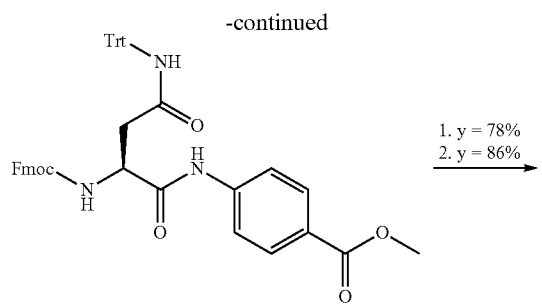

1

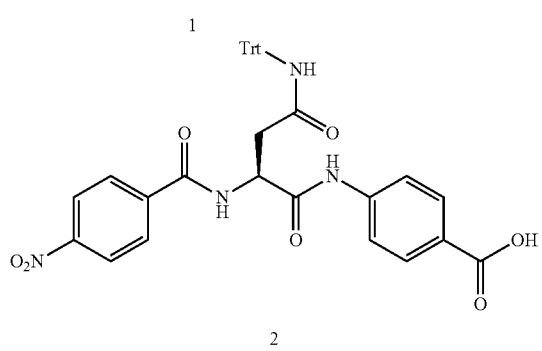

2 methyl (S)-4-(2-((((9H-fluoren-9-yl)methoxy)carbonyl)amino)-4-oxo-4-(tritylamino)butanamido)benzoate

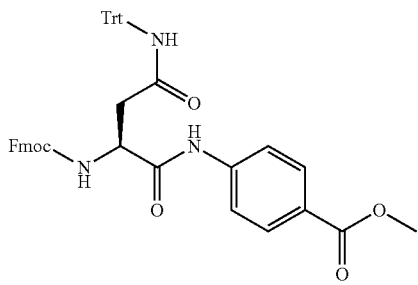

See: *J. Org. Chem.* (2012), 77, 6948-6958

POCl₃ (2.22 mL; 23.84 mmol) was added at 0° C. under N₂ atmosphere to a stirred solution of Fmoc-Asn(Trt)OH (14.22 g; 23.84 mmol), TEA (5.51 mL; 39.74 mmol) and methyl 4-aminobenzoate (3.00 g; 19.87 mmol) in DCM (330 mL). Reaction stirred at 0 C for 2 hours, quenched with HCl 1N and ice. Organic phase washed with HCL 1 N (300 mL), brine (330 mL) and dried over sodium sulphate. The solvent was removed under reduced pressure, the residue thus obtained was chromatographed on silica gel with a gradient 0-10% EA in DCM to give 13.97 g of a white solid (19.16 mmol; y=96%).

¹H NMR (700 MHz, DMSO) δ 10.44 (s, 1H), 8.62 (s, 1H), 7.91 (dd, J=15.9, 8.2 Hz, 4H), 7.80 (d, J=7.9 Hz, 1H), 7.78-7.72 (m, 4H), 7.41 (q, J=7.6 Hz, 2H), 7.30 (dt, J=22.8, 7.3 Hz, 2H), 7.23-7.15 (m, 15H), 4.48-4.43 (m, 1H), 4.36 (dd, J=10.6, 7.1 Hz, 1H), 4.30 (dd, J=10.5, 7.1 Hz, 1H), 4.23 (t, J=7.0 Hz, 1H), 2.75 (dd, J=14.6, 9.8 Hz, 1H), 2.62 (dd, J=14.6, 5.0 Hz, 1H).

¹³C NMR (176 MHz, DMSO) δ 170.9, 168.4, 165.8, 155.8, 144.7, 143.8, 143.8, 143.4, 140.7, 130.2, 128.6, 127.6, 127.4, 127.1, 126.3, 125.3, 125.2, 124.0, 120.1, 118.7, 69.4, 65.8, 52.9, 51.9, 46.7, 38.3, 20.8.

HRMS (ESI) calculated for C46H40N3O6 (M+H⁺) 730.2912, found 730.2925.

Marfey: 96.5% S enantiomer, 3.5% R enantiomer methyl (S)-4-(2-(4-nitrobenzamido)-4-oxo-4-(tritylamino)butanamido)benzoate

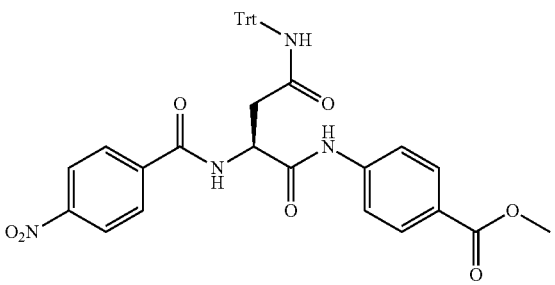

Methyl (S)-4-(2-((((9H-fluoren-9-yl)methoxy)carbonyl)amino)-4-oxo-4-(tritylamino)butan-amido)benzoate (12.26 g; 16.82 mmol) was dissolved in a 20% solution of diethylamine in acetonitrile (195 mL), solution stirred for 30 min. The solvent was removed under reduced pressure, the residue was dissolved in CH₃CN and evaporated twice. The pale yellow gum and 4-Nitrobenzoic acid (3.09 g; 18.5 mmol) were suspended in CH₃CN (140 mL), HBTU (7.02 g; 18.5 mmol) followed by DiPEA (6.754 mL, 38.85 mmol) were added at 0 C. The reaction mixture was stirred for 3 hours and quenched with NaHCO₃ saturated solution. The solvent was partially evaporated under reduced pressure, the residue was dissolved in EA (300 mL). Organic phase washed with NaHCO₃ saturated solution (300 mL), HCl 1 N (300 mL), brine (300 mL) dried over sodium sulphate and evaporated under vacuum. The residue thus obtained was triturated with Pet. Et. and chromatographed on silica gel with a gradient 0-10% EA in DCM to give 8.64 g of a yellow solid (13.17 mmol; y=78%).

¹H NMR (500 MHz, DMSO) δ 10.57 (s, 1H), 9.20 (d, J=7.6 Hz, 1H), 8.68 (s, 1H), 8.41-8.35 (m, 2H), 8.18-8.13 (m, 2H), 7.95-7.90 (m, 2H), 7.80-7.75 (m, 2H), 7.23-7.13 (m, 15H), 4.93 (m, 1H), 3.82 (s, 3H), 2.98 (dd, J=14.9, 10.5 Hz, 1H), 2.75 (dd, J=14.8, 4.6 Hz, 1H).

¹³C NMR (126 MHz, DMSO) δ 170.5, 168.3, 165.8, 164.6, 149.2, 144.7, 143.3, 139.3, 130.2, 129.0, 128.5, 127.4, 126.4, 124.1, 123.6, 118.8, 69.4, 52.1, 51.9, 37.9.

HRMS (ESI) calculated for C38H33N4O7 (M+H⁺) 657.2344, found 657.2348.

Marfey: 94.2% S enantiomer, 5.8% R enantiomer (S)-4-(2-(4-nitrobenzamido)-4-oxo-4-(tritylamino)butanamido)benzoic acid

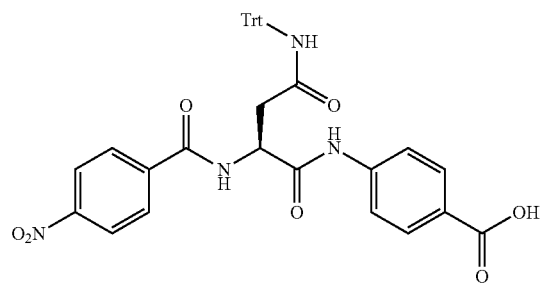

See: J. Org. Chem., 2016, 81 (3), pp 1137-1150

Methyl (S)-4-(2-(4-nitrobenzamido)-4-oxo-4-(tritylamino)butanamido)benzoate (5.7 g; 8.69 mmol) and lithium iodide (9.32 g; 69.52 mmol) were mixed in EA (80 mL) and heated to 90° C. for 5 days. After cooling, mixture diluted with EA (200 mL) and HCl 1 N (200 mL), organic phase washed with water (2×200 mL), brine (200 mL), dried over sodium sulphate and reduced under vacuum. The residue was chromatographed on silica gel with a gradient 0-20% MeOH in DCM to give 5.39 g of yellow solid (7.44 mmol; y=86%).

$^1$H NMR (700 MHz, DMSO) δ 12.72 (s, 1H), 10.52 (s, 1H), 9.19 (d, J=7.6 Hz, 1H), 8.67 (s, 1H), 8.40-8.36 (m, 2H), 8.17-8.13 (m, 2H), 7.91-7.88 (m, 2H), 7.76-7.72 (m, 2H), 7.22-7.14 (m, 15H), 4.93 (m, 1H), 2.98 (dd, J=14.9, 10.6 Hz, 1H), 2.75 (dd, J=14.9, 4.5 Hz, 1H).

$^{13}$C NMR (176 MHz, DMSO) δ 170.4, 168.3, 166.9, 164.6, 149.2, 144.7, 142.9, 139.3, 130.3, 129.0, 128.5, 127.4, 126.4, 123.6, 118.6, 69.4, 66.3, 52.0, 38.0. $^{13}$C NMR (176 MHz, DMSO) δ 170.4, 168.3, 166.9, 164.6, 149.2, 144.7, 142.9, 139.3, 130.3, 129.0, 128.5, 127.4, 126.4, 123.6, 118.6, 69.4, 52.0, 38.0.

HRMS (ESI) calculated for C37H29N4O7 (M−H) 641.2041, found 641.2045.

Marfey: 94.0% S enantiomer, 6.0% R enantiomer c. Fragments C1-4

Fragment C1

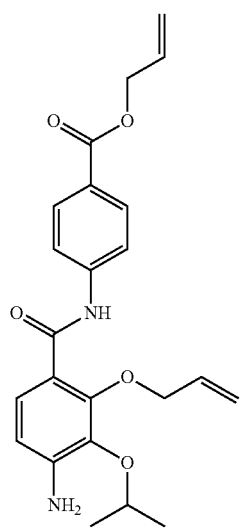

Synthesis:

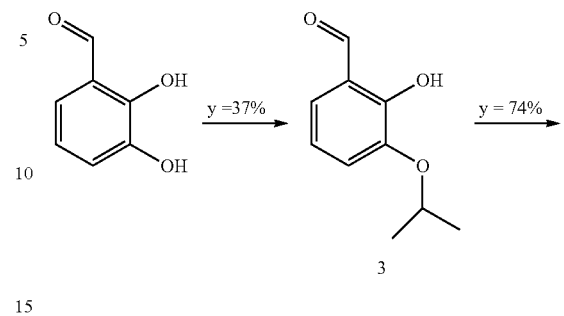

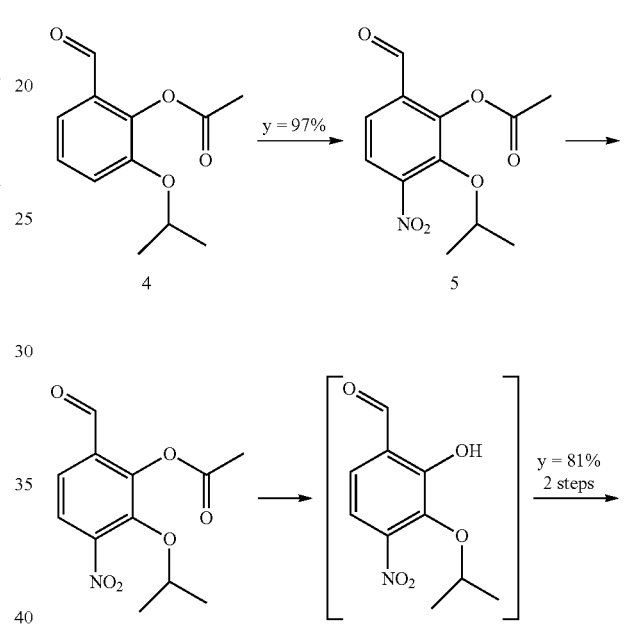

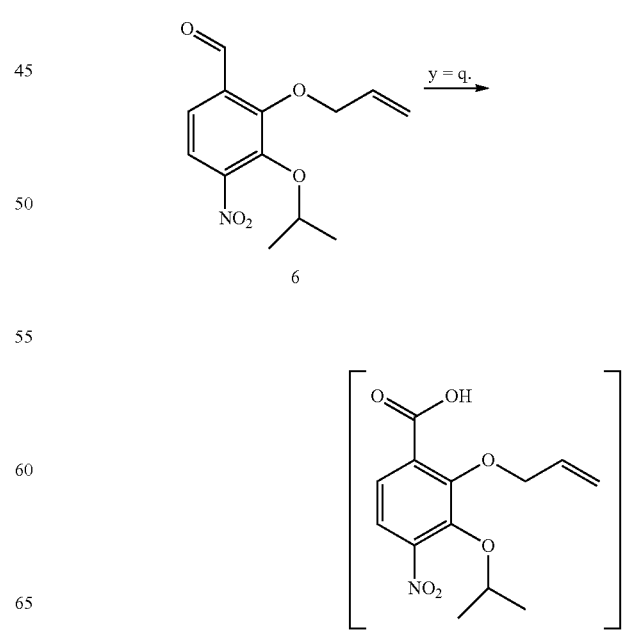

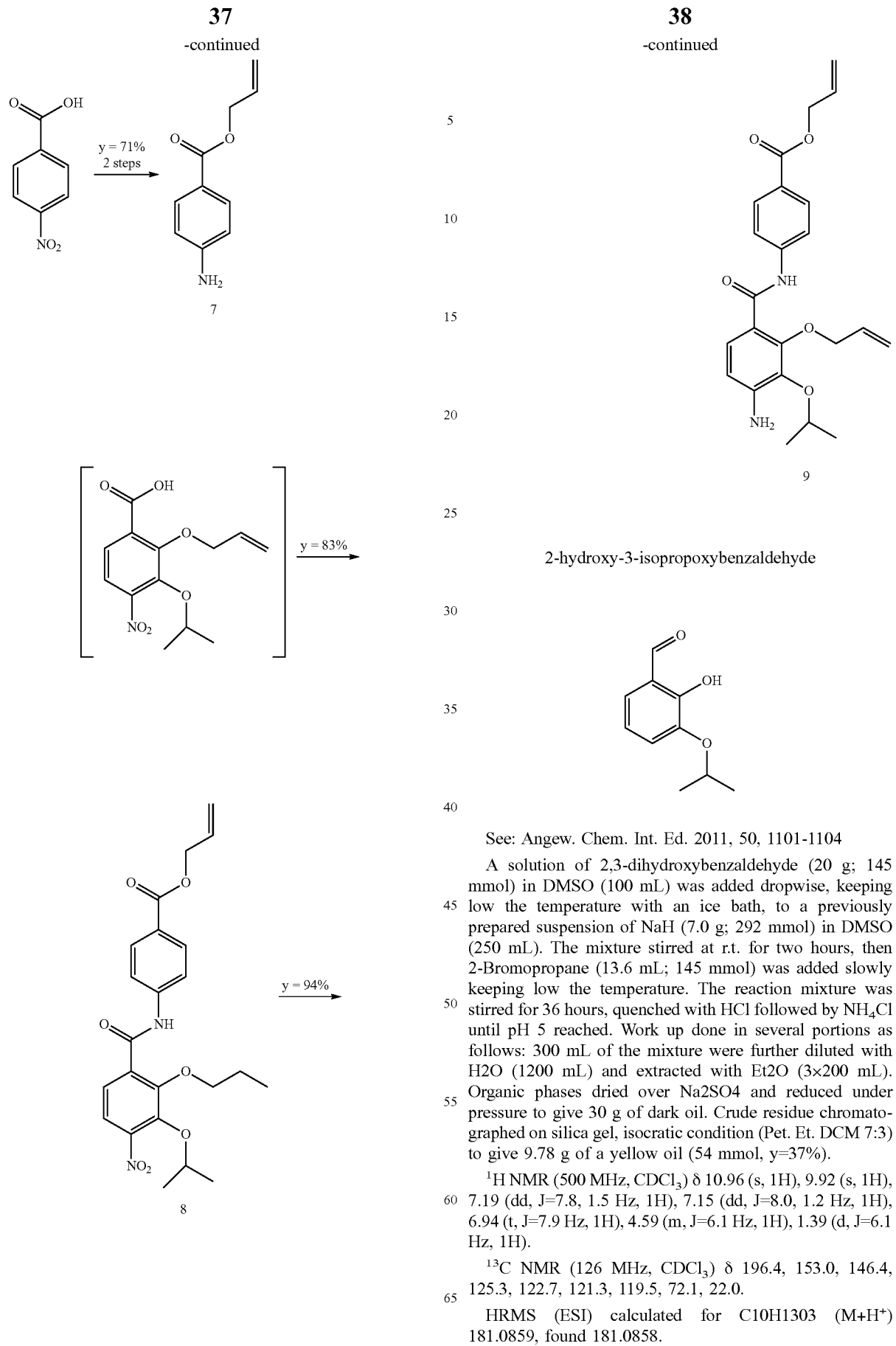

2-hydroxy-3-isopropoxybenzaldehyde

See: Angew. Chem. Int. Ed. 2011, 50, 1101-1104

A solution of 2,3-dihydroxybenzaldehyde (20 g; 145 mmol) in DMSO (100 mL) was added dropwise, keeping low the temperature with an ice bath, to a previously prepared suspension of NaH (7.0 g; 292 mmol) in DMSO (250 mL). The mixture stirred at r.t. for two hours, then 2-Bromopropane (13.6 mL; 145 mmol) was added slowly keeping low the temperature. The reaction mixture was stirred for 36 hours, quenched with HCl followed by $NH_4Cl$ until pH 5 reached. Work up done in several portions as follows: 300 mL of the mixture were further diluted with $H_2O$ (1200 mL) and extracted with $Et_2O$ (3×200 mL). Organic phases dried over $Na_2SO_4$ and reduced under pressure to give 30 g of dark oil. Crude residue chromatographed on silica gel, isocratic condition (Pet. Et. DCM 7:3) to give 9.78 g of a yellow oil (54 mmol, y=37%).

$^1$H NMR (500 MHz, $CDCl_3$) δ 10.96 (s, 1H), 9.92 (s, 1H), 7.19 (dd, J=7.8, 1.5 Hz, 1H), 7.15 (dd, J=8.0, 1.2 Hz, 1H), 6.94 (t, J=7.9 Hz, 1H), 4.59 (m, J=6.1 Hz, 1H), 1.39 (d, J=6.1 Hz, 1H).

$^{13}$C NMR (126 MHz, $CDCl_3$) δ 196.4, 153.0, 146.4, 125.3, 122.7, 121.3, 119.5, 72.1, 22.0.

HRMS (ESI) calculated for $C10H13O3$ $(M+H^+)$ 181.0859, found 181.0858.

2-formyl-6-isopropoxyphenyl acetate

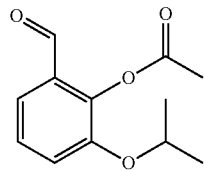 [SMILES: CC(=O)Oc1c(C=O)cccc1OC(C)C]

Acetyl chloride (4.25 mL; 59.76 mmol) was added dropwise to a stirred solution of 2-hydroxy-3-isopropoxybenzaldehyde (9.78 g; 54.33 mmol) and pyridine (9.65 mL; 119.53 mmol) in DCM (540 mL) at 0 C. Reaction stirred for 5 min. at 0° C. then temperature raised to r.t. Stirring prolonged for 1 h. Reaction quenched with HCl 1 N, organic phase partially reduced under vacuum, washed with HCl 1 N (200 mL), brine (200 mL), dried over sodium sulphate and reduced under vacuum to give 12.2 g of a yellow oil, which was chromatographed on silica gel with a gradient 2-10% EA in Pet. Et, to give 8.89 g of a pale yellow oil (40.04 mmol; y=74%).

$^1$H NMR (700 MHz, CDCl$_3$) δ 10.14 (s, 1H), 7.44 (dd, J=7.8, 1.5 Hz, 1H), 7.30 (t, J=8.0 Hz, 1H), 7.21 (dd, J=8.3, 1.3 Hz, 1H), 4.59-4.53 (m, 1H), 2.39 (s, 3H), 1.34 (d, J=6.1 Hz, 6H).

$^{13}$C NMR (176 MHz, CDCl$_3$) δ 188.8, 168.7, 150.2, 142.9, 129.5, 126.6, 121.0, 120.6, 71.9, 22.0, 20.5.

HRMS (ESI) calculated for C12H15O4 (M+H$^+$) 223.0965, found 223.0968.

6-formyl-2-isopropoxy-3-nitrophenyl acetate

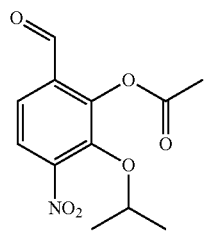 [SMILES: CC(=O)Oc1c(C=O)ccc([N+](=O)[O-])c1OC(C)C]

Fuming nitric acid (17.5 mL, 420 mmol) was cooled to −40° C. under a nitrogen atmosphere. A solution of 2-formyl-6-isopropoxyphenyl acetate (6.50 g, 29.3 mmol) in 40 mL of dry DCM was added dropwise while the mixture was vigorously stirred and kept at −40° C. The solution was stirred for an additional 1.5 hours before being poured into 150 mL of ice water. The mixture was then extracted with DCM (4×50 mL) and the combined organic extracts were dried over sodium sulphate. The solvent was removed under vacuum to afford the desired compound as an orange oil (7.59 g, 28.4 mmol, y=97%), containing around 17% of deactylated product.

$^1$H NMR (500 MHz, DMSO) δ 10.10 (d, J=0.5 Hz, 1H), 8.00 (dd, J=8.5, 0.4 Hz, 1H), 7.81 (d, J=8.5 Hz, 1H), 4.46 (hept, J=6.1 Hz, 1H), 2.44 (s, 3H), 1.22 (d, J=6.1 Hz, 6H).

$^{13}$C NMR (126 MHz, DMSO) δ 189.4, 168.3, 148.4, 145.5, 143.1, 131.8, 125.4, 122.0, 78.9, 22.1, 20.4.

HRMS (ESI) calculated for C12H14N06 (M+H$^+$) 268.0816, found 268.0811.

2-(allyloxy)-3-isopropoxy-4-nitrobenzaldehyde

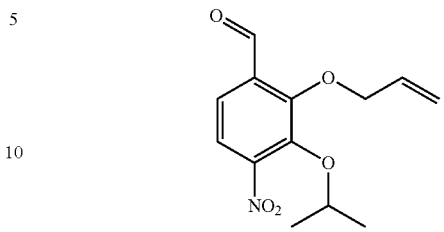

6-formyl-2-isopropoxy-3-nitrophenyl acetate (2.10 g; 7.9 mmol) was dissolved in THF (40 mL) and water (20 mL), then LiOH (1.89 g; 79.0 mmol) dissolved in water (20 mL) was added at 0 C, reaction stirred overnight. In the morning, pH adjusted to 1, solvent partially reduced under vacuum and watery phase extracted with CHCl3 (150 mL) three times, combined organic phases dried over sodium sulphate and reduced under vacuum to give a yellow oil, which was used in the next step without further purification. Residue was dissolved in DMF (20 mL), K$_2$CO$_3$ (2.18 g; 15.8 mmol) followed by allyl bromide (1.026 mL; 11.85 mmol) were added, reaction stirred 24 h at r.t. Reaction diluted with water (200 mL) and EA (200 mL), aqueous phase extracted with EA (150 mL). Combined organic phases washed with brine (300 mL), dried over sodium sulphate and reduced under vacuum to give 4 g of a crude material, which was chromatographed on silica gel with a gradient 0-10% EA in Pet. Et. to give 1.69 g a yellow oil (6.37 mmol; y=81%).

$^1$H NMR (500 MHz, CDCl$_3$) δ 10.39 (d, J=0.9 Hz, 1H), 7.64 (d, J=8.5 Hz, 1H), 7.51 (dd, J=8.5, 0.9 Hz, 1H), 6.05 (m, J=17.1, 10.3, 6.1 Hz, 1H), 5.40 (pseudo dq, J=17.1, 1.4 Hz, 1H), 5.33 (pseudo dq, J=10.3, 2.2, 1.0 Hz, 1H), 4.74-4.72 (m, 1H), 4.68 (m, 1H), 1.32 (d, J=6.2 Hz, 1H).

$^{13}$C NMR (126 MHz, CDCl$_3$) δ 188.7, 156.3, 150.0, 145.1, 133.0, 132.0, 122.3, 120.3, 119.5, 78.3, 75.7, 22.4.

HRMS (ESI) calculated for C13H15NO5Na (M+Na$^+$) 288.0842, found 288.0839.

2-(allyloxy)-3-isopropoxy-4-nitrobenzoic acid

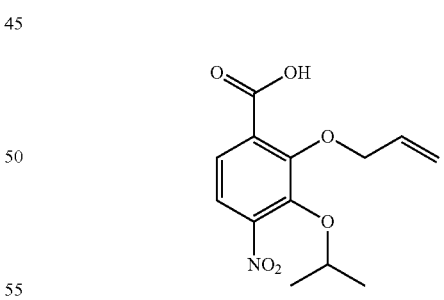

See: J. AM. CHEM. SOC. 2004, 126, 8396-8398 and J. Org. Chem. 2015, 80, 6076-6082

2-(allyloxy)-3-isopropoxy-4-nitrobenzaldehyde (1.69 g; 6.38 mmol) and 2-Methyl-2-butene (7.2 mL; 70 mmol) were dissolved in t-BuOH (48 mL). Then a solution of NaClO$_2$ 80% (0.87 g; 7.65 mmol) in Monosodium phosphate monohydrate solution 1 N (7.2 mL) was added dropwise to the solution. Reaction stirred for 1 h, then quenched by adding a solution of Na$_2$SO$_3$ (14.0 mmol in 10 mL). Mixture partially reduced under vacuum, diluted with EA (100 mL) and HCl 1 N (100 mL), aqueous phase extracted again with EA (50 mL), organic phases reunited washed with brine (150 mL) and dried over sodium sulphate. Solvent reduced under vacuum to give 1.9 g (6.38 mmol; y=q.) of a dark residue, which was used in the next step without further purification.

allyl 4-nitrobenzoate

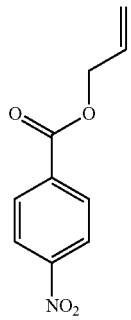

K$_2$CO$_3$ (2.5 g, 17.95 mmol) was added to a stirred mixture of 4-Nitrobenzoic acid (5.0 g; 30.0 mmol) and Allyl bromide (2.9 mL; 33.0 mmol) in DMF (50 mL). Reaction was stirred for 24 hours. Et$_2$O (500 mL) and water (500 mL) were added, the organic phase washed then with NaHCO$_3$ satured solution twice (400 mL) and once with brine (400 mL), dried over sodium sulphate, evaporated under reduced pressure to obtain 6.1 g (30.0 mmol; y=q.) of a yellow oil. Product was used in the next step without further purification.

allyl 4-aminobenzoate

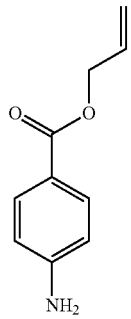

Zinc powder (27 g; 541 mmol) was added over 30 min to a solution of allyl 4-nitrobenzoate (5.6 g; 27 mmol) in acetic acid (100 mL). Reaction stirred overnight at r.t. It was quenched with NaHCO$_3$, watery phase extracted twice with EA, washed again with NaHCO$_3$ and brine, dried over sodium sulphate and reduced under vacuum to give around 4.5 g of a crude residue, which was chromatographed on silica gel with a gradient 5-30% EA in Pet. Et. to afford 3.42 g (19 mmol; y=71%) of a white solid.

$^1$H NMR (500 MHz, DMSO) δ 7.74-7.55 (m, 2H), 6.62-6.51 (m, 2H), 6.00 (m, 3H), 5.34 (pseudo dq, J=17.2, 1.7 Hz, 1H), 5.22 (pseudo dq, J=10.5, 1.4 Hz, 1H), 4.68 (dt, J=5.3, 1.5 Hz, 2H).

$^{13}$C NMR (126 MHz, DMSO) δ 165.5, 153.6, 133.3, 131.1, 117.2, 115.6, 112.6, 64.0.

HRMS (ESI) calculated for C10H12NO2 (M+H$^+$) 178.0863, found 178.0867.

allyl 4-(2-(allyloxy)-3-isopropoxy-4-nitrobenzamido)benzoate

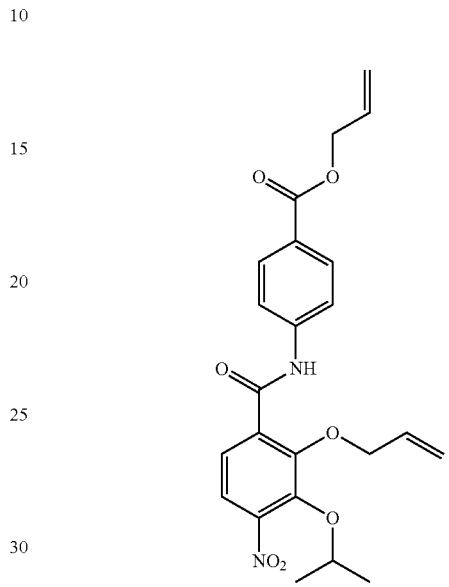

POCl$_3$ (0.68 mL; 7.32 mmol) was added at 0° C. to a stirred solution of 2-(allyloxy)-3-isopropoxy-4-nitrobenzoic acid (7.32 mmol, crude), TEA (1.7 mL; 12.20 mmol) and allyl 4-aminobenzoate (1.08 g; 6.10 mmol) in DCM (100 mL) under nitrogen. Reaction stirred for 3 h, then quenched with NaHCO$_3$ saturated solution, solvent partially reduced under vacuum, then diluted with EA (150 mL) and water (150 mL), aqueous phase extracted again twice with EA (2×100 mL), organic phases reunited washed with HCl 1 N (300 mL) and brine (300 mL), dried over sodium sulphate and reduced under vacuum to give a crude material, which was chromatographed on silica gel with a gradient 5-30% to give 2.22 g (5.04 mmol; y=83%) of a yellow oil.

$^1$H NMR (500 MHz, CDCl$_3$) δ 10.17 (s, 1H), 8.08 (d, J=8.7 Hz, 3H), 7.74 (d, J=8.6 Hz, 2H), 7.63 (d, J=8.8 Hz, 1H), 6.24-5.87 (m, 2H), 5.55-5.22 (m, 4H), 4.80 (dd, J=20.6, 5.9 Hz, 4H), 4.64 (hept, J=12.4, 6.3 Hz, 1H), 1.34 (d, J=6.2 Hz, 6H).

$^{13}$C NMR (176 MHz, CDCl$_3$) δ 165.7, 161.1, 151.5, 148.2, 144.7, 141.9, 132.3, 131.5, 131.0, 130.5, 126.2, 126.1, 121.1, 120.0, 119.4, 118.3, 78.7, 75.7, 65.5, 22.4.

HRMS (ESI) calculated for C23H25N2O7 (M+H$^+$) 441.1656, found 441.1654.

allyl 4-(2-(allyloxy)-4-amino-3-isopropoxyben-
zamido)benzoate

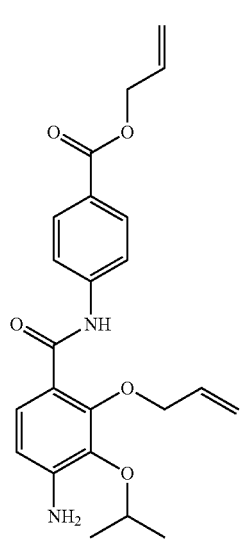 [SMILES: C=CCOC(=O)c1ccc(NC(=O)c2ccc([N+](=O)[O-])c(OC(C)C)c2OCC=C)cc1]

Tin(II) chloride dehydrate (4.3 g; 19.09 mmol), allyl 4-(2-(allyloxy)-3-isopropoxy-4-nitrobenzamido)benzoate (1.4 g; 3.18 mmol) were dissolved in EtOH (32 mL), the solution was stirred at r.t. overnight. The solvent was removed under vacuum, NaHCO$_3$ saturated solution (300 mL) and EA (300 mL) were added to the residue. The aqueous phase extracted again with EA (200 mL). The organic phases reunited were washed with brine (400 mL), dried over sodium sulphate and reduced under vacuum. The crude residue thus obtained was chromatographed on silica gel with a gradient EA 10-40% in Pet. Et. to give 1.22 g (2.98 mmol; 95%) of a yellow oil.

$^1$H NMR (500 MHz, DMSO) δ 10.26 (s, 1H), 8.01-7.86 (m, 2H), 7.86-7.74 (m, 2H), 7.39 (d, J=8.6 Hz, 1H), 6.56 (d, J=8.6 Hz, 1H), 6.26-5.93 (m, 2H), 5.59 (s, 2H), 5.48-5.35 (m, 2H), 5.30-5.20 (m, 2H) 4.78 (dt, J=5.4, 1.5 Hz, 2H), 4.61 (dt, J=5.6, 1.4 Hz, 2H), 4.46 (hept, J=6.1 Hz, 1H), 1.26 (d, J=6.1 Hz, 6H).

$^{13}$C NMR (126 MHz, DMSO) δ 165.0, 163.9, 150.6, 147.8, 143.7, 135.3, 133.6, 132.8, 130.3, 126.1, 123.6, 118.8, 118.1, 117.7, 114.6, 109.9, 74.4, 73.7, 64.8, 40.1, 40.0, 39.9, 39.8, 39.8, 39.7, 39.6, 39.5, 39.3, 39.2, 39.0, 22.2.

HRMS (ESI) calculated for C23H27N2O5 (M+H$^+$) 411.1914, found 411.1900.

Fragment C2

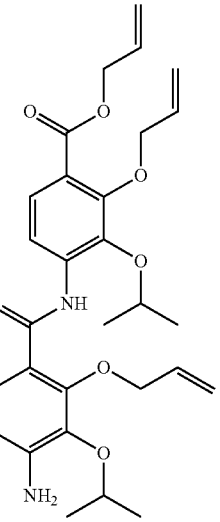

Synthesis:

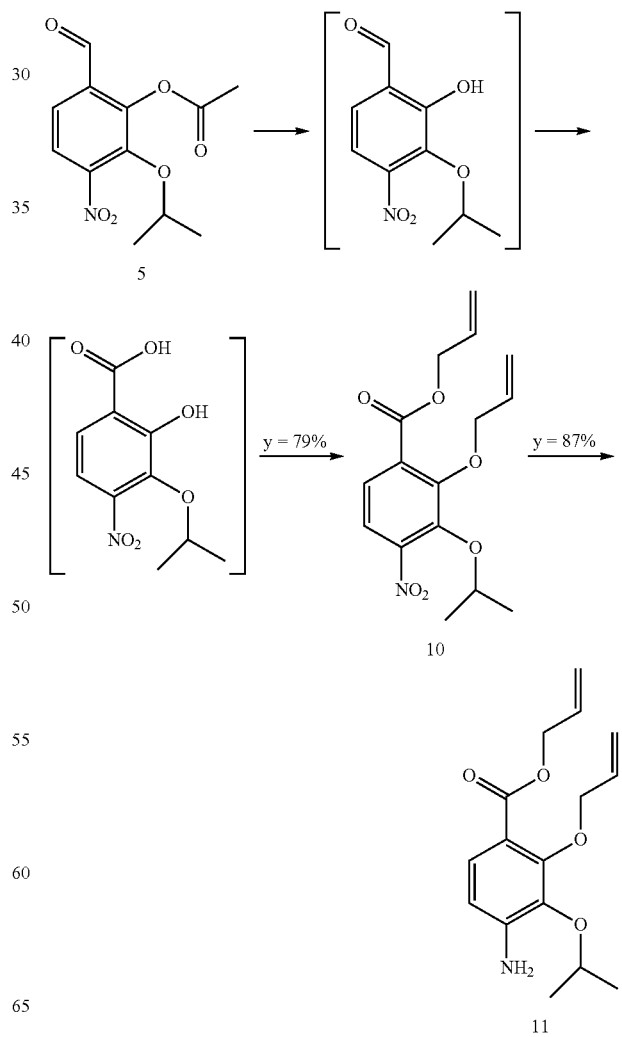

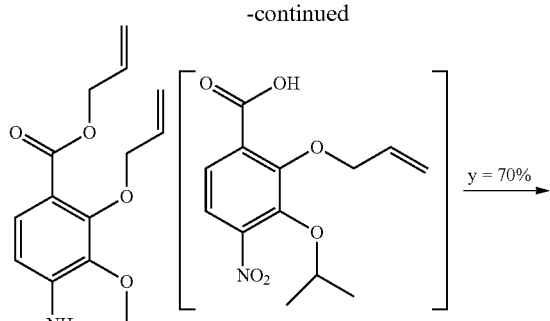

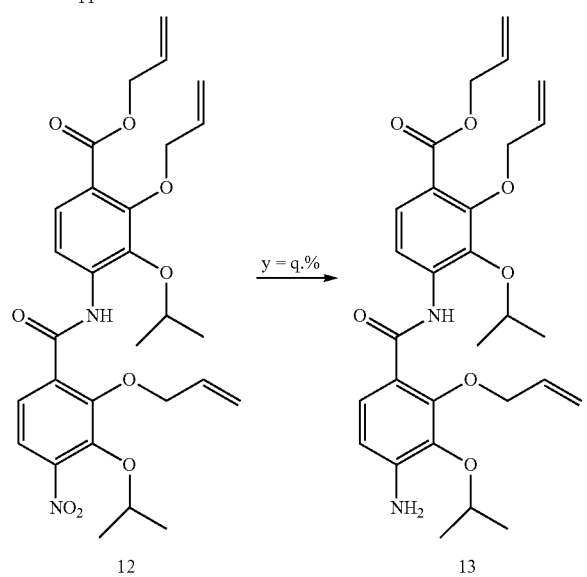

allyl 2-(allyloxy)-3-isopropoxy-4-nitrobenzoate

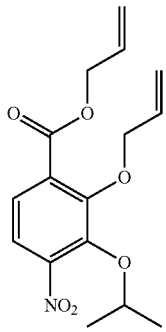

6-formyl-2-isopropoxy-3-nitrophenyl acetate (0.9 g; 3.37 mmol) was dissolved in THF (17 mL) and water (8.5 mL), then LiOH (0.81 g; 33.70 mmol) dissolved in water (8.5 mL) was added at 0 C, reaction stirred overnight. pH adjusted to 1, solvent partially reduced under vacuum and watery phase extracted with CHCl3 (100 mL) three times, combined organic phases dried over sodium sulphate and reduced under vacuum to give a yellow oil. Which was dissolved with 2-Methyl-2-butene (3.75 mL; 35.39 mmol) in t-BuOH (25 mL). Then a solution of NaClO$_2$ 80% (0.46 g; 4.04 mmol) in Monosodium phosphate monohydrate solution 1 N (3.75 mL) was added dropwise to the solution. Reaction stirred for 1 h, then quenched by adding a solution of Na$_2$SO$_3$ (8.0 mmol in 5 mL). Mixture partially reduced under vacuum, diluted with EA (100 mL) and HCl 1 N (100 mL), aqueous phase extracted again with EA (50 mL), organic phases reunited washed with brine (150 mL) and dried over sodium sulphate. Solvent removed under vacuum, the residue was dissolved in DMF (9.0 mL), K$_2$CO$_3$ (1.40 g; 10.11 mmol) followed by allyl bromide (0.73 mL; 8.43 mmol) were added, reaction stirred 24 h at r.t. Reaction diluted with water (100 mL) and EA (100 mL), aqueous phase extracted with EA (50 mL). Combined organic phases washed with brine (100 mL), dried over sodium sulphate and reduced under vacuum, the crude material was chromatographed on silica gel with a gradient 0-10% EA in Pet. Et. to give 0.84 g a yellow oil (2.63 mmol; y=79%).

$^1$H NMR (500 MHz, DMSO) δ 7.70 (d, J=8.5 Hz, 1H), 7.57 (d, J=8.5 Hz, 1H), 6.08-5.97 (m, 2H), 5.40 (m, 2H), 5.28 (m, 2H), 4.81 (dt, J=5.6, 1.4 Hz, 2H), 4.64 (dt, J=12.3, 6.1 Hz, 1H), 4.56 (dt, J=5.8, 1.4 Hz, 2H), 1.20 (d, J=6.1 Hz, 6H).

$^{13}$C NMR (126 MHz, DMSO) δ 164.1, 151.7, 147.8, 143.8, 133.2, 132.1, 130.4, 124.8, 119.1, 118.7, 118.5, 77.2, 74.8, 66.0, 22.0.

HRMS (ESI) calculated for C16H19NNaO6 (M+Na) 344.1105, found 344.1105.

allyl 2-(allyloxy)-4-amino-3-isopropoxybenzoate

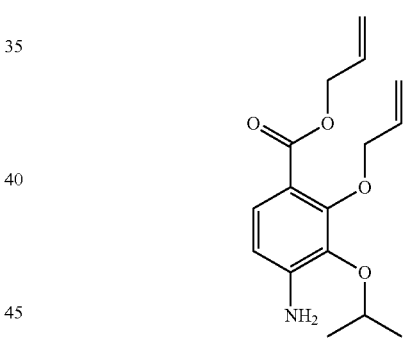

allyl 2-(allyloxy)-3-isopropoxy-4-nitrobenzoate 700 mg; 2.17 mmol) was dissolved in EtOH (19.8 mL) and AcOH (2.2 mL), the solution was cooled to 0° C. and to it Zn dust (1.42 g; 21.7 mmol) was added portion wise. Reaction stirred at r.t. for 4 hours then mixture filtered over a pad of celite and solvent reduced under vacuum, the residue was chromatographed on silica gel with a gradient 1-20% EA in Pet. Et. to afford 550 mg of desired compound (1.89 mmol; y=87%).

$^1$H NMR (500 MHz, DMSO) δ 7.33 (d, J=8.6 Hz, 1H), 6.46 (d, J=8.7 Hz, 1H), 6.10-5.94 (m, 2H), 5.62 (s, 2H), 5.34 (m, 2H), 5.20 (m, 2H), 4.66 (dt, J=5.4, 1.5 Hz, 2H), 4.45-4.38 (m, 3H), 1.21 (d, J=6.2 Hz, 6H).

$^{13}$C NMR (126 MHz, DMSO) δ 164.6, 153.1, 148.5, 136.2, 134.6, 133.2, 127.2, 117.5, 116.8, 111.0, 109.2, 74.1, 73.6, 64.2, 40.0, 39.9, 39.8, 39.8, 39.7, 39.5, 39.3, 39.2, 39.0, 22.1.

HRMS (ESI) calculated for C16H22NO4 (M+H) 292.1543, found 292.1541.

47
allyl 2-(allyloxy)-4-(2-(allyloxy)-3-isopropoxy-4-nitrobenzamido)-3-isopropoxybenzoate

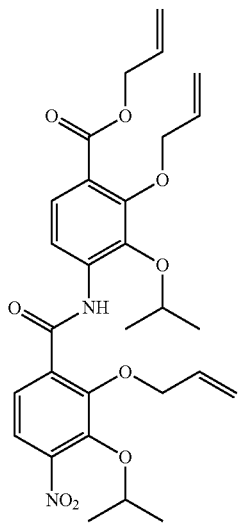 [SMILES: C=CCOC(=O)c1ccc(NC(=O)c2ccc([N+](=O)[O-])c(OC(C)C)c2OCC=C)c(OC(C)C)c1OCC=C]

Collidine (1.44 mL; 11.00 mmol) was added dropwise at 0° C. to a solution of 2-(allyloxy)-3-isopropoxy-4-nitrobenzoic acid (579 mg; 2.06 mmol) and Bis(trichloromethyl) carbonate (204 mg; 0.69 mmol) in THF (13 mL). Reaction stirred at r.t. for 20 min then added to a cooled solution of allyl 2-(allyloxy)-4-amino-3-isopropoxybenzoate (400 mg; 1.37 mmol) and DiPEA (2.38 mL; 13.7 mmol) in THF (13 mL). Reaction stirred for 20 hours at r.t., quenche with water and solvent partially reduced under vacuum, mixture diluted with Et$_2$O (50 mL) and HCl 1N (50 mL), watery phase extracted again with Et$_2$O (50 mL). The combined organic phases were washed with brine (100 mL), dried over sodium sulphate and reduced under vacuum. The crude was chromatographed on silica gel with a gradient 1-20% EA in Pet. Et. to give 535 mg of desired product (0.97 mmol; y=70%).

$^1$H NMR (500 MHz, CDCl$_3$) δ 10.73 (s, 1H), 8.42 (d, J=8.8 Hz, 1H), 8.02 (d, J=8.8 Hz, 1H), 7.68 (d, J=8.8 Hz, 1H), 7.62 (d, J=8.8 Hz, 1H), 6.18-6.00 (m, 3H), 5.45-5.35 (m, 2H), 5.34-5.27 (m, 2H), 5.26 (m, 2H), 4.83-4.76 (m, 5H), 4.65 (dt, J=12.3, 6.2 Hz, 1H), 4.58 (dt, J=5.9, 1.3 Hz, 2H), 1.37 (d, J=6.2 Hz, 6H), 1.28 (d, J=6.2 Hz, 6H).

$^{13}$C NMR (126 MHz, CDCl$_3$) δ 165.0, 161.3, 151.8, 151.2, 147.9, 145.0, 140.4, 137.4, 133.8, 132.2, 131.7, 131.6, 127.0, 125.9, 121.8, 121.1, 119.9, 118.5, 118.0, 115.1, 78.7, 76.3, 76.2, 74.9, 65.6, 22.5, 22.4.

HRMS (ESI) calculated for C29H35N2O9 (M+H) 555.2337, found 555.2335.

48
allyl 2-(allyloxy)-4-(2-(allyloxy)-4-amino-3-isopropoxybenzamido)-3-isopropoxybenzoate

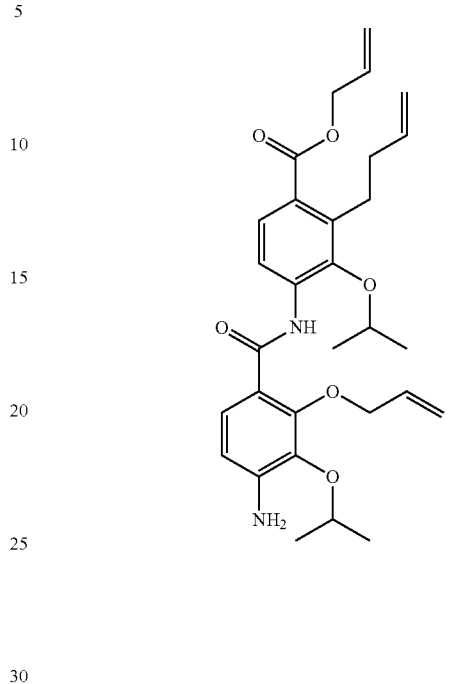

Allyl 2-(allyloxy)-4-(2-(allyloxy)-3-isopropoxy-4-nitrobenzamido)-3-isopropoxybenzoate (250 mg; 0.45 mmol) was dissolved in EtOH (9.0 mL) and AcOH (1.0 mL), the solution was cooled to 0° C. and to it Zn dust (295 mg; 4.50 mmol) was added portion wise. Reaction stirred at r.t. for 5 hours then mixture filtered over a pad of celite and solvent reduced under vacuum, residue dissolved in DCM (30 mL), organic phase washed with NaHCO$_3$ saturated solution and dried over sodium sulphate. Solvent removed under reduced pressure to give 220 mg of desired product (0.42 mmol; y=93%).

$^1$H NMR (500 MHz, DMSO) δ 10.75 (s, 1H), 8.34 (d, J=8.8 Hz, 1H), 7.55 (d, J=8.7 Hz, 1H), 7.53 (d, J=8.8 Hz, 1H), 6.58 (d, J=8.7 Hz, 1H), 6.12-5.98 (m, 3H), 5.70 (s, 2H), 5.43-5.36 (m, 2H), 5.31 (m, 2H), 5.27-5.19 (m, 2H), 4.75 (dt, J=5.5, 1.5 Hz, 2H), 4.67 (d, J=6.5 Hz, 2H), 4.61-4.55 (m, 1H), 4.53 (dt, J=5.7, 1.4 Hz, 2H), 4.45-4.39 (m, 1H), 1.29 (d, J=6.2 Hz, 6H), 1.23 (d, J=6.2 Hz, 6H).

$^{13}$C NMR (126 MHz, DMSO) δ 164.5, 162.9, 151.2, 150.6, 148.3, 139.5, 138.5, 135.1, 134.0, 133.0, 132.7, 126.7, 126.2, 119.8, 119.3, 118.1, 117.5, 114.2, 113.1, 110.3, 75.7, 74.8, 74.2, 74.1, 65.0, 22.2, 22.0.

HRMS (ESI) calculated for C29H37N2O7 (M+H) 525.2595, found 525.2591.

Fragment C3
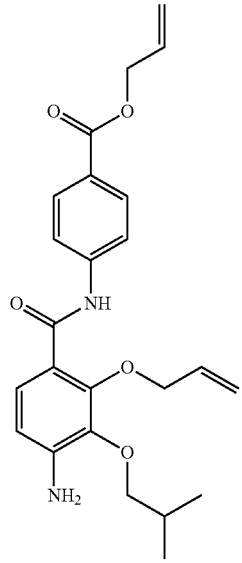
Synthesis:
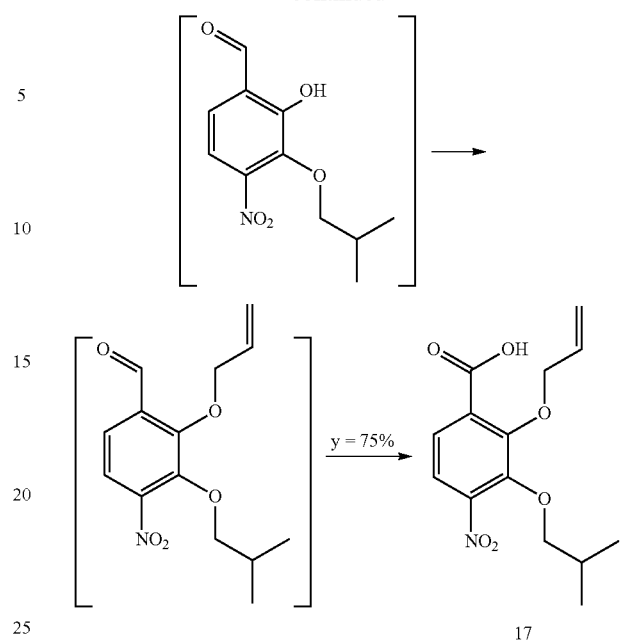
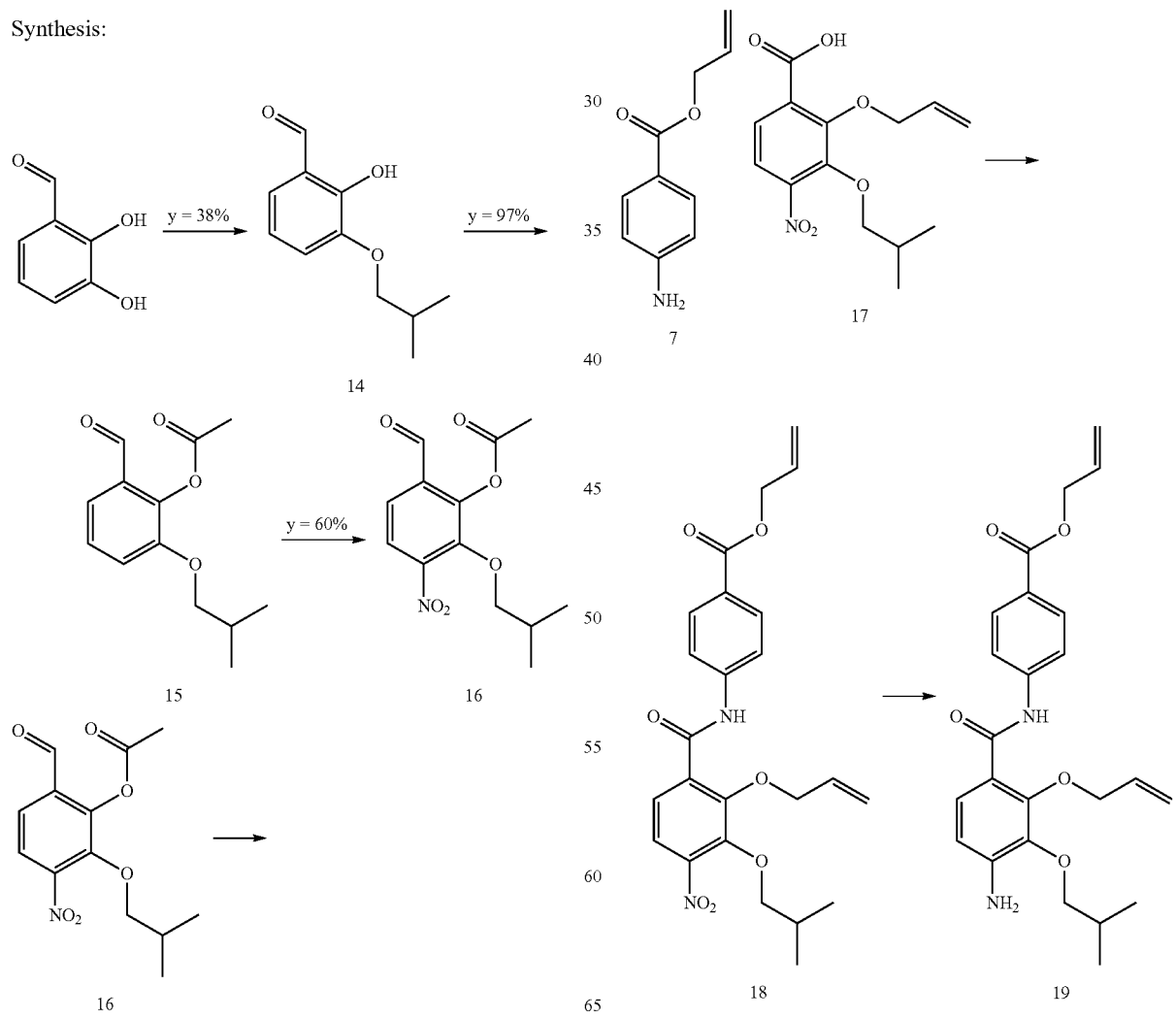

2-hydroxy-3-isobutoxybenzaldehyde

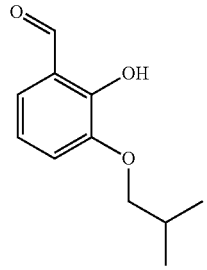

A solution of 2,3-dihydroxybenzaldehyde (15 g; 109 mmol) in DMSO (75 mL) was added drop wise, keeping low the temperature with an ice bath, to a previously prepared suspension of NaH (8.72 g; 218 mmol) in DMSO (180 mL). The mixture stirred at r.t. for two hours, then Isobutyl bromide (11.9 mL; 109 mmol) was added slowly keeping low the temperature. The reaction mixture was stirred for 42 hours, quenched with HCl followed by NH$_4$Cl until pH 5 reached. Work up done in several portions as follows: 300 mL of the mixture were further diluted with H$_2$O (1200 mL) and extracted with Et$_2$O (3×200 mL). Organic phases dried over Na$_2$SO$_4$ and reduced under pressure to give 30 g of dark oil. Crude residue chromatographed on silica gel, isocratic condition (Pet. Et. DCM 7:3) to give 8.04 g of a yellow oil (41 mmol, y=38%).

$^1$H NMR (500 MHz, CDCl$_3$) δ 10.98 (s, 1H), 9.92 (s, 1H), 7.17 (dd, J=7.8, 1.4 Hz, 1H), 7.11 (dd, J=8.0, 1.2 Hz, 1H), 6.93 (t, J=7.9 Hz, 1H), 3.81 (d, J=6.7 Hz, 2H), 2.17 (dp, J=13.3, 6.7 Hz, 1H), 1.05 (d, J=6.7 Hz, 6H).

2-formyl-6-isobutoxyphenyl acetate

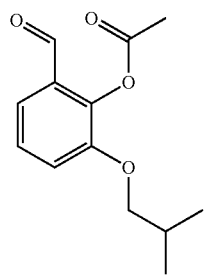 [SMILES: CC(=O)Oc1c(C=O)cccc1OCC(C)C]

Acetyl chloride (5.93 mL; 55.2 mmol) was added dropwise to a stirred solution of 2-hydroxy-3-isobutoxybenzaldehyde (7.15 g; 36.8 mmol) and pyridine (8.90 mL; 110.0 mmol) in DCM (340 mL) at 0 C. Reaction stirred for 5 min. at 0° C. then temperature raised to r.t. Stirring prolonged for 1 h. Reaction quenched with HCl 1 N, organic phase partially reduced under vacuum, washed with HCl 1 N (200 mL), brine (200 mL), dried over sodium sulphate and reduced under vacuum. The crude was chromatographed on silica gel with a gradient 2-10% EA in Pet. Et, to give 8.46 g of a pale yellow oil (35.85 mmol; y=97%).

$^1$H NMR (700 MHz, DMSO) δ 10.12 (s, 1H), 7.46 (dd, J=7.2, 2.5 Hz, 1H), 7.42-7.37 (m, 2H), 3.82 (d, J=6.3 Hz, 2H), 2.34 (s, 3H), 2.00 (dp, J=13.2, 6.6 Hz, 1H), 0.96 (d, J=6.8 Hz, 6H).

$^{13}$C NMR (176 MHz, DMSO) δ 190.0, 168.5, 150.9, 141.1, 128.9, 127.0, 120.4, 119.4, 74.6, 27.7, 20.2, 18.8.

HRMS (ESI) calculated for C13H16NaO4 (M+Na) 259.0941, found 259.0943.

6-formyl-2-isobutoxy-3-nitrophenyl acetate

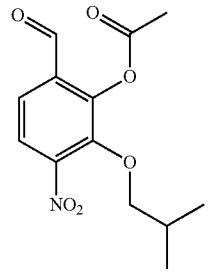 [SMILES: CC(=O)Oc1c(C=O)ccc([N+](=O)[O-])c1OCC(C)C]

Fuming nitric acid (5.0 mL, 118.4 mmol) was cooled to −40° C. under a nitrogen atmosphere. A solution of 2-formyl-6-isobutoxyphenyl acetate (3.50 g, 14.8 mmol) in 8.0 mL of dry DCM was added dropwise while the mixture was vigorously stirred and kept at −40° C. The solution was stirred for an additional 1.5 hours before being poured into 100 mL of ice water. The mixture was then extracted with DCM (4×50 mL) and the combined organic extracts were dried over sodium sulphate. The solvent was removed under vacuum, the crude thus obtained was chromatographed on silica gel with a gradient 5-40% EA in Pet. Et. to afford 2.45 g of the desired compound (8.73 mmol, y=97%).

$^1$H NMR (500 MHz, DMSO) δ 10.13-10.09 (s 1H), 8.03-8.00 (m, 1H), 7.83 (d, J=8.5 Hz, 1H), 3.84 (d, J=6.2 Hz, 2H), 2.44 (s, 3H), 2.01-1.93 (m, 1H), 0.94 (d, J=6.7 Hz, 6H).

$^{13}$C NMR (126 MHz, DMSO) δ 189.4, 168.5, 147.5, 145.2, 144.7, 132.0, 125.5, 122.3, 81.5, 28.5, 20.4, 18.5.

HRMS (ESI) calculated for C13H15NNaO6 (M+Na) 304.0792, found 304.0792.

2-(allyloxy)-3-isobutoxy-4-nitrobenzoic acid

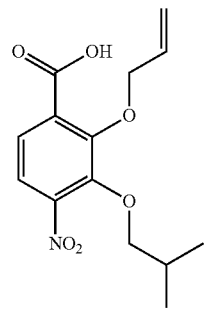 [SMILES: C=CCOc1c(C(=O)O)ccc([N+](=O)[O-])c1OCC(C)C]

6-formyl-2-isobutoxy-3-nitrophenyl acetate (4.10 g; 14.6 mmol) was dissolved in THF (70 mL) and water (35 mL), then LiOH (3.50 g; 146.0 mmol) dissolved in water (35 mL) was added at 0 C, reaction stirred overnight. In the morning, pH adjusted to 1, solvent partially reduced under vacuum and watery phase extracted with CHCl3 (150 mL) three times, combined organic phases dried over sodium sulphate and reduced under vacuum to give a yellow oil, which was used in the next step without further purification. Residue was dissolved in DMF (30 mL), K$_2$CO$_3$ (4.03 g; 29.2 mmol) followed by allyl bromide (1.89 mL; 21.9 mmol) were added, reaction stirred 24 h at r.t. Reaction diluted with water (200 mL) and EA (200 mL), aqueous phase extracted with EA (150 mL). Combined organic phases washed with brine (300 mL), dried over sodium sulphate and reduced under vacuum to give a crude material, which was dissolved with 2-Methyl-2-butene (15.5 mL; 146 mmol) in t-BuOH (100 mL). Then a solution of NaClO$_2$ 80% (1.98 g; 17.52 mmol) in Monosodium phosphate monohydrate solution 1 N (16.2 mL) was added dropwise to the solution. Reaction stirred for 1 h, then quenched by adding a solution of Na$_2$SO$_3$ (34.0 mmol in 10 mL). Mixture partially reduced under vacuum, diluted with EA (200 mL) and HCl 1 N (200 mL), aqueous phases extracted again with EA (100 mL), organic phases reunited washed with brine (250 mL) and dried over sodium sulphate. Solvent reduced under vacuum, crude chromatographed on silica gel with a gradient 0-10% MeOH in DCM to afford 3.01 g of the desired compound (10.22 mmol, y=70%).

$^1$H NMR (500 MHz, CDCl$_3$) δ 7.90 (d, J=8.7 Hz, 1H), 7.57 (d, J=8.7 Hz, 1H), 6.08 (m, 1H), 5.44 (dq, J=17.1, 1.3 Hz, 1H), 5.39 (ddd, J=10.3, 1.9, 0.9 Hz, 1H), 4.81-4.77 (m, 2H), 3.93 (d, J=6.5 Hz, 2H), 2.12 (dp, J=13.3, 6.7 Hz, 1H), 1.03 (d, J=6.7 Hz, 6H).

$^{13}$C NMR (126 MHz, CDCl$_3$) δ 165.0, 152.7, 148.2, 146.4, 131.1, 127.5, 126.8, 121.7, 119.8, 82.0, 76.5, 29.0, 19.0.

HRMS (ESI) calculated for C14H16NO6 (M−H) 294.0983, found 294.0995.

allyl 4-(2-(allyloxy)-3-isobutoxy-4-nitrobenzamido)benzoate

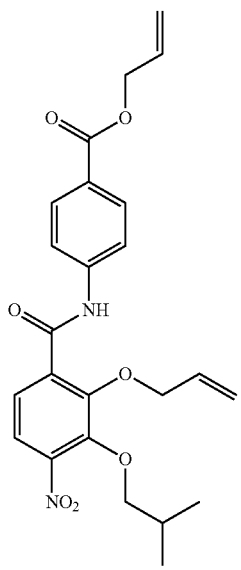 [SMILES: C=CCOC(=O)c1ccc(NC(=O)c2ccc([N+](=O)[O-])c(OCC(C)C)c2OCC=C)cc1]

To a stirred solution of 2-(allyloxy)-3-isobutoxy-4-nitrobenzoic acid (500 mg; 1.69 mmol), allyl 4-aminobenzoate (250 mg; 1.41 mmol) and TEA (0.38 mL; 2.82 mmol) in dry DCM (28 mL), POCl$_3$ (0.16 mL; 1.69 mmol) was added drop wise at 0° C. Reaction stirred for 4 hours then quenched by addition of NaHCO$_3$ saturated solution, solvent partially reduced under vacuum and residue dissolved in EA (50 mL). Organic phase washed with NaHCO$_3$ saturated solution (50 mL), HCl 1 N (50 mL), brine (50 mL), dried over sodium sulphate and reduced under vacuum. The crude thus obtained was purified on silica gel with a gradient 2-20% EA in Pet. Et. to give 400 mg of desired product (0.88 mmol; y=62%).

$^1$H NMR (500 MHz, CDCl$_3$) δ 10.13 (s, 1H), 8.09 (m, 3H), 7.79-7.73 (m, 2H), 7.64 (d, J=8.8 Hz, 1H), 6.08 (m, 2H), 5.48 (dq, J=17.1, 1.3 Hz, 1H), 5.45-5.39 (m, 2H), 5.30 (dq, J=10.5, 1.3 Hz, 1H), 4.83 (dt, J=5.7, 1.4 Hz, 2H), 4.76 (dt, J=6.1, 1.0 Hz, 2H), 3.97 (d, J=6.5 Hz, 2H), 2.20-2.11 (m, 1H), 1.06 (d, J=6.7 Hz, 6H).

$^{13}$C NMR (126 MHz, CDCl$_3$) δ 165.6, 161.1, 151.3, 147.3, 146.5, 141.8, 132.3, 131.5, 131.0, 130.8, 126.3, 126.1, 121.2, 120.1, 119.4, 118.3, 82.0, 76.2, 65.5, 29.1, 19.0.

HRMS (ESI) calculated for C24H27N2O7 (M+H) 455.1813, found 455.1806.

allyl 4-(2-(allyloxy)-4-amino-3-isobutoxybenzamido)benzoate

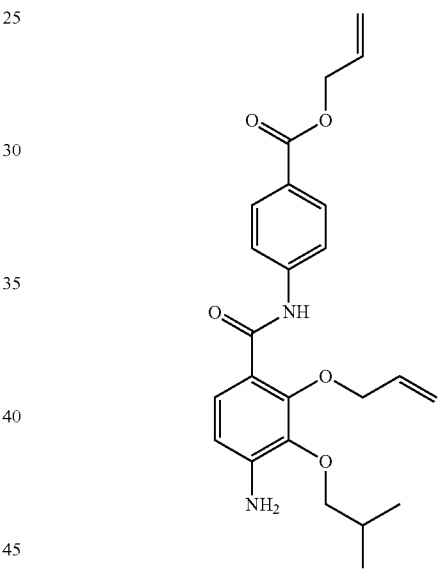

Allyl 4-(2-(allyloxy)-3-isobutoxy-4-nitrobenzamido)benzoate (350 mg; 0.77 mmol) was dissolved in EtOH (13.5 mL) and AcOH (1.5 mL), the solution was cooled to 0° C. and to it Zn dust (500 mg; 7.70 mmol) was added portion wise. Reaction stirred at r.t. for 4 hours then mixture filtered over a pad of celite and solvent reduced under vacuum to afford 295 mg of desired compound (0.70 mmol; y=90%).

$^1$H NMR (500 MHz, DMSO) δ 10.24 (s, 1H), 7.98-7.90 (m, 2H), 7.84-7.78 (m, 2H), 7.41-7.36 (m, 1H), 6.58 (d, J=8.6 Hz, 1H), 6.05 (m, 2H), 5.54 (s, 2H), 5.41 (ddq, J=17.1, 15.3, 1.6 Hz, 2H), 5.27 (m, 2H), 4.78 (dt, J=5.4, 1.5 Hz, 2H), 4.61 (dt, J=5.6, 1.3 Hz, 2H), 3.67 (d, J=6.5 Hz, 2H), 2.11 (tt, J=13.6, 6.8 Hz, 1H), 1.01 (d, J=6.7 Hz, 6H).

$^{13}$C NMR (126 MHz, DMSO) δ 165.0, 163.9, 150.4, 146.6, 143.6, 137.2, 133.5, 132.8, 130.3, 126.2, 123.7, 118.8, 118.3, 117.8, 114.8, 110.2, 78.5, 74.4, 64.8, 28.5, 19.2.

HRMS (ESI) calculated for C24H27N2O5 (M−H) 423.1925, found 423.1933.

Fragment C4

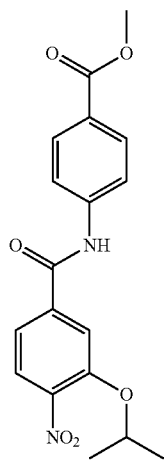 [SMILES: COC(=O)c1ccc(NC(=O)c2ccc([N+](=O)[O-])c(OC(C)C)c2)cc1]

Synthesis:

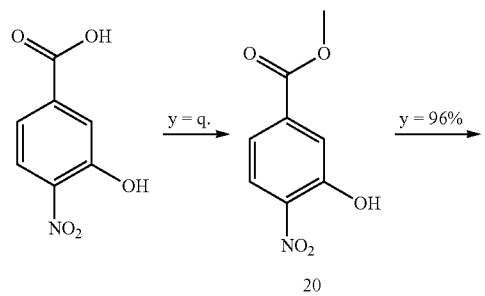

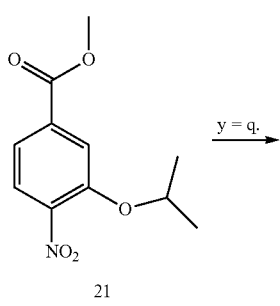

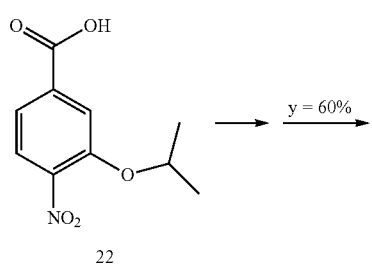

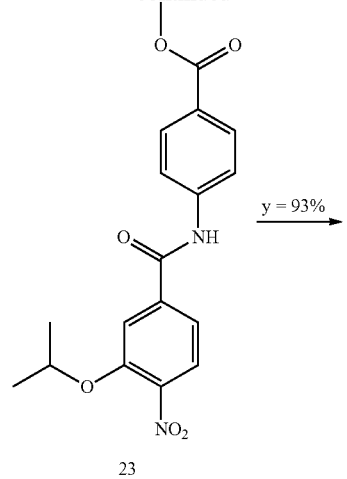

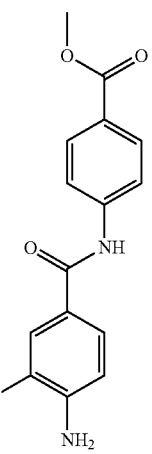

methyl 3-hydroxy-4-nitrobenzoate

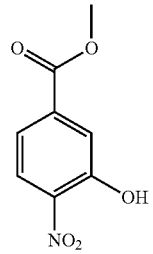

3-hydroxy-4-nitrobenzoic acid (2.5 g; 13.66 mmol) was dissolved in a MeOH (35.0 mL), Thionyl chloride (2.5 mL; 34.15 mmol) was added dropwise at 0° C., the solution was warmed to r.t. and then heated to 70° C. for 1 hour. The solvent was evaporated under reduced pressure, the residue was diluted with water (90 mL) and EA (90 mL), water again extracted twice with EA (2×90 mL). Combined organic phases washed with brine (150 mL), dried over sodium sulphate and evaporated under reduced pressure to give 2.64 g of a yellow solid.

$^1$H NMR (700 MHz, CDCl$_3$) δ 10.50 (s, 1H), 8.18 (d, J=8.8 Hz, 1H), 7.83 (d, J=1.8 Hz, 1H), 7.62 (dd, J=8.8, 1.8 Hz, 1H), 3.97 (s, 3H).

$^{13}$C NMR (176 MHz, CDCl$_3$) δ 164.9, 154.7, 138.0, 135.8, 125.3, 121.7, 120.6, 53.0.

HRMS (ESI) calculated for C8H6NO5 (M−H) 196.0251, found 196.0249.

methyl 3-isopropoxy-4-nitrobenzoate

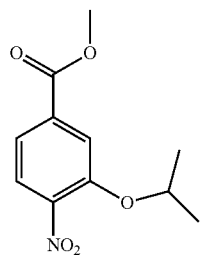 [SMILES: COC(=O)c1ccc([N+](=O)[O-])c(OC(C)C)c1]

Methyl 3-hydroxy-4-nitrobenzoate (1.94 g; 9.85 mmol) and K2CO3 (1.72 g; 11.82 mmol) were mixed in DMF (32 mL). 2-Bromopropane (1.55 mL; 15.76 mmol) was added and the mixture heated to 70° C. overnight. Reaction diluted with Et$_2$O (320 mL) and water (320 mL). Organic phase washed with brine (300 mL), dried over sodium sulphate and reduce under vacuum to give 2.25 g of a yellow oil.

$^1$H NMR (700 MHz, CDCl$_3$) δ 7.75 (d, J=8.3 Hz, 1H), 7.74 (d, J=1.6 Hz, 1H), 7.64 (dd, J=8.3, 1.6 Hz, 1H), 4.77 (hept, J=6.1 Hz, 1H), 3.96 (s, 3H), 1.41 (dd, J=6.0, 2.5 Hz, 6H).

$^{13}$C NMR (176 MHz, CDCl$_3$) δ 165.4, 150.8, 143.8, 134.5, 125.1, 121.1, 117.0, 73.0, 52.8, 21.8.

3-isopropoxy-4-nitrobenzoic acid

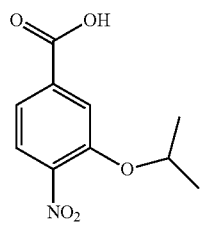 [SMILES: CC(C)Oc1cc(C(=O)O)ccc1[N+](=O)[O-]]

Methyl 3-isopropoxy-4-nitrobenzoate (1.45 g; 6.07 mmol) was dissolved in THF (33 mL) and water (15 mL). To this mixture, a solution of LiOH (1.45 g; 60.70 mmol) in water (18 mL) was added. Reaction stirred at r.t. for 3 h., pH adjusted to 1 and solvent partially reduced under vacuum. The precipitate thus formed was collected by filtration and washed with Pet. Et. twice to give 1.36 g of a pale yellow solid.

$^1$H NMR (500 MHz, CDCl$_3$) δ 7.82-7.77 (m, 2H), 7.73 (dd, J=8.3, 1.5 Hz, 1H), 4.79 (hept, J=6.1 Hz, 1H), 1.43 (d, J=6.1 Hz, 6H).

$^{13}$C NMR (126 MHz, CDCl$_3$) δ 169.4, 150.8, 133.3, 125.2, 121.8, 117.4, 73.2, 21.8.

HRMS (ESI) calculated for C10H10NO5 (M−H) 224.0564, found 224.0565.

methyl 4-(3-isopropoxy-4-nitrobenzamido)benzoate

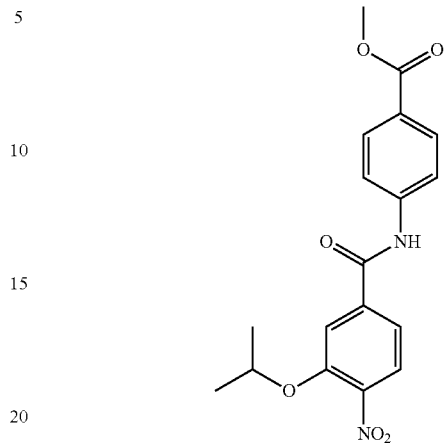

Methyl 4-aminobenzoate (79 mg; 0.52 mmol), 3-isopropoxy-4-nitrobenzoic acid (100 mg; 0.44) and HOAt (91; 0.67 mmol) were mixed together in DMF (1.2 mL). To this yellow solution, EDC (102 mg; 0.53 mmol) followed by lutidine (0.258 mL; 2.22 mmol) were added. Reaction stirred overnight, diluted with EA (20 mL) and HCl 1 N (20 mL), watery phase extracted again with EA (20 mL). Organic phases reunited dried over sodium sulphate and reduced under vacuum, the residue thus obtained chromatographed on silica gel with a gradient 3-40% EA in Pet. Et. to give 112 mg (0.31 mmol; y=60%) of a pale yellow solid.

$^1$H NMR (500 MHz, CDCl$_3$) δ 8.11-8.06 (m, 2H), 7.98 (s, 1H), 7.83 (d, J=8.3 Hz, 1H), 7.76-7.72 (m, 2H), 7.67 (d, J=1.6 Hz, 1H), 7.36 (dd, J=8.3, 1.7 Hz, 1H), 4.85-4.74 (m, 1H), 3.92 (s, 3H), 1.42 (d, J=6.1 Hz, 6H).

$^{13}$C NMR (126 MHz, CDCl$_3$) δ 166.5, 163.9, 151.7, 143.1, 141.4, 139.2, 131.0, 126.6, 125.7, 119.5, 117.2, 115.8, 73.3, 52.2, 21.8.

methyl 4-(4-amino-3-isopropoxybenzamido)benzoate

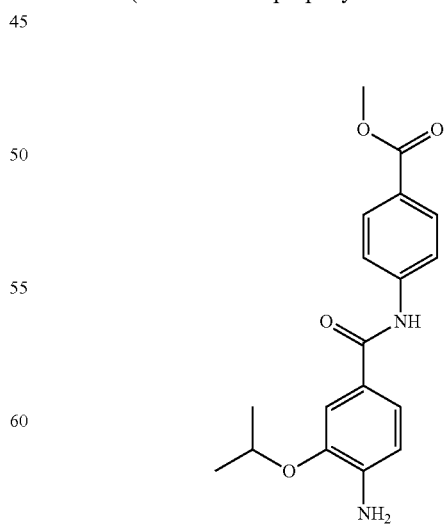

Methyl 4-(3-isopropoxy-4-nitrobenzamido)benzoate (800 mg; 2.23 mmol) was dissolved in MeOH (24 mL). The solution was degassed with Argon for 10 min. Pd (80 mg) was added, reaction stirred under an $H_2$ atmosphere overnight. Pd filtered out over a pad of celite and solvent evaporated under vacuum. The oil thus obtained was chromatographed on silica gel with a gradient 10-40% EA in Pet. Et. to give 790 mg (2.40 mmol; y=93%) of a white solid.

$^1$H NMR (500 MHz, CDCl$_3$) δ 8.08-8.03 (m, 1H), 8.03-7.98 (m, 2H), 7.78-7.71 (m, 2H), 7.46 (d, J=1.8 Hz, 1H), 7.28 (dd, J=8.2, 1.8 Hz, 1H), 6.80 (d, J=8.1 Hz, 1H), 4.71-4.62 (m, 1H), 3.91 (s, 3H), 1.37 (d, J=6.0 Hz, 6H).

$^{13}$C NMR (126 MHz, CDCl$_3$) δ 166.8, 165.5, 145.7, 142.7, 130.9, 125.4, 119.7, 119.0, 114.6, 112.9, 71.2, 52.1, 22.2.

HRMS (ESI) calculated for $C_{18}H_{21}N_2O_4$ (M+H) 329.1496, found 329.1495.

2.3 Assembling a. General Scheme Depicting the Final Steps of the Synthesis:

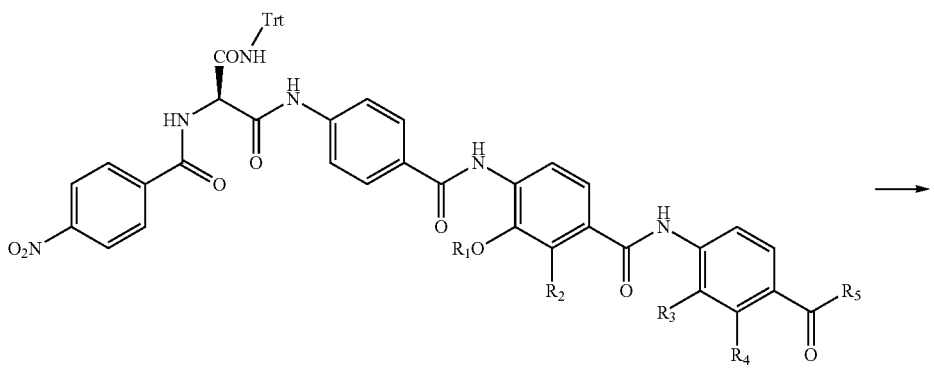

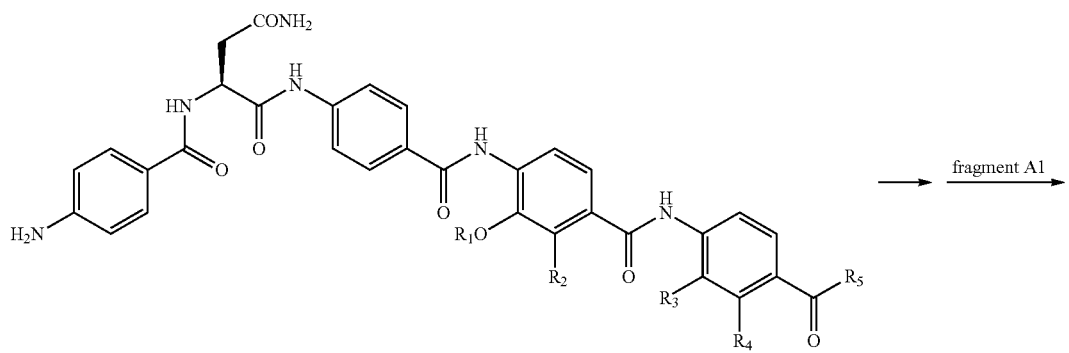

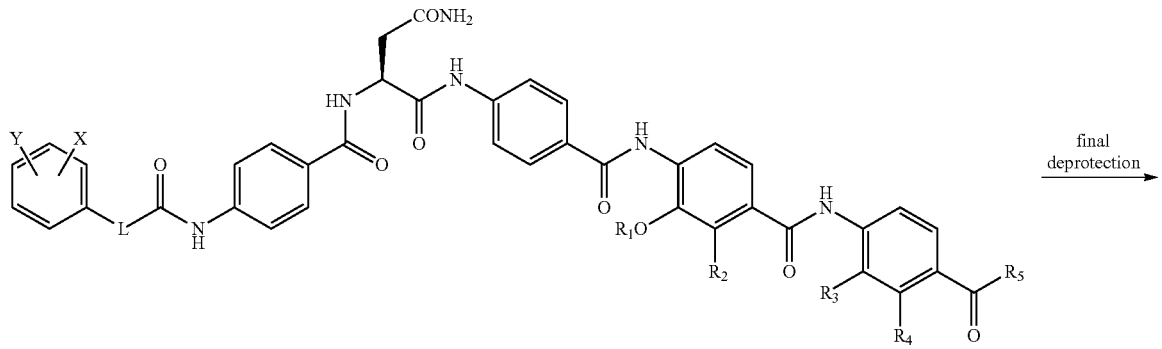

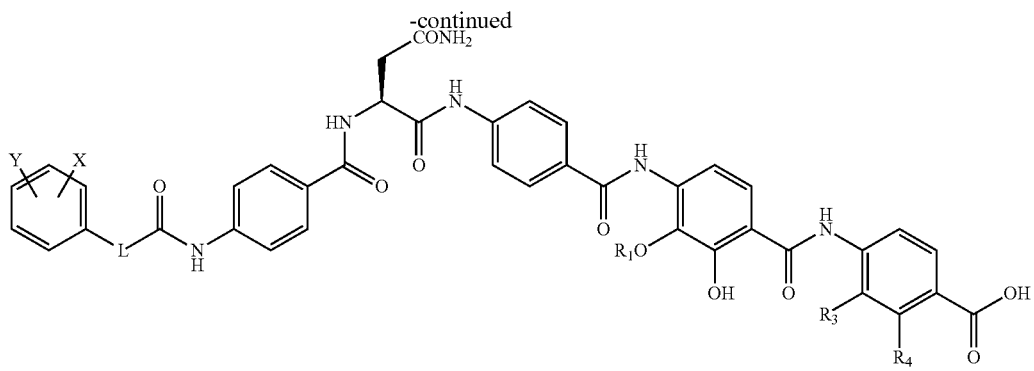

In the above formulas, groups X and Y independently represent H or R⁶.

b. General Procedures

Coupling:

The last aromatic ring was installed activating the carboxylic acid to acyl chloride or activated ester by means of:

A; BTC collidine
B; COCl via oxalyl chloride
C; EDC, HOAt

A. Collidine (8 eq.) added dropwise at 0° C. to a solution of desired carboxylic acid (3.5 eq.) and Bis(trichloromethyl) carbonate (1.05 eq.) in THF (M=0.02). Reaction stirred at r.t. for 20 min then added to a solution of allyl (S)-2-(allyloxy)-4-(2-(allyloxy)-4-(4-(2-(4-aminobenzamido)-3-cyanopropanamido)benzamido)-3-methoxybenzamido)-3-methoxybenzoate (1 eq.) and DiPEA (10 eq.) in THF (M=0.02). Reaction stirred for few hours then quenched with HCl 1 N and ice. Solvent partially reduced under vacuum, EA and HCl 1N were added, organic phase washed with NaHCO₃ saturated solution, brine and dried over sodium sulphate. The solvent was removed under reduced pressure, the residue was purified on silica gel or directly used in the next step without further purification.

B. Carboxylic acid activation: the desired carboxylic acid (1.0 eq.) is suspended in DCM (M=0.5), oxalyl chloride (1.5 eq.) followed by catalytic DMF were added at 0° C. Reaction stirred until all the carboxylic acid has reacted, reaction monitored by TLC. Solvent reduced under vacuum, residue dissolved again in DCM and evaporated twice.

The desired carbonyl chloride (1.5 eq.) as a solution in THF (M=0.08) was added at 0° C. to a stirred solution of allyl (S)-2-(allyloxy)-4-(2-(allyloxy)-4-(4-(2-(4-aminobenzamido)-3-cyanopropanamido)benzamido)-3-methoxybenzamido)-3-methoxybenzoate (1.0 eq.) and DiPEA (5 eq.) in THF (0.027 eq.), reaction stirred at 0° C. for 10 min then warmed to r.t., stirring prolonged for 1 h. Reaction quenched with HCl 1N/ice, solvent partially reduced under vacuum, mixture diluted with EA and HCl 1 N, organic phase washed with brine and dried over sodium sulphate. The residue thus obtained could be purified on silica gel or directly used in the next step without further purification.

C. Carboxylic acid (3.0 eq.), EDC (3.0 eq), HOAt (3.5 eq.) were mixed together in DMF (M=0.2), to this solution collidine was added (8.0 eq.), reaction stirred for 20 min then added to a solution of allyl (S)-2-(allyloxy)-4-(2-(allyloxy)-4-(4-(2-(4-aminobenzamido)-3-cyanopropanamido)benzamido)-3-methoxybenzamido)-3-methoxybenzoate (1.0 eq.) in DMF (M=0.02). Reaction heated to 50° C. for several hours until no more amine starting material present. Reaction diluted with EA and HCl 1 N, organic phase washed with brine and dried over sodium sulphate, solvent reduced under vacuum, the residue was used in the next step without further purification.

Final Deprotection

Phenyl silane (4.0 eq.) followed by Palladium-tetrakis (triphenylphosphine (0.25 eq.) was added to a solution of allyl protected cystobactamid derivative (1.0 eq.) in THF (M=0.01). Reaction stirred overnight and purified by preparative HPLC using condition A or B.

Condition A: gradient 20-95% CH₃CN+0.1% HCOOH in water+0.1% HCOOH in 40 min.

Condition B: gradient 10-95% CH₃CN in water 10 mM NH₄HCO₃ in 40 min.

c. A1+B1+C1

Synthesis:

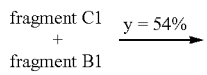

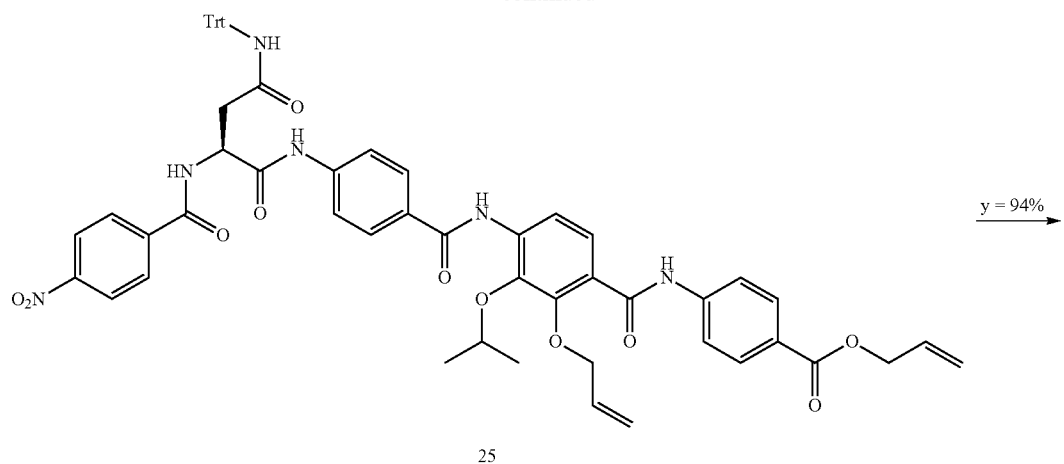
25
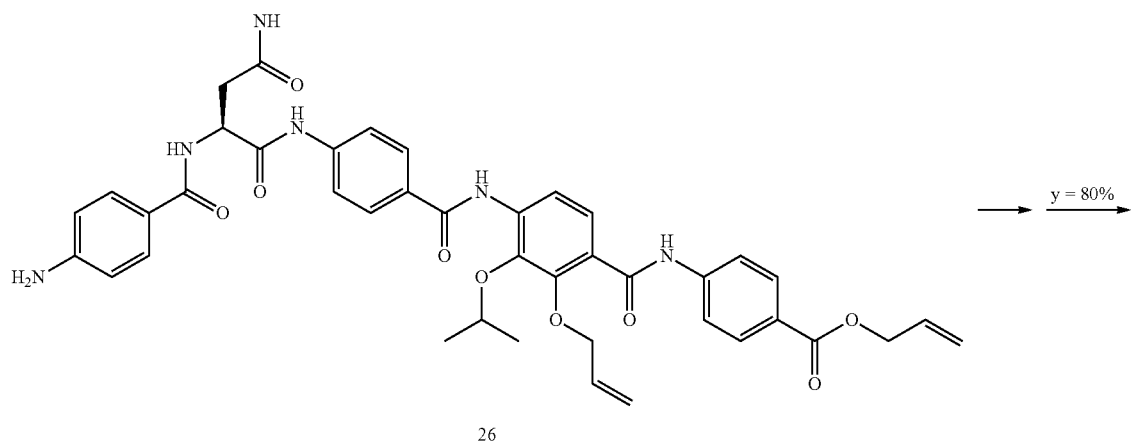
26
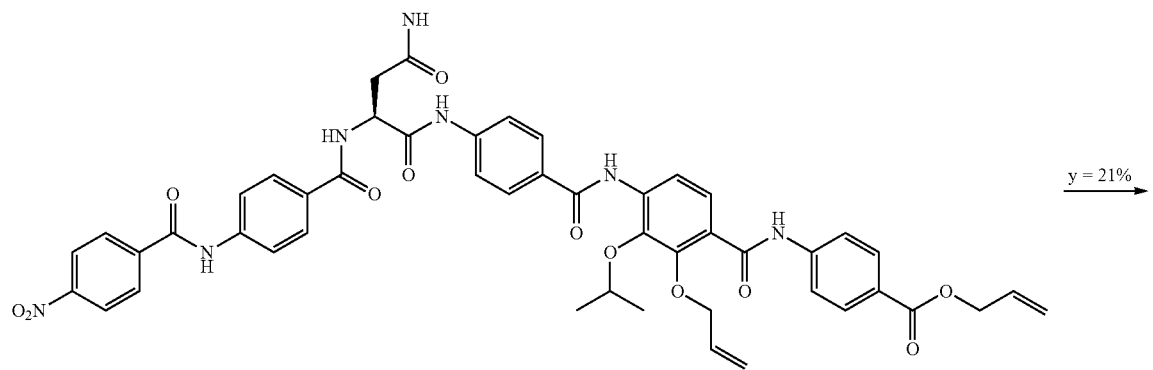
27

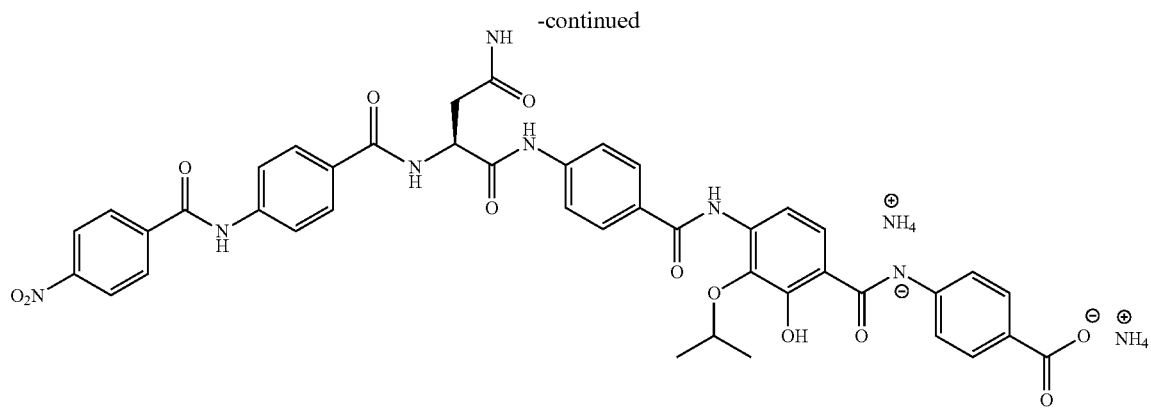

28 allyl (S)-4-(2-(allyloxy)-3-isopropoxy-4-(4-(2-(4-nitrobenzamido)-4-oxo-4-(tritylamino)butanamido)benzamido)benzamido)benzoate

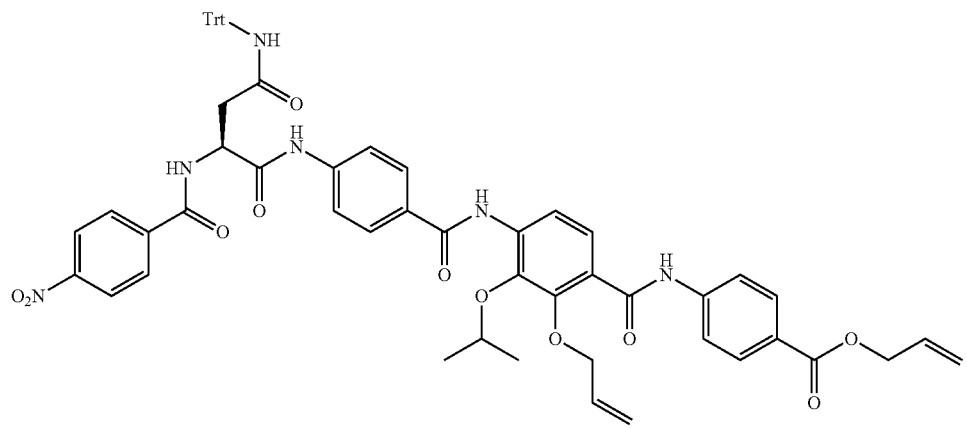

POCl₃ (3.20 mmol) as a solution in DCM (1:9) was added dropwise to a solution of allyl 4-(2-(allyloxy)-4-amino-3-isopropoxybenzamido)benzoate (0.53 g; 1.28 mmol) and (S)-4-(2-(4-nitrobenzamido)-4-oxo-4-(tritylamino)butanamido)benzoic acid (2.05 g, 3.20 mmol) in THF (13 mL) at 0° C., followed by DiPEA (1.78 mL; 10.24 mmol) as a solution in DCM (1:1). Reaction stirred at r.t. for 6 h, quenched with HCl 1 N and ice, solvent partially reduced under vacuum and residue diluted with EA (250 mL) and HCl 1N (250 mL), organic phase washed with brine (250 mL) and dried over sodium sulphate. Solvent removed under vacuum, the crude residue was chromatographed on silica gel with a gradient EA 20-75% in Pet. Et to give 940 mg of a orange residue (0.95 mmol; 54%).

¹H NMR (500 MHz, CDCl₃) δ 10.20 (s, 1H), 9.63 (s, 1H), 8.74 (s, 1H), 8.50 (d, J=8.9 Hz, 1H), 8.47 (d, J=6.2 Hz, 1H), 8.29 (d, J=8.8 Hz, 2H), 8.07 (dd, J=8.8, 4.9 Hz, 3H), 7.96 (d, J=8.8 Hz, 2H), 7.88 (d, J=8.7 Hz, 2H), 7.77 (d, J=8.7 Hz, 2H), 7.59 (d, J=8.7 Hz, 2H), 7.33-7.24 (m, 15H), 7.15 (s, 1H), 6.15 (m, 1H), 6.05 (m, 1H), 5.50 (dd, J=17.1, 1.2 Hz, 1H), 5.43 (m, 2H), 5.30 (dd, J=10.4, 1.1 Hz, 1H), 5.07 (m, 1H), 4.82 (d, J=5.6 Hz, 2H), 4.76 (dt, J=12.3, 6.2 Hz, 1H), 4.71 (d, J=5.9 Hz, 2H), 3.31 (dd, J=15.6, 2.7 Hz, 1H), 2.76 (dd, J=15.6, 7.3 Hz, 1H), 1.39 (dd, J=6.1, 3.9 Hz, 6H).

¹³C NMR (176 MHz, DMSO) δ 168.3, 166.9, 165.0, 164.6, 164.3, 149.5, 149.2, 144.7, 143.5, 142.6, 142.2, 139.3, 135.6, 133.7, 132.8, 130.6, 130.3, 129.0, 128.5, 128.4, 128.0, 127.4, 127.2, 126.4, 124.2, 123.6, 119.0, 118.9, 118.7, 117.8, 117.8, 76.3, 74.3, 69.4, 64.8, 52.1, 38.0, 22.3.

HRMS (ESI) calculated for C₆₀H₅₅N₆O₁₁ (M+H⁺) 1035.3923, found 1035.3943.

allyl (S)-4-(2-(allyloxy)-4-(4-(4-amino-2-(4-amino-benzamido)-4-oxobutanamido)benzamido)-3-iso-propoxybenzamido)benzoate

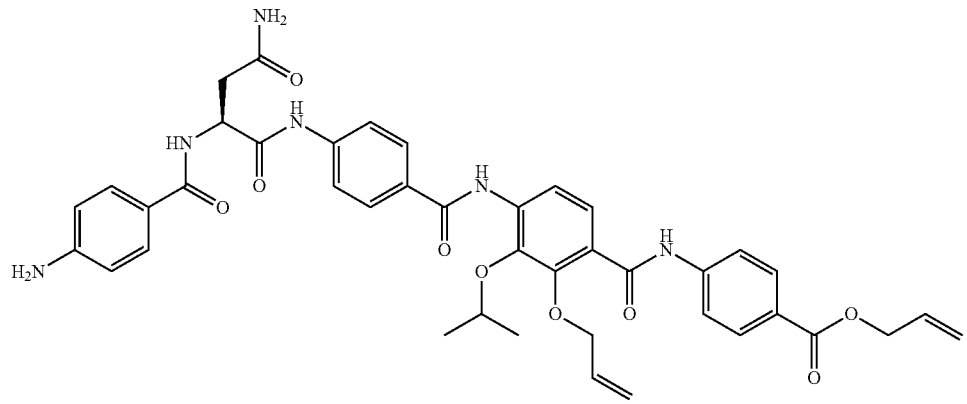 [SMILES: C=CCOC(=O)c1ccc(NC(=O)c2ccc(NC(=O)c3ccc(NC(=O)[C@H](CC(N)=O)NC(=O)c4ccc(N)cc4)cc3)c(OC(C)C)c2OCC=C)cc1]

Zn dust (0.95 g; 15.5 mmol) was added portionwise over few minutes to a stirred solution of allyl (S)-4-(2-(allyloxy)-3-isopropoxy-4-(4-(2-(4-nitrobenzamido)-4-oxo-4-(tritylamino)-butanamido)benzamido)benzamido)benzoate (1.30 g; 1.26 mmol) in THF (6.0 mL), EtOH (4.8 mL) and AcOH (1.2 mL). Reaction stirred for 5 h, the mixture was filtered through celite, the solvent was reduced under vacuum. The crude was used in the next step without further purification.

The residue was dissolved in DCM (18.7 mL), Tips (0.775 mL; 3.78 mmol) followed by TFA (6.3 mL) were added at 0 C. Reaction stirred 2 h at r.t. then solved removed under vacuum, residue take up and evaporated twice with DCM (15 mL) then triturated 3× with ice cold Pet. Et. The crude thus obtained was purified on silica gel with a gradient 0-10% MeOH in DCM to give 1.02 g of a yellow solid (1.18 mmol; y=94%).

$^1$H NMR (500 MHz, DMSO) δ 10.59 (s, 1H), 10.38 (s, 1H), 9.52 (s, 1H), 8.23 (d, J=7.3 Hz, 1H), 7.98 (t, J=9.4 Hz, 4H), 7.88 (d, J=8.8 Hz, 2H), 7.80 (dd, J=11.0, 8.7 Hz, 3H), 7.62 (d, J=8.7 Hz, 2H), 7.40 (d, J=8.5 Hz, 2H), 6.97 (s, 1H), 6.56 (d, J=8.7 Hz, 2H), 6.11-5.97 (m, 2H), 5.68 (s, 2H), 5.44-5.35 (m, 2H), 5.31-5.18 (m, 2H), 4.85 (dd, J=14.1, 7.1 Hz, 1H), 4.80 (d, J=5.3 Hz, 2H), 4.61 (d, J=5.5 Hz, 2H), 4.53-4.44 (m, 1H), 2.65 (d, J=7.0 Hz, 2H), 1.26 (d, J=6.1 Hz, 6H).

$^{13}$C NMR (126 MHz, DMSO) δ 171.5, 171.1, 166.4, 165.0, 164.7, 164.3, 151.9, 149.5, 143.5, 142.6, 142.5, 135.7, 133.7, 132.8, 130.4, 129.1, 128.4, 128.2, 127.1, 124.2, 123.6, 120.4, 119.0, 118.8, 117.8, 117.8, 116.0, 112.5, 76.3, 74.3, 64.9, 51.5, 40.1, 40.0, 39.9, 39.8, 39.8, 39.7, 39.6, 39.5, 39.3, 39.2, 39.0, 36.9, 22.3, 20.8.

HRMS (ESI) calculated for C41H43N6O9 (M+H$^+$) 763.3086, found 763.3085.

Marfey: 94.0% S enantiomer, 6.0% R enantiomer allyl (S)-4-(2-(allyloxy)-4-(4-(4-amino-2-(4-(4-nitrobenzamido)benzamido)-4-oxobutanamido)benzamido)-3-isopropoxybenzamido)benzoate

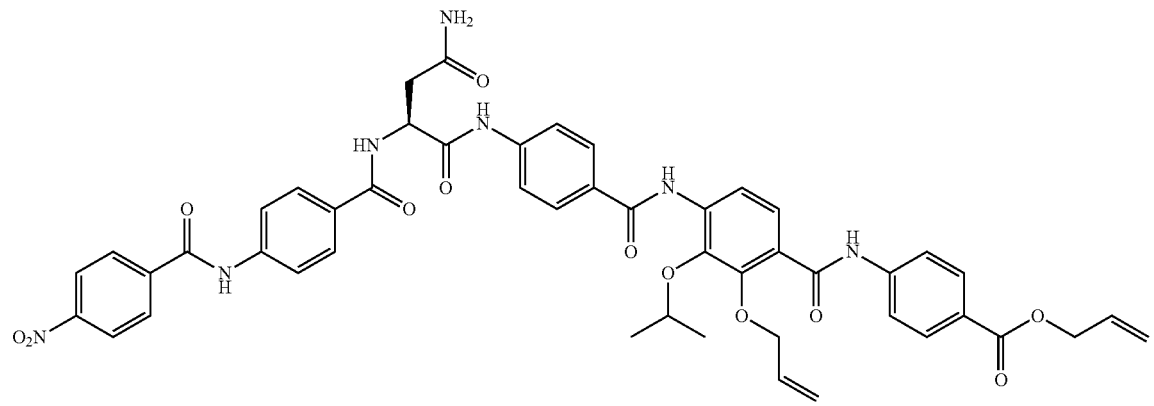 [SMILES: C=CCOC(=O)c1ccc(NC(=O)c2ccc(NC(=O)c3ccc(NC(=O)[C@H](CC(N)=O)NC(=O)c4ccc(NC(=O)c5ccc([N+](=O)[O-])cc5)cc4)cc3)c(OC(C)C)c2OCC=C)cc1]

See: Angew. Chem. Int. Ed. 2014, 53, 1-6

Collidine (0.166 mL; 1.26 mmol) was added dropwise at 0° C. to a solution of 4-nitro benzoic acid (92 mg; 0.551 mmol) and Bis(trichloromethyl) carbonate (49 mg; 0.165 mmol) in THF (10 mL). Reaction stirred at r.t. for 20 min then added to a solution of allyl (S)-2-(allyloxy)-4-(2-(allyloxy)-4-(4-(2-(4-aminobenzamido)-3-cyanopropanamido)benzamido)-3-methoxybenzamido)-3-methoxybenzoate (120 mg; 0.157 mmol) and DiPEA (0.273 mL; 1.57 mmol) in THF (10 mL). Reaction stirred for 4 h then quenched with HCl 1 N and ice. Solvent partially reduced under vacuum, EA (40 mL) and HCl 1N (40 mL) were added, organic phase washed with NaHCO₃ saturated solution (30 mL), brine (30 mL) and dried over sodium sulphate. The solvent was removed under reduced pressure, the residue was purified on silica gel with a gradient 0-10% MeOH in DCM to give 114 mg of a yellow residue (0.125 mmol; y=80%).

$^1$H NMR (700 MHz, DMSO) δ 10.79 (s, 1H), 10.58 (s, 1H), 10.45 (s, 1H), 9.52 (s, 1H), 8.68 (d, J=7.3 Hz, 1H), 8.41-8.36 (m, 2H), 8.23-8.19 (m, 2H), 8.00-7.95 (m, 4H), 7.94 (m, 2H), 7.91 (m, 2H), 7.87 (d, J=8.6 Hz, 2H), 7.81 (m, 3H), 7.40 (d, J=8.4 Hz, 2H), 6.99 (s, 1H), 6.04 (m, 2H), 5.39 (m, 2H), 5.28 (ddd, J=10.5, 2.9, 1.4 Hz, 1H), 5.20 (ddd, J=10.5, 2.9, 1.3 Hz, 1H), 4.92 (dd, J=14.0, 7.2 Hz, 1H), 4.79 (d, J=5.3 Hz, 2H), 4.61 (d, J=5.5 Hz, 2H), 4.49 (tt, J=12.2, 6.1 Hz, 1H), 2.69 (d, J=7.9 Hz, 2H), 1.26 (d, J=6.1 Hz, 6H).

$^{13}$C NMR (176 MHz, DMSO) δ 171.3, 170.7, 165.8, 164.9, 164.7, 164.3, 164.2, 149.5, 149.3, 143.5, 142.6, 142.4, 141.5, 140.3, 135.7, 133.7, 132.8, 130.3, 129.3, 129.2, 128.4, 128.3, 128.3, 127.1, 124.2, 123.6, 119.5, 119.0, 119.0, 118.8, 117.8, 117.8, 76.2, 74.3, 64.8, 51.6, 36.8, 22.3.

HRMS (ESI) calculated for C48H46N7O12 (M+H⁺) 912.3199, found 912.3196.

(S)-4-(4-(4-(4-amino-2-(4-(4-nitrobenzamido)benzamido)-4-oxobutanamido)benzamido)-2-hydroxy-3-isopropoxybenzamido)benzoic acid (28)

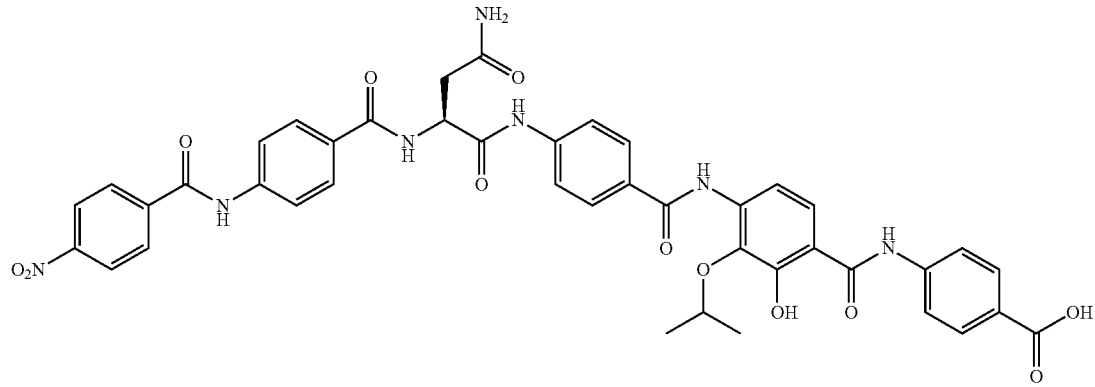 [SMILES: CC(C)Oc1c(NC(=O)c2ccc(NC(=O)[C@H](CC(N)=O)NC(=O)c3ccc(NC(=O)c4ccc([N+](=O)[O-])cc4)cc3)cc2)ccc(C(=O)Nc2ccc(C(=O)O)cc2)c1O]

Phenyl silane (0.012 mL; 0.099 mmol) followed by Palladium-tetrakis(triphenylphosphine (6.3 mg; 0.0055 mmol) was added to a solution of allyl (S)-4-(2-(allyloxy)-4-(4-(4-amino-2-(4-(4-nitrobenzamido)benzamido)-4-oxobutanamido)benzamido)-3-isopropoxybenzamido)benzoate (20 mg; 0.022 mmol) in THF (2.75 mL). Reaction stirred overnight and purified by preparative HPLC to afford to obtain 3.8 mg of a white material (0.0046 mmol; y=21%).

According to the purification method used, the desired structure could be obtained either in its protonated form or as ammonium salt.

Condition A: gradient 20-95% CH₃CN+0.1% HCOOH in water+0.1% HCOOH in 40 min.

Condition B: gradient 10-95% CH₃CN in water 10 mM NH₄HCO₃ in 40 min.

Condition A:

$^1$H NMR (700 MHz, DMSO) δ 12.82 (s, 1H), 12.29 (s, 1H), 10.79 (s, 1H), 10.60 (s, 1H), 10.46 (s, 1H), 9.40 (s, 1H), 8.68 (d, J=7.3 Hz, 1H), 8.41-8.35 (m, 2H), 8.24-8.18 (m, 2H), 7.99-7.92 (m, 6H), 7.90 (d, J=8.8 Hz, 2H), 7.85 (m, 3H), 7.82 (d, J=8.8 Hz, 2H), 7.70 (d, J=8.8 Hz, 1H), 7.40 (s, 1H), 6.99 (s, 1H), 4.92 (dd, J=14.1, 7.2 Hz, 1H), 4.57-4.51 (m, 1H), 2.69 (d, J=7.6 Hz, 2H), 1.26 (d, J=6.1 Hz, 6H).

(S)-4-(4-(4-(4-amino-2-(4-(4-nitrobenzamido)benzamido)-4-oxobutanamido)benzamido)-2-hydroxy-3-isopropoxybenzamido)benzoic acid as ammonium salts

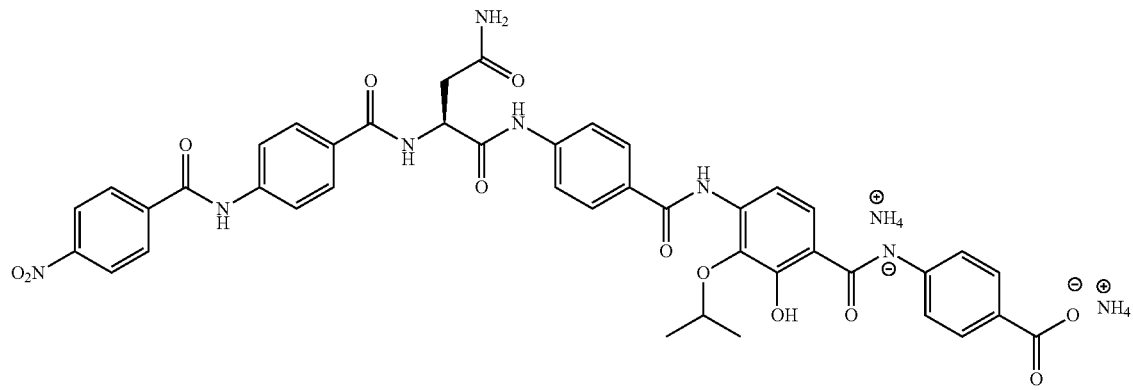 [SMILES: CC(C)Oc1c(NC(=O)c2ccc(NC(=O)[C@H](CC(N)=O)NC(=O)c3ccc(NC(=O)c4ccc([N+](=O)[O-])cc4)cc3)cc2)ccc(C(=O)[N-]c2ccc(C(=O)O)cc2)c1O ; [NH4+] ; [NH4+]]

Condition B:

$^1$H NMR (700 MHz, DMSO) δ 15.41 (br, 1H), 10.80 (s, 1H), 10.46 (s, 1H), 8.87 (s, 1H), 8.72 (d, J=7.3 Hz, 1H), 8.41-8.35 (m, 2H), 8.23-8.18 (m, 2H), 7.96-7.92 (m, 2H), 7.90 (d, J=8.8 Hz, 2H), 7.84 (d, J=8.9 Hz, 2H), 7.81 (d, J=8.9 Hz, 2H), 7.76 (d, J=7.8 Hz, 2H), 7.59 (br, 2H), 7.44 (d, J=8.7 Hz, 1H), 7.42 (s, 1H), 7.09 (d, J=8.7 Hz, 1H), 6.98 (s, 1H), 5.06-4.99 (m, 1H), 4.93 (q, J=7.1 Hz, 1H), 2.69 (d, J=7.4 Hz, 2H), 1.19 (d, J=6.2 Hz, 6H).

$^{13}$C NMR (176 MHz, DMSO) δ 171.3, 170.6, 166.9, 165.7, 165.3, 164.2, 163.1, 149.3, 142.0, 141.5, 140.3, 137.5, 129.5, 129.3, 129.3, 128.3, 127.6, 124.2, 123.7, 123.6, 119.5, 119.0, 117.7, 70.3, 51.6, 36.8, 22.7.

HRMS (ESI) calculated for C42H38N7O12 (M+H$^+$) 832.2573, found 832.2580.

Marfey: 91.2% S enantiomer, 8.8% R enantiomer d. Analogs Synthesized Modifying Building Block A1

Modifications of fragments A1 could give access to a series of derivatives, general synthetic scheme followed:

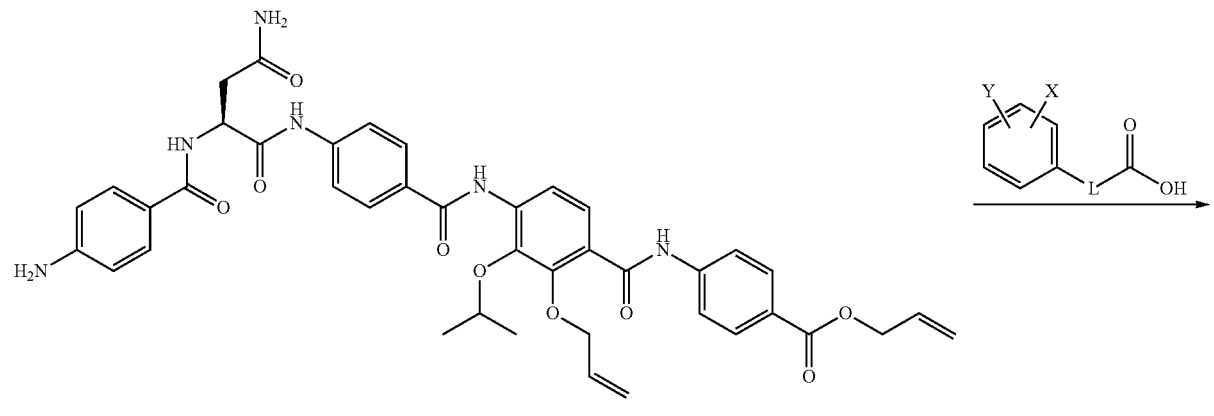

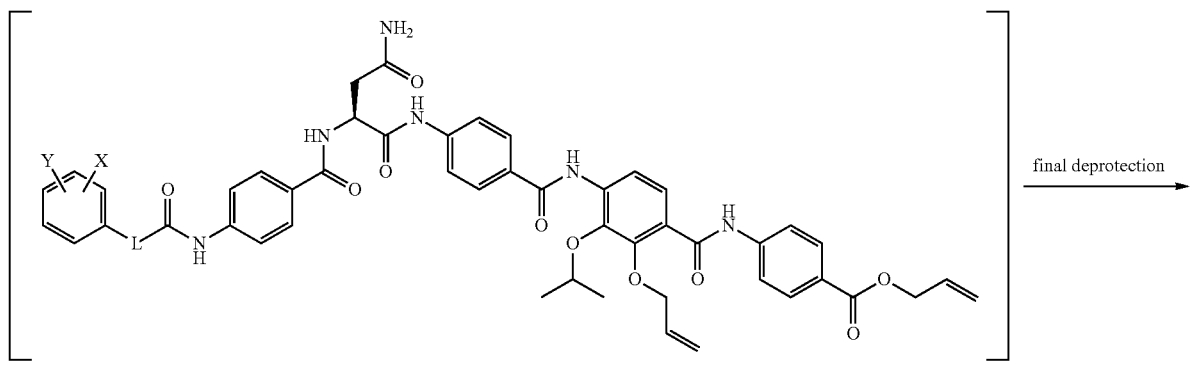

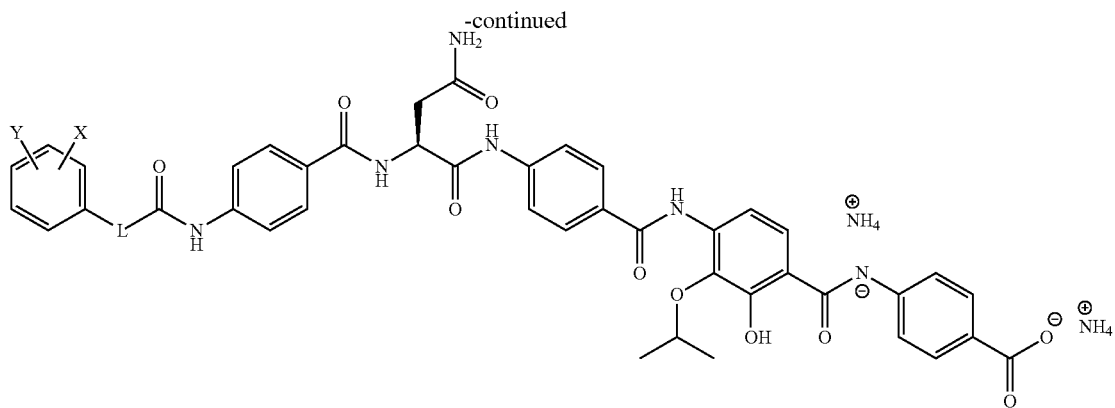

In the above formulas, X and Y independently represent H or $R^6$.

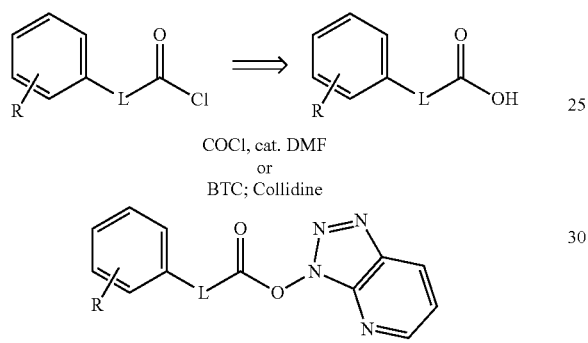

In the above formulas, R represents H or $R^6$.

Series of Final Compounds Synthesized Starting from Amine 26:

Coupling step, final deprotection and purification conditions are described in section 2.3b general procedures. Carbocylic acids employed in the coupling step with amine 26 were purchased or synthesized according to procedures described in section 2.2a.

All compounds purified according to condition B, preparative HPLC gradient 10-95% $CH_3CN$ in water 10 mM $NH_4HCO_3$ in 40 min, were obtained as ammonium salts.

(S)-4-(4-(4-(2-(4-(4-acetamidobenzamido)benzamido)-4-amino-4-oxobutanamido)benzamido)-2-hydroxy-3-isopropoxybenzamido)benzoic acid

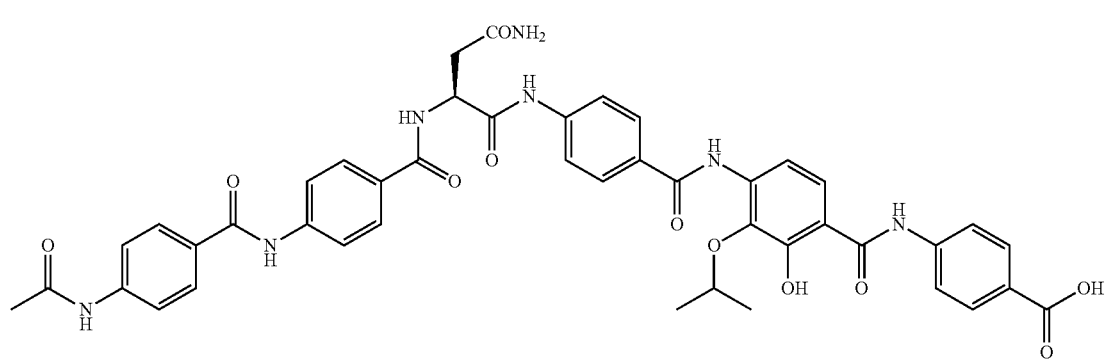

36

Amine 26 (15 mg, 0.016 mmol) coupled with carboxylic acid 31 using coupling conditions C followed by final deprotection.

Desired compound purified by preparative HPLC condition A, to obtain 1.1 mg of desired product as a white solid (0.0013 mmol, y=8%).

$^1$H NMR (700 MHz, DMSO) δ 12.78 (br, 1H), 12.29 (s, 1H), 10.60 (s, 1H), 10.45 (s, 1H), 10.33 (s, 1H), 10.23 (s, 1H), 9.40 (s, 1H), 8.63 (d, J=7.3 Hz, 1H), 7.95 (m, 6H), 7.92-7.87 (m, 3H), 7.85 (m, 3H), 7.82 (d, J=8.7 Hz, 2H), 7.71 (m, 3H), 7.39 (s, 1H), 7.35 (dd, J=8.0, 1.4 Hz, 1H), 6.99 (s, 1H), 4.92 (dd, J=14.0, 7.2 Hz, 1H), 4.54 (dt, J=12.3, 6.1 Hz, 1H), 2.69 (d, J=8.1 Hz, 2H), 2.09 (s, 3H), 1.26 (d, J=6.1 Hz, 6H).

$^{13}$C NMR (176 MHz, DMSO) δ 171.3, 170.8, 168.8, 168.5, 166.9, 165.8, 165.2, 164.2, 154.1, 142.5, 142.5, 142.2, 142.0, 137.0, 136.3, 133.9, 133.7, 130.2, 129.7, 128.7, 128.7, 128.5, 128.3, 128.2, 127.3, 126.3, 122.8, 120.7, 119.3, 119.0, 118.1, 112.4, 112.2, 74.9, 51.6, 36.8, 24.1, 22.3.

(S)-4-(4-(4-(4-amino-4-oxo-2-(4-(4-(3-(trifluoromethyl)-3H-diazirin-3-yl)benzamido)benzamido)butanamido)benzamido)-2-hydroxy-3-isopropoxybenzamido)benzoic acid $^1$H NMR (700 MHz, DMSO) δ 10.61 (s, 1H), 10.57 (s, 1H), 10.44 (s, 1H), 9.52 (s, 1H), 8.66 (d, J=7.3 Hz, 1H), 8.11-8.06 (m, 2H), 7.98 (dd, J=8.7, 6.8 Hz, 4H), 7.92 (d, J=8.9 Hz, 2H), 7.90-7.85 (m, 4H), 7.81 (dd, J=8.6, 6.6 Hz, 3H), 7.47 (d, J=8.1 Hz, 2H), 7.40 (d, J=8.4 Hz, 2H), 6.99 (s, 1H), 6.10-5.98 (m, 2H), 5.39 (m, 2H), 5.30-5.18 (m, 2H), 4.92 (dd, J=14.0, 7.3 Hz, 1H), 4.79 (d, J=5.3 Hz, 2H), 4.61 (d, J=5.5 Hz, 2H), 4.52-4.45 (m, 1H), 2.71-2.67 (m, 2H), 1.26 (d, J=6.1 Hz, 6H).

$^{13}$C NMR (176 MHz, DMSO) δ 171.3, 170.7, 165.8, 165.0, 164.8, 164.7, 164.3, 149.5, 143.5, 142.6, 142.4, 141.7, 136.3, 135.7, 133.7, 132.8, 130.7, 130.3, 129.0, 128.7, 128.4, 128.3, 127.1, 126.5, 124.2, 123.6, 122.5, 121.0, 119.4, 119.0, 119.0, 118.8, 117.8, 117.8, 76.2, 74.3, 64.8, 51.6, 36.8, 22.3.

Final Compound (37):

$^1$H NMR (700 MHz, DMSO) δ 12.81 (br, 1H), 12.29 (s, 1H), 10.61 (s, 2H), 10.46 (s, 1H), 9.39 (s, 1H), 8.66 (d, J=7.3 Hz, 1H), 8.09 (d, J=8.5 Hz, 2H), 7.96 (dd, J=12.4, 8.8 Hz, 3H), 7.90 (dd, J=26.1, 8.8 Hz, 4H), 7.87-7.83 (m, 3H), 7.82 (d, J=8.8 Hz, 2H), 7.70 (d, J=8.7 Hz, 2H), 7.47 (d, J=8.1 Hz, 2H), 7.39 (s, 1H), 6.99 (s, 1H), 4.92 (dd, J=14.0, 7.2 Hz, 1H), 4.58-4.51 (m, 1H), 2.69 (d, J=7.6 Hz, 2H), 1.26 (d, J=6.2 Hz, 6H).

37

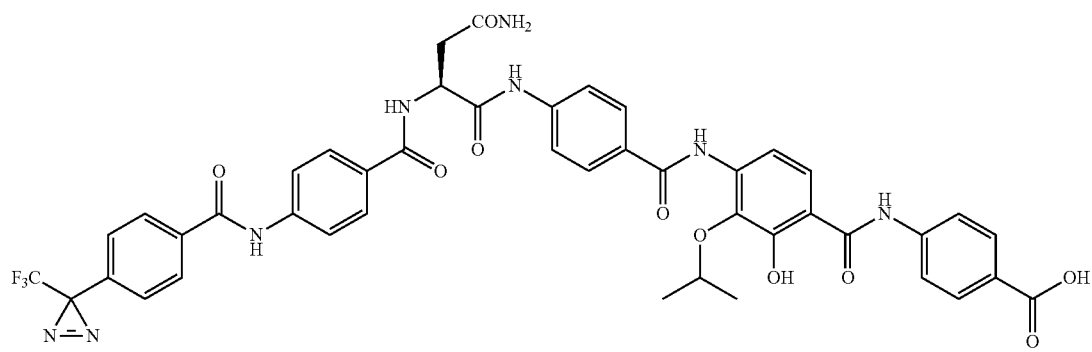

Amine 26 (28 mg, 0.037 mmol) coupled with 4-(3-(trifluoromethyl)-3H-diazirin-3-yl)benzoic acid using coupling conditions A, intermediate purified on silica gel with a gradient 0-10% MeOH in DCM to give 25 mg (0.027 mmol, y=70%) of allyl protected cystobactamid derivative. Followed final deprotection, desired compound purified by preparative HPLC condition A, to obtain 8.0 mg of desired product (0.009 mmol, y=31%).

Allyl Protected Intermediate $^{13}$C NMR (176 MHz, DMSO) δ 171.3, 170.7, 168.5, 166.9, 165.8, 164.8, 164.2, 142.5, 141.7, 137.0, 136.3, 136.3, 130.7, 130.2, 129.6, 129.0, 128.7, 128.3, 126.5, 122.8, 122.5, 121.0, 120.7, 119.4, 118.9, 112.4, 74.8, 51.6, 36.8, 22.1.

$^{19}$F NMR (471 MHz, DMSO) δ -64.40.

HRMS (ESI) calculated for C44H36F3N8O10 (M−H) 893.2512, found 893.2506.

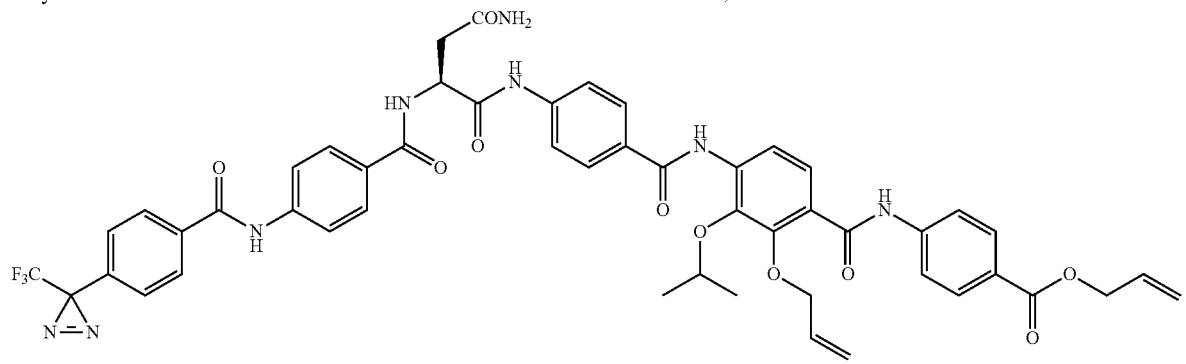

(S)-4-(4-(4-(4-amino-2-(4-benzamidobenzamido)-4-oxobutanamido)benzamido)-2-hydroxy-3-isopropoxybenzamido)benzoic acid

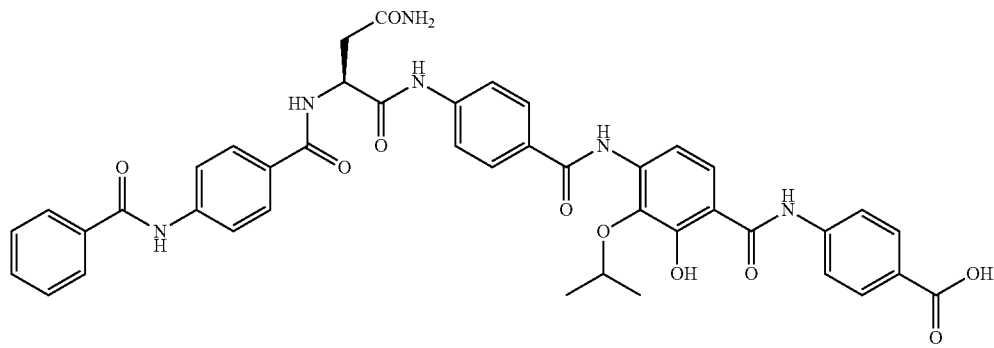

38

Amine 26 (40 mg, 0.052 mmol) coupled with benzoic acid using coupling conditions A followed by final deprotection.

Desired compound purified by preparative HPLC condition B, to obtain 13.8 mg of desired product as a white solid (0.018 mmol, y=34%).

$^1$H NMR (700 MHz, DMSO) δ 12.74 (br, 1H), 12.30 (br, 1H), 10.48 (s, 1H), 10.45 (s, 1H), 9.33 (br, 1H), 8.65 (d, J=7.3 Hz, 1H), 7.99-7.96 (m, 2H), 7.94 (dd, J=15.6, 6.5 Hz, 4H), 7.92-7.89 (m, 4H), 7.83 (dd, J=17.1, 8.7 Hz, 4H), 7.79 (s, 1H), 7.61 (dd, J=11.6, 4.2 Hz, 2H), 7.55 (t, J=7.6 Hz, 2H), 7.40 (s, 1H), 6.99 (s, 1H), 4.92 (dd, J=14.0, 7.2 Hz, 1H), 4.61 (s, 1H), 2.69 (d, J=7.9 Hz, 2H), 1.25 (d, J=6.1 Hz, 6H).

$^{13}$C NMR (176 MHz, DMSO) δ 171.3, 170.7, 168.3, 168.3, 166.9, 165.8, 164.0, 142.4, 142.1, 136.5, 134.7, 131.8, 130.2, 128.7, 128.4, 128.3, 128.2, 127.7, 127.4, 123.0, 120.4, 119.3, 118.9, 51.6, 36.8, 22.4.

HRMS (ESI) calculated for C42H37N6O10 (M−H) 785.2577, found 785.2577.

(S)-4-(4-(4-(4-amino-2-(4-(4-fluorobenzamido)benzamido)-4-oxobutanamido)benzamido)-2-hydroxy-3-isopropoxybenzamido)benzoic acid Amine 26 (40 mg, 0.052 mmol) coupled with 4-fluorobenzoic acid using coupling conditions A followed by final deprotection.

Desired compound purified by preparative HPLC condition B, to obtain 3.2 mg of desired product as a white solid (0.004 mmol, y=8%).

$^1$H NMR (500 MHz, DMSO) δ 12.80 (br, 1H), 12.29 (br, 1H), 10.62 (br, 1H), 10.49 (s, 1H), 10.46 (s, 1H), 9.39 (s, 1H), 8.65 (d, J=7.3 Hz, 1H), 8.09-8.03 (m, 2H), 7.96 (t, J=8.4 Hz, 4H), 7.90 (q, J=9.0 Hz, 4H), 7.84 (dd, J=17.4, 8.8 Hz, 5H), 7.68 (d, J=8.6 Hz, 1H), 7.43-7.35 (m, 3H), 6.99 (s, 1H), 4.92 (dd, J=14.1, 7.1 Hz, 1H), 4.59-4.51 (m, 1H), 2.69 (d, J=7.2 Hz, 2H), 1.26 (d, J=6.1 Hz, 6H).

$^{13}$C NMR (126 MHz, DMSO) δ 171.3, 170.8, 168.4, 166.9, 165.8, 164.7, 164.2, 163.2, 142.5, 142.0, 136.4, 131.1, 130.6, 130.5, 130.2, 128.8, 128.3, 122.8, 120.6, 119.4, 118.9, 115.5, 115.3, 112.5, 74.8, 51.6, 36.8, 22.3.

HRMS (ESI) calculated for C42H36FN6O10 (M−H) 803.2482, found 803.2498.

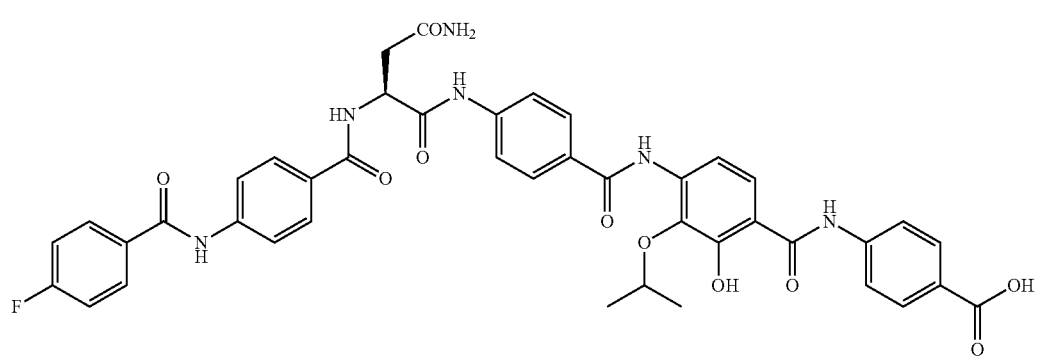

39

(S)-4-(4-(4-(4-amino-2-(4-(4-aminobenzamido)benzamido)-4-oxobutanamido)benzamido)-2-hydroxy-3-isopropoxybenzamido)benzoic acid

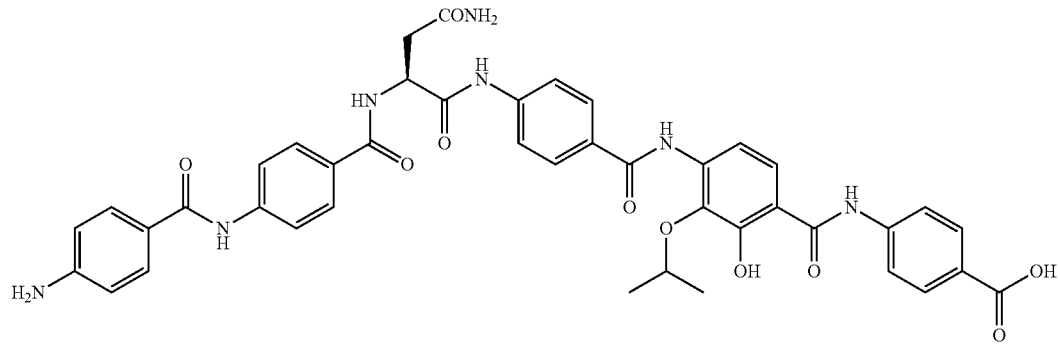

40

Compound 40 was isolated as a by-product of the synthesis of 28, obtained 0.7 mg.

$^1$H NMR (700 MHz, DMSO) δ 15.31 (s, 1H), 10.46 (s, 1H), 9.98 (s, 1H), 8.87 (s, 1H), 8.68 (d, J=7.0 Hz, 1H), 7.86 (d, J=9.9 Hz, 4H), 7.82 (dd, J=19.7, 8.8 Hz, 4H), 7.75 (dd, J=11.3, 8.6 Hz, 4H), 7.55 (d, J=8.5 Hz, 2H), 7.44 (d, J=8.7 Hz, 2H), 7.08 (d, J=8.7 Hz, 1H), 6.98 (s, 1H), 6.60 (d, J=8.6 Hz, 2H), 5.80 (s, 2H), 5.02 (dt, J=12.4, 6.1 Hz, 1H), 4.91 (dd, J=14.2, 7.2 Hz, 1H), 2.69 (d, J=7.0 Hz, 2H), 1.19 (d, J=6.1 Hz, 6H).

$^{13}$C NMR (176 MHz, DMSO) δ 171.3, 170.7, 169.8, 166.8, 165.9, 165.5, 165.3, 163.1, 152.4, 142.7, 142.0, 141.5, 137.5, 134.0, 129.6, 129.5, 128.2, 127.9, 127.5, 123.7, 120.7, 119.0, 119.0, 117.5, 116.1, 112.5, 100.6, 70.3, 51.7, 36.9, 22.7.

HRMS (ESI) calculated for C42H38N7O10 (M−H) 800.2686, found 800.2733.

(S)-4-(4-(4-(4-amino-2-(4-(3-nitrobenzamido)benzamido)-4-oxobutanamido)benzamido)-2-hydroxy-3-isopropoxybenzamido)benzoic acid

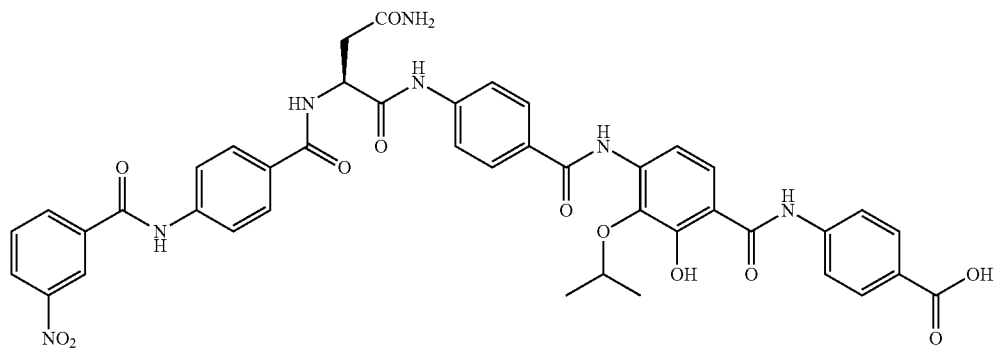

41

Amine 26 (40 mg, 0.052 mmol) coupled with 3-nitrobenzoic acid using coupling conditions A, intermediate purified on silica gel with a gradient 0-10% MeOH in DCM to give 45 mg (0.049 mmol, y=95%) of allyl protected cystobactamid derivative. Followed final deprotection on 20 mg of intermediate (0.022 mmol), desired compound purified by preparative HPLC condition B, to obtain 6.8 mg of desired product (0.008 mmol, y=31%) and 2.2 mg of compound 42, which was formed as a by-product of the reaction.

Allyl Protected Intermediate:

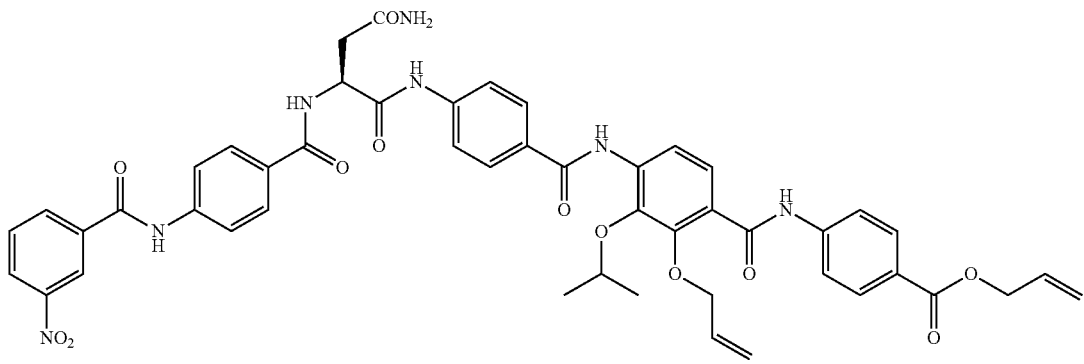 [SMILES: C=CCOC(=O)c1ccc(NC(=O)c2ccc(NC(=O)c3ccc(NC(=O)[C@H](CC(N)=O)NC(=O)c4ccc(NC(=O)c5cccc([N+](=O)[O-])c5)cc4)cc3)c(OC(C)C)c2OCC=C)cc1]

¹H NMR (700 MHz, DMSO) δ 10.80 (s, 1H), 10.58 (s, 1H), 10.45 (s, 1H), 9.52 (s, 1H), 8.82 (t, J=2.0 Hz, 1H), 8.68 (d, J=7.3 Hz, 1H), 8.46 (ddd, J=8.2, 2.3, 1.0 Hz, 1H), 8.44-8.41 (m, 1H), 8.00-7.96 (m, 4H), 7.96-7.93 (m, 2H), 7.93-7.89 (m, 2H), 7.86 (t, J=8.0 Hz, 3H), 7.83-7.79 (m, 3H), 7.40 (d, J=8.4 Hz, 2H), 6.99 (s, 1H), 6.08-5.99 (m, 2H), 5.39 (m, 2H), 5.24 (m, 2H), 4.93 (dd, J=14.0, 7.3 Hz, 1H), 4.79 (dd, J=3.9, 1.4 Hz, 2H), 4.61 (d, J=5.5 Hz, 2H), 4.52-4.46 (m, 1H), 2.71-2.68 (m, 2H), 1.26 (d, J=6.1 Hz, 6H).

¹³C NMR (176 MHz, DMSO) δ 171.3, 170.7, 165.8, 164.9, 164.7, 164.3, 163.6, 149.5, 147.8, 143.5, 142.6, 142.4, 141.5, 136.0, 135.7, 134.3, 133.7, 132.8, 130.3, 130.3, 129.2, 128.4, 128.3, 127.1, 126.4, 124.2, 123.6, 122.5, 119.6, 119.0, 118.8, 117.8, 117.8, 76.2, 74.3, 64.8, 51.6, 36.8, 22.3.

Final Compound 41:
¹H NMR (700 MHz, DMSO) δ 12.79 (br, 1H), 12.29 (br, 1H), 10.80 (s, 1H), 10.62 (br, 1H), 10.46 (s, 1H), 9.36 (s, 1H), 8.82 (t, J=1.8 Hz, 1H), 8.68 (d, J=7.2 Hz, 1H), 8.46 (dd, J=8.2, 1.5 Hz, 1H), 8.43 (d, J=7.9 Hz, 1H), 7.98-7.89 (m, 8H), 7.86 (dd, J=15.4, 7.9 Hz, 3H), 7.82 (d, J=8.7 Hz, 3H), 7.66 (br, 1H), 7.40 (s, 1H), 6.99 (s, 1H), 4.93 (dd, J=14.1, 7.2 Hz, 1H), 4.58 (s, 1H), 2.70 (d, J=7.5 Hz, 2H), 1.26 (d, J=6.1 Hz, 6H).

¹³C NMR (176 MHz, DMSO) δ 171.3, 170.7, 168.4, 166.9, 165.8, 164.1, 163.6, 147.8, 142.5, 141.5, 136.4, 136.0, 134.3, 130.3, 130.2, 129.2, 128.3, 128.3, 126.4, 122.9, 122.5, 120.6, 119.6, 118.9, 118.8, 74.5, 51.6, 36.8, 22.3.

HRMS (ESI) calculated for C42H38N7O12 (M+H) 832.2573, found 832.2565.

(S)-4-(4-(4-(4-amino-2-(4-(3-aminobenzamido)benzamido)-4-oxobutanamido)benzamido)-2-hydroxy-3-isopropoxybenzamido)benzoic acid

42

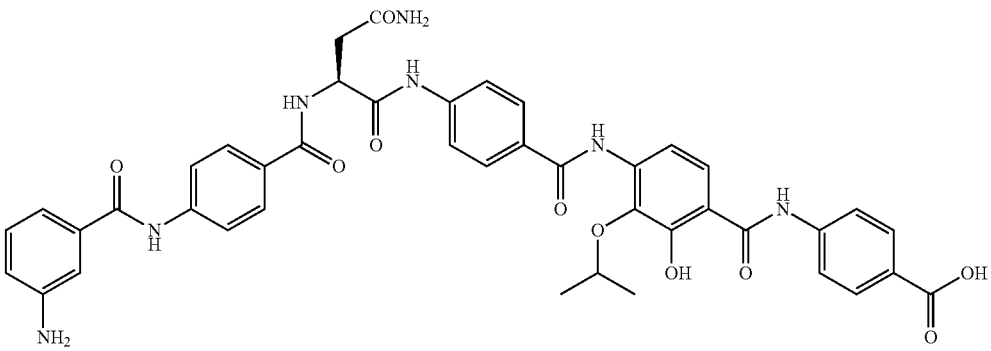

¹H NMR (700 MHz, DMSO) δ 15.86 (br, 1H), 12.45 (br, 1H), 10.43 (s, 1H), 10.30 (s, 1H), 8.94 (br, 1H), 8.62 (d, J=7.3 Hz, 1H), 7.91-7.83 (m, 9H), 7.79 (dd, J=20.6, 8.7 Hz, 4H), 7.49 (br, 1H), 7.40 (s, 1H), 7.16 (t, J=7.8 Hz, 1H), 7.10 (d, J=1.8 Hz, 1H), 7.08 (d, J=7.8 Hz, 1H), 6.98 (s, 1H), 6.76 (dd, J=7.9, 1.5 Hz, 1H), 5.33 (s, 2H), 4.95 (br, 1H), 4.92 (dd, J=14.0, 7.3 Hz, 1H), 2.71-2.66 (m, 2H), 1.20 (d, J=6.1 Hz, 6H).

¹³C NMR (176 MHz, DMSO) δ 171.3, 170.7, 167.5, 167.2, 166.6, 165.9, 163.3, 148.8, 142.3, 142.1, 135.6, 130.4, 128.8, 128.5, 128.2, 127.7, 123.6, 119.2, 119.0, 117.0, 114.8, 113.0, 51.6, 36.8, 22.6.

HRMS (ESI) calculated for C42H38N7O10 (M−H) 800.2686, found 800.2691.

(S)-4-(4-(4-(4-amino-2-(4-(2-nitrobenzamido)benzamido)-4-oxobutanamido)benzamido)-2-hydroxy-3-isopropoxybenzamido)benzoic acid

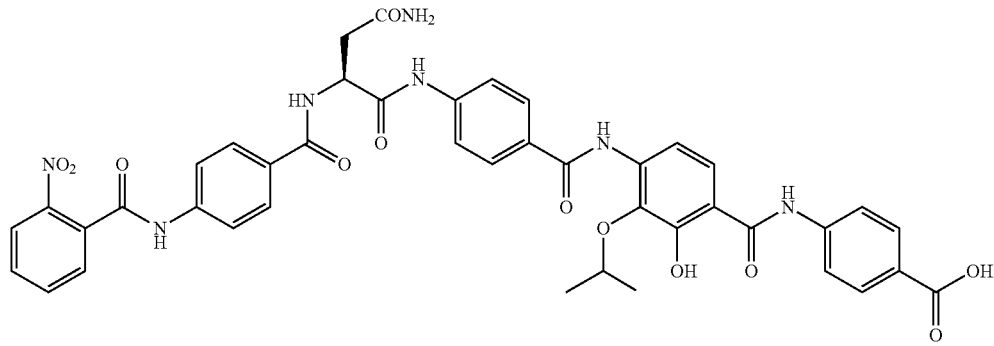

43

Amine 26 (20 mg, 0.026 mmol) coupled with 2-nitrobenzoic acid using coupling conditions B followed by final deprotection.

Desired compound purified by preparative HPLC condition B, to obtain 2.4 mg of desired product as a white solid (0.003 mmol, y=11%).

$^1$H NMR (700 MHz, DMSO) δ 12.72 (br, 1H), 12.30 (br, 1H), 10.91 (s, 1H), 10.45 (s, 1H), 9.29 (br, 1H), 8.67 (d, J=7.3 Hz, 1H), 8.17 (dd, J=8.2, 0.8 Hz, 1H), 7.93 (t, J=8.8 Hz, 6H), 7.89 (td, J=7.5, 0.9 Hz, 1H), 7.85-7.80 (m, 6H), 7.80-7.75 (m, 4H), 7.40 (s, 1H), 6.99 (s, 1H), 4.92 (dd, J=13.9, 7.3 Hz, 1H), 4.64 (br, 1H), 2.69 (dd, J=6.8, 3.4 Hz, 2H), 1.25 (d, J=6.1 Hz, 6H).

$^{13}$C NMR (176 MHz, DMSO) δ 171.3, 170.7, 168.2, 166.9, 165.7, 164.4, 164.0, 146.4, 142.4, 141.6, 136.6, 134.2, 132.4, 131.1, 130.3, 129.3, 129.0, 128.5, 128.1, 124.3, 123.0, 118.9, 118.7, 51.6, 36.8, 22.4.

HRMS (ESI) calculated for C42H36N7O12 (M−H) 830.2427, found 830.2439.

(S)-4-(4-(4-(4-amino-2-(4-(4-cyanobenzamido)benzamido)-4-oxobutanamido)benzamido)-2-hydroxy-3-isopropoxybenzamido)benzoic acid

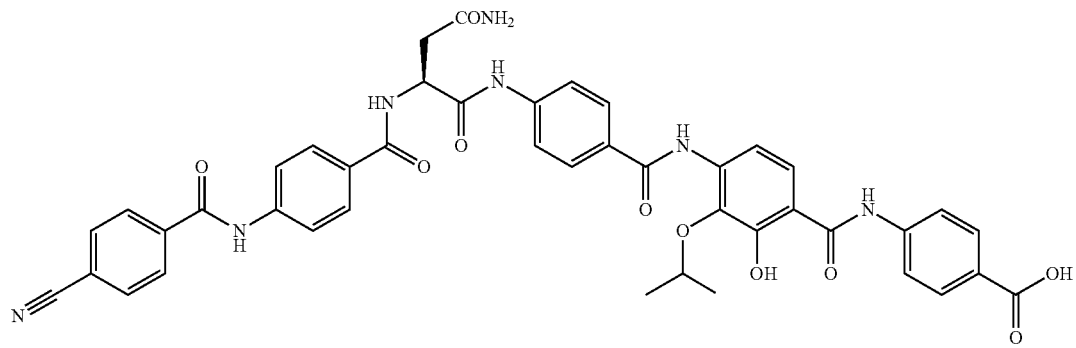

44

Amine 26 (25 mg, 0.033 mmol) coupled with 4-cyanobenzoic acid using coupling conditions A, intermediate purified on silica gel with a gradient 0-10% MeOH in DCM to give 18 mg (0.02 mmol, y=61%) of allyl protected cystobactamid derivative.

Final deprotection afforded the desired compound, which was purified by preparative HPLC condition B, to obtain 3.3 mg of desired product (0.004 mmol, y=20%).

Allyl Protected Intermediate:

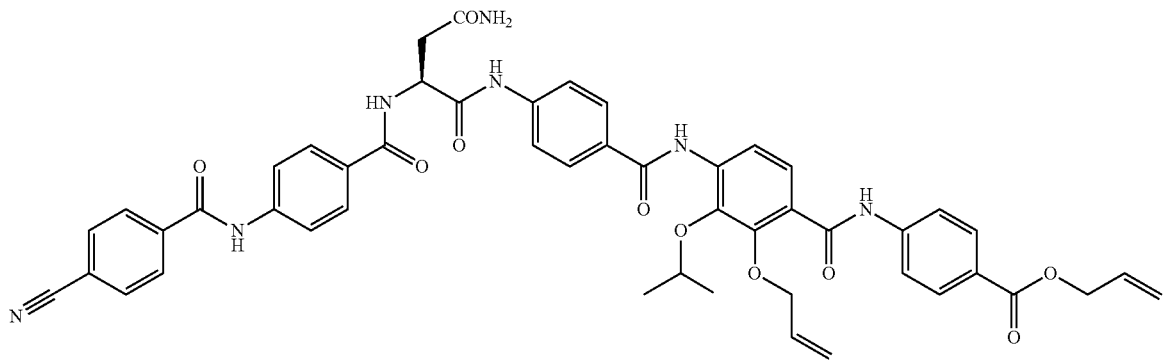 [SMILES: C=CCOC(=O)c1ccc(NC(=O)c2ccc(NC(=O)c3ccc(NC(=O)[C@H](CC(N)=O)NC(=O)c4ccc(NC(=O)c5ccc(C#N)cc5)cc4)cc3)c(OC(C)C)c2OCC=C)cc1]

¹H NMR (700 MHz, DMSO) δ 10.70 (s, 1H), 10.57 (s, 1H), 10.45 (s, 1H), 9.52 (s, 1H), 8.68 (d, J=7.3 Hz, 1H), 8.13 (d, J=8.4 Hz, 2H), 8.05 (d, J=8.4 Hz, 2H), 7.98 (dd, J=8.7, 6.9 Hz, 4H), 7.93 (d, J=8.8 Hz, 2H), 7.88 (dd, J=15.2, 8.7 Hz, 4H), 7.81 (dd, J=8.6, 5.6 Hz, 3H), 7.40 (d, J=8.4 Hz, 2H), 6.99 (s, 1H), 6.09-5.98 (m, 2H), 5.43-5.34 (m, 2H), 5.30-5.18 (m, 2H), 4.92 (dd, J=14.1, 7.2 Hz, 1H), 4.79 (d, J=5.3 Hz, 2H), 4.61 (d, J=5.4 Hz, 2H), 4.49 (dt, J=12.3, 6.1 Hz, 1H), 2.69 (d, J=7.5 Hz, 2H), 1.26 (d, J=6.1 Hz, 6H).

¹³C NMR (176 MHz, DMSO) δ 171.3, 170.7, 165.8, 165.0, 164.7, 164.5, 164.3, 149.5, 143.5, 142.6, 142.4, 141.6, 138.7, 135.7, 133.7, 132.8, 132.5, 130.3, 129.1, 128.6, 128.4, 128.3, 127.1, 124.2, 123.6, 119.5, 119.0, 118.8, 117.8, 117.8, 114.0, 76.3, 74.3, 64.8, 51.6, 36.8, 22.3.

Final Compound 44:

¹H NMR (500 MHz, DMSO) δ 12.81 (br, 1H), 12.29 (br, 1H), 10.70 (s, 1H), 10.61 (br, 1H), 10.46 (s, 1H), 9.37 (br, 1H), 8.67 (d, J=7.3 Hz, 1H), 8.15-8.10 (m, 2H), 8.07-8.03 (m, 2H), 7.98-7.93 (m, 4H), 7.93-7.87 (m, 4H), 7.83 (dd, J=16.0, 8.8 Hz, 5H), 7.67 (br, 1H), 7.40 (s, 1H), 6.99 (s, 1H), 4.92 (q, J=7.1 Hz, 1H), 4.56 (br, 1H), 2.69 (d, J=7.2 Hz, 2H), 1.26 (d, J=6.1 Hz, 6H).

¹³C NMR (176 MHz, DMSO) δ 171.3, 170.7, 168.4, 166.9, 165.8, 164.5, 164.1, 142.5, 141.6, 138.7, 136.4, 132.5, 130.2, 129.1, 128.6, 128.3, 128.3, 122.9, 120.6, 119.5, 118.9, 118.3, 114.0, 74.8, 51.6, 36.8, 22.3.

HRMS (ESI) calculated for C43H36N7O10 (M−H) 810.2529, found 810.2538.

(S)-4-(4-(4-(4-amino-4-oxo-2-(4-(4-(trifluoromethyl)benzamido)benzamido)butanamido)benzamido)-2-hydroxy-3-isopropoxybenzamido)benzoic acid

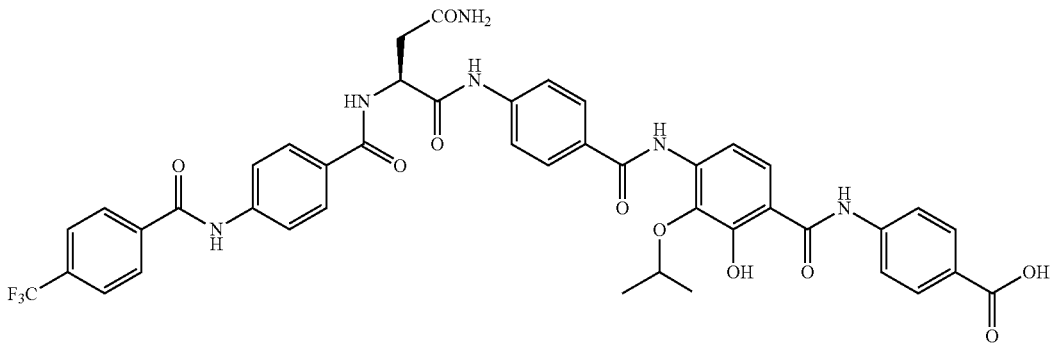

Amine 26 (15 mg, 0.020 mmol) coupled with 4-trifluoromethyl benzoic acid using coupling conditions A followed by final deprotection.

Desired compound purified by preparative HPLC condition B, to obtain 5.3 mg of desired product as a white solid (0.0062 mmol, y=31%).

¹H NMR (700 MHz, DMSO) δ 12.80 (br, 1H), 12.29 (br, 1H), 10.69 (s, 1H), 10.62 (br, 1H), 10.46 (s, 1H), 9.37 (br, 1H), 8.67 (d, J=7.3 Hz, 1H), 8.17 (d, J=8.1 Hz, 2H), 7.98-7.92 (m, 8H), 7.90 (d, J=8.9 Hz, 2H), 7.85 (d, J=8.7 Hz, 2H), 7.82 (d, J=8.8 Hz, 3H), 7.67 (br, 1H), 7.40 (s, 1H), 6.99 (s, 1H), 4.92 (q, J=7.2 Hz, 1H), 4.57 (br, 1H), 2.69 (d, J=7.6 Hz, 2H), 1.26 (d, J=6.1 Hz, 6H).

¹³C NMR (176 MHz, DMSO) δ 171.3, 170.7, 168.4, 166.9, 165.8, 164.7, 164.1, 142.5, 141.7, 138.5, 136.9, 136.4, 131.6, 131.4, 130.2, 129.1, 128.7, 128.3, 128.3, 125.4, 125.4, 124.7, 123.1, 122.9, 120.6, 119.5, 118.9, 74.7, 51.6, 36.8, 22.3.

HRMS (ESI) calculated for C43H36F3N6O10 (M−H) 853.2450, found 853.2438.

(S)-4-(4-(4-(4-amino-4-oxo-2-(4-(4-ureidobenzamido)benzamido)butanamido)benzamido)-2-hydroxy-3-isopropoxybenzamido)benzoic acid

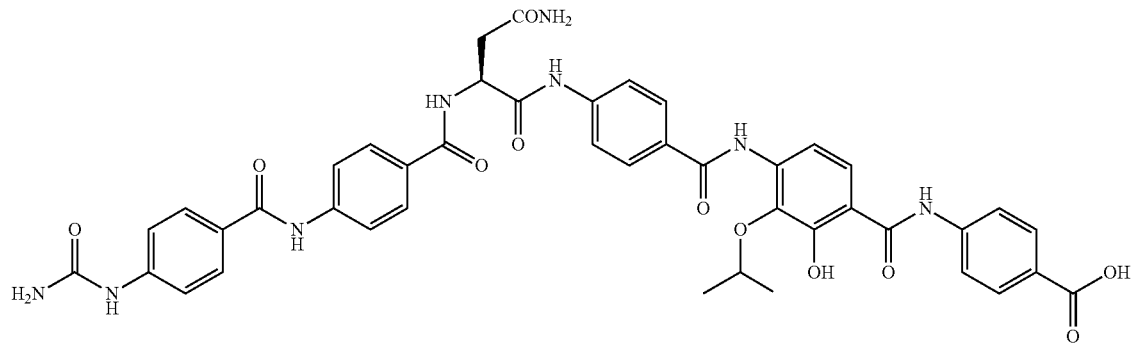

46

Amine 26 (20 mg, 0.026 mmol) coupled with carboxylic acid 32 using coupling conditions C followed by final deprotection.

Desired compound purified by preparative HPLC condition B, to obtain 6.2 mg of desired product as a white solid (0.0073 mmol, y=28%).

$^1$H NMR (700 MHz, DMSO) δ 12.55 (br, 1H), 10.44 (s, 1H), 10.26 (s, 1H), 9.15 (br, 1H), 8.89 (s, 1H), 8.63 (d, J=7.3 Hz, 1H), 7.93-7.87 (m, 10H), 7.81 (d, J=8.8 Hz, 4H), 7.66 (br, 1H), 7.56-7.52 (m, 2H), 7.39 (s, 1H), 6.99 (s, 1H), 6.01 (s, 2H), 4.92 (dd, J=14.0, 7.3 Hz, 1H), 4.77 (br, 1H), 2.69 (d, J=8.2 Hz, 2H), 1.23 (d, J=6.1 Hz, 6H).

$^{13}$C NMR (176 MHz, DMSO) δ 171.3, 170.7, 167.9, 167.0, 165.9, 165.3, 163.8, 155.7, 144.0, 142.3, 142.3, 130.3, 128.8, 128.4, 128.2, 128.0, 126.6, 123.2, 119.2, 119.0, 116.6, 51.6, 36.8, 22.5.

HRMS (ESI) calculated for C43H39N8O11 (M−H) 843.2744, found 843.2759.

(S)-4-(4-(4-(4-amino-2-(4-(4-(4-nitrobenzamido)benzamido)benzamido)-4-oxobutanamido)benzamido)-2-hydroxy-3-isopropoxybenzamido)benzoic acid Amine 26 (15 mg, 0.020 mmol) coupled with carboxylic acid 29 using coupling conditions C followed by final deprotection.

Desired compound purified by preparative HPLC condition B, to obtain 3.9 mg of desired product as a white solid (0.0041 mmol, y=20%).

$^1$H NMR (700 MHz, DMSO) δ 12.61 (br, 1H), 12.32 (br, 1H), 10.84 (s, 1H), 10.44 (s, 1H), 10.41 (s, 1H), 9.16 (br, 1H), 8.65 (d, J=7.2 Hz, 1H), 8.42-8.37 (m, 2H), 8.25-8.19 (m, 2H), 8.04 (d, J=8.7 Hz, 2H), 7.96 (d, J=8.8 Hz, 2H), 7.94-7.86 (m, 9H), 7.82 (d, J=8.7 Hz, 4H), 7.67 (br, 1H), 7.40 (s, 1H), 6.99 (s, 1H), 4.93 (dd, J=14.1, 7.2 Hz, 1H), 4.76 (br, 1H), 2.69 (d, J=7.7 Hz, 2H), 1.23 (d, J=6.1 Hz, 6H).

$^{13}$C NMR (176 MHz, DMSO) δ 171.3, 170.7, 167.0, 165.8, 165.1, 164.3, 163.7, 149.3, 142.3, 142.1, 141.9, 140.3, 130.3, 129.8, 129.3, 128.7, 128.6, 128.3, 128.0, 123.6, 123.2, 119.6, 119.3, 119.0, 51.6, 36.8, 22.5.

HRMS (ESI) calculated for C49H41N8O13 (M−H) 949.2799, found 949.2848.

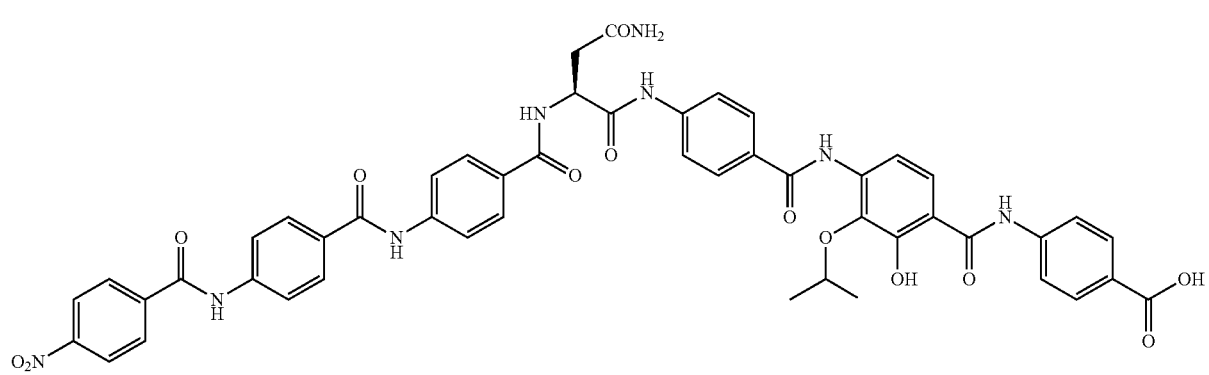

47

(S)-4-(4-(4-(4-amino-2-(4-(2-hydroxy-3-isopropoxy-4-nitrobenzamido)benzamido)-4-oxobutanamido)benzamido)-2-hydroxy-3-isopropoxybenzamido)benzoic acid

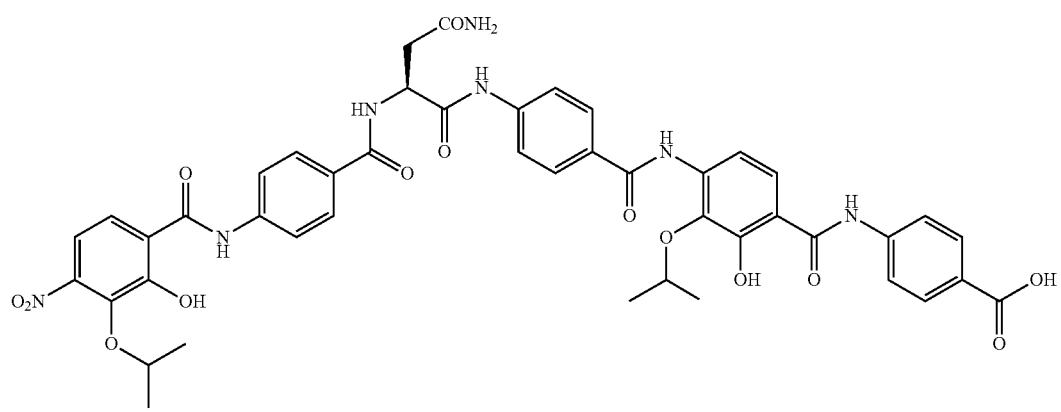

48

Amine 26 (40 mg, 0.052 mmol) coupled with carboxylic acid (see section 2.2c) using coupling conditions A, intermediate purified on silica gel with a gradient 0-10% MeOH in DCM to give 40 mg (0.095 mmol, y=87%) of allyl protected cystobactamid derivative.

Followed final deprotection on 15 mg of intermediate (0.015 mmol), desired compound purified by preparative HPLC condition B, to obtain 2.5 mg of desired product (0.0028 mmol, y=18%) and 1.2 mg of compound 49, which was formed as a by-product of the reaction.

Allyl Protected Intermediate:

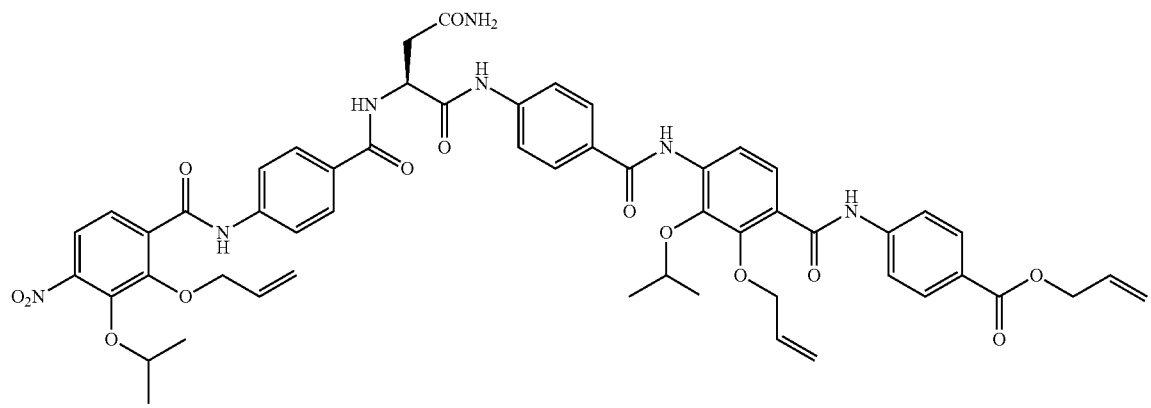 [SMILES: C=CCOC(=O)c1ccc(NC(=O)c2ccc(NC(=O)c3ccc(NC(=O)[C@H](CC(N)=O)NC(=O)c4ccc(NC(=O)c5ccc([N+](=O)[O-])c(OC(C)C)c5OCC=C)cc4)cc3)c(OC(C)C)c2OCC=C)cc1]

$^1$H NMR (700 MHz, DMSO) δ 10.66 (s, 1H), 10.58 (s, 1H), 10.44 (s, 1H), 9.52 (s, 1H), 8.66 (d, J=7.3 Hz, 1H), 7.98 (dd, J=8.7, 6.6 Hz, 4H), 7.92 (d, J=8.8 Hz, 2H), 7.87 (d, J=8.6 Hz, 2H), 7.83-7.76 (m, 5H), 7.72 (d, J=8.4 Hz, 1H), 7.46 (d, J=8.4 Hz, 1H), 7.40 (d, J=8.4 Hz, 2H), 6.99 (s, 1H), 6.09-5.93 (m, 3H), 5.43-5.36 (m, 2H), 5.36-5.26 (m, 2H), 5.22-5.16 (m, 2H), 4.92 (dd, J=13.9, 7.4 Hz, 1H), 4.81-4.78 (m, 2H), 4.70-4.65 (m, 1H), 4.62-4.59 (m, 4H), 4.52-4.46 (m, 1H), 2.71-2.67 (m, 1H), 1.26 (d, J=6.1 Hz, 6H), 1.24 (d, J=6.1 Hz, 6H).

$^{13}$C NMR (176 MHz, DMSO) δ 171.3, 170.7, 165.7, 164.9, 164.7, 164.3, 163.7, 149.9, 149.5, 146.8, 143.5, 143.4, 142.6, 142.4, 141.4, 136.1, 135.7, 133.7, 133.1, 132.8, 130.3, 129.1, 128.5, 128.4, 128.3, 127.1, 124.2, 123.6, 123.2, 119.2, 119.0, 118.8, 118.8, 118.3, 117.8, 117.8, 77.2, 76.2, 74.6, 74.3, 64.8, 51.6, 36.8, 22.3, 22.1.

Final Compound 48:

$^1$H NMR (700 MHz, DMSO) δ 12.82 (br, 1H), 12.29 (br, 1H), 10.61 (br, 1H), 10.43 (s, 1H), 9.40 (s, 1H), 8.60 (d, J=7.2 Hz, 1H), 7.96 (dd, J=14.7, 8.7 Hz, 4H), 7.91-7.75 (m, 9H), 7.69 (d, J=8.7 Hz, 1H), 7.59 (d, J=8.3 Hz, 1H), 7.40 (s, 1H), 6.98 (s, 1H), 6.48 (br, 1H), 5.10 (br, 1H), 4.91 (dd, J=13.9, 7.2 Hz, 1H), 4.54 (dt, J=11.9, 5.9 Hz, 1H), 2.69 (dd, J=6.7, 3.2 Hz, 2H), 1.26 (d, J=6.1 Hz, 6H), 1.14 (d, J=6.1 Hz, 6H).

$^{13}$C NMR (176 MHz, DMSO) δ 171.3, 170.8, 168.5, 166.3, 166.0, 164.2, 154.1, 147.2, 142.5, 137.0, 136.4, 130.2, 128.5, 128.3, 123.4, 122.8, 120.9, 120.7, 118.9, 118.8, 112.5, 112.2, 74.8, 51.6, 36.8, 22.3, 22.2.

HRMS (ESI) calculated for C45H44N7O14 (M+H) 906.2941, found 906.2940.

(S)-4-(4-(4-(4-amino-2-(4-(4-amino-2-hydroxy-3-isopropoxybenzamido)benzamido)-4-oxobutanamido)benzamido)-2-hydroxy-3-isopropoxybenzamido)benzoic acid

49

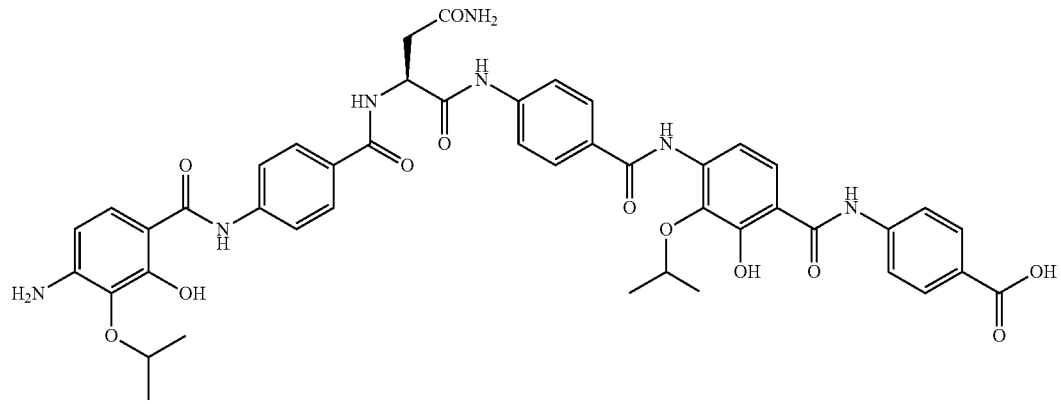

¹H NMR (700 MHz, DMSO) δ 12.82 (br, 1H), 12.63 (s, 1H), 12.28 (br, 1H), 10.61 (br, 1H), 10.45 (s, 1H), 10.11 (s, 1H), 9.39 (s, 1H), 8.65 (d, J=7.3 Hz, 1H), 7.95 (dd, J=12.0, 8.7 Hz, 4H), 7.89 (d, J=8.7 Hz, 2H), 7.83 (dd, J=24.7, 8.7 Hz, 4H), 7.78 (d, J=8.8 Hz, 2H), 7.68 (br, 2H), 7.59 (d, J=9.0 Hz, 1H), 7.40 (s, 1H), 6.99 (s, 1H), 6.26 (d, J=8.8 Hz, 1H), 5.63 (s, 2H), 4.92 (dd, J=14.0, 7.3 Hz, 1H), 4.55 (br, 1H), 4.46 (dt, J=12.3, 6.1 Hz, 1H), 2.70-2.67 (m, 2H), 1.26 (d, J=6.1 Hz, 6H), 1.22 (d, J=6.2 Hz, 6H).

¹³C NMR (176 MHz, DMSO) δ 171.3, 170.7, 169.4, 168.4, 166.9, 165.9, 164.2, 155.7, 148.1, 142.5, 142.0, 141.3, 137.0, 136.4, 130.2, 129.6, 128.8, 128.3, 128.3, 128.2, 123.6, 122.9, 120.6, 120.3, 118.9, 105.3, 103.4, 72.8, 51.6, 36.8, 22.3, 22.2.

HRMS (ESI) calculated for $C_{45}H_{46}N_7O_{12}$ (M+H) 876.3199, found 876.3200.

(S)-4-(4-(4-(4-amino-2-(4-(4-cyano-2-methylbenzamido)benzamido)-4-oxobutanamido)benzamido)-2-hydroxy-3-isopropoxybenzamido)benzoic acid Amine 26 (20 mg, 0.026 mmol) coupled with 4-Cyano-2-methylbenzoic acid using coupling conditions A followed by final deprotection.

Desired compound purified by preparative HPLC condition B, to obtain 4.5 mg of desired product as a white solid (0.005 mmol, y=21%).

¹H NMR (700 MHz, DMSO) δ 12.75 (br, 1H), 12.29 (br, 1H), 10.73 (s, 1H), 10.46 (s, 1H), 9.31 (br, 1H), 8.66 (d, J=7.3 Hz, 1H), 7.93 (m, 6H), 7.82 (m, 7H), 7.78 (br, 1H), 7.69 (d, J=7.9 Hz, 1H), 7.65-7.55 (br, 2H), 7.39 (s, 1H), 6.99 (s, 1H), 4.92 (dd, J=14.1, 7.2 Hz, 1H), 4.63 (br, 1H), 2.69 (d, J=8.1 Hz, 2H), 2.42 (s, 3H), 1.25 (d, J=6.1 Hz, 6H).

¹³C NMR (176 MHz, DMSO) δ 171.3, 170.7, 168.3, 166.9, 166.6, 165.7, 164.0, 142.4, 141.6, 141.1, 136.8, 136.5, 134.0, 130.2, 129.7, 129.0, 128.4, 128.2, 123.0, 120.3, 118.9, 118.9, 118.4, 112.3, 51.6, 36.8, 22.4, 18.8.

HRMS (ESI) calculated for $C_{44}H_{38}N_7O_{10}$ (M-H) 824.2686, found 824.2705.

50

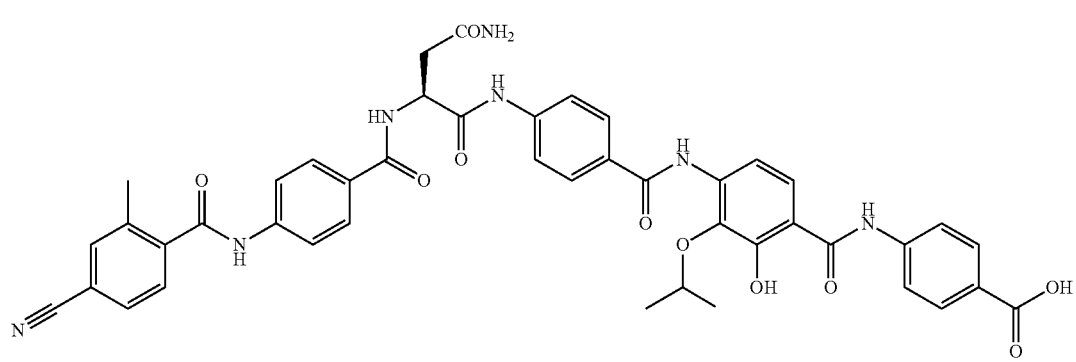

(S)-4-(4-(4-(4-amino-2-(4-(4-cyano-3-fluorobenzamido)benzamido)-4-oxobutanamido)benzamido)-2-hydroxy-3-isopropoxybenzamido)benzoic acid

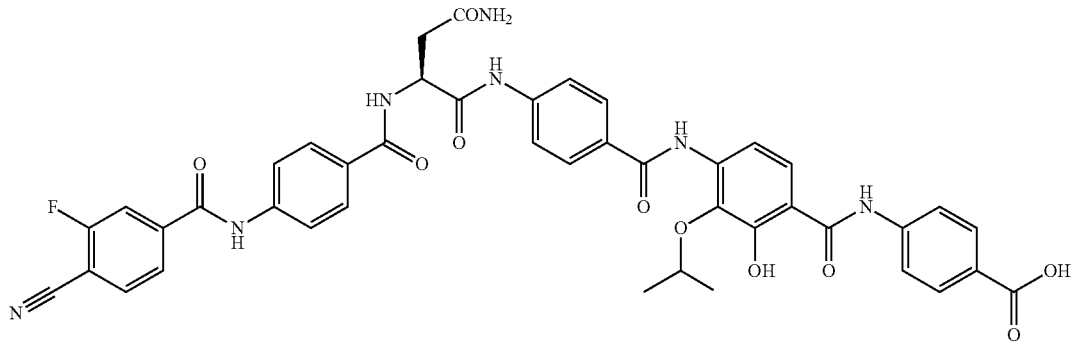

51

Amine 26 (20 mg, 0.026 mmol) coupled with 4-Cyano-3-fluorobenzoic acid using coupling conditions A followed by final deprotection.

Desired compound purified by preparative HPLC condition B, to obtain 5.7 mg of desired product as a white solid (0.007 mmol, y=27%).

$^1$H NMR (500 MHz, DMSO) δ 12.78 (br, 1H), 12.29 (br, 1H), 10.74 (s, 1H), 10.46 (s, 1H), 9.35 (br, 1H), 8.68 (d, J=7.3 Hz, 1H), 8.15 (dd, J=8.0, 6.7 Hz, 1H), 8.08 (dd, J=10.1, 1.5 Hz, 1H), 7.97 (m, 2H), 7.94 (d, J=8.7 Hz, 5H), 7.88 (d, J=8.9 Hz, 2H), 7.83 (dd, J=15.2, 8.8 Hz, 5H), 7.64 (br, 1H), 7.40 (s, 1H), 6.99 (s, 1H), 4.92 (dd, J=14.1, 7.1 Hz, 1H), 4.59 (br, 1H), 2.69 (d, J=7.2 Hz, 2H), 1.26 (d, J=6.1 Hz, 6H).

$^{13}$C NMR (176 MHz, DMSO) δ 171.2, 170.7, 168.4, 166.9, 165.7, 164.1, 161.5, 142.5, 141.5, 141.5, 141.3, 136.4, 134.3, 129.3, 128.4, 128.2, 124.7, 124.7, 122.9, 120.5, 119.6, 118.9, 115.8, 115.7, 113.6, 102.9, 102.8, 51.6, 36.8, 22.3.

$^{19}$F NMR (471 MHz, DMSO) δ -107.68 (dd, J=9.8, 6.8 Hz).

HRMS (ESI) calculated for C43H35FN7O10 (M−H) 828.2435, found 28.2447.

(S)-4-(4-(4-(4-amino-2-(4-(4-cyano-3-methylbenzamido)benzamido)-4-oxobutanamido)benzamido)-2-hydroxy-3-isopropoxybenzamido)benzoic acid Amine 26 (20 mg, 0.026 mmol) coupled with 4-Cyano-3-methylbenzoic acid using coupling conditions A followed by final deprotection.

Desired compound purified by preparative HPLC condition B, to obtain 5.2 mg of desired product as a white solid (0.006 mmol, y=24%).

$^1$H NMR (700 MHz, DMSO) δ 12.77 (br, 1H), 12.29 (br, 1H), 10.66 (s, 1H), 10.46 (s, 1H), 9.34 (br, 1H), 8.67 (d, J=7.3 Hz, 1H), 8.02 (s, 1H), 7.98-7.90 (m, 8H), 7.90-7.87 (m, 2H), 7.87-7.76 (m, 5H), 7.67-7.58 (br, 1H), 7.40 (s, 1H), 6.99 (s, 1H), 4.92 (dd, J=14.1, 7.2 Hz, 1H), 4.60 (br, 1H), 2.69 (d, J=7.5 Hz, 2H), 2.59 (s, 3H), 1.25 (d, J=6.1 Hz, 6H).

$^{13}$C NMR (176 MHz, DMSO) δ 171.3, 170.7, 168.3, 166.9, 165.8, 164.6, 164.1, 142.4, 141.9, 141.6, 138.6, 136.5, 132.8, 132.6, 130.2, 129.4, 129.2, 129.1, 128.3, 128.2, 125.8, 125.4, 122.9, 120.4, 119.5, 118.9, 117.5, 114.4, 51.6, 36.8, 22.3, 20.0.

HRMS (ESI) calculated for C44H38N7O10 (M−H) 824.2686, found 824.2694.

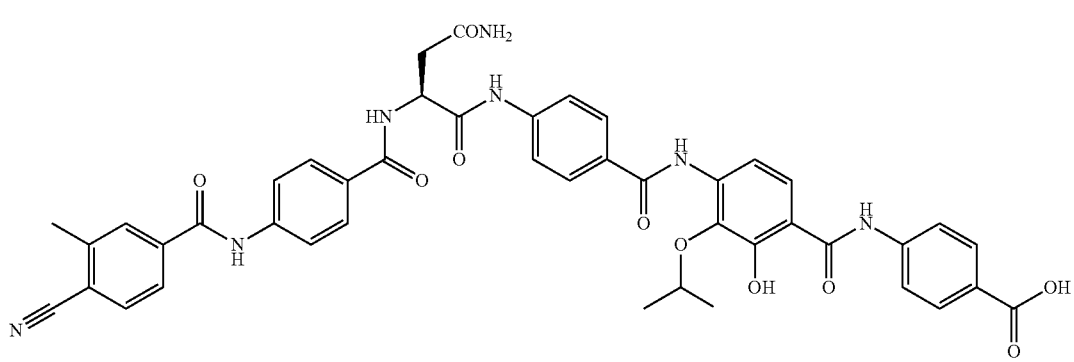

52

(S,E)-4-(4-(4-(4-amino-2-(4-(3-(4-hydroxyphenyl)-2-methylacrylamido)benzamido)-4-oxobutanamido)benzamido)-2-hydroxy-3-isopropoxybenzamido)benzoic acid

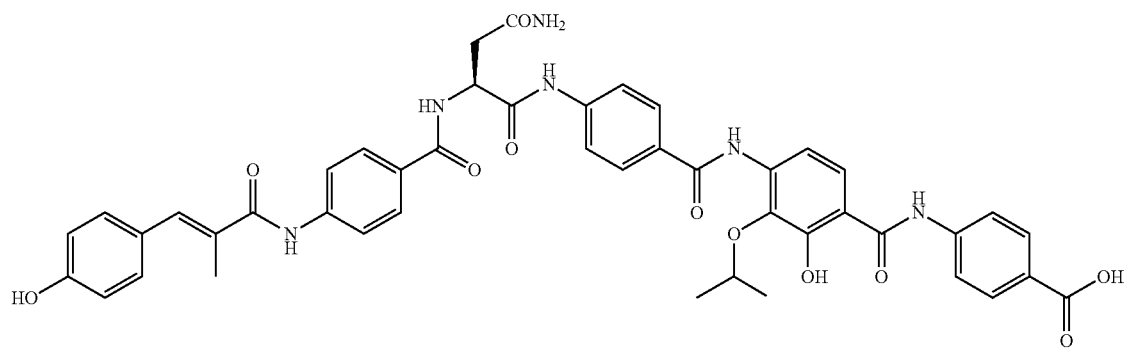

53

Amine 26 (40 mg, 0.052 mmol) coupled with carboxylic acid 30 coupling conditions A, intermediate purified on silica gel with a gradient 0-10% MeOH in DCM to give 50 mg (0.052 mmol, y=q.) of allyl protected cystobactamid derivative.

Followed final deprotection on 15 mg of intermediate (0.016 mmol), desired compound purified by preparative HPLC condition B, to obtain 1.0 mg of desired product (0.0012 mmol, y=7%).

Allyl Protected Intermediate:

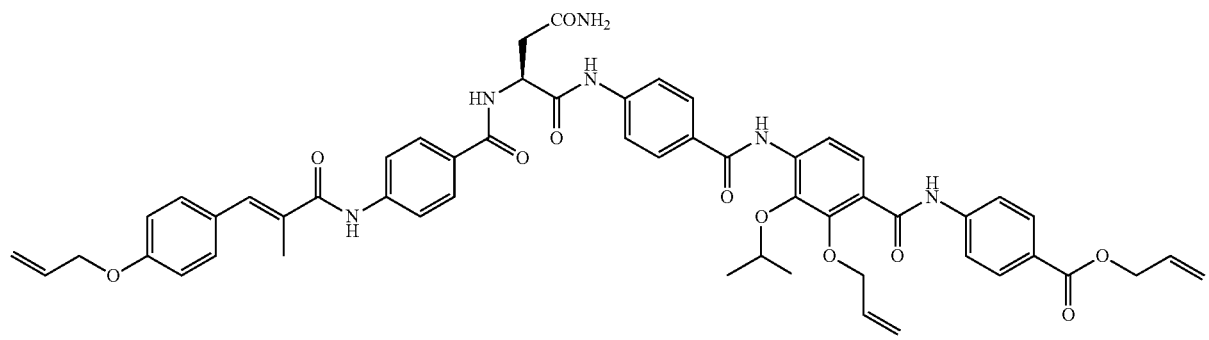 [SMILES: C=CCOC(=O)c1ccc(NC(=O)c2ccc(NC(=O)c3ccc(NC(=O)[C@H](CC(N)=O)NC(=O)c4ccc(NC(=O)/C(C)=C/c5ccc(OCC=C)cc5)cc4)cc3)c(OC(C)C)c2OCC=C)cc1]

$^{1}$H NMR (700 MHz, DMSO) δ 10.58 (s, 1H), 10.44 (s, 1H), 10.12 (s, 1H), 9.52 (s, 1H), 8.62 (d, J=7.3 Hz, 1H), 7.98 (dd, J=8.8, 7.0 Hz, 4H), 7.90-7.85 (m, 4H), 7.85-7.79 (m, 5H), 7.45 (d, J=8.8 Hz, 2H), 7.40 (d, J=8.4 Hz, 2H), 7.30 (s, 1H), 7.06-7.01 (m, 2H), 6.99 (s, 1H), 6.09-5.98 (m, 3H), 5.44-5.35 (m, 3H), 5.28 (dq, J=10.5, 1.4 Hz, 2H), 5.20 (ddd, J=10.5, 2.9, 1.3 Hz, 1H), 4.91 (dd, J=14.0, 7.2 Hz, 1H), 4.79 (dd, J=4.0, 1.4 Hz, 2H), 4.63-4.60 (m, 4H), 4.49 (dt, J=12.3, 6.2 Hz, 1H), 3.85-3.73 (m, 1H), 2.69 (d, J=7.8 Hz, 2H), 2.12 (d, J=1.3 Hz, 3H), 1.26 (d, J=6.1 Hz, 6H).

$^{13}$C NMR (176 MHz, DMSO) δ 171.3, 170.8, 168.7, 165.9, 165.0, 164.7, 164.3, 158.0, 149.5, 143.5, 142.6, 142.4, 142.3, 135.7, 133.7, 133.6, 133.3, 132.8, 131.1, 130.7, 130.3, 128.4, 128.3, 128.2, 127.1, 124.2, 123.6, 119.1, 119.0, 118.8, 117.8, 117.8, 117.6, 114.7, 107.0, 97.2, 76.3, 74.3, 68.2, 64.8, 51.6, 36.8, 22.3, 14.5.

Final Compound 53:

$^{1}$H NMR (700 MHz, DMSO) δ 12.79 (br, 1H), 12.29 (br, 1H), 10.60 (br, 1H), 10.45 (s, 1H), 10.08 (s, 1H), 9.76 (s, 1H), 9.38 (br, 1H), 8.61 (d, J=7.2 Hz, 1H), 7.98-7.90 (m, 4H), 7.90-7.76 (m, 10H), 7.39 (s, 1H), 7.35 (d, J=8.7 Hz, 2H), 7.26 (s, 1H), 6.99 (s, 1H), 6.84 (d, J=8.6 Hz, 2H), 4.91 (dd, J=14.1, 7.2 Hz, 1H), 4.56 (br, 1H), 2.68 (d, J=7.5 Hz, 2H), 2.11 (d, J=1.2 Hz, 3H), 1.26 (d, J=6.1 Hz, 6H).

$^{13}$C NMR (176 MHz, DMSO) δ 171.3, 170.8, 168.8, 166.9, 165.9, 164.1, 162.3, 162.2, 157.5, 142.4, 133.8, 131.3, 130.2, 129.5, 128.2, 127.3, 126.6, 122.8, 120.6, 119.0, 118.9, 115.4, 51.6, 36.8, 22.3, 14.5.

HRMS (ESI) calculated for $C_{45}H_{41}N_6O_{11}$ (M-H) 841,2839, found 841,2844.

4-(4-(4-(((2S)-4-amino-4-oxo-2-(4-(2-phenoxypropanamido)benzamido)butanamido)benzamido)-2-hydroxy-3-isopropoxybenzamido)benzoic acid

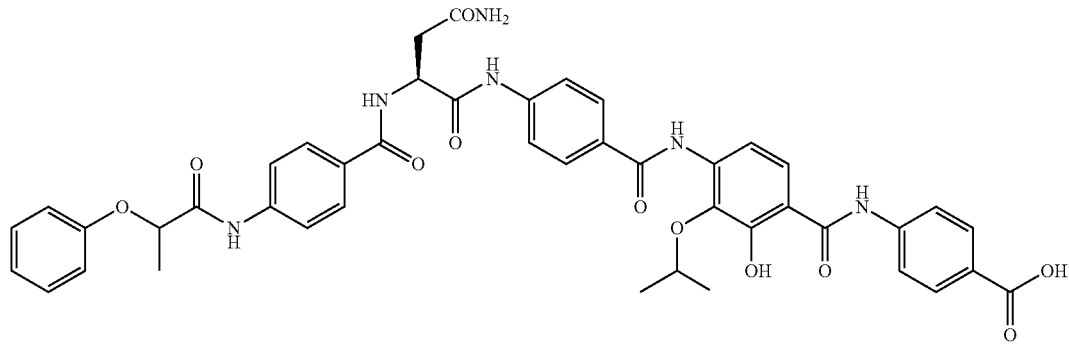

54

Amine 26 (40 mg, 0.052 mmol) coupled with 2-phenoxypropanoic acid using coupling conditions A, intermediate purified on silica gel with a gradient 0-10% MeOH in DCM to give 30 mg (0.033 mmol, y=63%) of allyl protected cystobactamid derivative.

Followed final deprotection on 15 mg of intermediate (0.016 mmol), desired compound purified by preparative HPLC condition B, to obtain 7.5 mg of desired product (0.009 mmol, y=56%).

Allyl Protected Intermediate:

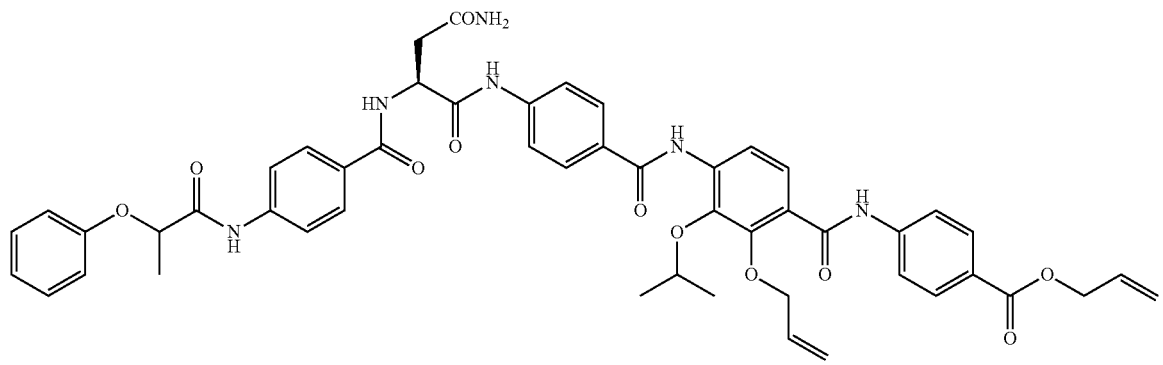 [SMILES: C=CCOC(=O)c1ccc(NC(=O)c2ccc(NC(=O)c3ccc(NC(=O)[C@H](CC(N)=O)NC(=O)c4ccc(NC(=O)C(C)Oc5ccccc5)cc4)cc3)c(OC(C)C)c2OCC=C)cc1]

55

$^1$H NMR (500 MHz, Acetone) δ 10.25 (s, 1H), 10.02 (s, 1H), 9.52 (s, 1H), 8.99 (s, 1H), 8.40 (dd, J=8.8, 2.3 Hz, 1H), 8.37 (d, J=7.5 Hz, 1H), 8.08-8.03 (m, 2H), 8.00-7.96 (m, 2H), 7.94-7.88 (m, 4H), 7.88-7.82 (m, 5H), 7.34-7.29 (m, 2H), 7.15 (s, 1H), 7.05-7.01 (m, 2H), 6.99 (tt, J=7.4, 1.0 Hz, 1H), 6.54 (s, 1H), 6.27-6.17 (m, 1H), 6.14-6.04 (m, 1H), 5.50 (m, 2H), 5.32 (m, 2H), 5.10-5.05 (m, 1H), 4.89 (q, J=6.7 Hz, 1H), 4.83-4.76 (m, 5H), 2.93 (qd, J=15.9, 6.0 Hz, 2H), 1.61 (d, J=6.7 Hz, 3H), 1.39 (d, J=6.2 Hz, 6H).

$^{13}$C NMR (176 MHz, Acetone) δ 173.7, 171.5, 171.0, 167.2, 166.0, 165.0, 163.9, 158.3, 150.7, 144.4, 143.6, 142.6, 140.8, 138.6, 138.3, 134.1, 133.9, 131.5, 130.6, 130.4, 130.2, 130.1, 129.2, 126.9, 126.2, 123.8, 122.7, 122.0, 120.2, 120.1, 120.0, 119.6, 118.1, 116.7, 116.6, 116.6, 115.9, 77.5, 75.9, 75.6, 65.9, 52.5, 37.1, 22.9, 18.8.

Final Compound 54:

$^1$H NMR (700 MHz, DMSO) δ 12.76 (br, 1H), 12.29 (br, 1H), 10.71 (br, 1H), 10.44 (s, 1H), 10.36 (s, 1H), 9.33 (br, 1H), 8.62 (d, J=7.3 Hz, 1H), 7.94 (dd, J=15.5, 8.6 Hz, 4H), 7.85 (dd, J=16.2, 8.7 Hz, 4H), 7.80 (d, J=8.7 Hz, 3H), 7.74 (d, J=8.8 Hz, 2H), 7.62 (br, 1H), 7.38 (s, 1H), 7.30 (dd, J=8.6, 7.4 Hz, 2H), 6.96 (dd, J=13.2, 7.6 Hz, 4H), 4.93-4.87 (m, 2H), 4.60 (br, 1H), 2.69-2.65 (m, 2H), 1.56 (d, J=6.6 Hz, 3H), 1.25 (d, J=6.1 Hz, 6H).

$^{13}$C NMR (176 MHz, DMSO) δ 170.9, 170.3, 170.1, 168.0, 166.6, 165.3, 163.7, 156.8, 142.1, 140.9, 136.1, 129.9, 129.2, 128.4, 128.0, 127.8, 122.6, 120.9, 120.0, 118.5, 118.4, 114.7, 73.3, 51.2, 36.4, 22.0, 18.2.

HRMS (ESI) calculated for C44H41N6O11 (M−H) 829.2839, found 829.2830.

(S)-4-(4-(4-(4-amino-2-(4-(isonicotinamido)benzamido)-4-oxobutanamido)benzamido)-2-hydroxy-3-isopropoxybenzamido)benzoic acid

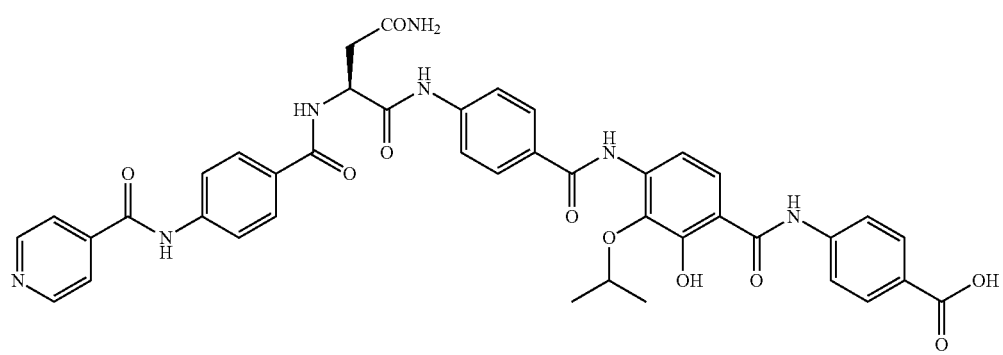

55

Amine 26 (25 mg, 0.032 mmol) coupled with isonicotinic acid using coupling conditions A followed by final deprotection.

Desired compound purified by preparative HPLC condition B, to obtain 5.5 mg of desired product as a white solid (0.007 mmol, y=22%).

$^1$H NMR (700 MHz, DMSO) δ 15.70 (br, 1H), 12.48 (br, 1H), 10.73 (s, 1H), 10.46 (s, 1H), 8.88 (s, 1H), 8.80 (d, J=5.8 Hz, 2H), 8.73 (d, J=7.0 Hz, 1H), 7.94 (d, J=8.7 Hz, 2H), 7.91-7.86 (m, 4H), 7.86-7.77 (m, 6H), 7.70 (br, 2H), 7.45 (d, J=8.7 Hz, 1H), 7.42 (s, 1H), 7.10 (d, J=8.7 Hz, 1H), 6.98 (s, 1H), 5.01 (dt, J=12.2, 6.0 Hz, 1H), 4.92 (q, J=7.1 Hz, 1H), 2.69 (d, J=7.0 Hz, 2H), 1.20 (d, J=6.1 Hz, 6H).

$^{13}$C NMR (176 MHz, DMSO) δ 171.3, 170.7, 167.1, 165.7, 165.3, 164.3, 163.2, 150.3, 142.0, 141.7, 141.4, 137.5, 134.2, 130.0, 129.5, 129.3, 128.3, 127.6, 124.2, 123.7, 121.6, 119.5, 119.0, 117.9, 115.7, 100.9, 70.4, 51.7, 36.8, 22.7.

HRMS (ESI) calculated for C41H38N7O10 (M–H) 788.2675, found 788.2659.

(S)-4-(4-(4-(4-amino-2-(4-(4-(methylsulfonyl)benzamido)benzamido)-4-oxobutanamido)benzamido)-2-hydroxy-3-isopropoxybenzamido)benzoic acid Amine 26 (25 mg, 0.032 mmol) coupled with 4-(methylsulfonyl)benzoic acid using coupling conditions A followed by final deprotection.

Desired compound purified by preparative HPLC condition B, to obtain 8.6 mg of desired product as a white solid (0.010 mmol, y=31%).

$^1$H NMR (700 MHz, DMSO) δ 15.35 (s, 1H), 10.76 (s, 1H), 10.57 (s, 1H), 8.90 (s, 1H), 8.87 (s, 1H), 8.21 (d, J=8.1 Hz, 2H), 8.09 (d, J=8.1 Hz, 2H), 7.96 (d, J=8.5 Hz, 2H), 7.90 (d, J=8.4 Hz, 2H), 7.83 (s, 4H), 7.79 (d, J=8.0 Hz, 2H), 7.58 (d, J=8.0 Hz, 2H), 7.51 (s, 1H), 7.45 (d, J=8.7 Hz, 1H), 7.08 (d, J=8.7 Hz, 1H), 6.98 (s, 1H), 5.02 (dt, J=12.0, 5.9 Hz, 1H), 4.92 (dd, J=13.4, 7.2 Hz, 1H), 3.30 (s, 3H), 2.73 (dd, J=14.8, 8.7 Hz, 1H), 2.68 (dd, J=14.8, 5.1 Hz, 1H), 1.20 (d, J=5.7 Hz, 6H).

$^{13}$C NMR (176 MHz, DMSO) δ 171.3, 170.7, 166.9, 165.7, 165.3, 164.6, 163.1, 143.3, 142.0, 141.8, 141.6, 139.2, 137.5, 134.0, 133.4, 129.7, 129.5, 129.2, 128.8, 128.4, 128.3, 127.6, 127.1, 127.0, 126.8, 123.7, 119.5, 119.0, 117.6, 116.0, 100.6, 70.3, 51.9, 43.3, 36.9, 22.7.

HRMS (ESI) calculated for C43H39N6O12S (M–H) 863.2352, found 863.2364.

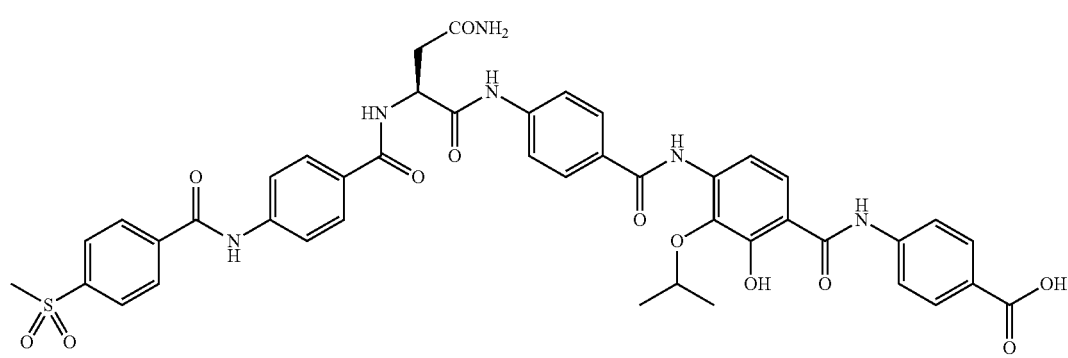

56

(S)-4-(4-(4-(4-amino-4-oxo-2-(4-(1-oxo-1,3-dihydroisobenzofuran-5-carboxamido)benzamido)butanamido)benzamido)-2-hydroxy-3-isopropoxybenzamido)benzoic acid

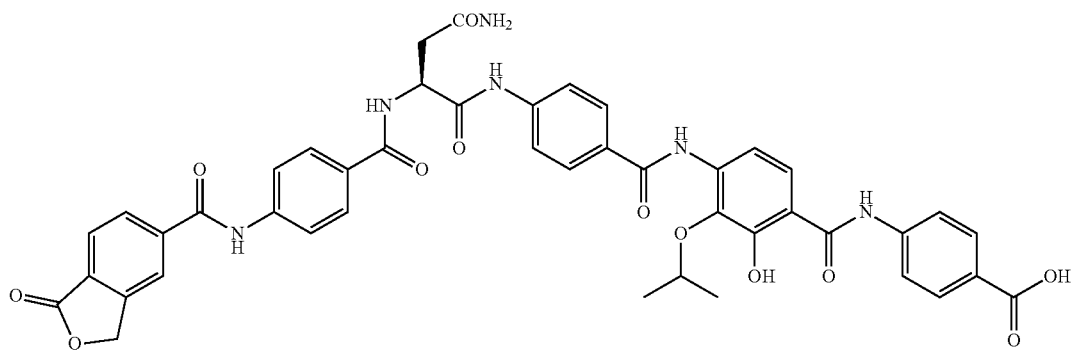

57

Amine 26 (25 mg, 0.032 mmol) coupled with 1-oxo-1,3-dihydroisobenzofuran-5-carboxylic acid using coupling conditions A followed by final deprotection.

Desired compound purified by preparative HPLC condition B, to obtain 4.9 mg of desired product as a white solid (0.0058 mmol, y=18%).

$^{1}$H NMR (700 MHz, DMSO) δ 15.33 (s, 1H), 10.81 (s, 1H), 10.56 (s, 1H), 8.87 (s, 2H), 8.23 (s, 1H), 8.14 (d, J=8.1 Hz, 1H), 8.01 (d, J=8.0 Hz, 1H), 7.95 (d, J=8.8 Hz, 2H), 7.91 (d, J=8.7 Hz, 2H), 7.83 (q, J=9.1 Hz, 4H), 7.77 (d, J=8.4 Hz, 2H), 7.56 (d, J=8.5 Hz, 2H), 7.51 (s, 1H), 7.44 (d, J=8.7 Hz, 1H), 7.08 (d, J=8.7 Hz, 1H), 6.98 (s, 1H), 5.51 (s, 2H), 5.05-5.00 (m, 1H), 4.92 (dd, J=13.9, 7.6 Hz, 1H), 2.73 (dd, J=15.1, 8.6 Hz, 1H), 2.68 (dd, J=15.1, 5.5 Hz, 1H), 1.19 (d, J=6.1 Hz, 6H).

$^{13}$C NMR (176 MHz, DMSO) δ 171.3, 170.7, 170.0, 166.8, 165.7, 165.3, 165.0, 163.1, 147.4, 142.0, 141.6, 140.0, 137.5, 134.0, 133.4, 131.2, 129.7, 129.5, 129.1, 128.5, 128.3, 128.1, 127.5, 127.4, 127.1, 125.0, 124.2, 123.7, 122.5, 120.0, 119.5, 119.0, 117.5, 116.0, 100.6, 70.3, 70.1, 51.9, 36.9, 22.7.

HRMS (ESI) calculated for C44H37N6O12 (M–H) 841.2475, found 841.2478.

(S,E)-4-(4-(4-(4-amino-2-(4-(3-(4-cyanophenyl)-2-methylacrylamido)benzamido)-4-oxobutanamido)benzamido)-2-hydroxy-3-isopropoxybenzamido)benzoic acid

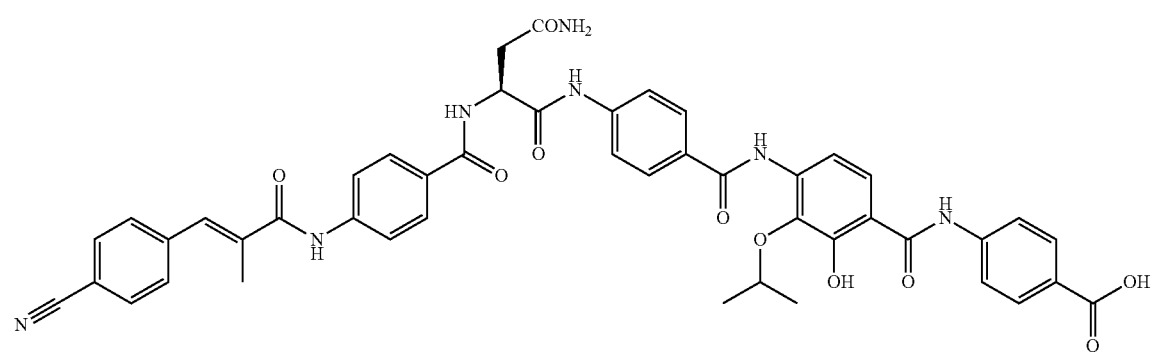

58

Amine 26 (25 mg, 0.032 mmol) coupled with carboxylic acid 35 using coupling conditions A followed by final deprotection.

Desired compound purified by preparative HPLC condition B, to obtain 6.4 mg of desired product as a white solid (0.0075 mmol, y=24%).

$^1$H NMR (700 MHz, DMSO) δ 12.80 (br, 1H), 12.29 (br, 1H), 10.65 (br, 1H), 10.47 (s, 1H), 10.26 (s, 1H), 9.37 (s, 1H), 8.64 (d, J=7.2 Hz, 1H), 7.95 (dd, J=11.5, 8.8 Hz, 4H), 7.91 (dd, J=10.4, 8.6 Hz, 4H), 7.88-7.80 (m, 7H), 7.67 (d, J=8.3 Hz, 3H), 7.40 (s, 1H), 7.37 (s, 1H), 6.99 (s, 1H), 4.92 (q, J=7.1 Hz, 1H), 4.59-4.53 (m, 1H), 2.69 (d, J=7.0 Hz, 2H), 1.26 (d, J=6.1 Hz, 6H).

$^{13}$C NMR (176 MHz, DMSO) δ 171.3, 170.8, 168.4, 168.1, 166.9, 165.8, 164.1, 142.5, 142.1, 142.0, 140.6, 136.9, 136.4, 135.8, 132.4, 132.0, 131.7, 130.2, 130.1, 128.6, 128.3, 126.9, 126.1, 122.9, 120.6, 119.2, 118.9, 118.7, 112.5, 110.3, 74.7, 51.6, 36.8, 22.3, 14.6.

HRMS (ESI) calculated for C46H41N7NaO10 (M+Na$^+$) 874.2807, found 874.2814.

(S)-4-(4-(4-(4-amino-2-(4-(6-cyanonicotinamido)benzamido)-4-oxobutanamido)benzamido)-2-hydroxy-3-isopropoxybenzamido)benzoic acid

95

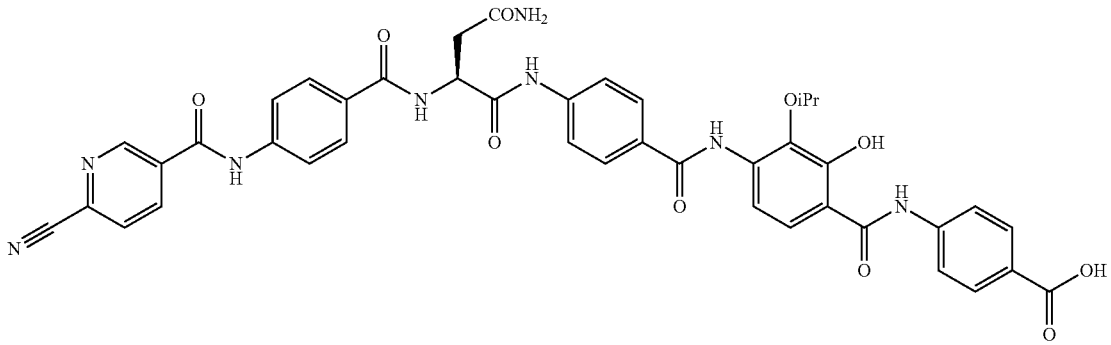

Amine 26 (25 mg, 0.033 mmol) coupled with 6-cyanonicotinic acid using coupling conditions A followed by final deprotection.

Desired compound purified by preparative HPLC condition B, to obtain 4.6 mg of desired product (0.0057 mmol, y=17%).

$^1$H NMR (500 MHz, DMSO) δ 12.76 (br, 1H), 12.31 (br, 1H), 10.87 (s, 1H), 10.47 (s, 1H), 9.34 (br, 1H), 9.26-9.22 (m, 1H), 8.69 (d, J=7.2 Hz, 1H), 8.54 (dd, J=8.1, 2.2 Hz, 1H), 8.26 (d, J=8.1 Hz, 1H), 7.95 (dt, J=6.7, 3.2 Hz, 6H), 7.91-7.74 (m, 7H), 7.63 (br, 1H), 7.40 (s, 1H), 6.99 (s, 1H), 4.92 (dd, J=14.1, 7.1 Hz, 1H), 4.60 (s, 1H), 2.69 (d, J=7.0 Hz, 2H), 1.25 (d, J=6.1 Hz, 6H).

$^{13}$C NMR (176 MHz, DMSO) δ 171.2, 170.7, 168.3, 166.9, 165.7, 164.1, 163.0, 150.2, 142.4, 141.3, 137.3, 136.5, 134.5, 133.4, 130.2, 129.4, 128.8, 128.4, 128.2, 122.9, 120.4, 119.5, 118.9, 117.1, 74.4, 51.6, 36.8, 22.3.

HRMS (ESI) calculated for C42H35N8O10 (M–H) 811.2482, found 811.2480.

(S)-4-(4-(4-(4-amino-2-(4-(5-cyanopicolinamido)benzamido)-4-oxobutanamido)benzamido)-2-hydroxy-3-isopropoxybenzamido)benzoic acid

96

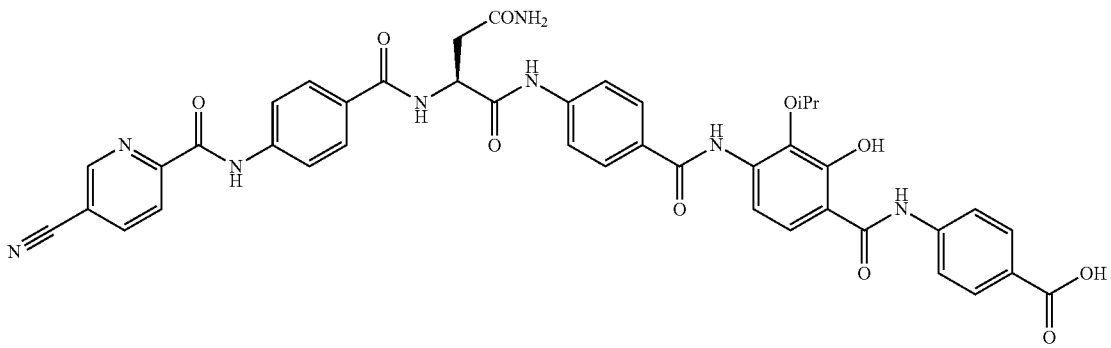

Amine 26 (25 mg, 0.033 mmol) coupled with 5-cyanopicolinic acid using coupling conditions A followed by final deprotection.

Desired compound purified by preparative HPLC condition B, to obtain 2.5 mg of desired product (0.0031 mmol, y=9%).

$^1$H NMR (500 MHz, DMSO) δ 12.76 (br, 1H), 12.30 (br, 1H), 11.03 (s, 1H), 10.46 (s, 1H), 9.33 (br, 1H), 9.22 (d, J=1.3 Hz, 1H), 8.68 (d, J=7.3 Hz, 1H), 8.60 (dd, J=8.2, 2.0 Hz, 1H), 8.31 (d, J=8.1 Hz, 1H), 8.05 (d, J=8.8 Hz, 2H), 8.00-7.89 (m, 6H), 7.83 (dd, J=13.2, 8.8 Hz, 5H), 7.62 (s, 1H), 7.40 (s, 1H), 6.99 (s, 1H), 4.92 (dd, J=14.1, 7.2 Hz, 1H), 4.60 (br, 1H), 2.69 (d, J=7.3 Hz, 2H), 1.25 (d, J=6.1 Hz, 6H).

$^{13}$C NMR (176 MHz, DMSO) δ 171.3, 170.7, 168.3, 166.9, 165.8, 164.0, 161.6, 152.3, 151.5, 142.4, 142.3, 140.9, 136.5, 130.2, 129.4, 128.3, 128.2, 122.9, 122.5, 120.3, 119.7, 118.9, 116.6, 111.7, 51.6, 36.8, 22.4.

HRMS (ESI) calculated for C42H35N8O10 (M−H) 811.2482, found 811.2461.

(S)-4-(4-(4-(4-amino-2-(4-(3-chloro-4-cyanobenzamido)benzamido)-4-oxobutanamido)benzamido)-2-hydroxy-3-isopropoxybenzamido)benzoic acid

97

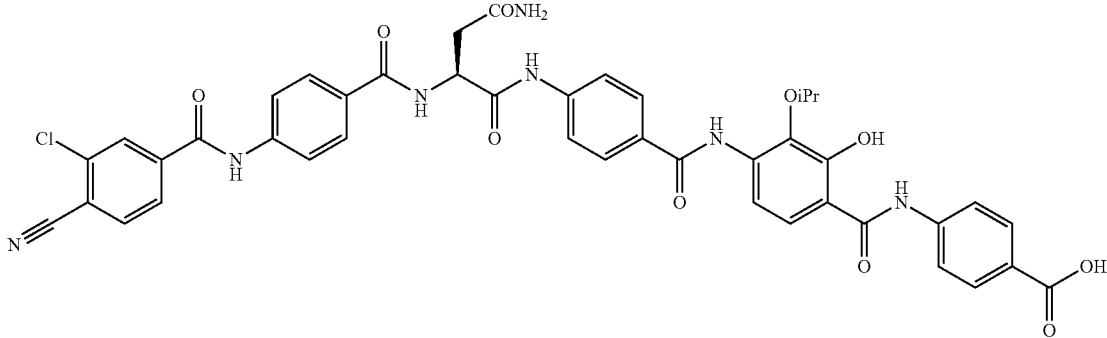

Amine 26 (25 mg, 0.033 mmol) coupled with 3-chloro-4-cyanobenzoic acid using coupling conditions A followed by final deprotection.

Desired compound purified by preparative HPLC condition B, to obtain 4.5 mg of desired product (0.0053 mmol, y=16%).

$^1$H NMR (500 MHz, DMSO) δ 12.78 (br, 1H), 12.30 (br, 1H), 10.76 (s, 1H), 10.46 (s, 1H), 9.36 (br, 1H), 8.68 (d, J=7.3 Hz, 1H), 8.29 (d, J=1.6 Hz, 1H), 8.19 (d, J=8.1 Hz, 1H), 8.07 (dd, J=8.1, 1.6 Hz, 1H), 7.98-7.91 (m, 5H), 7.91-7.78 (m, 6H), 7.65 (br, 1H), 7.40 (s, 1H), 6.99 (s, 1H), 4.92 (q, J=7.1 Hz, 1H), 4.57 (br, 1H), 2.69 (d, J=7.1 Hz, 2H), 1.26 (d, J=6.1 Hz, 6H).

$^{13}$C NMR (176 MHz, DMSO) δ 171.2, 170.7, 168.4, 166.9, 165.7, 164.1, 163.1, 142.5, 141.3, 140.3, 136.4, 135.6, 134.9, 130.2, 129.3, 128.9, 128.4, 128.2, 127.3, 122.9, 120.5, 119.5, 118.9, 115.6, 114.5, 51.6, 36.8, 22.3.

HRMS (ESI) calculated for C43H37ClN7O10 (M+H) 846.2285, found 846.2297.

(S)-4-(4-(4-(4-amino-2-(4-(5-cyanothiophene-2-carboxamido)benzamido)-4-oxobutanamido)benzamido)-2-hydroxy-3-isopropoxybenzamido)benzoic acid

98

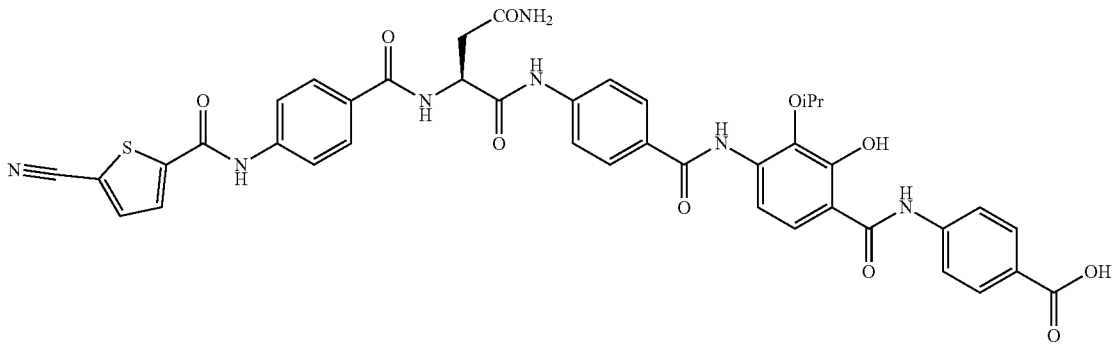

Amine 26 (25 mg, 0.033 mmol) coupled with 5-cyano-thiophene-2-carboxylic acid using coupling conditions A followed by final deprotection.

Desired compound purified by preparative HPLC condition B, to obtain 6.6 mg of desired product (0.0053 mmol, y=24%).

$^1$H NMR (500 MHz, DMSO) δ 12.71 (br, 1H), 12.35 (br, 1H), 10.79 (s, 1H), 10.46 (s, 1H), 9.34 (br, 1H), 8.70 (d, J=7.3 Hz, 1H), 8.15 (d, J=4.1 Hz, 1H), 8.08 (d, J=4.1 Hz, 1H), 7.98-7.92 (m, 6H), 7.87-7.77 (m, 7H), 7.64 (br, 1H), 7.40 (s, 1H), 7.00 (s, 1H), 4.93 (dd, J=14.1, 7.1 Hz, 1H), 4.61 (br, 1H), 2.70 (d, J=7.3 Hz, 2H), 1.26 (d, J=6.2 Hz, 6H).

$^{13}$C NMR (176 MHz, DMSO) δ 171.2, 170.7, 168.3, 166.9, 165.7, 164.1, 158.5, 146.8, 142.4, 140.8, 139.7, 136.7, 136.5, 130.2, 129.5, 129.2, 128.4, 128.2, 125.8, 122.9, 120.4, 119.7, 118.9, 113.8, 112.8, 112.5, 74.3, 51.6, 36.8, 22.3.

HRMS (ESI) calculated for C41H36N7O10S (M+H) 818.2239, found 818.2237.

(S)-4-(4-(4-(4-amino-2-(4-(4-cyano-3-methoxybenzamido)benzamido)-4-oxobutanamido)benzamido)-2-hydroxy-3-isopropoxybenzamido)benzoic acid

99

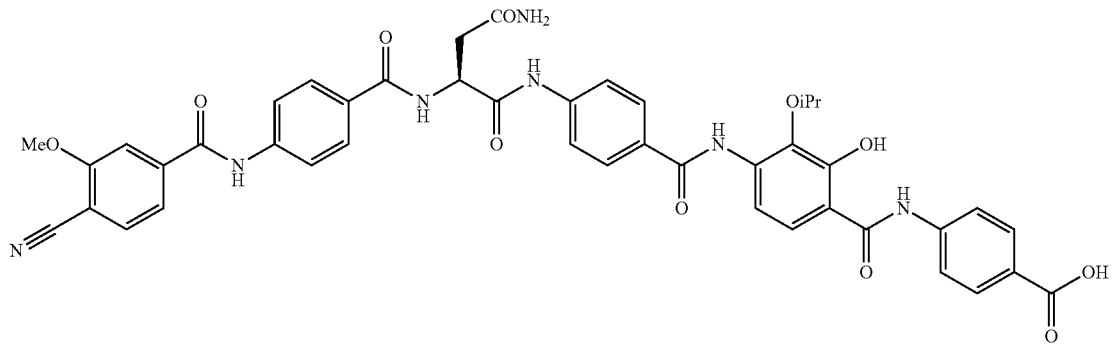

Amine 26 (25 mg, 0.033 mmol) coupled with 4-cyano-3-methoxybenzoic acid using coupling conditions A followed by final deprotection.

Desired compound purified by preparative HPLC condition B, to obtain 4.8 mg of desired product (0.0057 mmol, y=17%).

$^1$H NMR (500 MHz, DMSO) δ 12.80 (br, 1H), 12.29 (br, 1H), 10.66 (s, 1H), 10.47 (s, 1H), 9.38 (s, 1H), 8.68 (d, J=7.3 Hz, 1H), 7.98-7.92 (m, 7H), 7.91-7.79 (m, 7H), 7.72 (d, J=1.3 Hz, 1H), 7.69-7.63 (m, 2H), 7.40 (s, 1H), 7.00 (s, 1H), 4.92 (q, J=7.1 Hz, 1H), 4.61-4.53 (m, 1H), 4.03 (s, 3H), 2.69 (d, J=7.1 Hz, 2H), 1.25 (t, J=8.4 Hz, 6H).

$^{13}$C NMR (176 MHz, DMSO) δ 171.2, 170.7, 168.4, 166.9, 165.7, 164.4, 164.1, 160.8, 142.5, 142.1, 141.5, 140.7, 136.9, 136.4, 133.9, 130.2, 129.2, 128.3, 128.3, 126.1, 122.9, 120.6, 120.1, 119.6, 118.9, 115.9, 112.6, 111.4, 103.0, 74.6, 56.6, 51.6, 36.8, 22.3.

HRMS (ESI) calculated for C44H40N7O11 (M+H) 842.2780, found 842.2784.

(S)-4-(4-(4-(4-amino-2-(4-(3-(4-cyanophenyl)propanamido)benzamido)-4-oxobutanamido)benzamido)-2-hydroxy-3-isopropoxybenzamido)benzoic acid

100

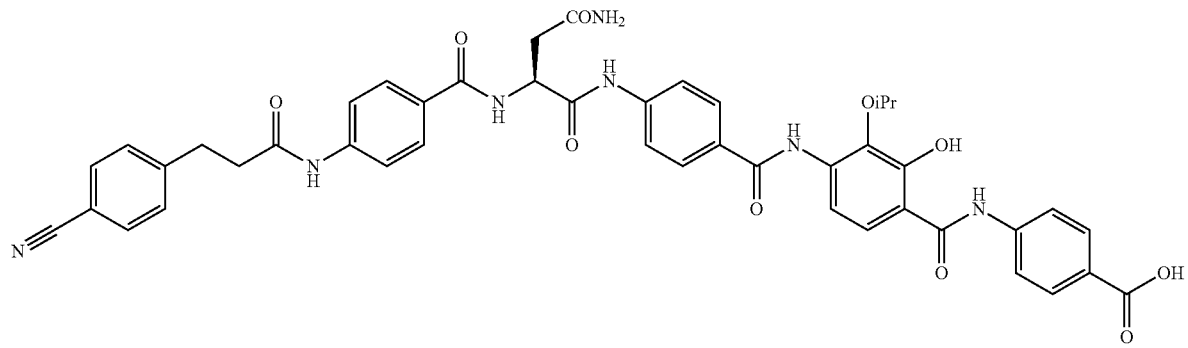

Amine 26 (25 mg, 0.033 mmol) coupled with 3-(4-cyanophenyl)propanoic acid using coupling conditions A followed by final deprotection.

Desired compound purified by preparative HPLC condition B, to obtain 4.7 mg of desired product (0.0057 mmol, y=17%).

¹H NMR (500 MHz, DMSO) δ 12.80 (br, 1H), 12.29 (br, 1H), 10.63 (br, 1H), 10.44 (s, 1H), 10.19 (s, 1H), 9.39 (s, 1H), 8.60 (d, J=7.3 Hz, 1H), 8.00-7.91 (m, 4H), 7.89-7.78 (m, 7H), 7.78-7.74 (m, 2H), 7.72-7.64 (m, 3H), 7.48 (d, J=8.4 Hz, 2H), 7.38 (s, 1H), 6.98 (s, 1H), 4.90 (dd, J=14.1, 7.2 Hz, 1H), 4.55 (dt, J=12.1, 6.0 Hz, 1H), 3.01 (t, J=7.6 Hz, 2H), 2.71 (t, J=7.6 Hz, 2H), 2.67 (d, J=7.6 Hz, 2H), 1.26 (d, J=6.1 Hz, 6H).

¹³C NMR (176 MHz, DMSO) δ 171.3, 170.7, 170.4, 168.4, 166.9, 165.8, 164.2, 147.3, 142.5, 142.0, 141.9, 137.0, 136.3, 132.2, 130.2, 129.4, 128.4, 128.3, 128.2, 126.2, 122.8, 120.6, 119.0, 118.9, 118.1, 112.5, 112.2, 108.9, 74.8, 51.6, 37.1, 36.8, 30.6, 22.3.

HRMS (ESI) calculated for C45H42N7O10 (M+H) 840.2988, found 840.2971.

(S)-4-(4-(4-(4-amino-2-(4-(2-(4-cyanophenyl)acetamido)benzamido)-4-oxobutanamido)benzamido)-2-hydroxy-3-isopropoxybenzamido)benzoic acid

101

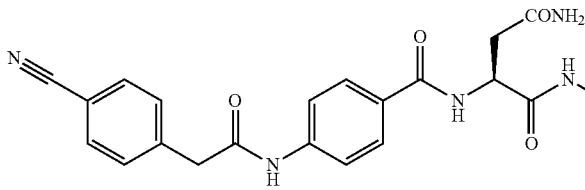
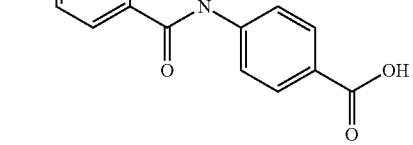

Amine 26 (25 mg, 0.033 mmol) coupled with 2-(4-cyanophenyl)acetic acid using coupling conditions A followed by final deprotection.

Desired compound purified by preparative HPLC condition B, to obtain 6.4 mg of desired product (0.0078 mmol, y=24%).

¹H NMR (500 MHz, DMSO) δ 12.74 (br, 1H), 12.30 (br, 1H), 10.49 (s, 1H), 10.44 (s, 1H), 9.35 (br, 1H), 8.62 (d, J=7.3 Hz, 1H), 7.94 (dd, J=11.1, 8.9 Hz, 4H), 7.90-7.74 (m, 9H), 7.68 (d, J=8.8 Hz, 2H), 7.65 (br, 1H), 7.54 (d, J=8.2 Hz, 2H), 7.39 (s, 1H), 6.98 (s, 1H), 4.90 (q, J=7.1 Hz, 1H), 4.58 (s, 1H), 3.82 (s, 2H), 2.67 (d, J=7.0 Hz, 2H), 1.25 (d, J=6.1 Hz, 6H).

¹³C NMR (176 MHz, DMSO) δ 171.3, 170.7, 168.5, 168.4, 166.9, 165.7, 164.1, 142.4, 141.8, 141.5, 136.4, 132.2, 132.1, 131.9, 130.5, 130.2, 128.4, 128.2, 122.9, 122.5, 120.5, 118.9, 118.2, 109.5, 74.4, 51.6, 43.0, 36.8, 22.3.

HRMS (ESI) calculated for C44H38N7O10 (M−H) 824.2686, found 824.2689.

(S)-4-(4-(4-(4-amino-2-(4-(4-cyano-1-methyl-1H-pyrrole-2-carboxamido)benzamido)-4-oxobutanamido)benzamido)-2-hydroxy-3-isopropoxybenzamido)benzoic acid

102

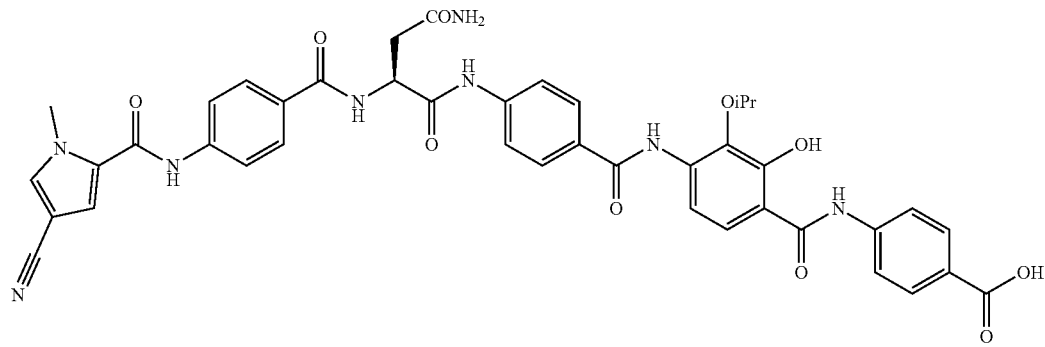

Amine 26 (20 mg, 0.033 mmol) coupled with 4-cyano-1-methyl-1H-pyrrole-2-carboxylic acid using coupling conditions C, intermediate purified on silica gel with a gradient 0-10% MeOH in DCM.

Final deprotection afforded the desired compound, which was purified by preparative HPLC condition B, to obtain 1.4 mg of desired product (0.002 mmol, y=8%).

$^1$H NMR (500 MHz, DMSO) δ 12.51 (br, 1H), 10.43 (s, 1H), 10.24 (s, 1H), 8.99 (br, 1H), 8.64 (d, J=7.3 Hz, 1H), 7.92-7.88 (m, 2H), 7.88-7.83 (m, 5H), 7.83-7.75 (m, 6H), 7.53 (br, 1H), 7.45 (d, J=1.8 Hz, 1H), 7.39 (s, 1H), 7.23 (br, 1H), 6.98 (s, 1H), 4.92 (dd, J=14.1, 7.1 Hz, 2H), 3.92 (s, 3H), 2.68 (d, J=7.2 Hz, 2H), 1.21 (d, J=6.2 Hz, 6H).

$^{13}$C NMR (176 MHz, DMSO) δ 171.3, 170.7, 167.6, 167.1, 165.7, 163.4, 158.6, 142.1, 141.6, 135.0, 130.4, 129.2, 128.7, 128.3, 127.8, 126.9, 123.5, 119.1, 119.0, 116.4, 115.9, 90.0, 51.6, 37.1, 36.8, 22.6.

HRMS (ESI) calculated for C42H39N8O10 (M+H) 815.2784, found 815.2777.

4-(4-(4-((2S)-4-amino-2-(4-(2-(4-cyanophenoxy)propanamido)benzamido)-4-oxobutanamido)benzamido)-2-hydroxy-3-isopropoxybenzamido)benzoic acid

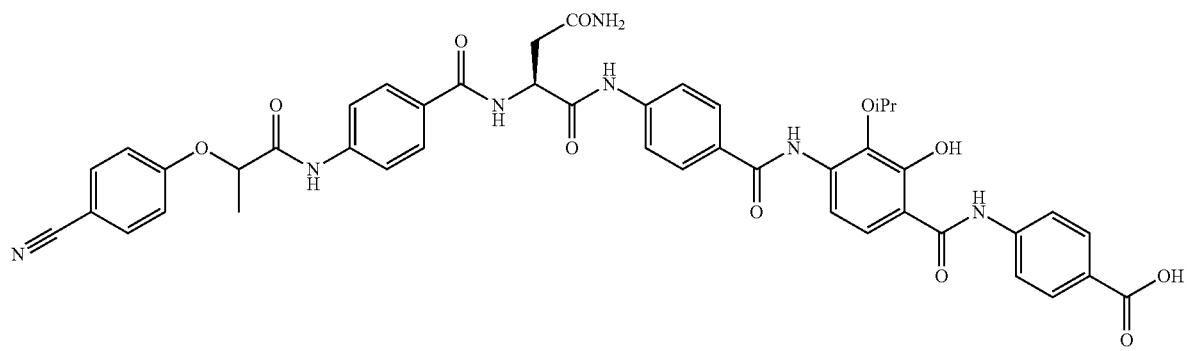

103

Amine 26 (25 mg, 0.033 mmol) coupled with 2-(4-cyanophenoxy)propanoic acid using coupling conditions A followed by final deprotection.

Desired compound purified by preparative HPLC condition B, to obtain 6.9 mg of desired product (0.0081 mmol, y=24%).

$^1$H NMR (500 MHz, DMSO) δ 12.61 (br, 2H), 10.45 (s, 2H), 9.27 (br, 1H), 8.64 (d, J=7.3 Hz, 1H), 7.97-7.85 (m, 6H), 7.85-7.77 (m, 6H), 7.75 (br, 1H), 7.71 (d, J=8.8 Hz, 2H), 7.55 (br, 1H), 7.39 (s, 1H), 7.15-7.08 (m, 2H), 6.98 (s, 1H), 5.07 (q, J=6.6 Hz, 1H), 4.90 (q, J=7.1 Hz, 1H), 4.66 (br, 1H), 2.70-2.65 (m, 2H), 1.59 (d, J=6.6 Hz, 3H), 1.24 (d, J=6.2 Hz, 6H).

$^{13}$C NMR (176 MHz, DMSO) δ 171.3, 171.0, 169.4, 168.2, 167.0, 165.7, 163.9, 160.7, 142.4, 141.1, 136.6, 134.3, 130.3, 128.9, 128.6, 128.4, 128.1, 123.0, 120.1, 119.0, 118.9, 118.9, 116.0, 103.5, 73.7, 51.6, 36.8, 22.4, 18.3.

HRMS (ESI) calculated for C45H42N7O11 (M+H) 856.2937, found 856.2938.

4-(4-(4-((2S)-4-amino-2-(4-(2-((4-cyanophenyl)thio) propanamido)benzamido)-4-oxobutanamido)benzamido)-2-hydroxy-3-isopropoxybenzamido)benzoic acid

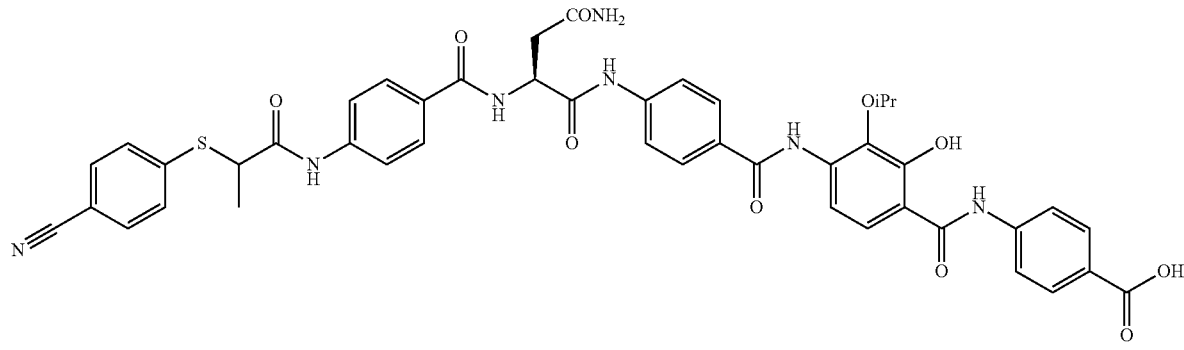

104

Amine 26 (25 mg, 0.033 mmol) coupled with 2-((4-cyanophenyl)thio)propanoic acid using coupling conditions A followed by final deprotection.

Desired compound purified by preparative HPLC condition B, to obtain 6.0 mg of desired product (0.0069 mmol, y=21%).

HRMS (ESI) calculated for $C_{45}H_{42}N_7O_{10}S$ (M+H) 872.2708, found 872.2715.

(S)-4-(4-(4-(4-amino-2-(4-(5-nitroquinoline-8-carboxamido)benzamido)-4-oxobutanamido)benzamido)-2-hydroxy-3-isopropoxybenzamido)benzoic acid

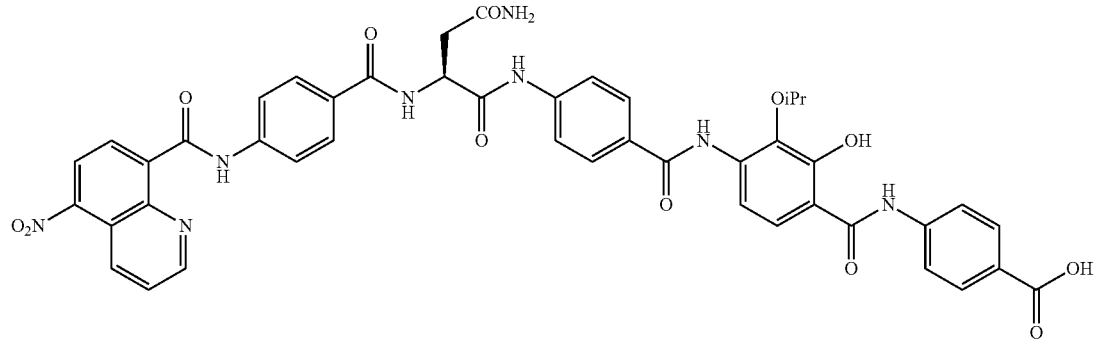

105

Amine 26 (25 mg, 0.033 mmol) coupled with 5-nitroquinoline-8-carboxylic acid using coupling conditions A followed by final deprotection.

Desired compound purified by preparative HPLC condition B, to obtain 2.1 mg of desired product (0.0024 mmol, y=7%).

$^1$H NMR (500 MHz, DMSO) δ 12.83 (br, 1H), 12.29 (br, 1H), 12.08 (s, 1H), 10.62 (br, 1H), 10.48 (s, 1H), 9.40 (s, 1H), 9.25 (dd, J=4.2, 1.5 Hz, 1H), 8.93 (dd, J=8.9, 1.6 Hz, 1H), 8.71 (d, J=7.3 Hz, 1H), 8.56 (d, J=8.0 Hz, 1H), 8.45 (d, J=8.0 Hz, 1H), 8.02-7.90 (m, 8H), 7.84 (dd, J=13.5, 8.7 Hz, 5H), 7.69 (d, J=8.7 Hz, 1H), 7.41 (s, 1H), 7.01 (s, 1H), 4.94 (dd, J=14.1, 7.0 Hz, 1H), 4.59-4.51 (m, 1H), 2.74-2.67 (m, 2H), 1.26 (d, J=6.1 Hz, 6H).

HRMS (ESI) calculated for $C_{45}H_{39}N_8O_{12}$ (M+H) 883.2682, found 883.2682.

(S)-4-(4-(4-(4-amino-2-(4-(4-amino-2,3,5,6-tet-rafluorobenzamido)benzamido)-4-oxobutanamido) benzamido)-2-hydroxy-3-isopropoxybenzamido) benzoic acid

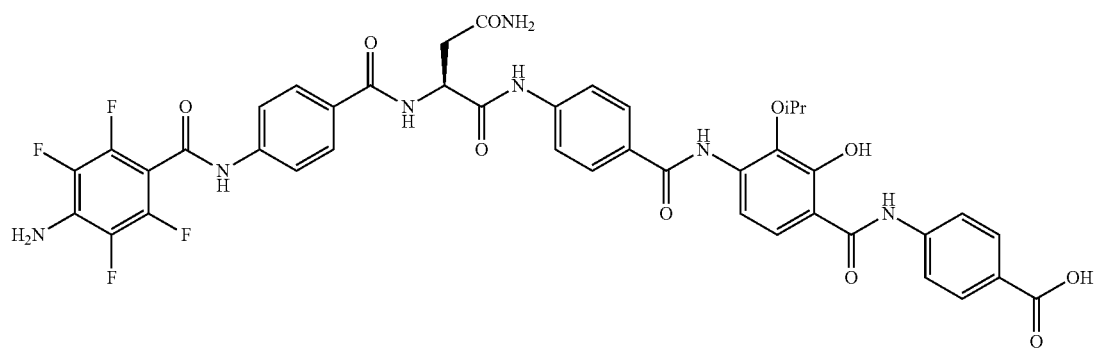

106

Amine 26 (25 mg, 0.033 mmol) coupled with 4-azido-2, 3,5,6-tetrafluorobenzoic acid using coupling conditions A followed by final deprotection.

Purification by preparative HPLC following condition B was done, to obtain 4.3 mg of amine xx, as a degradation byproduct of desired azide (0.0069 mmol, y=15%).

$^1$H NMR (500 MHz, DMSO) δ 12.64 (br, 2H), 10.83 (s, 1H), 10.45 (s, 1H), 9.23 (br, 1H), 8.67 (d, J=7.3 Hz, 1H), 7.96-7.88 (m, 6H), 7.82 (dd, J=8.7, 7.1 Hz, 4H), 7.76 (d, J=8.7 Hz, 2H), 7.72 (br, 1H), 7.51 (br, 1H), 7.39 (s, 1H), 6.99 (s, 1H), 6.49 (s, 2H), 4.92 (dd, J=14.1, 7.2 Hz, 1H), 4.70 (br, 1H), 2.70-2.66 (m, 2H), 1.24 (d, J=6.2 Hz, 6H).

$^{13}$C NMR (176 MHz, DMSO) δ 171.3, 170.7, 168.1, 167.0, 165.7, 163.9, 157.2, 144.4, 143.0, 142.3, 141.2, 136.7, 135.8, 134.3, 130.3, 129.2, 128.6, 128.1, 123.1, 119.9, 118.9, 118.6, 100.95 (t, J=19.5 Hz, C), 51.6, 36.8, 22.4.

$^{19}$F NMR (471 MHz, DMSO) δ −145.12 (d, J=16.0 Hz), −161.56 (d, J=16.1 Hz).

HRMS (ESI) calculated for C42H36F4N7O10 (M+H) 874.2454, found 874.2458.

Amine 26 (25 mg, 0.033 mmol) coupled with 4,5-bis (allyloxy)picolinic acid using coupling conditions A followed by final deprotection.

Purification by preparative HPLC following condition B was done, to obtain 11.5 mg of desired compound (0.0136 mmol, y=41%).

$^1$H NMR (700 MHz, DMSO) δ 15.83 (br, 1H), 10.51 (s, 1H), 10.41 (s, 1H), 8.88 (s, 1H), 8.62 (d, J=7.4 Hz, 1H), 8.49 (s, 1H), 7.96 (d, J=8.8 Hz, 2H), 7.88 (d, J=8.8 Hz, 2H), 7.83 (t, J=8.0 Hz, 5H), 7.80 (d, J=8.8 Hz, 2H), 7.74 (d, J=8.2 Hz, 2H), 7.45 (d, J=8.7 Hz, 1H), 7.39 (s, 1H), 7.32 (br, 1H), 7.11 (d, J=8.7 Hz, 1H), 6.97 (s, 1H), 5.03-4.98 (m, 1H), 4.91 (dd, J=14.1, 7.3 Hz, 1H), 2.68 (d, J=8.1 Hz, 2H), 1.19 (d, J=6.1 Hz, 6H).

$^{13}$C NMR (176 MHz, DMSO) δ 171.4, 170.7, 170.3, 166.9, 165.9, 165.3, 164.6, 163.1, 142.0, 141.7, 137.5, 134.0, 131.1, 129.7, 129.5, 128.3, 128.1, 127.6, 127.5, 127.0, 124.2, 123.7, 119.1, 118.0, 117.6, 116.0, 107.7, 100.7, 70.4, 51.7, 36.9, 22.7.

HRMS (ESI) calculated for C41H38N7O12 (M+H) 820.2573, found 820.2571.

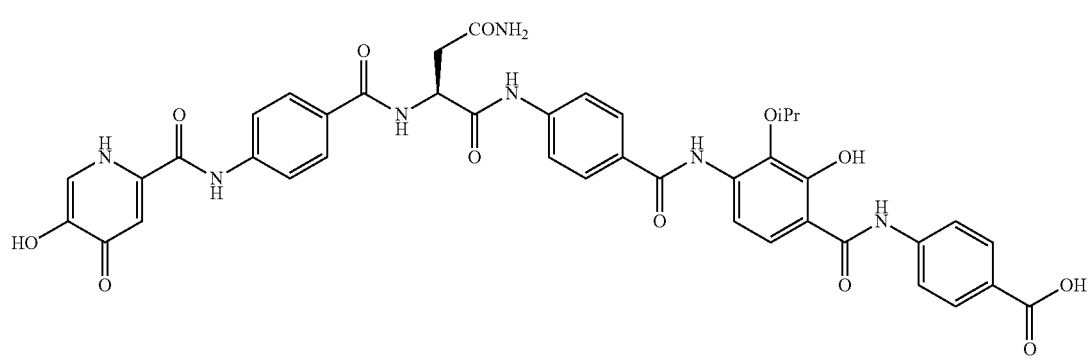

107

Synthetic Scheme Depicting the Synthesis of Compound 109:

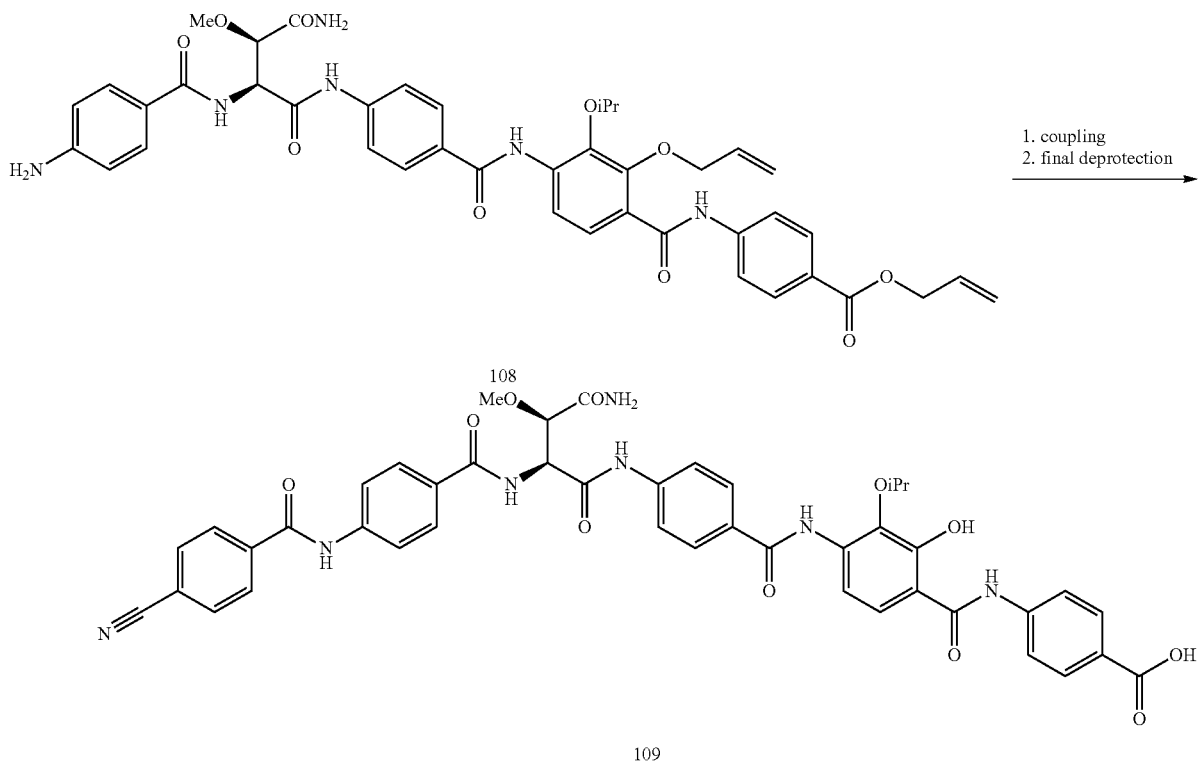

Amine 108 was synthesis following experimental procedure reported in DOI: 10.1002/anie.201705913R1.

4-(4-(4-((2S,3R)-4-amino-2-(4-(4-cyanobenzamido)benzamido)-3-methoxy-4-oxobutanamido)benzamido)-2-hydroxy-3-isopropoxybenzamido)benzoic acid

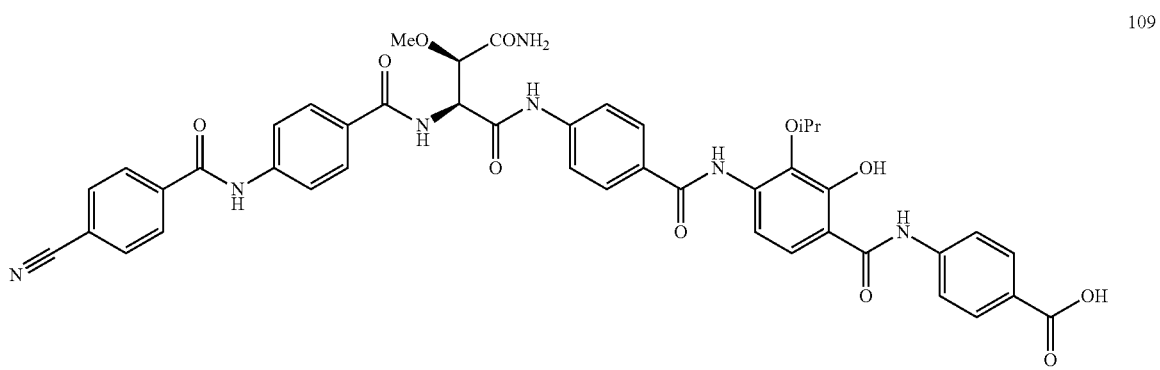 [SMILES: CO[C@@H](C(N)=O)[C@H](NC(=O)c1ccc(NC(=O)c2ccc(C#N)cc2)cc1)C(=O)Nc1ccc(C(=O)Nc2ccc(C(=O)Nc3ccc(C(=O)O)cc3)c(O)c2OC(C)C)cc1]

Amine 108 (12 mg, 0.015 mmol) was coupled to 4-cyanobenzoic acid using coupling conditions A followed by final deprotection.

Purification by preparative HPLC using condition B afforded 5.2 mg of desired compound (0.0062 mmol, y=41%).

$^1$H NMR (700 MHz, DMSO) δ 12.70 (br, 1H), 12.28 (br, 1H), 10.72 (s, 1H), 10.57 (s, 1H), 9.34 (br, 1H), 8.46 (d, J=8.1 Hz, 1H), 8.14-8.11 (m, 2H), 8.04 (d, J=8.4 Hz, 2H), 7.95 (dd, J=8.2, 5.4 Hz, 4H), 7.92-7.86 (m, 4H), 7.84 (d, J=8.6 Hz, 4H), 7.80 (br, 1H), 7.62 (br, 1H), 7.54 (s, 1H), 7.47 (s, 1H), 4.92 (t, J=8.1 Hz, 1H), 4.60 (br, 1H), 4.09 (d, J=8.1 Hz, 1H), 3.31 (s, 3H), 1.26 (d, J=6.1 Hz, 6H).

$^{13}$C NMR (176 MHz, DMSO) δ 170.9, 168.7, 168.3, 166.9, 165.5, 164.5, 164.1, 142.2, 141.8, 138.7, 136.5, 132.5, 130.2, 128.9, 128.6, 128.3, 122.9, 120.4, 119.6, 119.0, 118.3, 114.0, 107.0, 80.0, 57.7, 55.8, 45.8, 22.4.
HRMS (ESI) calculated for C44H40N7O11 (M+H) 842.2780, found 842.2771.
The same synthetic scheme was also pursued with different building blocks C (C2-4)
e. A1+B1+C2
Synthesis:
fragment C 2
+
fragment B 1 →
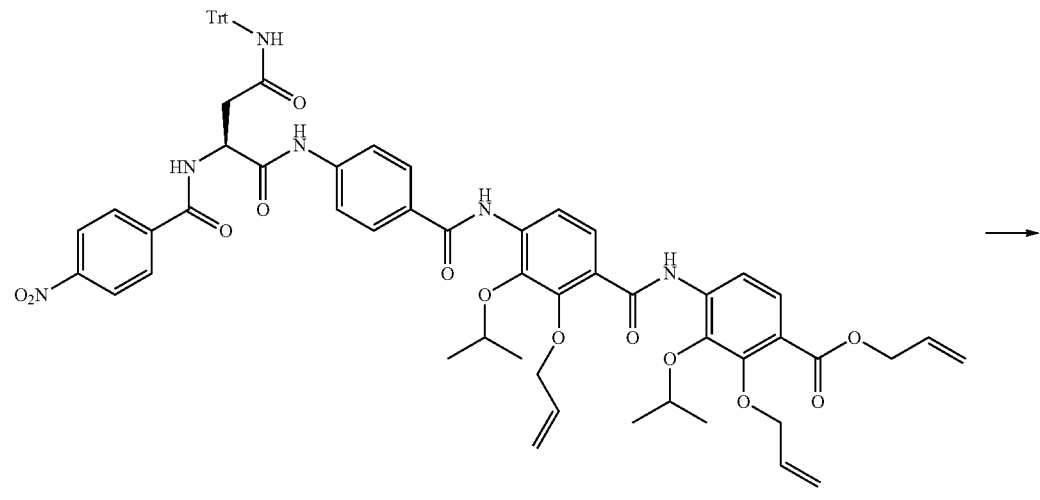
59
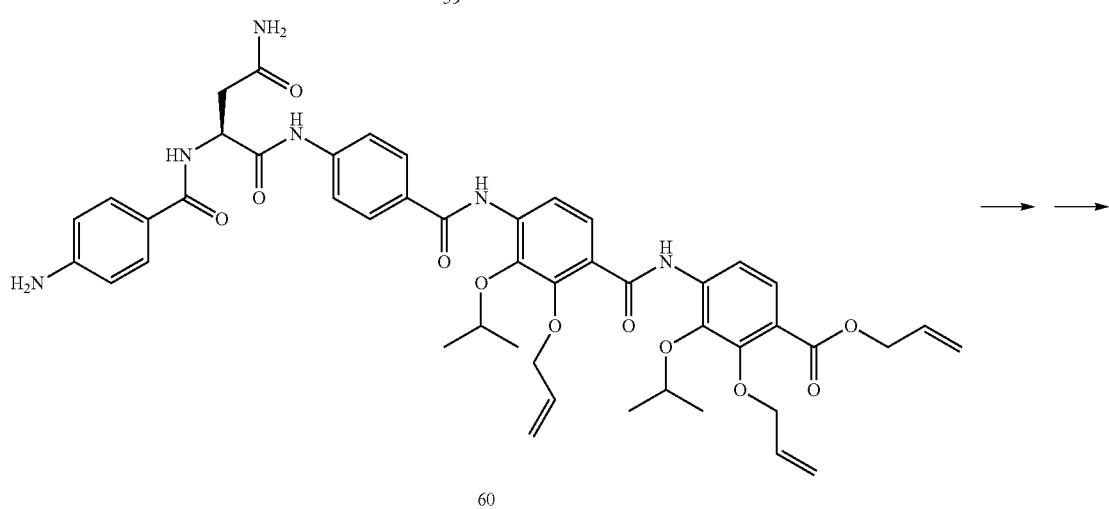
60
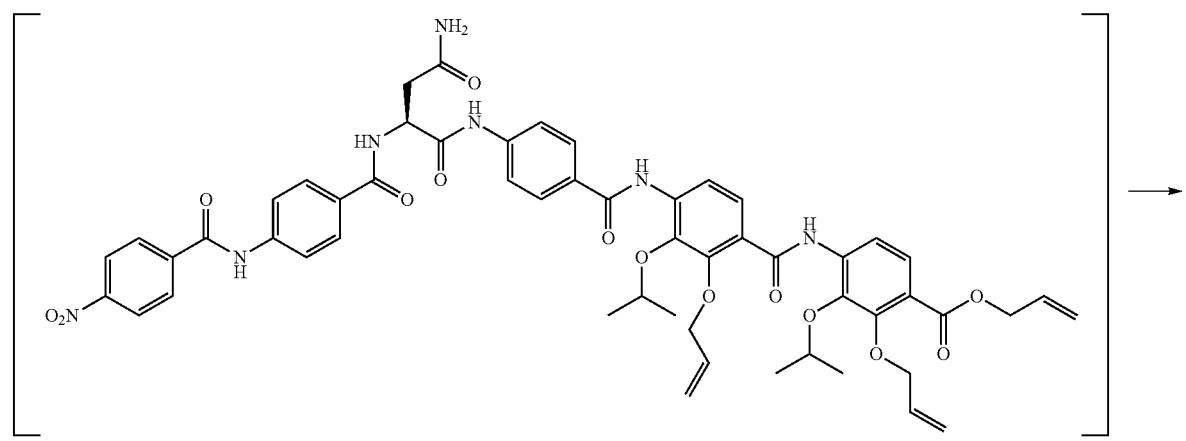

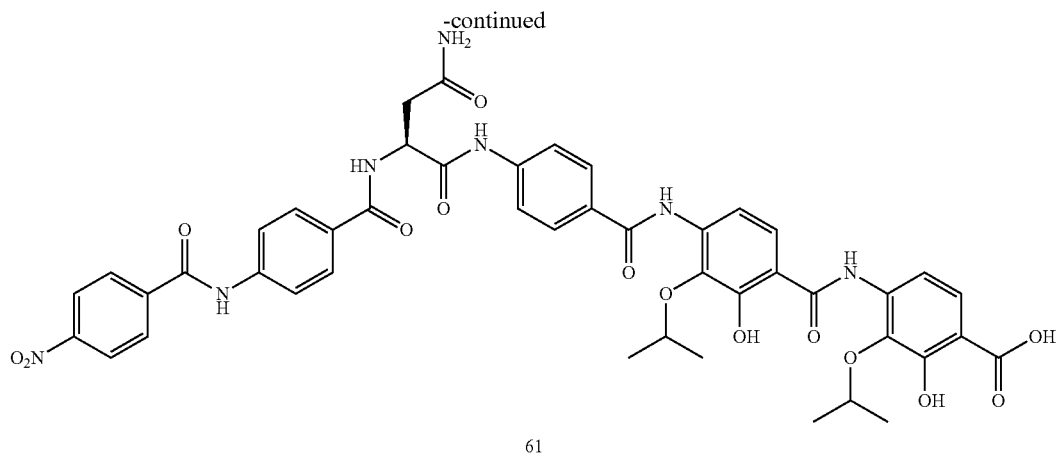

61 allyl (S)-2-(allyloxy)-4-(2-(allyloxy)-3-isopropoxy-4-(4-(2-(4-nitrobenzamido)-4-oxo-4-(tritylamino)butanamido)benzamido)benzamido)-3-isopropoxybenzoate

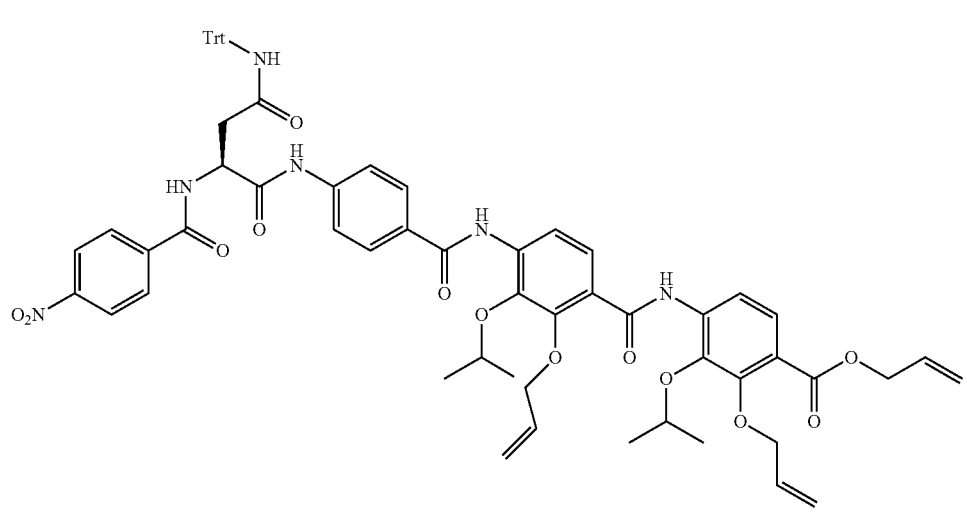

59

POCl₃ (1.42 mmol) as a solution in DCM (1:9) was added dropwise to a solution of allyl 2-(allyloxy)-4-(2-(allyloxy)-4-amino-3-isopropoxybenzamido)-3-isopropoxybenzoate (0.300 g; 0.57 mmol) and (S)-4-(2-(4-nitrobenzamido)-4-oxo-4-(tritylamino)butanamido)benzoic acid (0.914 g, 1.42 mmol) in THF (7.2 mL) and DCM (5.0 mL) at 0° C., followed by DiPEA (0.79 mL; 4.56 mmol) as a solution in DCM (1:1). Reaction stirred at r.t. for 5 h, quenched with HCl 1 N and ice, solvent partially reduced under vacuum and residue diluted with EA (200 mL) and HCl 1N (200 mL), organic phase washed with brine (200 mL) and dried over sodium sulphate. Solvent removed under vacuum, the crude residue was chromatographed on silica gel with a gradient EA 20-90% in Pet. Et to give 407 mg of an orange residue (0.35 mmol; 62%).

¹H NMR (500 MHz, CDCl₃) δ 10.73 (s, 1H), 9.63 (s, 1H), 8.74 (s, 1H), 8.47 (d, J=2.3 Hz, 1H), 8.45 (d, J=2.4 Hz, 1H), 8.44 (s, 1H), 8.27-8.24 (m, 2H), 8.00 (d, J=8.9 Hz, 1H), 7.97-7.93 (m, 3H), 7.86 (d, J=8.8 Hz, 2H), 7.67 (d, J=8.8 Hz, 1H), 7.60-7.57 (m, 2H), 7.30-7.22 (m, 15H), 6.20-6.00 (m, 3H), 5.40 (tq, J=17.2, 1.5 Hz, 2H), 5.33-5.25 (m, 2H), 5.25-5.21 (m, 2H), 5.12-5.06 (m, 1H), 4.80 (dt, J=5.7, 1.3 Hz, 2H), 4.79-4.72 (m, 2H), 4.70 (d, J=6.7 Hz, 2H), 4.59 (dt, J=5.9, 1.3 Hz, 2H), 3.34-3.22 (m, 1H), 2.78 (dd, J=15.6, 7.2 Hz, 1H), 1.41 (dd, J=6.1, 3.3 Hz, 6H), 1.29 (d, J=6.2 Hz, 6H).

¹³C NMR (126 MHz, CDCl₃) δ 171.1, 168.8, 165.6, 165.1, 164.1, 162.8, 151.9, 149.9, 149.0, 143.9, 141.1, 140.2, 139.2, 138.3, 138.2, 137.2, 133.9, 132.9, 132.3, 128.6, 128.1, 128.0, 127.3, 127.2, 127.0, 123.8, 122.6, 120.7, 120.3, 119.8, 119.4, 119.2, 118.4, 117.8, 115.5, 115.0, 76.6, 76.0, 75.7, 74.8, 71.2, 65.5, 51.2, 37.6, 22.8, 22.5.

HRMS (ESI) calculated for C66H65N6O13 (M+H) 1149.4604, found 1149.4593.

allyl (S)-2-(allyloxy)-4-(2-(allyloxy)-4-(4-(4-amino-2-(4-aminobenzamido)-4-oxobutanamido)benzamido)-3-isopropoxybenzamido)-3-isopropoxybenzoate

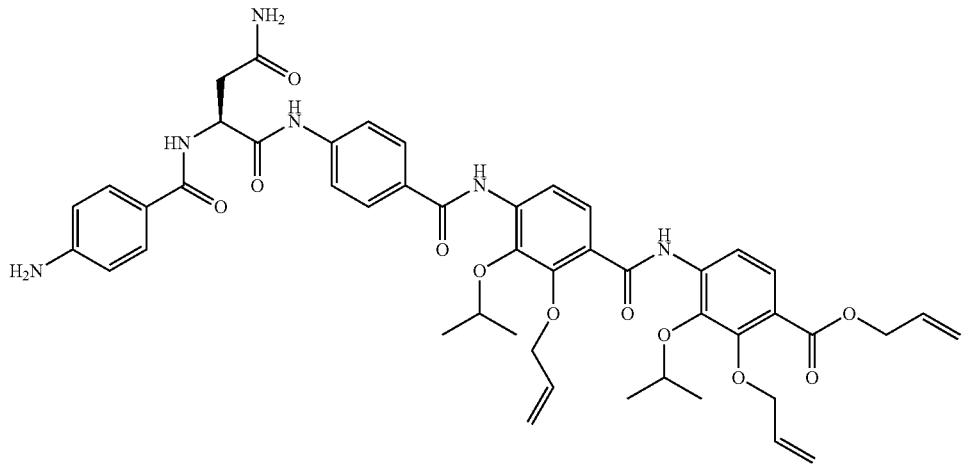

60

Zn dust (0.56 g; 8.6 mmol) was added portionwise over few minutes to a stirred solution of allyl (S)-4-(2-(allyloxy)-3-isopropoxy-4-(4-(2-(4-nitrobenzamido)-4-oxo-4-(tritylamino)-butanamido)benzamido)benzamido)benzoate (0.49 g; 0.43 mmol) in THF (2.7 mL), EtOH (2.4 mL) and AcOH (0.27 mL). Reaction stirred for 5 h, the mixture was filtered through celite, the solvent was reduced under vacuum. The crude was used in the next step without further purification.

The residue was dissolved in DCM (16.5 mL), Tips (0.264 mL; 1.29 mmol) followed by TFA (5.5 mL) were added at 0 C. Reaction stirred 2 h at r.t. then solved removed under vacuum, residue take up and evaporated twice with DCM (10 mL) then triturated 3× with ice cold Pet. Et. The crude thus obtained was purified on silica gel with a gradient 0-10% MeOH in DCM to give 263 mg of a yellow solid (0.30 mmol; y=70%).

$^1$H NMR (500 MHz, DMSO) δ 10.89-10.54 (m, 1H), 10.39 (t, J=7.9 Hz, 1H), 9.58-9.53 (m, 1H), 8.35 (d, J=8.8 Hz, 1H), 8.22 (d, J=7.4 Hz, 1H), 7.97 (d, J=8.7 Hz, 2H), 7.92 (d, J=8.8 Hz, 1H), 7.84-7.77 (m, 3H), 7.63-7.59 (m, 2H), 7.56 (dd, J=11.9, 8.7 Hz, 1H), 7.38 (s, 1H), 6.97 (s, 1H), 6.58-6.53 (m, 2H), 6.13-5.86 (m, 3H), 5.67 (br, 2H), 5.46-5.22 (m, 5H), 5.10-5.01 (m, 1H), 4.86 (m, 2H), 4.81-4.71 (m, 2H), 4.68 (d, J=5.4 Hz, 1H), 4.62 (dt, J=12.3, 6.1 Hz, 1H), 4.54 (d, J=5.7 Hz, 1H), 4.46 (m, 2H), 2.64 (d, J=7.1 Hz, 2H), 1.29 (dd, J=12.4, 7.4 Hz, 3H), 1.24 (m, 6H), 1.19 (d, J=6.1 Hz, 3H).

$^{13}$C NMR (126 MHz, DMSO) δ 171.5, 171.1, 168.7, 166.4, 164.5, 164.4, 152.9, 151.9, 149.8, 142.4, 141.3, 139.9, 137.7, 137.4, 136.6, 136.3, 134.0, 132.7, 132.2, 129.1, 128.5, 126.2, 125.5, 123.5, 120.4, 118.8, 118.5, 118.1, 117.7, 116.5, 114.6, 112.5, 76.6, 75.4, 74.2, 65.7, 65.1, 51.5, 36.9, 22.3, 22.1.

HRMS (ESI) calculated for C47H53N6O11 (M+H) 877.3767, found 877.3780.

(S)-4-(4-(4-(4-amino-2-(4-(4-nitrobenzamido)benzamido)-4-oxobutanamido)benzamido)-2-hydroxy-3-isopropoxybenzamido)-2-hydroxy-3-isopropoxybenzoic acid

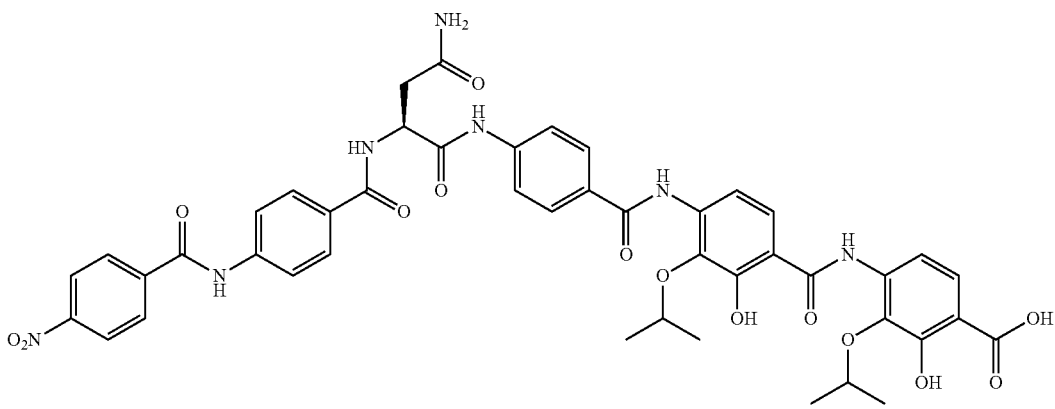

61

Collidine (0.036 mL; 0.272 mmol) was added dropwise at 0° C. to a solution of 4-nitro benzoic acid (20 mg; 0.12 mmol) and Bis(trichloromethyl) carbonate (11.6 mg; 0.039 mmol) in THF (1.75 mL). Reaction stirred at r.t. for 20 min then added to a solution of amine 60 (30 mg; 0.034 mmol) and DiPEA (0.060 mL; 0.34 mmol) in THF (1.75 mL). Reaction stirred for 3 h then quenched with HCl 1 N and ice. Solvent partially reduced under vacuum, EA (25 mL) and HCl 1N (25 mL) were added, organic phase washed with NaHCO$_3$ saturated solution (20 mL), brine (20 mL) and dried over sodium sulphate. The solvent was removed under reduced pressure, the residue thus obtained was used in the next step without further purification.

Phenyl silane (0.026 mL; 0.21 mmol) followed by Palladium-tetrakis(triphenylphosphine (9.8 mg; 0.0085 mmol) was added to a solution of the crude residue (0.034 mmol) in THF (3.5 mL). Reaction stirred overnight and purified by preparative HPLC with a gradient 10-95% CH$_3$CN in water 10 mM NH$_4$HCO$_3$ in 40 min to afford 1.7 mg of desired product (0.0046 mmol; y=6%).

$^1$H NMR (700 MHz, DMSO) δ 11.26 (s, 1H), 10.90 (s, 1H), 10.79 (s, 1H), 10.45 (s, 1H), 9.60 (s, 1H), 8.68 (d, J=7.3 Hz, 1H), 8.42-8.35 (m, 2H), 8.24-8.18 (m, 2H), 7.99-7.88 (m, 8H), 7.80 (dd, J=8.7, 5.3 Hz, 4H), 7.54-7.48 (m, 2H), 7.40 (s, 1H), 6.99 (s, 1H), 4.92 (dd, J=14.0, 7.2 Hz, 1H), 4.69 (dt, J=12.3, 6.1 Hz, 1H), 4.31 (dt, J=12.2, 6.1 Hz, 1H), 2.71-2.65 (m, 2H), 1.31-1.23 (m, 12H).

$^{13}$C NMR (176 MHz, DMSO) δ 171.3, 170.7, 165.8, 164.3, 164.2, 163.6, 162.3, 150.4, 149.3, 142.4, 141.5, 140.3, 138.4, 136.3, 134.0, 129.3, 129.2, 128.4, 128.3, 125.0, 124.8, 123.6, 119.5, 118.8, 116.4, 115.3, 112.5, 109.9, 75.7, 74.0, 51.6, 36.8, 22.0, 21.9.

HRMS (ESI) calculated for C45H42N7O14 (M−H) 904.2795, found 904.2786.

(S)-4-(4-(4-(4-amino-2-(4-(4-cyanobenzamido)benzamido)-4-oxobutanamido)benzamido)-2-hydroxy-3-isopropoxybenzamido)-2-hydroxy-3-isopropoxybenzoic acid

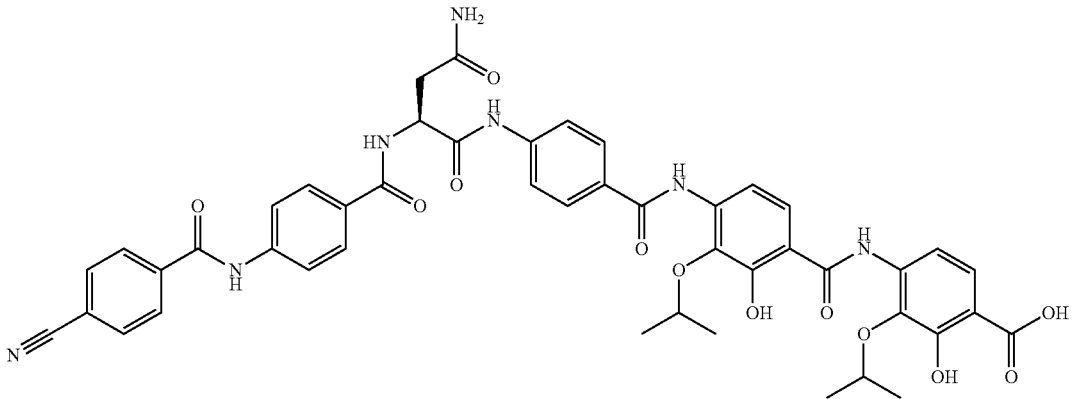

62

Compound 62 was synthesized starting from amine 60 (30 mg; 0.034 mmol) and 4-Cyanobenzoic acid (18 mg; 0.12 mmol) using the same experimental procedure employed for the synthesis of compound 61.

Preparative HPLC (gradient 10-95% CH$_3$CN in water 10 mM NH$_4$HCO$_3$ in 40 min) afforded 8.7 mg of desired product (0.010 mmol; y=29%).

$^1$H NMR (700 MHz, DMSO) δ 11.25 (s, 1H), 10.93 (s, 1H), 10.70 (s, 1H), 10.44 (s, 1H), 9.60 (s, 1H), 8.67 (d, J=7.3 Hz, 1H), 8.13 (d, J=8.4 Hz, 2H), 8.05 (d, J=8.4 Hz, 2H), 7.96 (t, J=8.9 Hz, 3H), 7.91 (dd, J=26.2, 8.8 Hz, 4H), 7.80 (m, 3H), 7.54 (d, J=8.8 Hz, 1H), 7.51 (d, J=8.8 Hz, 1H), 7.40 (s, 1H), 6.99 (s, 1H), 4.92 (dd, J=14.0, 7.3 Hz, 1H), 4.69 (dp, J=12.3, 6.1 Hz, 1H), 4.30 (td, J=12.1, 6.0 Hz, 1H), 2.71-2.67 (m, 2H), 1.27 (dd, J=7.5, 6.3 Hz, 12H).

$^{13}$C NMR (176 MHz, DMSO) δ 172.0, 171.3, 170.7, 165.8, 164.5, 164.3, 163.6, 150.4, 142.4, 141.6, 138.7, 138.4, 136.3, 133.9, 132.5, 129.1, 128.6, 128.4, 128.3, 125.0, 124.9, 119.5, 118.8, 118.3, 116.4, 115.4, 114.0, 110.1, 75.7, 74.1, 51.6, 40.0, 39.9, 39.8, 39.6, 39.5, 39.4, 39.3, 39.2, 36.8, 22.0, 21.9.

HRMS (ESI) calculated for C46H42N7O12 (M−H) 884.2897, found 884.2917.

(S)-4-(4-(4-(4-amino-2-(4-(5-cyanopicolinamido)benzamido)-4-oxobutanamido)benzamido)-2-hydroxy-3-isopropoxybenzamido)-2-hydroxy-3-isopropoxybenzoic acid

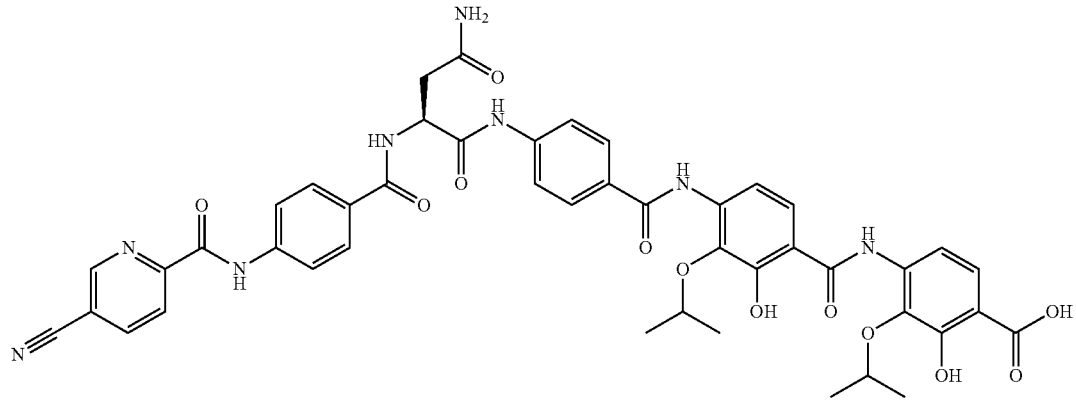

120

Compound 120 was synthesized starting from amine 60 (20 mg; 0.023 mmol) and 5-cyanopicolinic acid (12 mg; 0.08 mmol) using the same experimental procedure employed for the synthesis of compound 61.

Preparative HPLC (gradient 10-95% CH$_3$CN in water 10 mM NH$_4$HCO$_3$ in 40 min) afforded 5.6 mg of desired product (0.0063 mmol; y=27%).

$^1$H NMR (700 MHz, DMSO) δ 11.26 (s, 1H), 11.03 (s, 1H), 10.89 (s, 1H), 10.43 (s, 1H), 9.59 (s, 1H), 9.22 (dd, J=1.9, 0.7 Hz, 1H), 8.67 (d, J=7.3 Hz, 1H), 8.60 (dd, J=8.2, 2.0 Hz, 1H), 8.35-8.27 (m, 1H), 8.04 (d, J=8.8 Hz, 2H), 7.97 (d, J=8.8 Hz, 2H), 7.93 (d, J=8.7 Hz, 3H), 7.80 (dd, J=8.7, 4.8 Hz, 3H), 7.51 (t, J=9.5 Hz, 2H), 7.40 (s, 1H), 6.99 (s, 1H), 4.92 (dd, J=13.9, 7.4 Hz, 1H), 4.72-4.66 (m, 1H), 4.31 (dt, J=12.2, 6.1 Hz, 1H), 2.73-2.65 (m, 2H), 1.27 (dd, J=5.8, 5.1 Hz, 12H).

$^{13}$C NMR (176 MHz, DMSO) δ 171.9, 171.3, 170.7, 165.8, 164.3, 163.6, 161.6, 152.3, 151.5, 150.4, 142.4, 142.3, 140.9, 138.4, 136.3, 134.0, 129.4, 128.4, 128.3, 124.9, 124.8, 122.5, 119.7, 118.8, 116.6, 116.4, 115.3, 111.7, 109.9, 75.7, 74.0, 51.6, 36.8, 22.0, 21.9.

(S)-4-(4-(4-(4-amino-2-(4-(5-cyanothiophene-2-carboxamido)benzamido)-4-oxobutanamido)benzamido)-2-hydroxy-3-isopropoxybenzamido)-2-hydroxy-3-isopropoxybenzoic acid Compound 121 was synthesized starting from amine 60 (20 mg; 0.023 mmol) and 5-cyanothiophene-2-carboxylic acid (12 mg; 0.08 mmol) using the same experimental procedure employed for the synthesis of compound 61.

Preparative HPLC (gradient 10-95% CH$_3$CN in water 10 mM NH$_4$HCO$_3$ in 40 min) afforded 4.7 mg of desired product (0.0053 mmol; y=23%).

$^1$H NMR (700 MHz, DMSO) δ 11.27 (br, 1H), 10.88 (br, 1H), 10.78 (s, 1H), 10.44 (s, 1H), 9.59 (s, 1H), 8.68 (d, J=7.3 Hz, 1H), 8.14 (d, J=4.1 Hz, 1H), 8.08 (d, J=4.0 Hz, 1H), 7.97 (d, J=8.7 Hz, 2H), 7.94 (d, J=8.7 Hz, 2H), 7.92 (br, 1H), 7.84 (d, J=8.7 Hz, 2H), 7.80 (m, 3H), 7.51 (t, J=7.8 Hz, 2H), 7.39 (s, 1H), 6.98 (s, 1H), 4.92 (dd, J=14.0, 7.2 Hz, 1H), 4.69 (dt, J=12.3, 6.1 Hz, 1H), 4.31 (dt, J=12.2, 6.1 Hz, 1H), 2.73-2.65 (m, 2H), 1.27 (m, 12H).

$^{13}$C NMR (176 MHz, DMSO) δ 171.9, 171.3, 170.7, 165.7, 164.3, 163.6, 158.5, 150.4, 146.8, 142.4, 140.8, 139.7, 138.4, 136.2, 134.0, 129.5, 129.2, 128.4, 124.9, 124.7, 119.7, 118.8, 116.4, 115.3, 113.8, 112.5, 109.9, 75.7, 73.9, 51.6, 36.8, 22.0, 21.9.

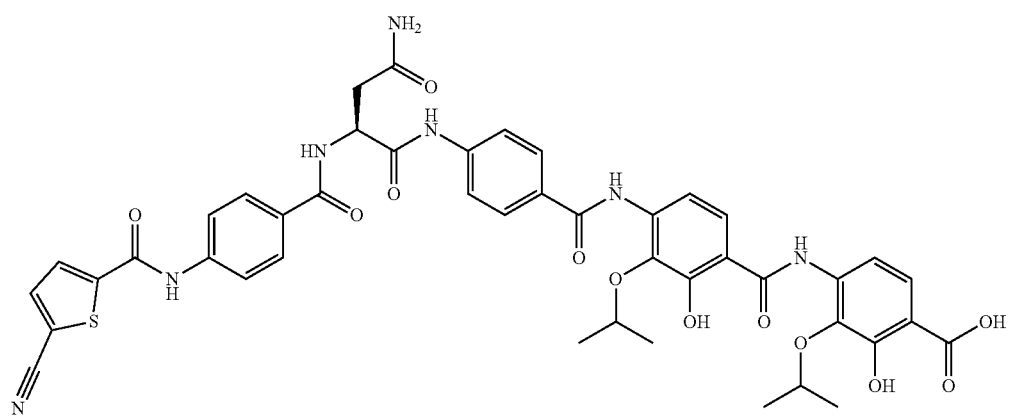

121 f. A1+B1+C3
fragment C 3
+
fragment B 1
→
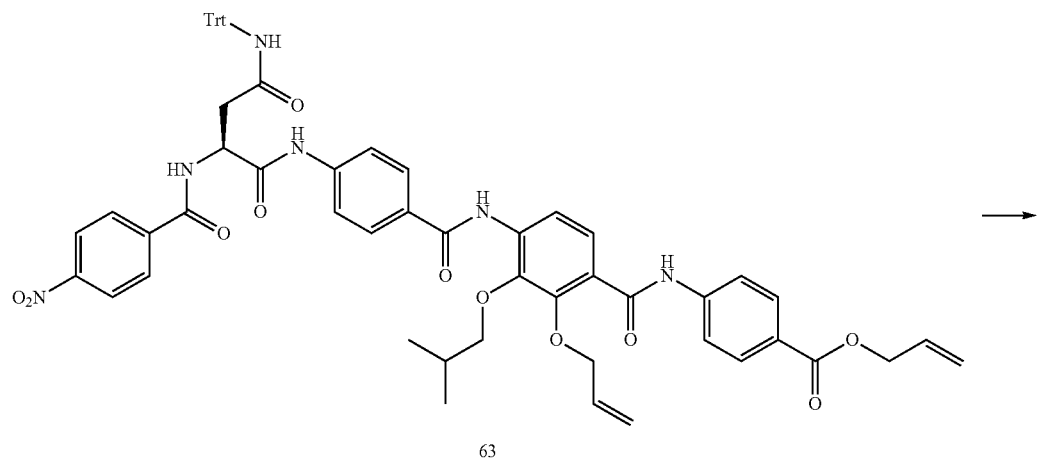
63
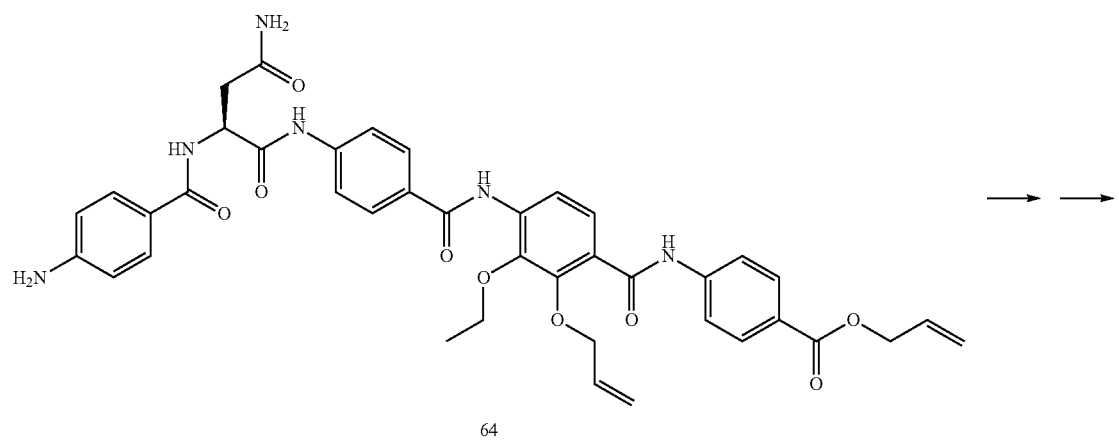
64
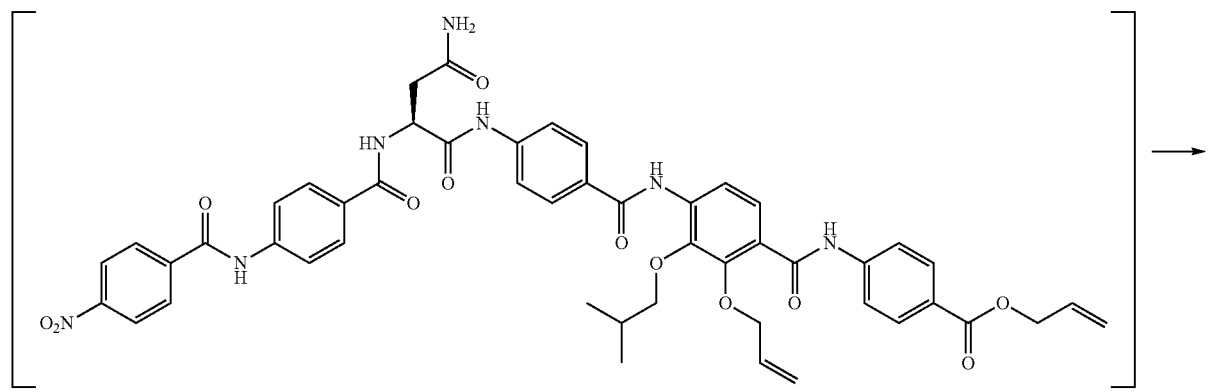

-continued

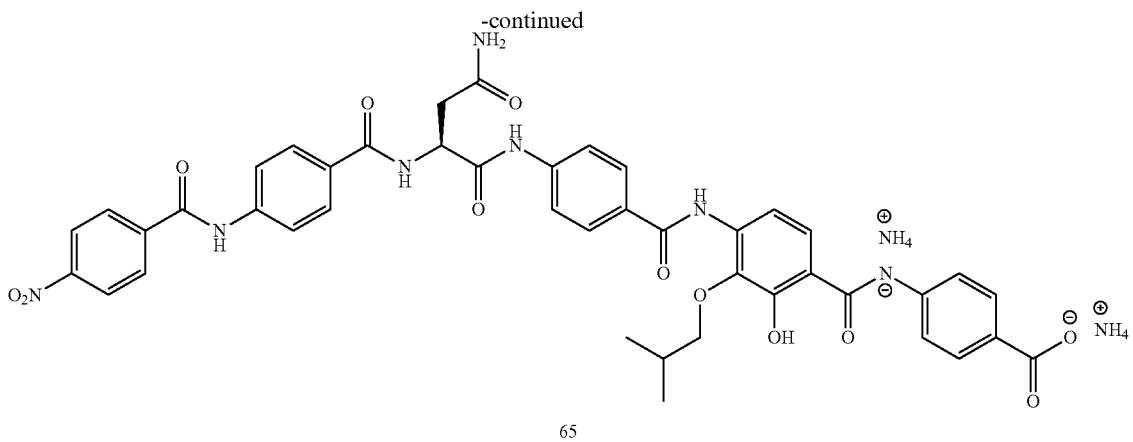

65 allyl (S)-4-(2-(allyloxy)-3-isobutoxy-4-(4-(2-(4-nitrobenzamido)-4-oxo-4-(tritylamino)butanamido)benzamido)benzamido)benzoate

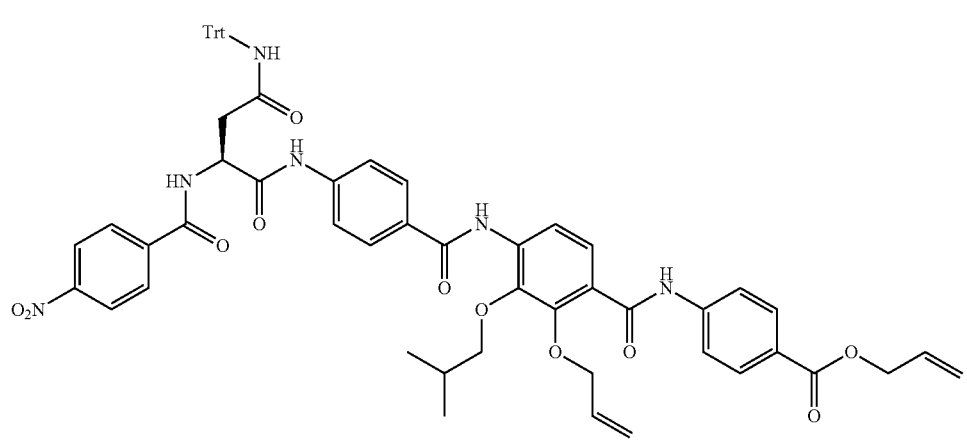

63

POCl₃ (2.3 mmol) as a solution in DCM (1:9) was added dropwise to a solution allyl 4-(2-(allyloxy)-4-amino-3-isobutoxybenzamido)benzoate (0.390 g; 0.92 mmol) and (S)-4-(2-(4-nitrobenzamido)-4-oxo-4-(tritylamino)butanamido)benzoic acid (1.48 g, 2.3 mmol) in THF (9.2 mL) and DCM (7.0 mL) at 0° C., followed by DiPEA (1.28 mL; 7.36 mmol) as a solution in DCM (1:1). Reaction stirred at r.t. for 4 h, quenched with HCL 1 N and ice, solvent partially reduced under vacuum and residue diluted with EA (200 mL) and HCl 1N (200 mL), organic phase washed with brine (200 mL) and dried over sodium sulphate. Solvent removed under vacuum, the crude residue was chromatographed on silica gel with a gradient EA 20-90% in Pet. Et to give 626 mg of an orange residue (0.60 mmol; 65%).

¹H NMR (500 MHz, DMSO) δ 10.58 (s, 1H), 10.52 (s, 1H), 9.58 (s, 1H), 9.21 (d, J=7.6 Hz, 1H), 8.70 (s, 1H), 8.41-8.37 (m, 2H), 8.19-8.15 (m, 2H), 7.99 (dd, J=8.8, 2.0 Hz, 4H), 7.87 (d, J=8.7 Hz, 2H), 7.78 (d, J=8.8 Hz, 2H), 7.69 (d, J=8.5 Hz, 1H), 7.40 (d, J=8.4 Hz, 1H), 7.23-7.14 (m, 15H), 6.10-5.96 (m, 2H), 5.44-5.38 (m, 1H), 5.36 (ddd, J=17.2, 3.1, 1.6 Hz, 1H), 5.28 (ddd, J=10.5, 2.6, 1.3 Hz, 1H), 5.19 (dd, J=10.5, 1.3 Hz, 1H), 4.97-4.91 (m, 1H), 4.79 (d, J=5.3 Hz, 2H), 4.60 (d, J=5.5 Hz, 2H), 3.82 (d, J=6.2 Hz, 2H), 3.00 (dd, J=14.8, 10.3 Hz, 1H), 2.77 (dd, J=14.8, 4.5 Hz, 1H), 1.99 (tt, J=13.4, 6.7 Hz, 1H), 0.94 (d, J=6.7 Hz, 6H).

¹³C NMR (126 MHz, DMSO) δ 168.3, 164.9, 164.6, 164.5, 149.4, 149.2, 144.8, 144.7, 143.5, 142.2, 139.3, 134.8, 133.6, 132.8, 130.3, 129.0, 128.5, 128.5, 127.6, 127.4, 126.4, 124.2, 123.6, 119.9, 119.0, 118.7, 117.8, 79.4, 74.6, 69.4, 64.8, 52.1, 38.0, 28.6, 19.0.

HRMS (ESI) calculated for C61H57N6O11 (M+H) 1049.4080, found 1049.4096.

allyl (S)-4-(2-(allyloxy)-4-(4-(4-amino-2-(4-aminobenzamido)-4-oxobutanamido)benzamido)-3-isobutoxybenzamido)benzoate

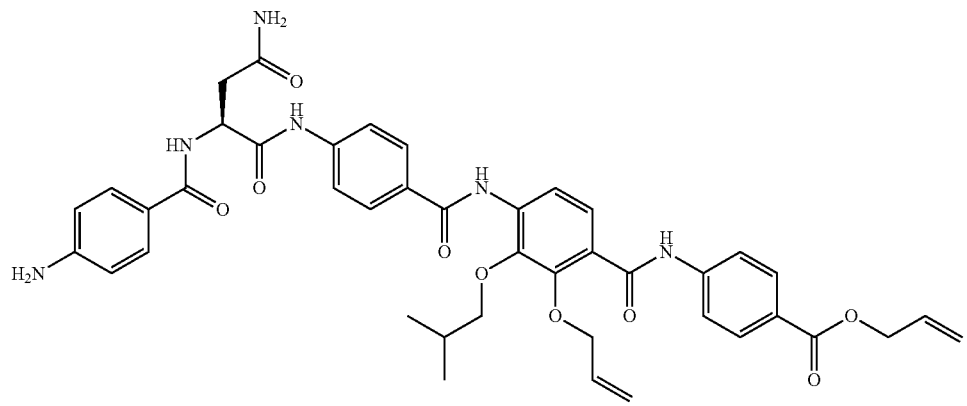

64

Zn dust (0.314 g; 4.8 mmol) was added portion wise over few minutes to a stirred solution of intermediate 63 (0.25 g; 0.24 mmol) in THF (1.5 mL), EtOH (1.4 mL) and AcOH (0.15 mL). Reaction stirred for 5 h, the mixture was filtered through celite, the solvent was reduced under vacuum. The crude was used in the next step without further purification.

The residue was dissolved in DCM (9.0 mL), Tips (0.148 mL; 0.72 mmol) followed by TFA (3.0 mL) were added at 0 C. Reaction stirred 2 h at r.t. then solved removed under vacuum, residue take up and evaporated twice with DCM (5 mL) then triturated 3× with ice cold Pet. Et. The crude thus obtained was purified on silica gel with a gradient 0-10% MeOH in DCM to give 140 mg of a yellow solid (0.18 mmol; y=76%).

$^1$H NMR (500 MHz, DMSO) δ 10.58 (s, 1H), 10.36 (s, 1H), 9.56 (s, 1H), 8.22 (d, J=7.4 Hz, 1H), 7.98 (dd, J=11.9, 5.0 Hz, 4H), 7.87 (d, J=8.8 Hz, 2H), 7.77 (d, J=8.9 Hz, 2H), 7.69 (d, J=8.5 Hz, 1H), 7.63-7.59 (m, 2H), 7.39 (d, J=8.4 Hz, 2H), 6.97 (s, 1H), 6.58-6.54 (m, 2H), 6.10-5.96 (m, 2H), 5.70 (br, 2H), 5.41 (dq, J=17.2, 1.7 Hz, 1H), 5.36 (dq, J=17.2, 1.7 Hz, 1H), 5.28 (ddd, J=10.5, 3.0, 1.4 Hz, 1H), 5.19 (ddd, J=10.5, 3.0, 1.3 Hz, 1H), 4.84 (dd, J=14.1, 7.2 Hz, 1H), 4.79 (dt, J=5.3, 1.4 Hz, 2H), 4.60 (d, J=5.5 Hz, 2H), 3.81 (d, J=6.2 Hz, 2H), 2.66-2.62 (m, 2H), 1.99 (dp, J=13.2, 6.6 Hz, 1H), 0.94 (d, J=6.7 Hz, 6H).

$^{13}$C NMR (126 MHz, DMSO) δ 171.5, 171.0, 166.4, 165.0, 164.6, 164.5, 151.8, 149.4, 144.7, 143.5, 142.4, 134.8, 133.6, 132.8, 130.4, 129.1, 128.4, 128.3, 127.6, 124.2, 123.5, 120.4, 119.9, 119.0, 118.6, 117.8, 112.5, 79.4, 74.6, 64.9, 51.5, 36.8, 28.6, 19.0.

HRMS (ESI) calculated for C42H45N6O9 (M+H) 777.3243, found 777.3225.

(S)-4-(4-(4-(4-amino-2-(4-(4-nitrobenzamido)benzamido)-4-oxobutanamido)benzamido)-2-hydroxy-3-isobutoxybenzamido)benzoic acid

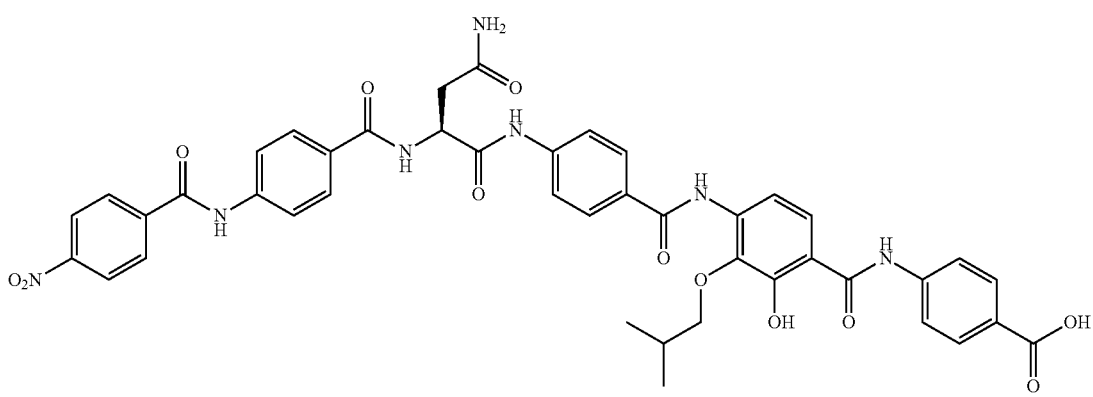

65

Collidine (0.048 mL; 0.36 mmol) was added dropwise at 0° C. to a solution of 4-nitro benzoic acid (26 mg; 0.16 mmol) and Bis(trichloromethyl) carbonate (14.0 mg; 0.047 mmol) in THF (2.3 mL). Reaction stirred at r.t. for 20 min then added to a solution of amine 64 (35 mg; 0.045 mmol) and DiPEA (0.078 mL; 0.45 mmol) in THF (2.3 mL). Reaction stirred for 3 h then quenched with HCl 1 N and ice. Solvent partially reduced under vacuum, EA (25 mL) and HCl 1N (25 mL) were added, organic phase washed with NaHCO₃ saturated solution (20 mL), brine (20 mL) and dried over sodium sulphate. The solvent was removed under reduced pressure, the residue thus obtained was used in the next step without further purification.

Phenyl silane (0.022 mL; 0.18 mmol) followed by Palladium-tetrakis(triphenylphosphine (13.0 mg; 0.011 mmol) was added to a solution of the crude residue (0.045 mmol) in THF (4.5 mL). Reaction stirred for 3 hours and purified by preparative HPLC with a gradient 10-95% CH₃CN in water 10 mM NH₄HCO₃ in 40 min to afford 3.0 mg of desired product (0.0036 mmol; y=8%).

¹H NMR (700 MHz, DMSO) δ 12.78 (br, 1H), 12.27 (br, 1H), 10.79 (s, 1H), 10.61 (br, 1H), 10.44 (s, 1H), 9.36 (br, 1H), 8.68 (d, J=7.3 Hz, 1H), 8.41-8.36 (m, 2H), 8.24-8.19 (m, 2H), 7.99-7.92 (m, 6H), 7.90 (d, J=8.8 Hz, 2H), 7.85 (d, J=8.6 Hz, 2H), 7.79 (d, J=8.8 Hz, 3H), 7.53 (br, 1H), 7.40 (s, 1H), 6.99 (s, 1H), 4.92 (dd, J=13.9, 7.3 Hz, 1H), 3.83 (d, J=6.4 Hz, 2H), 2.69 (dd, J=6.9, 2.9 Hz, 2H), 2.01 (dp, J=13.3, 6.6 Hz, 1H), 0.95 (d, J=6.7 Hz, 6H).

¹³C NMR (176 MHz, DMSO) δ 171.3, 170.7, 168.3, 166.9, 165.7, 164.3, 164.2, 149.3, 142.4, 141.5, 140.3, 130.2, 129.3, 129.2, 128.3, 128.3, 123.6, 122.9, 120.4, 119.5, 118.7, 78.5, 51.6, 36.8, 28.6, 19.1.

HRMS (ESI) calculated for C43H38N7O12 (M−H) 844.2584, found 844.2593.

g. A1+B1+C4

Synthesis:

The synthesis was accomplished with minor modifications of the general synthetic scheme (section 2.3a).

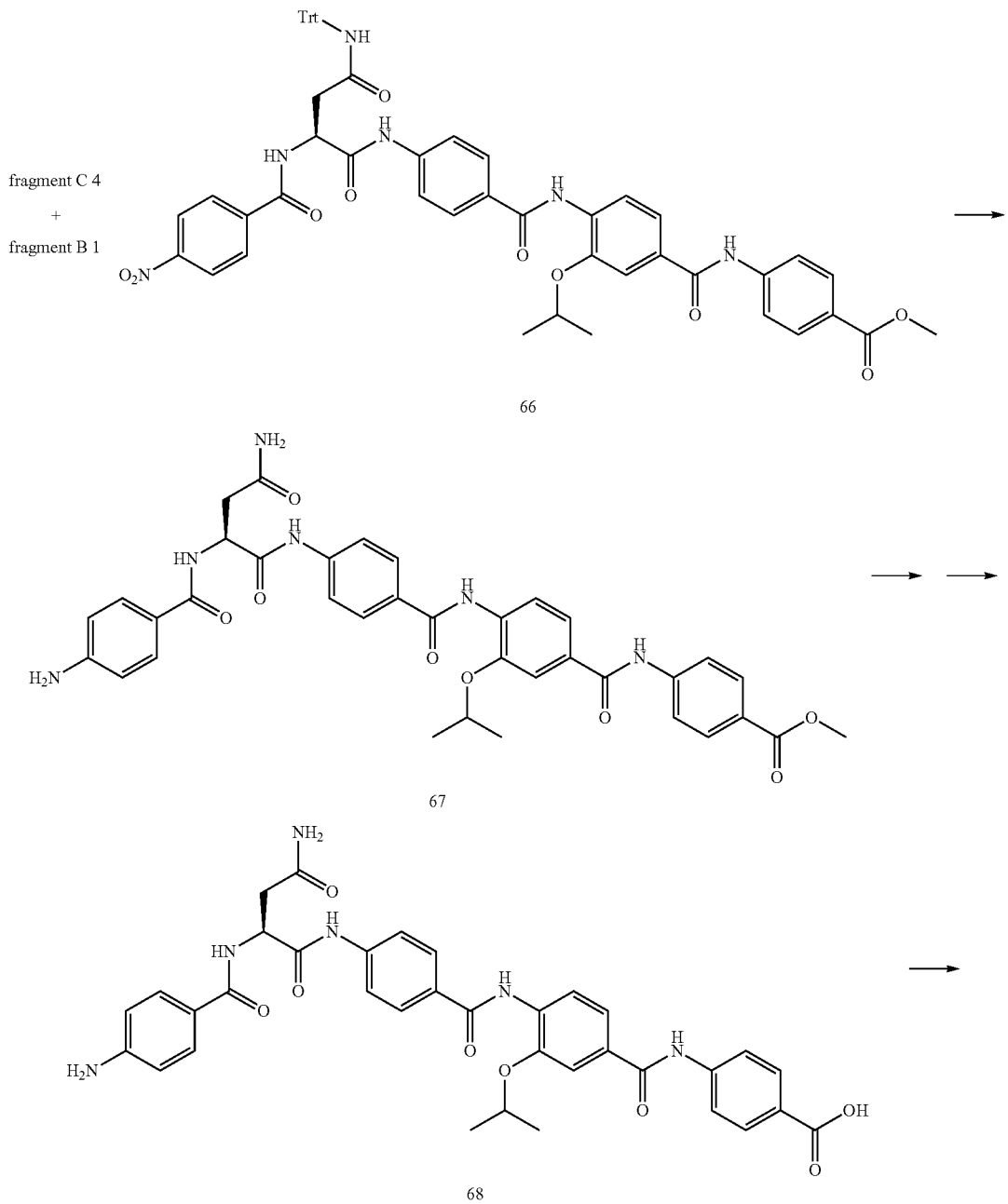

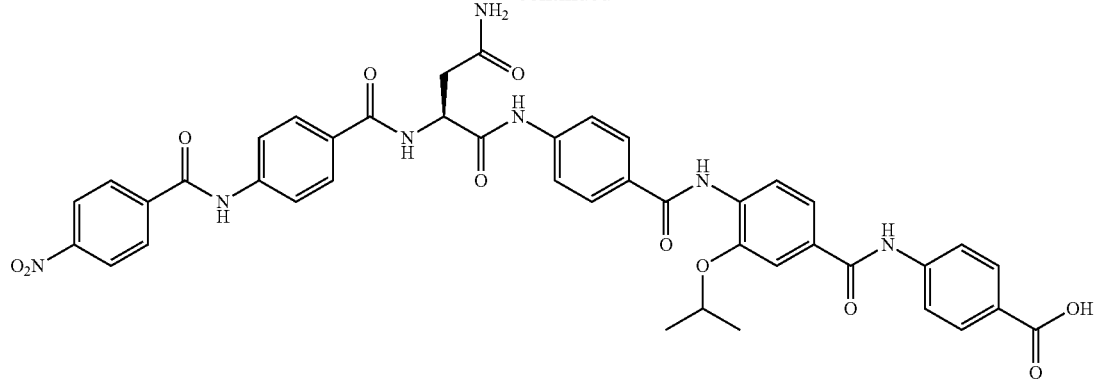

69 methyl (S)-4-(3-isopropoxy-4-(4-(2-(4-nitrobenzamido)-4-oxo-4-(tritylamino)butanamido)benzamido)benzamido)benzoate

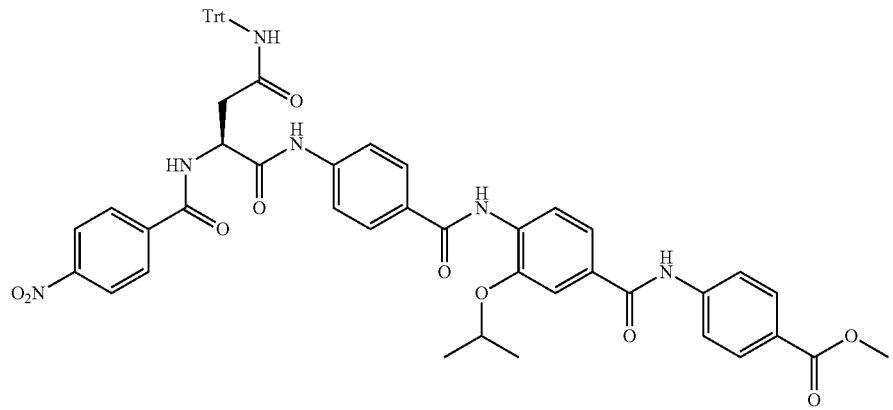

(S)-4-(2-(4-nitrobenzamido)-4-oxo-4-(tritylamino)butanamido)benzoic acid (325 mg; 0.506 mmol), methyl 4-(4-amino-3-isopropoxybenzamido)benzoate (194 mg; 0.592 mmol), HOAt (103 mg; 0.759 mmol) were mixed in DMF (1.25 mL). To this solution, EDC (116 mg; 0.607 mmol) followed by lutidine (0.295 mL; 2.530 mmol) were added. Reaction stirred at r.t. for 6 days, reaction diluted with EA (75 mL) and HCl 1 N (75 mL), the organic phase washed with NaHCO$_3$ saturated solution (50 mL) and brine (50 mL), dried over sodium sulphate and reduced under vacuum to give an orange material, which was chromatographed on silica gel with a gradient 0-3% MeOH in DCM to give 220 mg of desired product (0.23 mmol; y=46%).

$^1$H NMR (500 MHz, CDCl$_3$) δ 9.61 (s, 1H), 8.80 (s, 1H), 8.69 (d, J=8.4 Hz, 1H), 8.48 (d, J=6.3 Hz, 1H), 8.31-8.26 (m, 2H), 8.09-8.05 (m, 2H), 7.99 (s, 1H), 7.98-7.94 (m, 2H), 7.88-7.84 (m, 2H), 7.78-7.74 (m, 2H), 7.61 (d, J=1.9 Hz, 1H), 7.60-7.55 (m, 2H), 7.41 (dd, J=8.5, 1.9 Hz, 1H), 7.32-7.24 (m, 15H), 7.14 (s, 1H), 5.09-5.04 (m, 1H), 4.88-4.76 (m, 1H), 3.92 (s, 3H), 3.31 (dd, J=15.7, 2.7 Hz, 1H), 2.75 (dd, J=15.6, 7.3 Hz, 1H), 1.47 (dd, J=6.0, 2.9 Hz, 6H).

$^{13}$C NMR (176 MHz, CDCl$_3$) δ 171.2, 168.8, 166.6, 165.7, 165.1, 164.5, 150.1, 146.6, 143.9, 142.2, 141.0, 138.3, 132.4, 131.0, 130.4, 129.4, 128.6, 128.6, 128.2, 128.2, 127.4, 125.8, 124.0, 119.8, 119.2, 118.9, 118.8, 112.1, 72.0, 71.4, 52.1, 51.2, 37.5, 22.3.

HRMS (ESI) calculated for C55H49N6O10 (M+H) 953.3505, found 953.3483.

methyl (S)-4-(4-(4-(4-amino-2-(4-aminobenzamido)-4-oxobutanamido)benzamido)-3-isopropoxybenzamido)benzoate

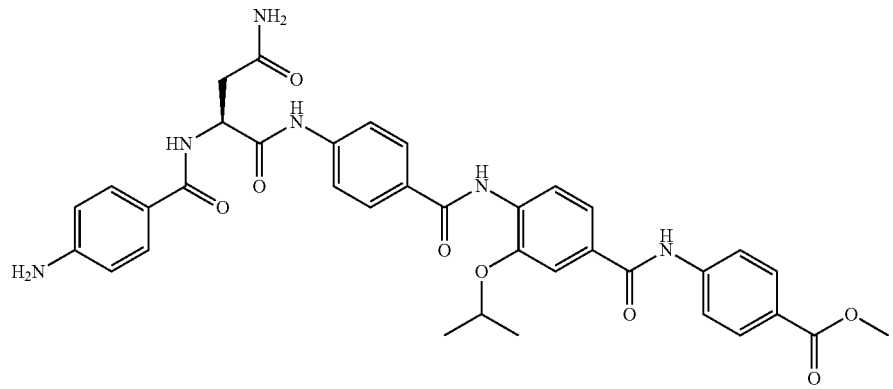 [SMILES: COC(=O)c1ccc(NC(=O)c2ccc(NC(=O)c3ccc(NC(=O)[C@H](CC(N)=O)NC(=O)c4ccc(N)cc4)cc3)c(OC(C)C)c2)cc1]

Methyl (S)-4-(3-isopropoxy-4-(4-(2-(4-nitrobenzamido)-4-oxo-4-(tritylamino)butanamido)-benzamido)benzamido)benzoate (238 mg; 0.25 mmol) was dissolved in DCM (7.5 mL), Tips (0.154 mL; 0.75 mmol) followed by TFA (2.5 mL) were added at 0° C. Reaction stirred 2 h at r.t. then solved removed under vacuum, residue take up and evaporated twice with DCM (10 mL) then triturated 3× with ice cold Pet. Et.

Tin(II) chloride dehydrate (338 mg; 1.50 mmol) was mixed with the crude residue coming from the former step (0.25 mmol) in EtOH (5 mL), the solution was stirred at r.t. overnight.

Solvent was evaporated under vacuum, the residue dissolved in EA (50 mL), washed with NaHCO₃ (50 mL) saturated solution, which was extracted twice again with EA (2×30 mL). Organic phases reunited washed with brine (100 mL), dried over sodium sulphate and reduced under vacuum. The residue was chromatographed on silica gel with a gradient 0-10% MeOH in DCM to give 50 mg of desired product (0.082 mmol; y=33%).

¹H NMR (700 MHz, DMSO) δ 10.47 (s, 1H), 10.38 (s, 1H), 9.25 (s, 1H), 8.22 (d, J=7.4 Hz, 1H), 8.20 (d, J=8.9 Hz, 1H), 7.99-7.90 (m, 6H), 7.82-7.78 (m, 2H), 7.64 (dd, J=6.9, 1.8 Hz, 2H), 7.62-7.59 (m, 2H), 7.37 (s, 1H), 6.97 (s, 1H), 6.57-6.54 (m, 2H), 5.67 (s, 2H), 4.85 (q, J=7.1 Hz, 1H), 4.79 (hept, J=6.0 Hz, 1H), 3.84 (s, 3H), 2.64 (d, J=7.1 Hz, 2H), 1.37 (d, J=6.0 Hz, 6H).

¹³C NMR (176 MHz, DMSO) δ 171.4, 171.1, 166.4, 165.8, 165.3, 164.2, 151.9, 147.8, 143.7, 142.5, 131.7, 130.4, 130.1, 129.1, 128.4, 128.3, 124.2, 121.3, 120.5, 120.4, 119.7, 118.8, 113.1, 112.4, 71.5, 51.9, 51.5, 36.9, 21.8.

(S)-4-(4-(4-(4-amino-2-(4-aminobenzamido)-4-oxobutanamido)benzamido)-3-isopropoxybenzamido)benzoic acid

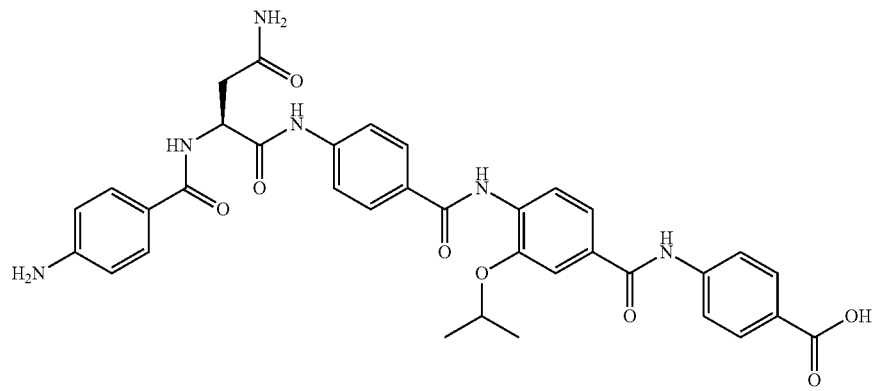 [SMILES: CC(C)Oc1cc(C(=O)Nc2ccc(C(=O)O)cc2)ccc1NC(=O)c1ccc(NC(=O)[C@H](CC(N)=O)NC(=O)c2ccc(N)cc2)cc1]

Methyl (S)-4-(4-(4-(4-amino-2-(4-aminobenzamido)-4-oxobutanamido)benzamido)-3-iso-propoxybenzamido)benzoate (20 mg, 0.029 mmol) was mixed into THF (1.4 mL) and water (1.4 mL). To this mixture, a solution 0.1 M of LiOH (0.59 mL; 0.059 mmol) was added at 0° C. Reaction stirred for 2.5 days. Reaction quenched with acetic acid, solvent reduced under vacuum and residue purified by preparative HPLC with a gradient 20-90% CH$_3$CN in water both phases +0.1% TFA to obtain 4.8 mg of desired product (0.0073 mmol; y=25%).

$^1$H NMR (500 MHz, DMSO) δ 12.78 (br, 1H), 10.45 (s, 1H), 10.40 (s, 1H), 9.26 (s, 1H), 8.24 (d, J=7.2 Hz, 1H), 8.19 (d, J=8.9 Hz, 1H), 7.92 (m, 6H), 7.80 (d, J=8.8 Hz, 2H), 7.66-7.59 (m, 4H), 7.38 (s, 1H), 6.98 (s, 1H), 6.57 (d, J=8.6 Hz, 2H), 5.72 (br, 1H), 4.85 (q, J=7.0 Hz, 1H), 4.79 (dt, J=12.1, 6.0 Hz, 1H), 2.67-2.60 (m, 2H), 1.37 (d, J=6.0 Hz, 6H).

$^{13}$C NMR (176 MHz, DMSO) δ 171.4, 171.0, 166.9, 166.4, 165.2, 164.2, 147.8, 143.3, 142.5, 131.7, 130.4, 130.2, 129.1, 128.5, 128.3, 125.4, 121.3, 120.5, 119.6, 118.8, 113.1, 112.6, 71.6, 51.5, 36.9, 21.8.

HRMS (ESI) calculated for C35H35N6O8 (M+H) 667.2511, found 667.2512.

(S)-4-(4-(4-(4-amino-2-(4-(4-nitrobenzamido)benzamido)-4-oxobutanamido)benzamido)-3-isopropoxybenzamido)benzoic acid (69)

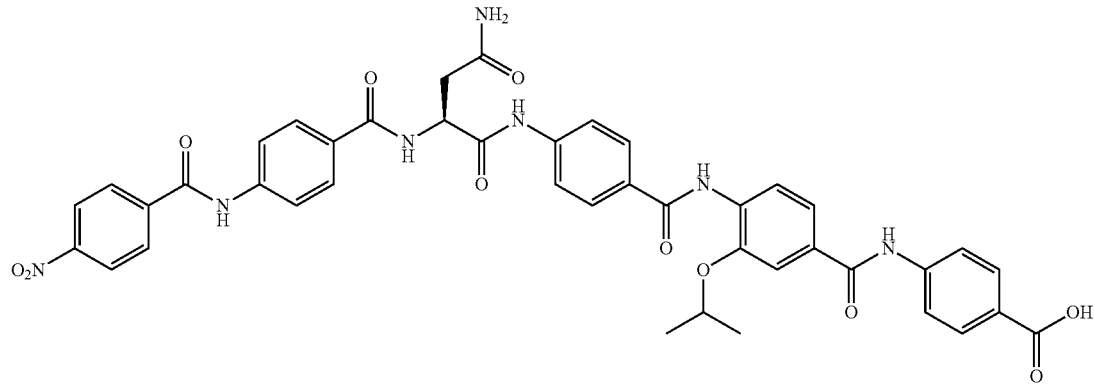 [SMILES: CC(C)Oc1cc(C(=O)Nc2ccc(C(=O)O)cc2)ccc1NC(=O)c1ccc(NC(=O)[C@H](CC(N)=O)NC(=O)c2ccc(NC(=O)c3ccc([N+](=O)[O-])cc3)cc2)cc1]

To a suspension of (S)-4-(4-(4-(4-amino-2-(4-aminobenzamido)-4-oxobutanamido)benz-amido)-3-isopropoxybenzamido)benzoic acid (4.8 mg; 0.0072 mmol) in THF (0.25 mL) and NaHCO$_3$ saturated solution (0.25 mL), 4-nitrobenzoyl chloride (2.6 mg; 0.014 mmol) was added at 0° C. Reaction stirred for 2.5 hours then quenched with AcOH, solvent partially removed under vacuum, residue dissolved in DMSO, salts filtered out, and purified by preparative HPLC with a gradient 20-90% CH$_3$CN in water both phases +0.1% TFA to obtain 1 mg of desired compound (0.0012 mmol; y=16%).

$^1$H NMR (700 MHz, DMSO) δ 12.75 (br, 1H), 10.79 (s, 1H), 10.46 (s, 1H), 10.44 (s, 1H), 9.26 (s, 1H), 8.68 (d, J=7.3 Hz, 1H), 8.40-8.37 (m, 2H), 8.21 (dt, J=17.0, 6.2 Hz, 3H), 7.96-7.89 (m, 10H), 7.82 (d, J=8.8 Hz, 2H), 7.65-7.63 (m, 2H), 7.40 (s, 1H), 6.99 (s, 1H), 4.93 (dd, J=14.0, 7.2 Hz, 1H), 4.79 (hept, J=6.1 Hz, 1H), 2.69 (d, J=7.8 Hz, 2H), 1.37 (d, J=6.0 Hz, 6H).

$^{13}$C NMR (176 MHz, DMSO) δ 171.3, 170.7, 166.9, 165.8, 165.2, 164.2, 149.3, 147.8, 143.3, 141.5, 140.3, 131.7, 130.5, 130.2, 129.3, 129.2, 128.6, 128.3, 128.3, 125.4, 123.6, 121.4, 120.5, 119.6, 118.9, 113.1, 71.6, 51.6, 36.8, 21.8.

HRMS (ESI) calculated for C42H38N7O11 (M+H$^+$) 816.2624, found 816.2633.

3. Synthesis 2

3.1 Retrosynthetic Disconnection fragments

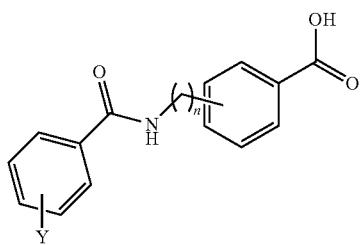

-continued

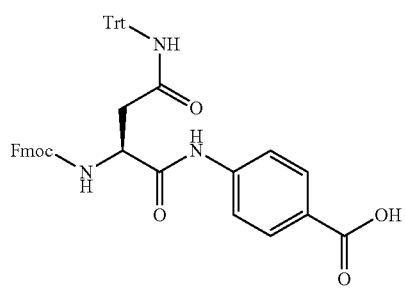

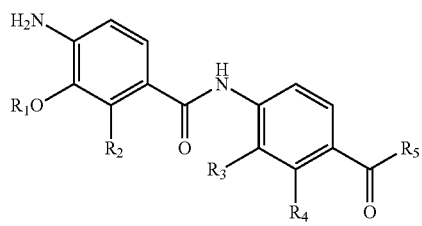

In the above formula A2, n represents 0 or m and Y represents H or R$^6$.

3.2 Building Blocks Synthesis
a. Fragments A2

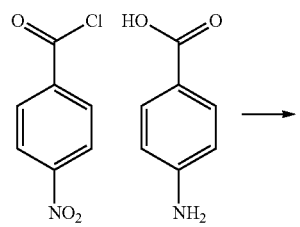

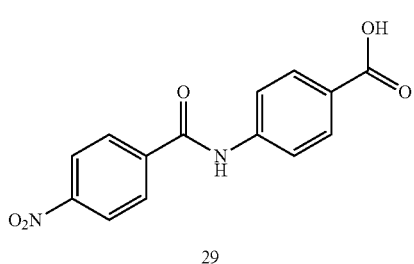

See synthesis of compound 29 inn section 2.2a.

With the same retrosynthetic approach, the following building blocks have also been prepared:

4-(4-cyanobenzamido)benzoic acid

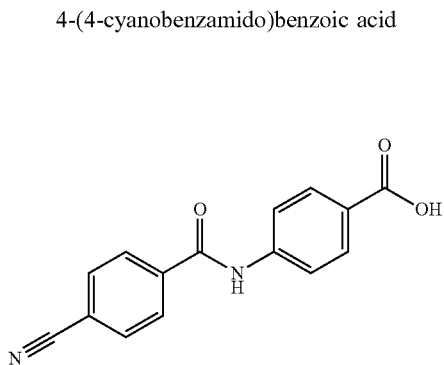

4-Aminobenzoic acid (213 mg; 1.56 mmol) was dissolved in THF (1.2 mL) and NaHCO$_3$ saturated solution (1.2 mL), to it 4-cyanobenzoyl chloride (285 mg; 1.73 mmol) was added at 0° C. Reaction stirred for 2 hours, precipitate collected by filtration, washed with water and triturated with Et$_2$O, dried at high vacuum to give 300 mg of a solid (1.13 mmol; y=72%).

$^1$H NMR (500 MHz, DMSO) δ 12.81 (br, 1H), 10.77 (s, 1H), 8.14-8.11 (m, 2H), 8.07-8.03 (m, 2H), 7.98-7.94 (m, 2H), 7.94-7.90 (m, 2H).

$^{13}$C NMR (126 MHz, DMSO) δ 167.4, 165.1, 143.3, 139.1, 133.0, 130.8, 129.1, 126.4, 120.1, 118.8, 114.6.

HRMS (ESI) calculated for C15H9N2O3 (M–H) 265.0619, found 265.0622.

3-(4-cyanobenzamido)benzoic acid

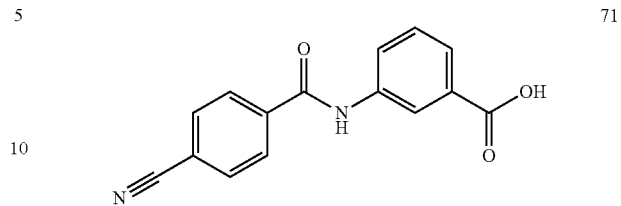

3-Aminobenzoic acid (230 mg; 1.68 mmol) was dissolved in THF (1.2 mL) and NaHCO$_3$ saturated solution (1.2 mL), to it 4-cyanobenzoyl chloride (277 mg; 1.68 mmol) was added at 0° C. Reaction stirred for 2 hours, pH adjusted to 1, precipitate collected by filtration, washed with HCl 1 N, triturated with Et$_2$O and dried at high vacuum to give 280 mg of a solid (1.05 mmol; y=63%).

$^1$H NMR (500 MHz, DMSO) δ 13.02 (br, 1H), 10.67 (s, 1H), 8.42 (t, J=1.8 Hz, 1H), 8.14 (d, J=8.4 Hz, 2H), 8.04 (d, J=8.4 Hz, 3H), 7.71 (d, J=7.8 Hz, 1H), 7.50 (t, J=7.9 Hz, 1H).

$^{13}$C NMR (126 MHz, DMSO) δ 167.1, 164.3, 139.0, 138.6, 132.5, 131.3, 129.0, 128.6, 124.8, 124.5, 121.2, 118.3, 114.0.

HRMS (ESI) calculated for C15H9N2O3 (M–H) 265.0619, found 265.0606.

4-((4-cyanobenzamido)methyl)benzoic acid

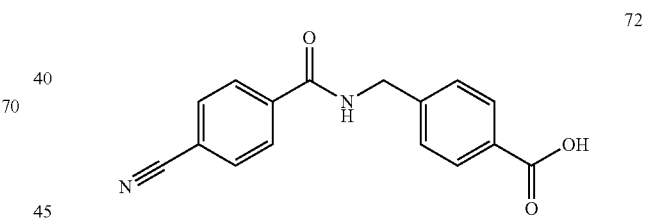

4-(aminomethyl)benzoic acid (287 mg; 1.9 mmol) was dissolved in THF (2.0 mL) and NaOH 1 N (5.7 mL), to it 4-cyanobenzoyl chloride (314 mg; 1.9 mmol) was added at 0° C. Reaction stirred for 2 hours, pH adjusted to 1, compound extracted with EA (50 mL), organic phase washed with brine (50 mL) dried over sodium sulphate and reduced under vacuum, crude chromatographed on silica gel with a gradient 0-10% MeOH in DCM to give 100 mg of a white solid (0.36 mmol; y=19%).

$^1$H NMR (500 MHz, DMSO) δ 12.87 (br, 1H), 9.37 (t, J=5.9 Hz, 1H), 8.08-8.02 (m, 2H), 8.01-7.96 (m, 2H), 7.94-7.88 (m, 2H), 7.43 (d, J=8.5 Hz, 2H), 4.56 (d, J=5.9 Hz, 2H).

$^{13}$C NMR (126 MHz, DMSO) δ 167.2, 165.0, 144.3, 138.1, 132.5, 129.4, 128.1, 127.2, 118.3, 113.7, 42.6.

HRMS (ESI) calculated for C$_{16}$H$_{11}$N$_2$O$_3$ (M–H) 279.0775, found 279.0794.

145
4-(2-(4-cyanobenzamido)ethyl)benzoic acid

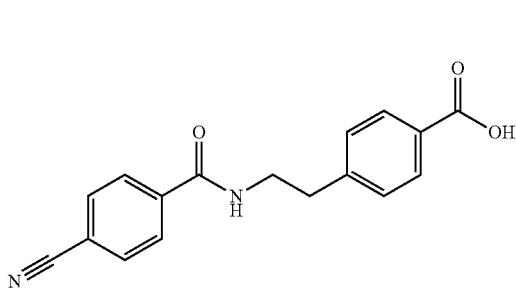

73

4-(2-aminoethyl)benzoic acid (165 mg; 0.82 mmol) was dissolved in THF (3.0 mL) and NaOH 1 N (3.5 mL), to it 4-cyanobenzoyl chloride (108 mg; 0.66 mmol) was added at 0° C. Reaction stirred for 1.5 hours, pH adjusted to 1, compound extracted with EA (30 mL), organic phase washed with brine (30 mL) dried over sodium sulphate and reduced under vacuum, crude chromatographed on silica gel with a gradient 0-10% MeOH in DCM to give 45 mg of a white solid (0.14 mmol; y=21%).

$^1$H NMR (500 MHz, DMSO) δ 12.82 (br, 1H), 8.83 (t, J=5.6 Hz, 1H), 7.98-7.92 (m, 4H), 7.88-7.84 (m, 2H), 7.36 (d, J=8.3 Hz, 2H), 3.53 (dd, J=13.0, 7.1 Hz, 2H), 2.93 (t, J=7.2 Hz, 2H).

$^{13}$C NMR (126 MHz, DMSO) δ 167.2, 164.8, 144.7, 138.5, 132.4, 129.4, 128.9, 128.0, 118.3, 113.5, 40.5, 34.8.

HRMS (ESI) calculated for $C_{17}H_{13}N_2O_3$ (M–H) 293.0932, found 293.0951.

146
4-((4-cyanophenyl)sulfonamido)benzoic acid

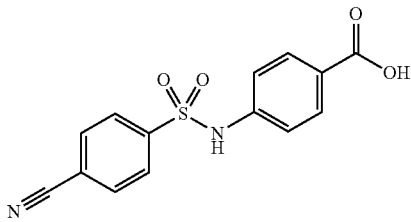 [SMILES: N#Cc1ccc(S(=O)(=O)Nc2ccc(C(=O)O)cc2)cc1]

Tert-butyl 4-aminobenzoate (140 mg; 0.725 mmol) and pyridine (0.58 mL; 7.25 mmol) were dissolved in THF (10 mL), to this solution a solution of 4-cyanobenzenesulfonyl chloride (146 mg; 0.725 mmol) in THF (2 mL) was added at r.t. Reaction stirred overnight, quenched with HCl 1 N and ice, solvent partially reduced under vacuum, residue diluted with EA (30 mL) and water (30 mL), organic phase washed with NaHCO$_3$ saturated solution (30 mL), brine (30 mL) and dried over sodium sulphate. Solvent evaporated under reduced pressure and crude used in the next step without further purification.

The crude residue was dissolved in DCM (6.0 mL) and TFA (1.2 mL) was added at 0° C. Reaction stirred for 1.5 h, solvent reduced under vacuum, residue dissolved in EA (40 mL), washed with HCl 1 N (40 mL), brine (40 mL) and dried over sodium sulphate. Solvent removed under vacuum to afford 160 mg of pure product (0.52; y=72%).

$^1$H NMR (500 MHz, DMSO) δ 12.81 (br, 1H), 11.05 (s, 1H), 8.10-8.04 (m, 2H), 8.00-7.95 (m, 2H), 7.86-7.80 (m, 2H), 7.23-7.18 (m, 2H).

$^{13}$C NMR (126 MHz, DMSO) δ 167.1, 143.7, 141.7, 134.1, 131.3, 127.9, 126.7, 119.2, 118.0, 116.2.

HRMS (ESI) calculated for C14H9N2O4S (M–H) 301.0289, found 301.0301.

b. Fragment B2
Synthesis:

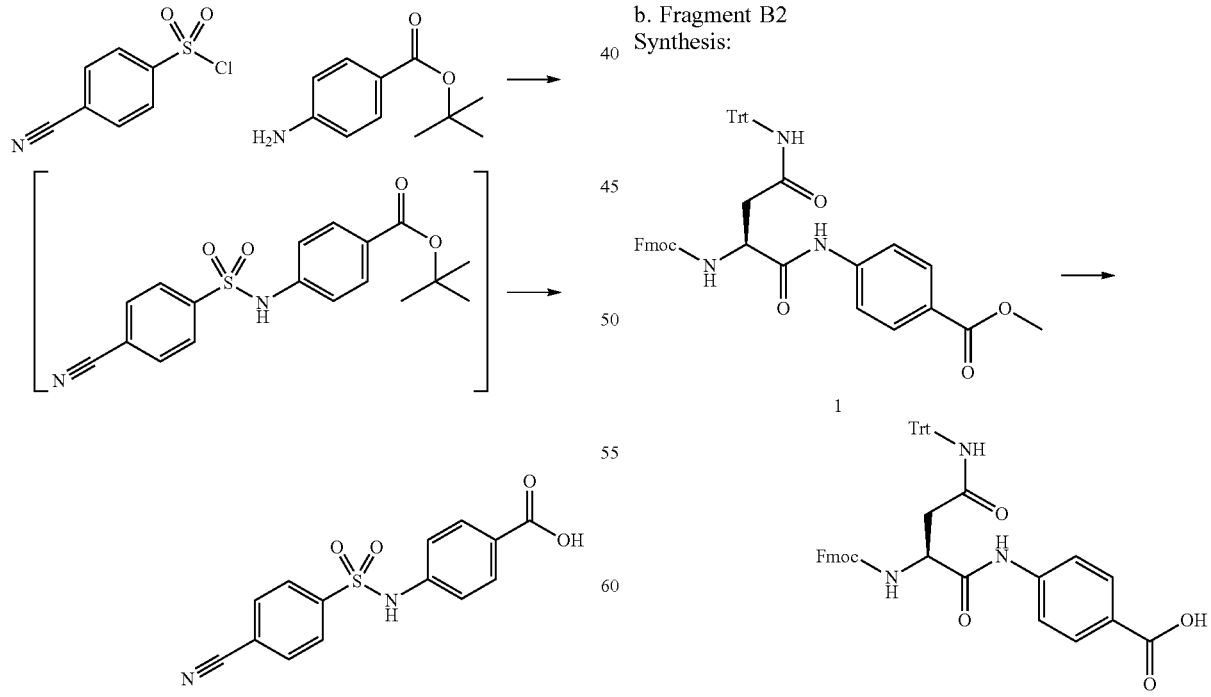

(S)-4-(2-((((9H-fluoren-9-yl)methoxy)carbonyl)amino)-4-oxo-4-(tritylamino)butanamido)benzoic acid

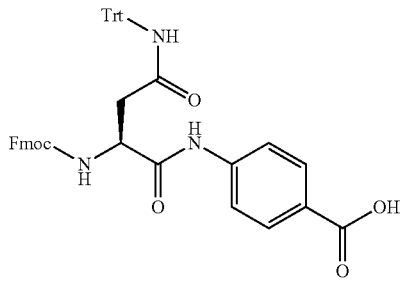

Methyl (S)-4-(2-((((9H-fluoren-9-yl)methoxy)carbonyl)amino)-4-oxo-4-(tritylamino)butan-amido)benzoate (1.0 g; 1.37 mmol), lithium iodide (1.8 g; 13.72 mmol) were mixed in EA (14 mL) and heated at 110° C. in for 12 h in a microwave synthesizer. Mixture was diluted with EA (100 mL) and HCL 1N (100 mL), organic phase washed with brine (100 mL), dried over sodium sulphate and reduced under vacuum. The residue was chromatographed on silica gel with a gradient 0-5% MeOH in DCM to give 0.74 g of a white solid (1.03 mmol; y=75%).

$^1$H NMR (500 MHz, DMSO) δ 12.70 (s, 1H), 10.41 (s, 1H), 8.62 (s, 1H), 7.90 (dd, J=8.1, 3.9 Hz, 4H), 7.80 (d, J=7.9 Hz, 1H), 7.77-7.70 (m, 4H), 7.42 (dd, J=13.7, 7.0 Hz, 2H), 7.34-7.26 (m, 2H), 7.25-7.14 (m, 15H), 4.49-4.41 (m, 1H), 4.36 (dd, J=10.4, 7.0 Hz, 1H), 4.30 (dd, J=10.4, 7.0 Hz, 1H), 4.23 (t, J=6.9 Hz, 1H), 2.75 (dd, J=14.6, 9.8 Hz, 1H), 2.66-2.58 (dd, J=14.0, 4.4 Hz, 1H).

$^{13}$C NMR (126 MHz, DMSO) δ 170.8, 168.4, 166.9, 155.8, 144.7, 143.8, 143.0, 140.7, 130.3, 128.6, 127.6, 127.4, 127.1, 126.3, 125.3, 125.2, 120.1, 118.6, 69.4, 65.8, 52.8, 46.7, 38.4.

HRMS (ESI) calculated for C45H38N3O6 (M+H$^+$) 716.2755, found 716.2745.

Marfey: 93.9% S enantiomer, 6.1% R enantiomer

For synthesis of fragment C1 see section 2.2c.

3.3 Assembling a. General Scheme fragment C1
+
fragment B2
→

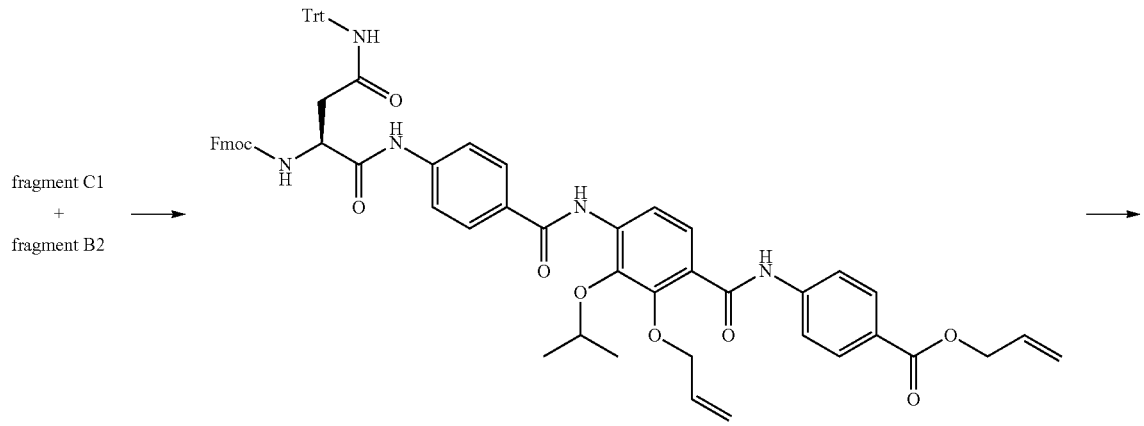

76

→

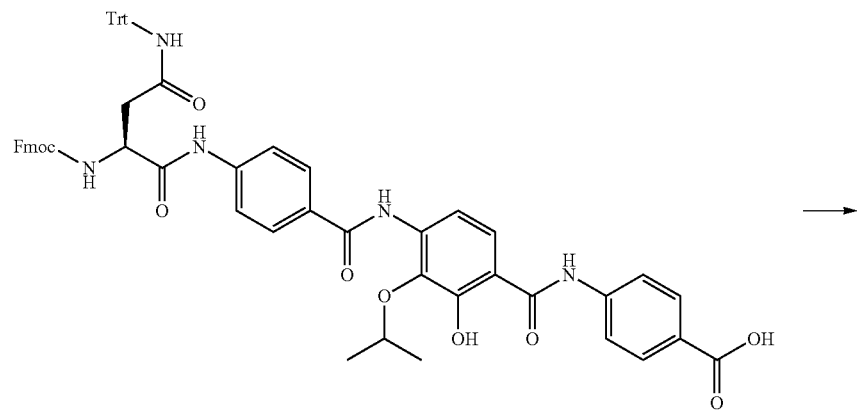

77

→

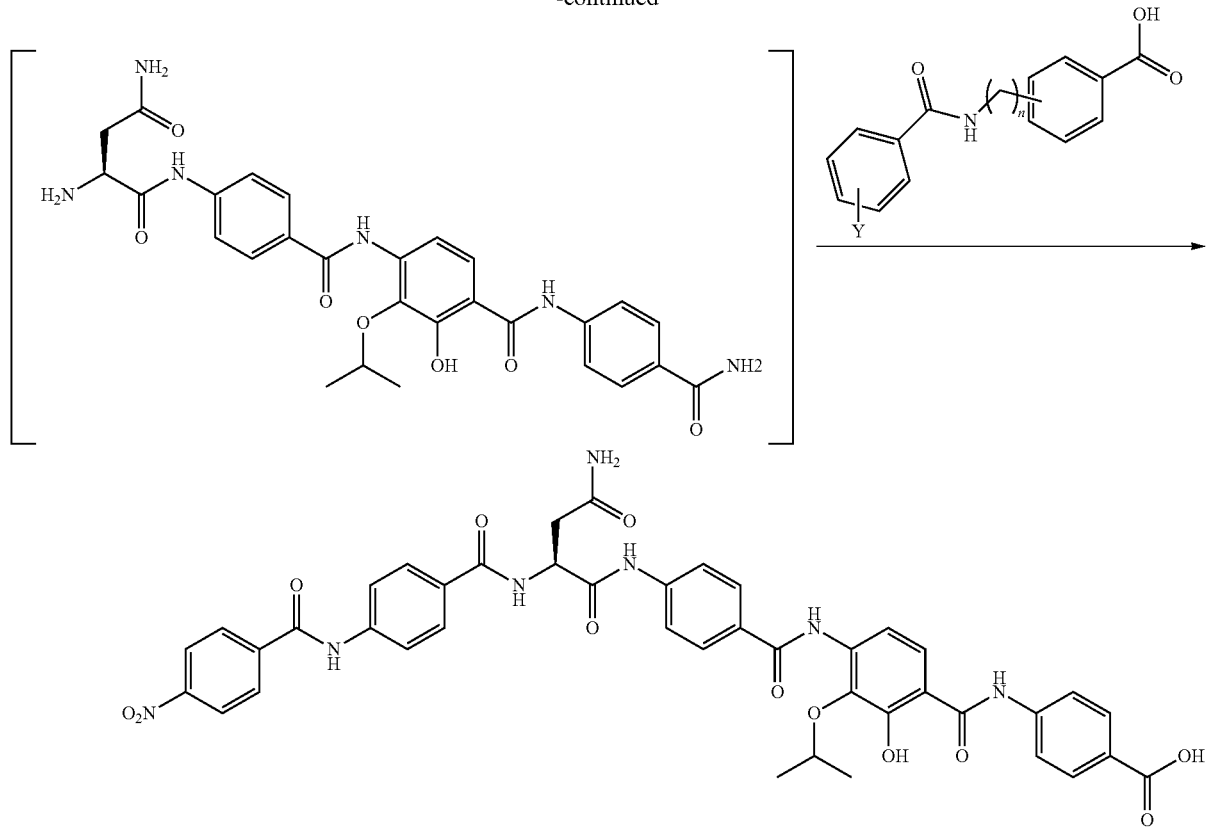

In the above Scheme, n represents 0 or m and Y represents H or R[6].

b. General Procedures

Trityl Deprotection

Compound was dissolved in DCM (M=0.1), Tips (3 eq.) followed by TFA (20%) were added at 0 C. Reaction stirred 2 h at r.t. then solved removed under vacuum, residue suspended and evaporated twice with DCM, finally triturated 3× with ice cold Pet. Et.

Fmoc Deprotection

Compound was dissolved in a 20% solution of diethylamine in acetonitrile (M=0.05-0.1), reaction stirred for 30 min. The solvent was removed under reduced pressure, the residue was dissolved in CH$_3$CN and evaporated twice.

c. A2+B2+C1

Synthesis:

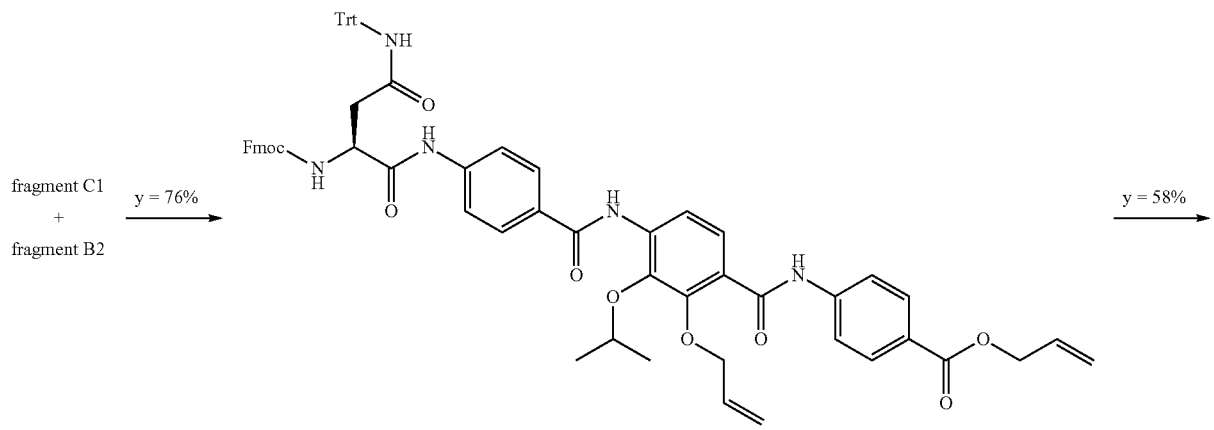

-continued
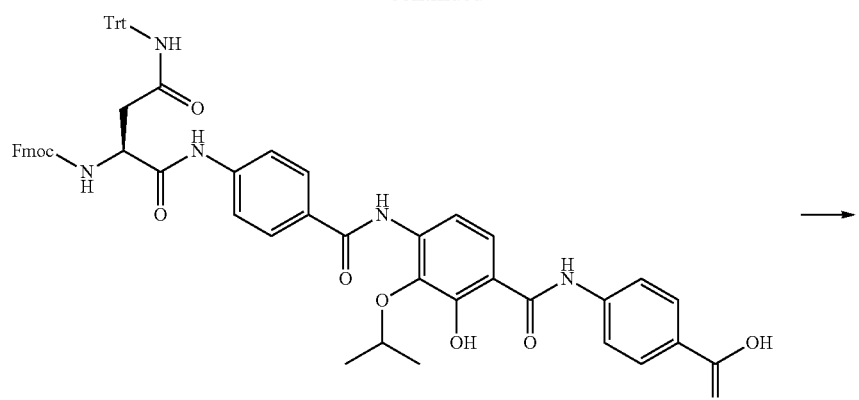
77
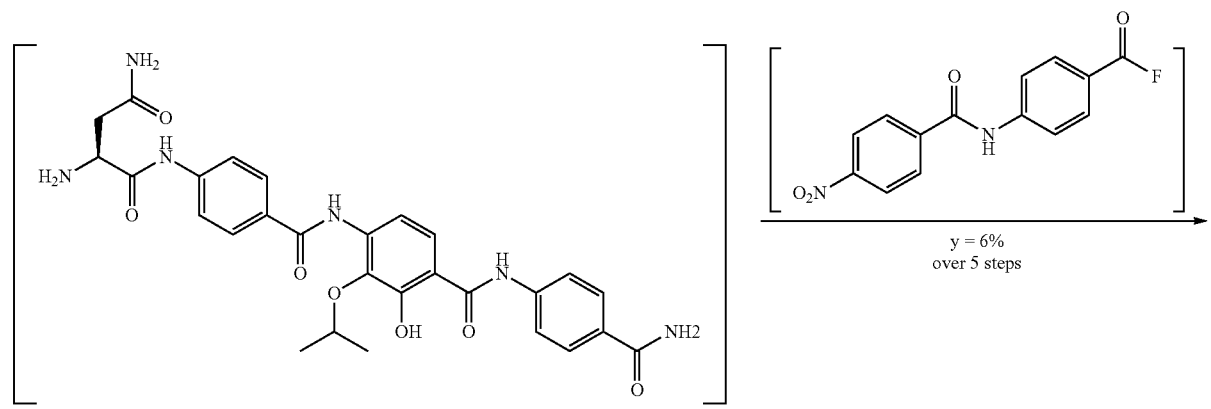
y = 6%
over 5 steps
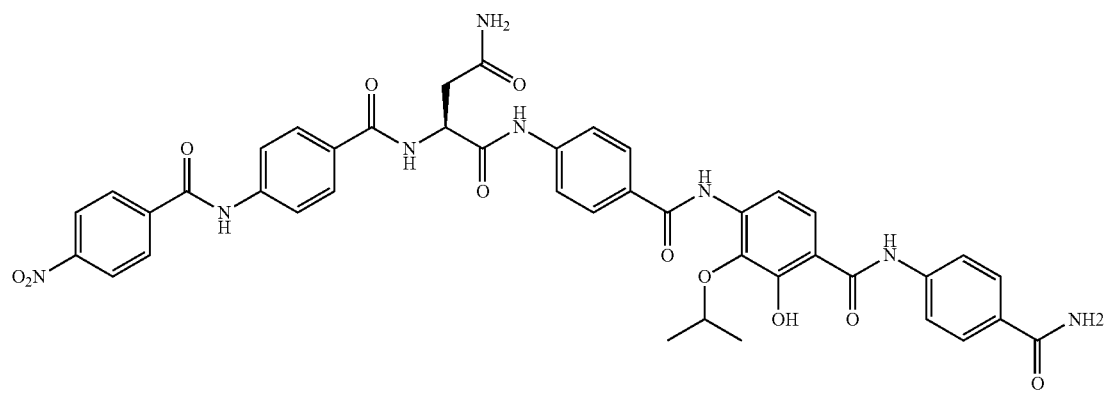
78 allyl (S)-4-(4-(4-(2-((((9H-fluoren-9-yl)methoxy)
carbonyl)amino)-4-oxo-4-(tritylamino)butanamido)
benzamido)-2-(allyloxy)-3-isopropoxybenzamido)
benzoate

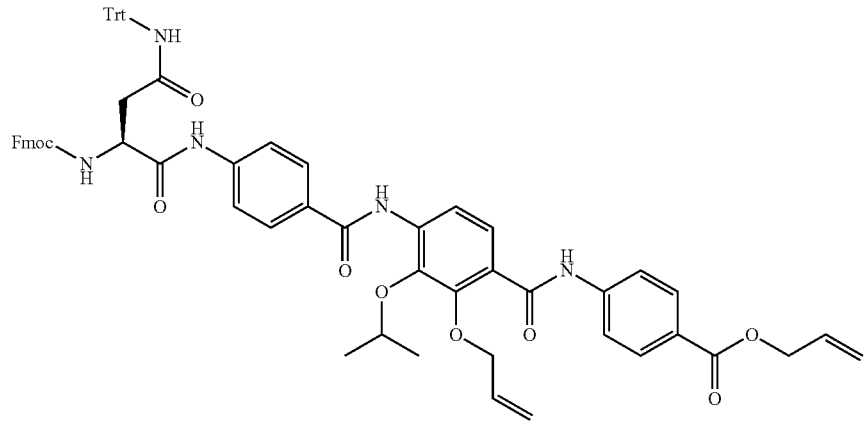

POCl₃ (1.92 mmol) as a solution in DCM (1:9) was added dropwise to a solution of allyl 4-(2-(allyloxy)-4-amino-3-isopropoxybenzamido)benzoate (0.315 g; 0.77 mmol) and (S)-4-(2-((((9H-fluoren-9-yl)methoxy)carbonyl)amino)-4-oxo-4-(tritylamino)butanamido)benzoic acid (1.37 g, 1.92 mmol) in THF (8 mL) and DCM (4 mL) at 0° C., followed by DiPEA (1.78 mL; 10.24 mmol) as a solution in DCM (1:1). Reaction stirred at r.t. for 6 h, quenched with HCL 1 N and ice, solvent partially reduced under vacuum and residue diluted with EA (200 mL) and HCl 1N (200 mL), organic phase washed with brine (200 mL) and dried over sodium sulphate. Solvent removed under vacuum, the crude residue was chromatographed on silica gel with a gradient EA 20-75% in Pet. Et to give 750 mg of a orange residue (0.68 mmol; 76%).

¹H NMR (700 MHz, DMSO) δ 10.58 (s, 1H), 10.42 (s, 1H), 9.53 (s, 1H), 8.64 (s, 1H), 7.99 (d, J=8.6 Hz, 2H), 7.93-7.85 (m, 4H), 7.81 (m, 4H), 7.78-7.72 (m, 3H), 7.42 (m, 3H), 7.35-7.26 (m, 3H), 7.26-7.14 (m, 15H), 6.04 (m, 2H), 5.39 (m, 2H), 5.24 (m, 2H), 4.80 (d, J=5.3 Hz, 2H), 4.62 (d, J=5.5 Hz, 2H), 4.52-4.44 (m, 2H), 4.37 (m, 1H), 4.31 (m, 1H), 4.24 (dd, J=14.3, 7.1 Hz, 1H), 2.77 (td, J=14.1, 9.9 Hz, 1H), 2.64 (td, J=15.1, 5.0 Hz, 1H), 1.26 (d, J=6.1 Hz, 6H).

¹³C NMR (176 MHz, DMSO) δ 170.8, 168.5, 166.9, 165.0, 164.7, 164.3, 155.8, 149.5, 144.7, 143.8, 143.5, 143.0, 142.6, 142.3, 140.7, 135.7, 133.7, 132.8, 130.3, 128.6, 127.4, 127.1, 126.3, 125.3, 125.2, 124.2, 123.6, 120.1, 119.0, 118.8, 118.6, 117.8, 117.8, 76.3, 74.3, 69.4, 65.8, 64.8, 52.9, 46.7, 30.4, 22.3.

HRMS (ESI) calculated for C68H62N5O10 (M+H⁺) 1108.4491, found 1108.4514.

(S)-4-(4-(4-(2-((((9H-fluoren-9-yl)methoxy)carbo-
nyl)amino)-4-oxo-4-(tritylamino)butanamido)ben-
zamido)-2-hydroxy-3-isopropoxybenzamido)benzoic
acid

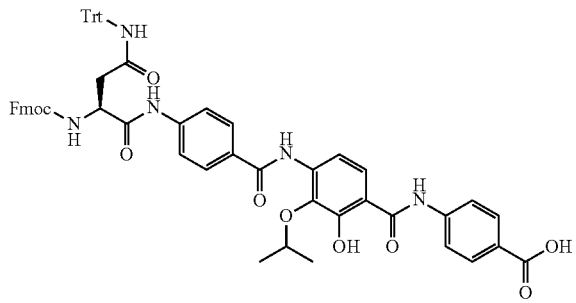

Phenyl silane (0.25 mL; 2.02 mmol) followed by Palladium-tetrakis(triphenylphosphine (138 mg; 0.12 mmol) was added to a solution of allyl (S)-4-(4-(4-(2-((((9H-fluoren-9-yl)methoxy)carbonyl)amino)-4-oxo-4-(tritylamino)butanamido)benzamido)-2-(allyloxy)-3-isopropoxybenzamido)benzoate (530 mg; 0.48 mmol) in THF (19.0 mL). Reaction stirred for 3 h, quenched by addition of few drops of acetic acid and filtered through celite. Solvent removed under reduced pressure, the crude residue was purified on silica gel with a gradient 0-10% MeOH in DCM +1% acetic acid to give 285 mg of a yellow solid (0.28 mmol; y=58%).

¹H NMR (500 MHz, DMSO) δ 12.36 (br, 1H), 12.30 (s, 1H), 10.61 (s, 1H), 10.43 (s, 1H), 9.41 (s, 1H), 8.64 (s, 1H), 8.00-7.93 (m, 3H), 7.90 (d, J=7.6 Hz, 2H), 7.86 (m, 3H), 7.81 (dd, J=8.0, 4.8 Hz, 3H), 7.75 (dd, J=7.4, 3.8 Hz, 2H), 7.71 (d, J=8.9 Hz, 1H), 7.42 (dd, J=12.6, 7.4 Hz, 2H), 7.35-7.27 (m, 3H), 7.27-7.15 (m, 15H), 4.58-4.51 (m, 1H), 4.48 (dd, J=14.2, 8.4 Hz, 1H), 4.38 (dd, J=10.4, 7.1 Hz, 1H), 4.31 (dd, J=10.5, 7.0 Hz, 1H), 4.24 (t, J=6.8 Hz, 1H), 2.78 (dd, J=14.5, 9.7 Hz, 1H), 2.64 (dd, J=14.2, 5.2 Hz, 1H), 1.27 (d, J=6.1 Hz, 6H).

¹³C NMR (176 MHz, DMSO) δ 172.0, 170.8, 168.5, 168.5, 166.9, 164.2, 155.8, 154.1, 144.7, 143.8, 142.4, 142.0, 140.7, 137.0, 136.3, 130.2, 128.6, 128.3, 127.7, 127.4, 127.1, 126.3, 126.3, 125.3, 125.2, 124.9, 122.8, 120.7, 120.1, 118.9, 112.4, 112.2, 74.9, 69.4, 65.8, 52.9, 46.7, 30.4, 22.3.

HRMS (ESI) calculated for C62H52N5O10 (M−H) 1026.3720, found 1026.3716.

Marfey: 96.2% S enantiomer, 3.8% R enantiomer 4-(4-nitrobenzamido)benzoyl fluoride

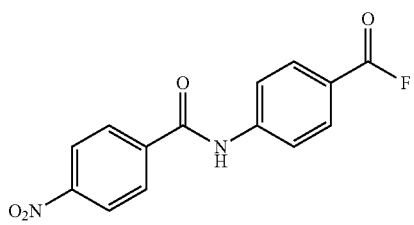 [SMILES: O=C(F)c1ccc(NC(=O)c2ccc([N+](=O)[O-])cc2)cc1]

Diethylaminosulfur trifluoride (13 μL; 0.095 mmol) was added was added at 0° C. to a mixture of 4-(4-nitrobenzamido)benzoic acid (50 mg; 0.17 mmol) in DCM (1.5 mL). Reaction stirred for 20 minutes, diluted with DCM and washed with ice water, organic phase dried over sodium sulphate and reduced under vacuum to give 4-(4-nitrobenzamido)benzoyl fluoride.

(S)—N1-(4-((4-((4-carbamoylphenyl)carbamoyl)-3-hydroxy-2-isopropoxyphenyl)carbamoyl)phenyl)-2-(4-(4-nitrobenzamido)benzamido)succinamide (78)

Diethylaminosulfur trifluoride (13 μL; 0.095 mmol) was added at 0° C. to a mixture of (S)-4-(4-(4-(2-((((9H-fluoren-9-yl)methoxy)carbonyl)amino)-4-oxo-4-(tritylamino)butanamido)benzamido)-2-hydroxy-3-isopropoxybenzamido) benzoic acid (65 mg; 0.063 mmol) in DCM (0.7 mL). Reaction stirred for 20 minutes, diluted with DCM (20 mL) and washed with ice water (20 mL), organic phase dried over sodium sulphate and reduced under vacuum.

The residue was dissolved in THF (0.5 mL), the solution added to a NH3 in MeOH 7N at 0° C. Reaction stirred 15 min then solvent removed under vacuum. Compound dissolved in DCM (2 mL), Tips (0.1 mL) followed by TFA (0.5 mL) were added at 0° C. Reaction stirred 2 h, solvent reduced under vacuum, residue dissolved again in DCM and evaporated twice. The crude thus obtained was dissolved in a 20% solution of diethylamine in acetonitrile (2 mL), solution stirred for 30 min. The solvent was removed under reduced pressure, the residue was dissolved in CH3CN and evaporated twice. Residue triturated three times with Pet. Et. And used in the coupling step.

A solution of 4-(4-nitrobenzamido)benzoyl fluoride (0.069 mmol) in THF (1 mL) added to a solution of the crude from the previous step (0.048 mmol) and DiPEA (42 μL; 0.24 mmol) in DCM/THF 1:1 (1 mL). Reaction stirred for 3 h and then purified by prep HPLC using method B, to obtain 3.2 mg of desired compound (0.0039 mmol; y=6%).

$^1$H NMR (700 MHz, DMSO) δ 12.40 (br, 1H), 10.79 (s, 1H), 10.58 (br, 1H), 10.46 (s, 1H), 9.35 (br, 1H), 8.68 (d, J=7.3 Hz, 1H), 8.41-8.37 (m, 2H), 8.23-8.19 (m, 2H), 7.94 (dd, J=8.9, 2.2 Hz, 4H), 7.90 (dd, J=8.6, 5.7 Hz, 5H), 7.82 (d, J=8.8 Hz, 3H), 7.78 (d, J=8.7 Hz, 2H), 7.66 (br, 1H), 7.40 (s, 1H), 7.28 (br, 1H), 6.99 (s, 1H), 4.93 (dd, J=14.0, 7.2 Hz, 1H), 4.58 (br, 1H), 2.69 (d, J=7.7 Hz, 2H), 1.26 (d, J=6.1 Hz, 6H).

$^{13}$C NMR (176 MHz, DMSO) δ 171.3, 170.7, 168.4, 167.3, 165.8, 164.2, 164.1, 149.3, 142.5, 141.5, 140.3, 136.4, 129.3, 129.2, 128.6, 128.2, 123.6, 122.8, 120.5, 119.6, 118.9, 51.6, 36.8, 22.3.

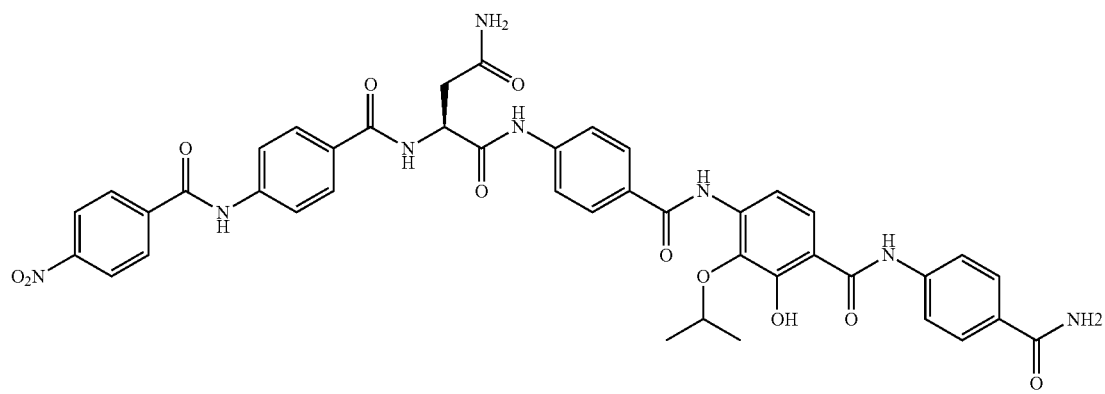 [SMILES: CC(C)Oc1c(NC(=O)c2ccc(NC(=O)[C@H](CC(N)=O)NC(=O)c3ccc(NC(=O)c4ccc([N+](=O)[O-])cc4)cc3)cc2)ccc(C(=O)Nc2ccc(C(N)=O)cc2)c1O]

HRMS (ESI) calculated for C42H37N8O11 (M−H) 829.2587, found 829.2588.

d. Analogs Synthesized Modifying Building Block A2

Building block A2 could be commercially available or synthesized as described in section 3.2a.

Synthesis:
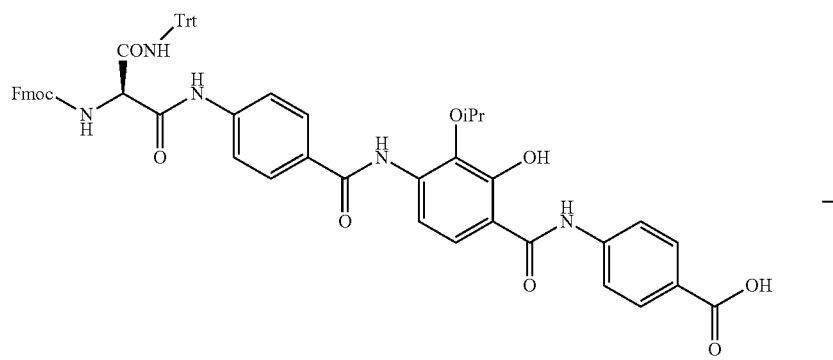
77
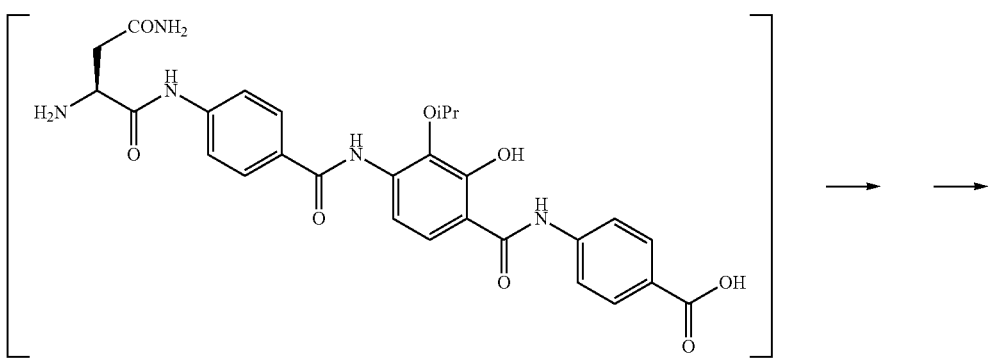
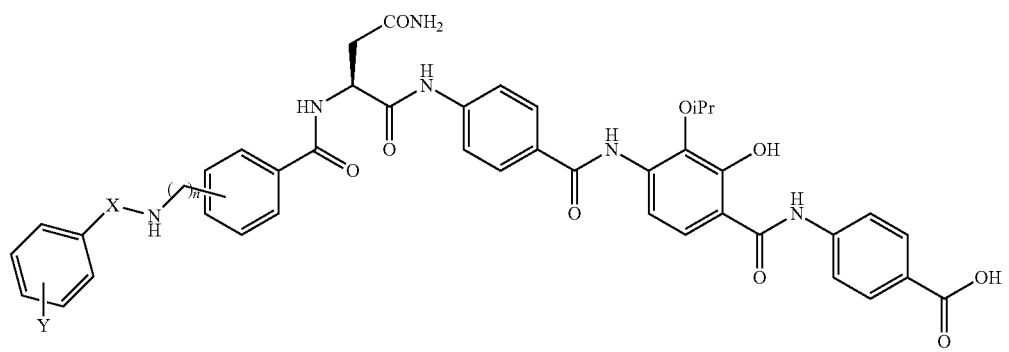
In the above formula, n represents 0 or m, Y represents H or $R^6$ and X represents CO or $SO_2$.
Starting from intermediate 77, after Trityl and Fmoc deprotection (see general procedures section 3.3b), crude amine was coupled to a desired carboxylic acid (fragment A2) to obtain the following compounds.

(S,E)-4-(4-(4-(4-amino-4-oxo-2-(4-(phenyldiazenyl)benzamido)butanamido)benzamido)-2-hydroxy-3-isopropoxybenzamido)benzoic acid

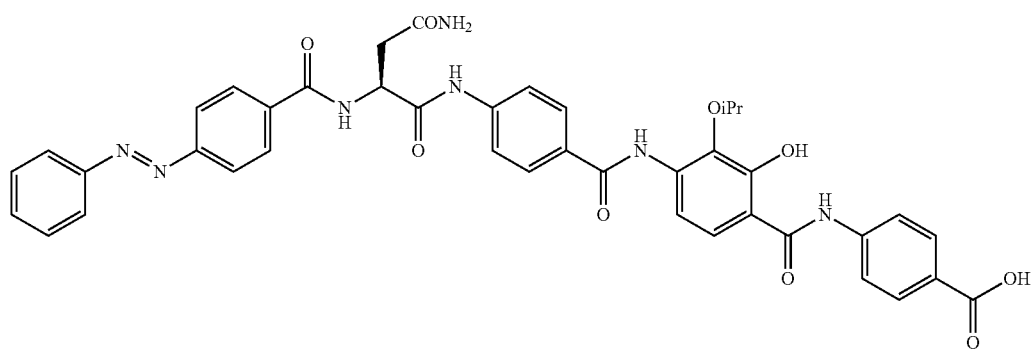

79

Carboxylic acid (0.039 mmol) was mixed with HBTU (0.039 mmol) in DMF (0.1 mL), to this solution DiPEA (0.117 mmol) was added. Reaction stirred 15 min. then added to the crude amine (0.019 mmol). Reaction stirred overnight and purified by preparative HPLC with a gradient 10-95% $CH_3CN$ in water 10 mM $NH_4HCO_3$ in 40 min. to give 2.5 mg of desired product (0.0032 mmol; y=17%).

$^1$H NMR (700 MHz, DMSO) δ 12.79 (br, 1H), 12.29 (br, 1H), 10.62 (br, 1H), 10.49 (s, 1H), 9.36 (br, 1H), 8.94 (d, J=7.3 Hz, 1H), 8.14-8.10 (m, 2H), 8.01-7.98 (m, 2H), 7.98-7.92 (m, 6H), 7.87-7.81 (m, 5H), 7.66 (br, 1H), 7.64-7.60 (m, 3H), 7.41 (s, 1H), 7.01 (s, 1H), 4.97 (dd, J=13.9, 7.3 Hz, 1H), 4.58 (br, 1H), 2.74-2.70 (m, 2H), 1.26 (d, J=6.1 Hz, 6H).

$^{13}$C NMR (176 MHz, DMSO) δ 171.2, 170.5, 168.4, 166.9, 165.6, 164.1, 153.4, 151.9, 142.4, 136.4, 136.0, 132.0, 130.2, 129.6, 128.9, 128.2, 122.9, 122.8, 122.3, 120.5, 118.9, 51.7, 36.7, 22.3.

HRMS (ESI+): m/z for $C_{41}H_{38}N_7O_9$ [M+H]$^+$: calculated: 772.2726, found: 772.2724.

(S)-4-(4-(4-(4-amino-2-(3-(4-cyanobenzamido)benzamido)-4-oxobutanamido)benzamido)-2-hydroxy-3-isopropoxybenzamido)benzoic acid

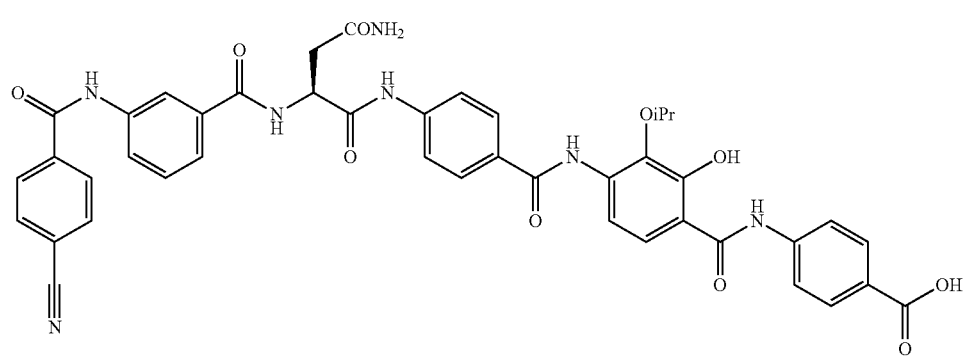

110

The carboxylic acid coupling partner (71) was activated to the corresponding pentafluorophenyl ester as reported in DOI: 10.1002/ange.201705387.

Activated ester (17.3 mg; 0.04 mmol) was dissolved in DMF (0.1 mL) and added at 0° C. to a stirred solution of crude amine (0.02 mmol) and DiPEA (18 μL; 0.10 mmol). Reaction stirred three hours at r.t. then diluted with EA and a solution of ice cold HCl, organic phase washed with brine and evaporated under vacuum. Residue purified by preparative HPLC with a gradient 10-95% $CH_3CN$ in water 10 mM $NH_4HCO_3$ in 40 min. to give 0.9 mg of desired product (0.0011 mmol; y=5%).

$^1$H NMR (700 MHz, DMSO) δ 15.36 (br, 1H), 10.70 (s, 1H), 10.48 (s, 1H), 8.87 (s, 1H), 8.83 (d, J=6.6 Hz, 1H), 8.54 (s, 1H), 8.25 (s, 1H), 8.15 (d, J=8.3 Hz, 2H), 8.04 (d, J=8.3 Hz, 2H), 8.01 (d, J=7.9 Hz, 1H), 7.82 (dd, J=22.5, 8.7 Hz, 4H), 7.76 (d, J=8.3 Hz, 2H), 7.68 (d, J=7.8 Hz, 1H), 7.57 (d, J=7.7 Hz, 2H), 7.49 (t, J=7.9 Hz, 1H), 7.44 (d, J=8.7 Hz, 2H), 7.08 (d, J=8.7 Hz, 1H), 6.97 (s, 1H), 5.02 (dt, J=12.3, 6.1 Hz, 1H), 4.93 (dd, J=13.9, 7.3 Hz, 1H), 2.72-2.68 (m, 2H), 1.19 (d, J=6.1 Hz, 6H).

$^{13}$C NMR (176 MHz, DMSO) δ 171.3, 170.5, 166.2, 165.4, 165.2, 164.2, 163.1, 142.0, 138.8, 137.5, 134.6, 134.0, 132.5, 129.7, 129.5, 128.6, 127.6, 123.7, 123.3, 122.9, 120.1, 119.0, 118.3, 117.6, 116.0, 113.9, 100.7, 70.3, 51.7, 36.8, 22.7.

(S)-4-(4-(4-(4-amino-2-(4-((4-cyanobenzamido)methyl)benzamido)-4-oxobutanamido)benzamido)-2-hydroxy-3-isopropoxybenzamido)benzoic acid

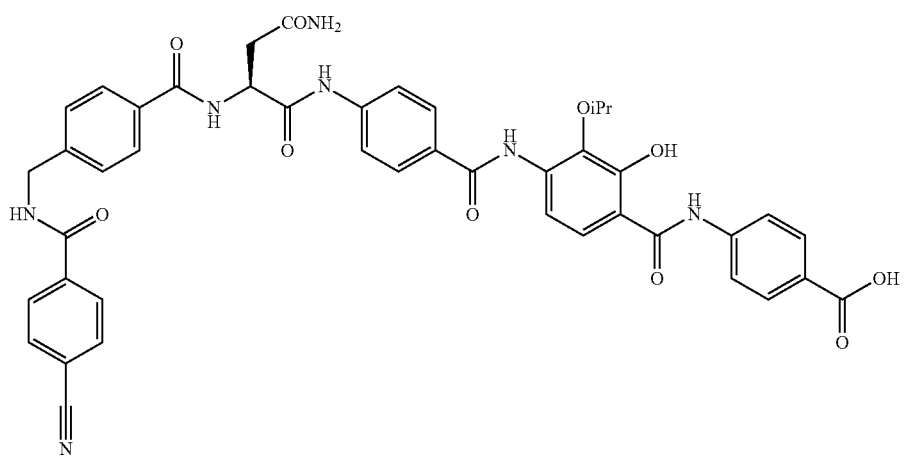

111

The carboxylic acid coupling partner (72) was activated to the corresponding pentafluorophenyl ester as reported in DOI: 10.1002/ange.201705387.

Activated ester (18.0 mg; 0.04 mmol) was dissolved in DMF (0.1 mL) and added at 0° C. to a stirred solution of crude amine (0.02 mmol) and DiPEA (18 µL; 0.10 mmol). Reaction stirred three hours at r.t. then diluted with EA and a solution of ice cold HCl, organic phase washed with brine and evaporated under vacuum. Residue purified by preparative HPLC with a gradient 10-95% CH$_3$CN in water 10 mM NH$_4$HCO$_3$ in 40 min. to give 3.2 mg of desired product (0.0039 mmol; y=19%).

$^1$H NMR (700 MHz, DMSO) δ 12.49 (br, 1H), 10.44 (s, 1H), 9.36 (t, J=5.9 Hz, 1H), 9.26 (s, 1H), 8.69 (d, J=7.3 Hz, 1H), 8.05 (d, J=8.4 Hz, 2H), 7.98 (d, J=8.4 Hz, 2H), 7.93 (dd, J=13.9, 8.6 Hz, 4H), 7.88-7.78 (m, 6H), 7.75 (d, J=7.8 Hz, 1H), 7.55 (br, 1H), 7.43 (d, J=8.2 Hz, 2H), 7.38 (s, 1H), 6.98 (s, 1H), 4.91 (dd, J=13.9, 7.3 Hz, 1H), 4.65 (br, 1H), 4.56 (d, J=5.9 Hz, 2H), 2.68 (dd, J=6.6, 4.4 Hz, 2H), 1.24 (d, J=6.1 Hz, 6H).

$^{13}$C NMR (176 MHz, DMSO) δ 171.3, 170.6, 168.2, 167.0, 166.1, 165.0, 163.9, 142.8, 142.4, 138.2, 136.6, 132.5, 130.3, 128.6, 128.1, 127.6, 127.0, 123.0, 120.1, 118.9, 118.3, 113.7, 51.6, 42.6, 36.8, 22.4.

(S)-4-(4-(4-(4-amino-2-(4-(2-(4-cyanobenzamido)ethyl)benzamido)-4-oxobutanamido)benzamido)-2-hydroxy-3-isopropoxybenzamido)benzoic acid

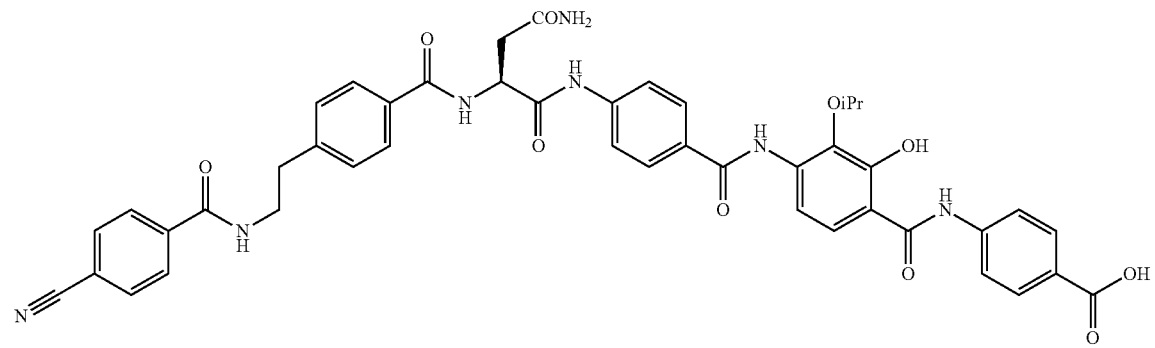

112

The carboxylic acid coupling partner (73) was activated to the corresponding pentafluorophenyl ester as reported in DOI: 10.1002/ange.201705387.

Activated ester (18.4 mg; 0.04 mmol) was dissolved in DMF (0.1 mL) and added at 0° C. to a stirred solution of crude amine (0.02 mmol) and DiPEA (18 µL; 0.10 mmol). Reaction stirred three hours at r.t. then diluted with EA and a solution of ice cold HCl, organic phase washed with brine and evaporated under vacuum. Residue purified by preparative HPLC with a gradient 10-95% CH$_3$CN in water 10 mM NH$_4$HCO$_3$ in 40 min. to give 5.3 mg of desired product (0.0063 mmol; y=32%).

$^1$H NMR (700 MHz, DMSO) δ 15.34 (s, 1H), 10.53 (s, 1H), 8.85 (m, 3H), 7.95 (s, 4H), 7.82 (ddd, J=25.7, 15.6, 8.3 Hz, 8H), 7.57 (d, J=8.4 Hz, 2H), 7.47 (s, 1H), 7.44 (d, J=8.7 Hz, 1H), 7.35 (d, J=8.2 Hz, 2H), 7.08 (d, J=8.7 Hz, 1H), 6.96 (s, 1H), 5.02 (dt, J=12.3, 6.1 Hz, 1H), 4.90 (dd, J=13.8, 7.6

Hz, 1H), 3.54 (dd, J=13.2, 6.9 Hz, 2H), 2.92 (t, J=7.1 Hz, 2H), 2.68 (ddd, J=20.6, 15.1, 7.1 Hz, 2H), 1.19 (d, J=6.0 Hz, 6H).
$^{13}$C NMR (176 MHz, DMSO) δ 171.3, 170.7, 166.9, 166.1, 165.3, 164.8, 163.1, 143.1, 142.0, 141.7, 138.5, 137.5, 134.0, 132.4, 131.9, 129.7, 129.5, 128.6, 128.0, 127.6, 127.5, 124.2, 123.7, 119.0, 118.3, 117.6, 116.0, 113.5, 100.6, 70.3, 51.8, 40.7, 36.9, 34.7, 22.7.
4. Synthesis 3
4.1 Retrosynthetic Disconnection
fragments
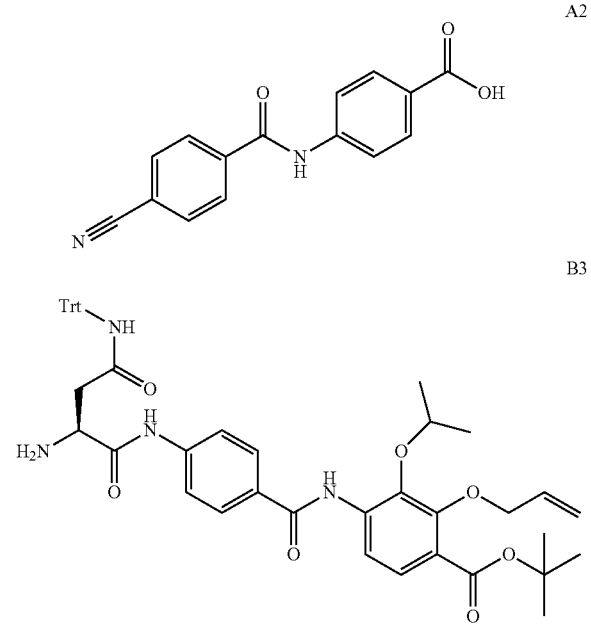
In the above formula, R represents group A.
4.2 Building Blocks Synthesis
For synthesis of fragment A2 see section 3.2a.
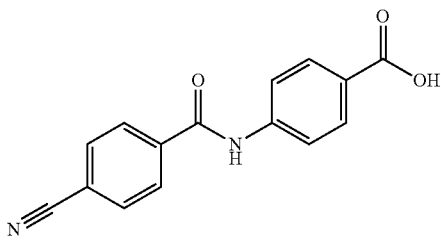
a. Fragment B3:
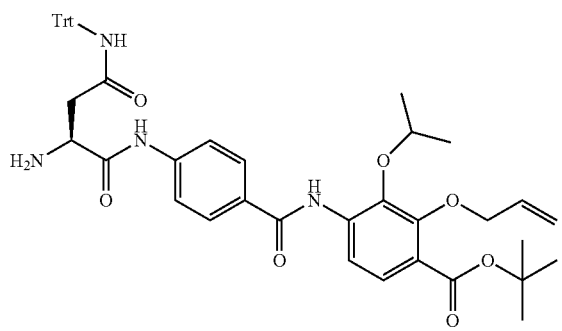
Synthesis:
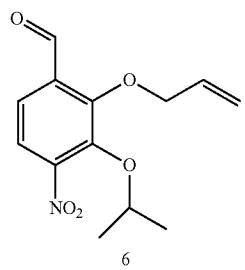
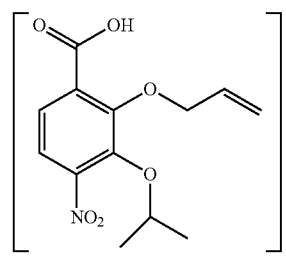
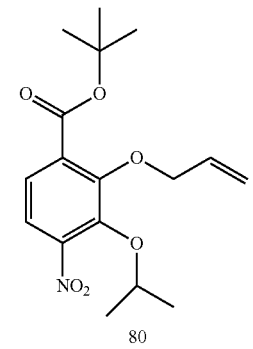
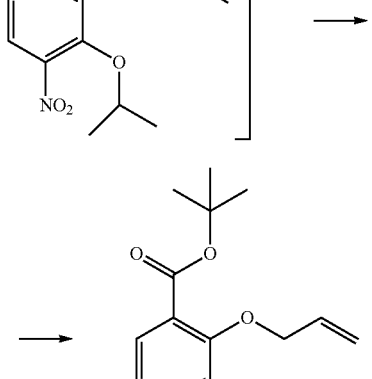

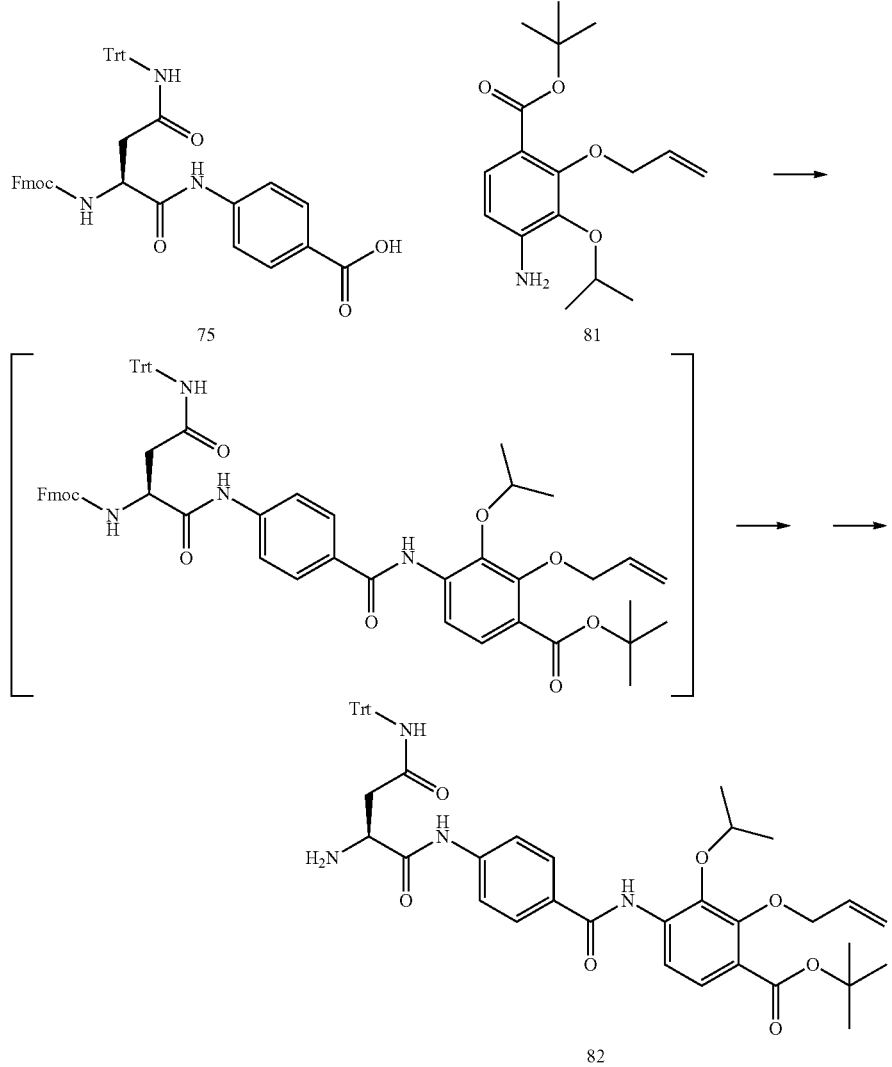

tert-butyl 2-(allyloxy)-3-isopropoxy-4-nitrobenzoate

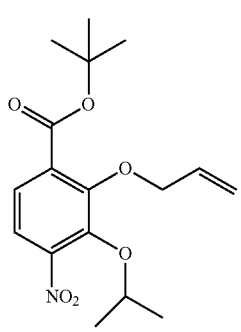

2-Alloxy-3-isopropoxy-4-nitrobenzoic acid (2.18 g; 7.75 mmol), DMAP (95 mg; 0.78 mmol) and tert-butyl alcohol (7.3 mL; 77.5 mmol) were dissolved in 17 mL of dry DCM. The stirred solution was cooled to 0° C. and DCC (1.76 g; 7.75 mmol) was added in small portions. Stirring continued at 0° C. for 10 minutes, before the mixture was allowed to warm to room temperature and stirred for an additional 5 hours. The precipitate was removed by filtration.

The clear solution was diluted with ethyl acetate (100 mL), washed with 0.5M HCl (2×100 mL) and saturated aqueous $NaHCO_3$ solution (100 mL) and dried over anhydrous $Na_2SO_4$. The solvent was removed by distillation at reduced pressure and the crude product was purified by flash chromatography (petroleum ether/ethyl acetate) affording tert-butyl 2-allyloxy-3-isopropoxy-4-nitrobenzoate as a pale yellow oil (1.85 g; 5.48 mmol; 71%).

$^1$H-NMR (500 MHz, DMSO): δ (ppm)=7.67 (d, J=8.5 Hz, 1H), 7.44 (d, J=8.5 Hz, 1H), 6.06 (ddt, J=17.2, 10.7, 5.4 Hz, 1H), 5.40 (dq, J=17.2, 1.5 Hz, 1H), 5.28 (dq, J=10.5, 1.5 Hz, 1H), 4.62 (hept, J=6.2 Hz, 1H), 4.57 (dt, J=5.4, 1.5 Hz, 2H), 1.54 (s, 9H), 1.19 (d, J=6.2 Hz, 6H).

$^{13}$C-NMR (126 MHz, DMSO-$d_6$): δ (ppm)=164.0, 150.8, 147.3, 143.8, 133.1, 132.6, 124.2, 119.2, 117.8, 82.5, 77.2, 74.2, 27.6, 22.0.

HRMS (ESI+): m/z for $C_{17}H_{23}NO_6$ [M+Na]$^+$: calculated: 360.1418, found: 360.1419.

tert-butyl 2-(allyloxy)-4-amino-3-isopropoxybenzoate

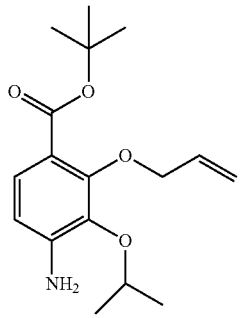 [SMILES: C=CCOc1c(C(=O)OC(C)(C)C)ccc([N+](=O)[O-])c1OC(C)C]

To a stirred solution of tert-Butyl 2-allyloxy-3-isopropoxy-4-nitrobenzoate (1.71 g; 5.07 mmol) in THF (9.0 mL) and EtOH (7.2 mL) was added glacial acidic acid (1.8 mL). The solution was cooled to 0° C. and zinc dust (3.31 g; 50.7 mmol) was added in small portions. The mixture was stirred at room temperature for 30 minutes, before the solid was filtered off. The filtrate was diluted with saturated aqueous NaHCO$_3$ solution (50 mL) and extracted with ethyl acetate (3×50 mL). The combined organic extracts were dried over Na$_2$SO$_4$ and the solvent was removed by distillation at reduced pressure. The crude material was purified by flash chromatography (petrol ether/ethyl acetate) and dried at high vacuum yielding tert-butyl 2-allyloxy-4-amino-3-isopropoxybenzoate as a white solid (1.39 g; 4.53 mmol; 89%).

$^1$H-NMR (500 MHz, DMSO): δ (ppm)=7.20 (d, J=8.5 Hz, 1H), 6.43 (d, J=8.5 Hz, 1H), 6.06 (ddt, J=17.3, 10.5, 5.2 Hz, 1H), 5.48 (s, 2H), 5.35 (dd, J=17.3, 1.8 Hz, 1H), 5.20 (dd, J=10.5, 1.8 Hz, 1H), 4.45-4.38 (m, 3H), 1.48 (s, 9H), 1.20 (d, J=6.1 Hz, 6H).

$^{13}$C-NMR (126 MHz, DMSO): δ (ppm)=164.9, 152.4, 147.7, 136.1, 134.8, 126.9, 116.2, 113.6, 109.1, 79.2, 74.0, 73.3, 28.0, 22.2.

HRMS (ESI+): m/z for C$_{17}$H$_{25}$NO$_4$ [M+H]$^+$: calculated: 308.1852, found: 308.1856.

tert-butyl (S)-2-(allyloxy)-4-(4-(2-amino-4-oxo-4-(tritylamino)butanamido)benzamido)-3-isopropoxybenzoate

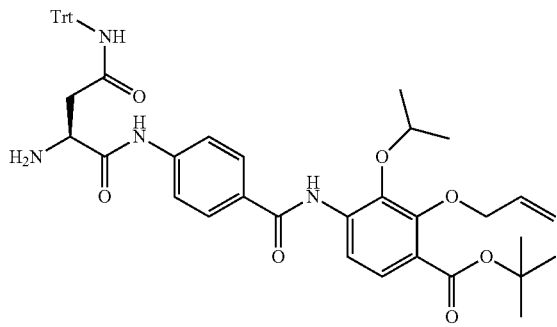

A stirred solution of (S)-4-(2-((((9H-fluoren-9-yl)methoxy)carbonyl)amino)-4-oxo-4-(tritylamino)butanamido)benzoic acid (1.29 g; 1.81 mmol) and tert-butyl 2-Allyloxy-4-amino-3-isopropoxybenzoate (327 mg; 1.06 mmol) in 10.5 mL of dry DCM and 10.5 mL of dry THF under N$_2$ atmosphere was cooled to 0° C. POCl$_3$ (0.17 mL; 1.81 mmol) and DIPEA (0.93 mL; 5.31 mmol) were added dropwise and the reaction mixture was allowed to warm to room temperature after stirring for 10 minutes. The solution was stirred for 6.5 hours before the reaction was quenched by addition of water (20 mL). The mixture was diluted with brine (50 mL) and extracted with ethyl acetate (3×50 mL). The organic extracts were combined, washed with 1N HCl (50 mL), saturated aqueous NaHCO$_3$ solution (50 mL) and brine (50 mL) and dried over anhydrous Na$_2$SO$_4$. The solvent was removed by distillation at reduced pressure.

The crude reaction product was then dissolved in MeCN (40 mL) and diethylamine (10 mL) was added. The solution was stirred at room temperature for 20 minutes before the solvent was removed by distillation at reduced pressure. Purification by flash chromatography afforded the desired product as an off-white solid (545 mg; 0.70 mmol; 66%).

$^1$H-NMR (500 MHz, DMSO): δ (ppm)=9.45 (s, 1H), 9.23 (s, 1H), 7.97 (d, J=8.7 Hz, 2H), 7.83 (pseudo t, J=8.4 Hz, 3H), 7.29-7.16 (m, 16H), 6.10 (ddt, J=17.2, 10.5, 5.3 Hz, 1H), 5.40 (dq, J=17.2, 1.8 Hz, 1H), 5.26 (dq, J=10.5, 1.5 Hz, 1H), 4.54 (dt, J=5.4, 1.5 Hz, 2H), 4.47 (hept, J=6.1 Hz, 1H), 3.73 (dd, J=8.2, 5.1 Hz, 1H), 2.64-2.53 (m, 2H), 1.53 (s, 1H), 1.23 (d, J=6.1 Hz, 6H).

$^{13}$C-NMR (126 MHz, DMSO): δ (ppm)=173.8, 169.9, 164.8, 164.2, 150.1, 144.9, 142.4, 136.5, 134.1, 128.5, 128.4, 128.2, 127.5, 126.3, 124.9, 123.9, 118.7, 118.0, 116.9, 81.0, 76.1, 73.8, 69.3, 52.9, 41.0, 27.8, 22.3.

HRMS (ESI+): m/z for C$_{47}$H$_{50}$N$_4$O$_7$ [M+H]$^+$: calculated: 783.3752, found: 783.3757.

b. Fragment C5

It can be any aromatic or aliphatic amine, which could be synthesized or purchased.

Amine Synthesized:

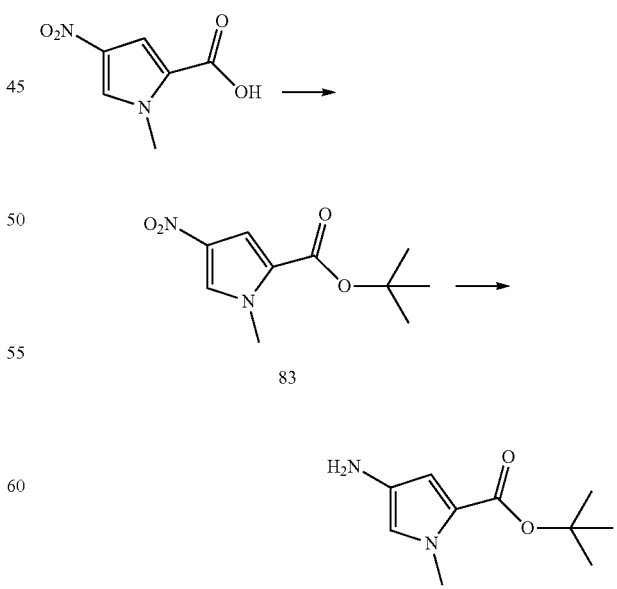

tert-butyl 1-methyl-4-nitro-1H-pyrrole-2-carboxylate

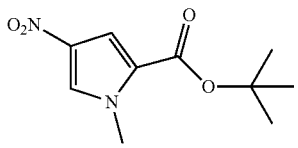

1-methyl-4-nitro-1H-pyrrole-2-carboxylic acid (500 mg; 2.94 mmol) and DMAP (36 mg; 0.29 mmol) were suspended in a mixture of dry DCM (6.0 mL) and tBuOH (2.8 mL; 29.4 mmol) under a nitrogen atmosphere. The mixture was cooled to 0° C. and DCC (667 mg, 3.23 mmol) was added in small portions. The mixture was stirred for 5 minutes at 0° C. before being allowed to warm to room temperature. Stirring continued overnight and the solid was filtered off. The solvent was removed by distillation at reduced pressure and the crude product was purified by flash chromatography (petroleum ether/ethyl acetate) yielding tert-butyl 1-methyl-4-nitro-1H-pyrrole-2-carboxylate as a white solid (550 mg; 2.43 mmol; 83%).

$^1$H-NMR (500 MHz, DMSO): δ (ppm)=8.22 (dd, J=2.1, 0.6 Hz, 1H), 7.22 (d, J=2.1 Hz, 1H), 3.90 (d, J=0.6 Hz, 3H), 1.25 (s, 9H).

$^{13}$C-NMR (126 MHz, DMSO): δ (ppm)=158.7, 133.9, 129.2, 124.0, 111.4, 81.7, 37.6, 27.8.

HRMS (ESI+): m/z for $C_{10}H_{14}N_2O_4$ [M+H]+: calculated: 227.1026, found: 227.1033.

tert-butyl 4-amino-1-methyl-1H-pyrrole-2-carboxylate

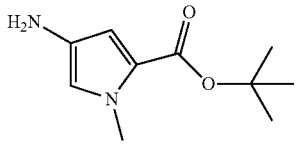 [SMILES: Cn1cc([N+](=O)[O-])cc1C(=O)OC(C)(C)C]

tert-butyl 1-methyl-4-nitro-1H-pyrrole-2-carboxylate (200 mg, 0.88 mmol, 1.0 eq.) was dissolved in dry MeOH (30 mL) under a nitrogen atmosphere. The solution was purged with nitrogen for 10 minutes, before Pd/C (10% wt, 100 mg) was added. The mixture was then purged with hydrogen for 5 minutes and set under a hydrogen atmosphere. After stirring overnight, the mixture was filtered through a pad of celite and the solvent was removed by distillation at reduced pressure. The product was dried at high vacuum affording the desired compound as a yellow oil (160 mg; 0.81 mmol; 92%). The product was stored under nitrogen at −20° C. to prevent decomposition.

$^1$H-NMR (500 MHz, DMSO): δ (ppm)=6.33 (d, J=2.2 Hz, 1H), 6.14 (d, J=2.2 Hz, 1H), 3.88 (br s, 2H), 3.66 (s, 3H), 1.46 (s, 9H). 13C-NMR (126 MHz, DMSO): δ (ppm)=160.0, 132.2, 120.1, 116.1, 106.8, 79.0, 35.8, 28.1.

HRMS (ESI+): m/z for $C_{10}H_{16}N_2O_2$ [M+H]+: calculated: 197.1285, found: 197.1289.

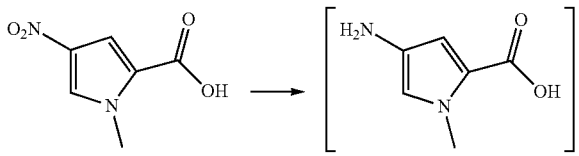

1-methyl-4-nitro-1H-pyrrole-2-carboxylic acid (170 mg, 1.00 mmol, 1.0 eq.) was dissolved in dry DMF (5.0 mL) under a nitrogen atmosphere. The solution was purged with nitrogen for 15 minutes before Pd/C (80 mg, 10% wt) was added. The mixture was then purged with hydrogen for 5 minutes, set under a hydrogen atmosphere and stirred overnight. The mixture was then passed through a syringe filter (CHROMAFIL® PET-45/15, 45 μm pore size, 15 mm diameter) and 730 μL of this solutions were used directly for the synthesis of compound 88 following the general coupling conditions (section 4.3b) under a nitrogen atmosphere.

4.3 Building Blocks Synthesis a. General Scheme

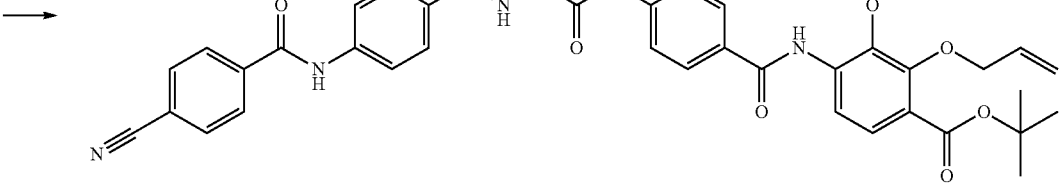

fragment A2 + fragment B3 →

-continued

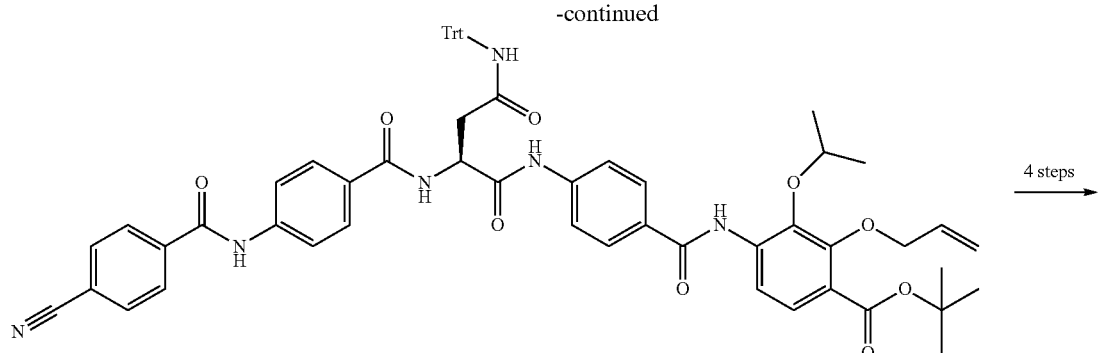

85

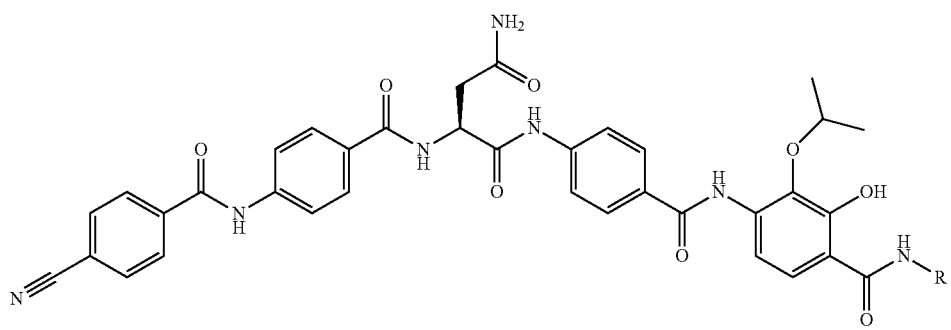

In the above formula, R represents group A.

b. General Procedures

Deprotection

Compound 85 (20.0 mg-30.0 mg, 19.4 µmol-29.1 µmol, 1.0 eq.) was dissolved in 800 µL of dry DCM. TIPS (12 µL-18 µL, 38.8 µmol-58.2 µmol, 2.0 eq.) was added and the solution was cooled to 0° C. 200 µL of TFA were added to the mixture and the solution was allowed to warm to room temperature and stirred for 1.5 hours. The solvent was removed by distillation at reduced pressure. The residue was taken up in 1 mL of DCM and the solvent was evaporated again. This procedure was repeated twice.

Coupling

HATU (6.2 mg-11.1 mg, 19.4 µmol-29.1 µmol, 1.0 eq.), DMF (300 µL) and DIPEA (17 µL-25 µL, 97.0 µmol-146 µmol, 5.0 eq.) were then added to the residue. The solution was stirred at room temperature for 30 minutes before a solution of the amine (5.0 eq., 3.0 eq. in case of the presence of a free acid moiety) in DMF (300 µL) was added. The mixture was then stirred until completion. The reaction mixture was quenched by addition of 25 mL of 1M HCl (or 25 mL of water in the presence of a pyridine or amine moiety in the product), diluted with brine (25 mL) and extracted with ethyl acetate (3×25 mL). The combined organic extracts were washed with water (25 mL) and brine (25 mL) and dried over $Na_2SO_4$. The solvent was removed by distillation at reduced pressure.

Allyl Deprotection

The residue was then dissolved in dry THF (1.0 mL) under a nitrogen atmosphere. $PhSiH_3$ (4.8 µL-6.3 µL, 38.3 µmol-58 µmol, 2.0 eq.) and a freshly prepared solution of $Pd(PPh_3)_4$ (5.6 mg-8.4 mg, 4.9-7.3 µmol, 0.25 eq.) in 0.9 mL of dry THF were added and the reaction mixture was stirred for 3 hours. The solvent was then removed by distillation at reduced pressure.

tert-Butyl or Boc Deprotection

In case of the presence of a tert-butyl ester or Boc protecting group on the coupled amine, the residue was dissolved in dry DCM (800 µL) and cooled to 0° C. TFA (200 µL) was added and the reaction mixture was stirred until full conversion was observed by LCMS. The solvent was removed by distillation at reduced pressure. The residue was taken up in 1 mL of DCM and the solvent was evaporated again. This procedure was repeated twice.

Purification

The crude product was then purified by reversed-phase HPLC with a gradient 10-95% $CH_3CN$ in 10 mM aqueous $NH_4HCO_3$.

c. A2+B3+C5
Synthesis:

tert-butyl (S)-2-(allyloxy)-4-(4-(2-(4-(4-cyanobenzamido)benzamido)-4-oxo-4-(trityl-amino)butanamido)benzamido)-3-isopropoxybenzoate

5

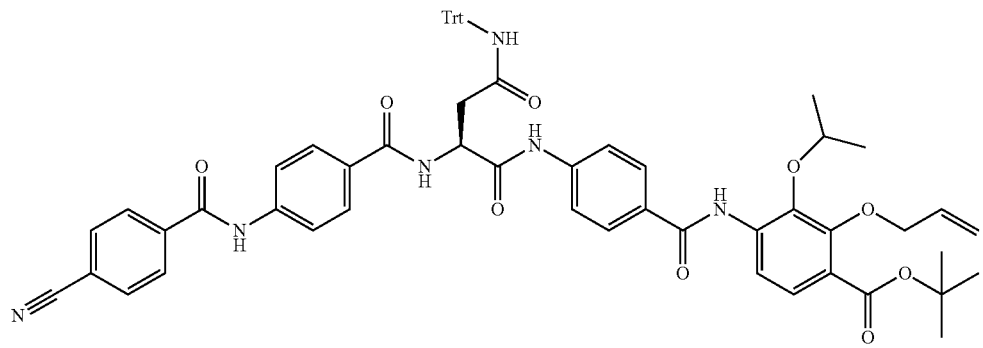

To a solution of 4-(4-cyanobenzamido)benzoic acid (173 mg; 0.77 mmol) and HBTU (292 mg; 0.77 mmol) in dry DMF (1.5 mL) was added DIPEA (0.4 mL; 2.30 mmol). The mixture was stirred for 15 minutes before being added to a solution of tert-butyl (S)-2-(allyloxy)-4-(4-(2-amino-4-oxo-4-(trityl amino)butanamido)benzamido)-3-isopropoxybenzoate (500 mg; 0.64 mmol) in dry DMF (3.5 mL). The solution was stirred for 6 hours, diluted with brine (50 mL) and water (50 mL) and extracted with ethyl acetate (3×50 mL). The combined organic extracts were washed with 1N HCl (50 mL), saturated aqueous NaHCO$_3$ solution (50 mL) and brine (50 mL). After drying over anhydrous Na$_2$SO$_4$, the solvent was removed by distillation at reduced pressure and the residue was subjected to flash chromatography (DCM/MeOH) to afford the desired product as an off-white solid (440 mg; 0.43 mmol; 67%).

$^1$H-NMR (500 MHz, DMSO): δ (ppm)=10.73 (s, 1H), 10.51 (s, 1H), 9.45 (s, 1H), 8.78 (d, J=7.5 Hz, 1H), 8.68 (s, 1H), 8.17-8.04 (m, 4H), 8.00-7.90 (m, 6H), 7.85-7.77 (m, 3H), 7.40 (d, J=8.6 Hz, 1H), 7.25-7.15 (m, 15H), 6.10 (ddt, J=17.3, 10.5, 5.3 Hz, 1H), 5.40 (dq, J=17.3, 1.8 Hz, 1H), 5.26 (dq, J=10.5, 1.6 Hz, 1H), 4.95-4.88 (m, 1H), 4.54 (d, J=5.7 Hz, 1H), 4.46 (hept, J=6.1 Hz, 1H), 3.06-2.96 (m, 1H), 2.74-2.69 (m, 1H), 1.53 (s, 9H), 1.22 (d, J=6.2 Hz, 6H).

$^{13}$C-NMR (125 MHz, DMSO): δ (ppm)=170.9, 168.4, 165.7, 164.8, 164.5, 164.2, 150.7, 144.7, 142.5, 142.4, 141.6, 138.7, 136.5, 134.1, 132.5, 129.1, 128.6, 128.6, 128.4, 128.3, 127.4, 126.4, 124.9, 123.9, 119.5, 118.8, 118.3, 118.1, 116.9, 114.0, 81.0, 76.1, 73.8, 69.5, 52.0, 38.2, 27.8, 22.3.

HRMS (ESI+): m/z for C$_{62}$H$_{58}$N$_6$O$_9$ [M+H]$^+$: calculated: 1031.4338, found: 1031.4334.

d. Analogs Synthesized Modifying Building Block C5

(S)-4-(4-(4-amino-2-(4-(4-cyanobenzamido)benzamido)-4-oxobutanamido)benzamido)-2-hydroxy-3-isopropoxybenzoic acid

86

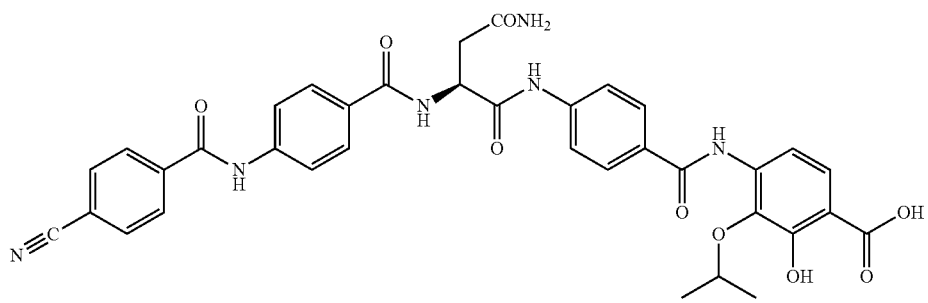

Compound 86 was synthesized according to the general procedures (section 4.3b) using intermediate 85 (30.0 mg, 29.1 μmol, 1.0 eq.) and skipping the coupling step yielding a white solid (17.24 mg, 24.9 μmol, 86%).

$^1$H-NMR (500 MHz, DMSO): δ (ppm)=10.71 (s, 1H), 10.46 (s, 1H), 9.28 (s, 1H), 8.68 (d, J=7.3 Hz, 1H), 8.15-8.03 (m, 4H), 7.95-7.88 (m, 6H), 7.83-7.80 (m, 2H), 7.65 (d, J=8.8 Hz, 1H), 7.54 (d, J=8.8 Hz, 1H), 7.40 (s, 1H), 6.99 (s, 1H), 4.92 (pseudo q, J=7.1 Hz, 1H), 4.56 (hept, J=6.2 Hz, 1H), 2.69 (d, J=7.1 Hz, 2H), 1.25 (d, J=6.2 Hz, 6H).

$^{13}$C-NMR (126 MHz, DMSO): δ (ppm)=172.0, 171.3, 170.7, 165.7, 164.4, 164.1, 155.1, 142.5, 141.6, 138.7, 137.4, 135.4, 132.5, 129.1, 128.6, 128.4, 128.3, 128.2, 124.6, 119.5, 118.9, 118.3, 114.0, 111.4, 74.6, 51.6, 36.8, 22.4.

HRMS (ESI+): m/z for C$_{36}$H$_{33}$N$_6$O$_9$ [M+H]+: calculated: 693.2304, found: 693.2288.

(S)-2-(4-(4-cyanobenzamido)benzamido)-N1-(4-((3-hydroxy-2-isopropoxy-4-((1-methyl-1H-pyrrol-3-yl)carbamoyl)phenyl)carbamoyl)phenyl)succinamide

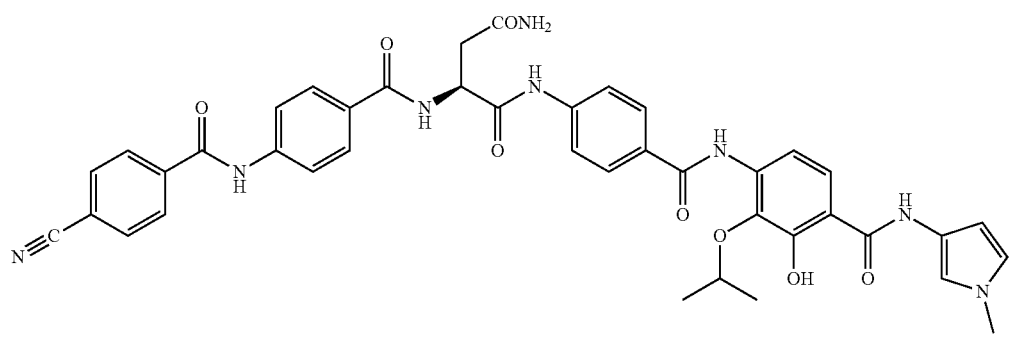

87

Compound 87 was synthesized according to the general procedures (section 4.3b) using intermediate 85 (20.0 mg, 19.4 μmol, 1.0 eq.) and amine 84 (19.0 mg, 97.0 μmol, 5.0 eq.) yielding a white solid (9.00 mg, 11.7 μmol, 60%).

$^1$H-NMR (700 MHz, DMSO): δ (ppm)=13.33 (s, 1H), 10.70 (s, 1H), 10.46 (s, 1H), 10.40 (s, 1H), 9.31 (s, 1H), 8.67 (d, J=7.4 Hz, 1H), 8.15-8.02 (m, 4H), 7.97-7.87 (m, 6H), 7.84-7.77 (m, 3H), 7.65 (d, J=8.9 Hz, 1H), 7.40 (s, 1H), 7.17 (t, J=2.1 Hz, 1H), 6.99 (s, 1H), 6.62 (t, J=2.5 Hz, 1H), 6.17 (dd, J=2.8, 1.7 Hz, 1H), 4.92 (q, J=7.1 Hz, 1H), 4.56 (hept, J=6.1 Hz, 1H), 3.61 (s, 3H), 2.69 (d, J=7.1 Hz, 2H), 1.25 (d, J=6.1 Hz, 6H).

$^{13}$C-NMR (176 MHz, DMSO): δ (ppm)=171.3, 170.7, 166.4, 165.8, 164.5, 164.1, 154.6, 142.5, 141.6, 138.7, 136.2, 136.1, 133.0, 132.5, 132.4, 129.1, 128.3, 128.2, 121.9, 121.6, 119.8, 119.5, 118.9, 118.3, 114.0, 113.1, 111.6, 111.5, 101.2, 74.6, 51.6, 36.8, 36.0, 22.4.

HRMS (ESI+): m/z for $C_{41}H_{38}N_8O_8$ [M+H]$^+$: calculated: 771.2885, found: 771.2890.

(S)-4-(4-(4-(4-amino-2-(4-(4-cyanobenzamido)benzamido)-4-oxobutanamido)benzamido)-2-hydroxy-3-isopropoxybenzamido)-1-methyl-1H-pyrrole-2-carboxylic acid Compound 88 was synthesized according to the general procedures (section 4.3b) using intermediate 85 (30.0 mg, 29.1 μmol, 1.0 eq.) and the previously prepared solution of crude 4-amino-1-methyl-1H-pyrrole-2-carboxylic acid (730 μL, 146 μmol, 5.0 eq.), see section 4.2b, yielding a white solid (6.16 mg, 7.7 μmol, 26%).

$^1$H-NMR (700 MHz, DMSO): δ (ppm)=10.71 (s, 1H), 10.47 (s, 1H), 9.26 (s, 1H), 8.69 (d, J=7.3 Hz, 1H), 8.15-8.02 (m, 4H), 7.95-7.88 (m, 6H), 7.81 (d, J=8.7 Hz, 2H), 7.72 (br s, 1H), 7.68-7.50 (m, 2H), 7.45 (d, J=2.0 Hz, 1H), 7.40 (s, 1H), 6.99 (s, 1H), 6.89 (pseudo br s, 1H), 4.92 (pseudo q, J=7.1 Hz, 1H), 4.63 (pseudo br s, 1H), 3.86 (s, 3H), 2.69 (d, J=7.0 Hz, 2H), 1.24 (d, J=6.1 Hz, 6H).

$^{13}$C-NMR (176 MHz, DMSO): δ (ppm)=171.3, 170.7, 166.7, 165.7, 164.4, 163.9, 162.0, 142.4, 141.6, 138.7, 136.3, 132.5, 129.1, 128.6, 128.5, 128.3, 128.1, 120.8, 119.5, 118.9, 118.3, 114.0, 108.7, 51.6, 36.8, 36.2, 22.4.

HRMS (ESI+): m/z for $C_{42}H_{38}N_8O_{10}$ [M+H]$^+$: calculated: 815.2784, found: 815.2793.

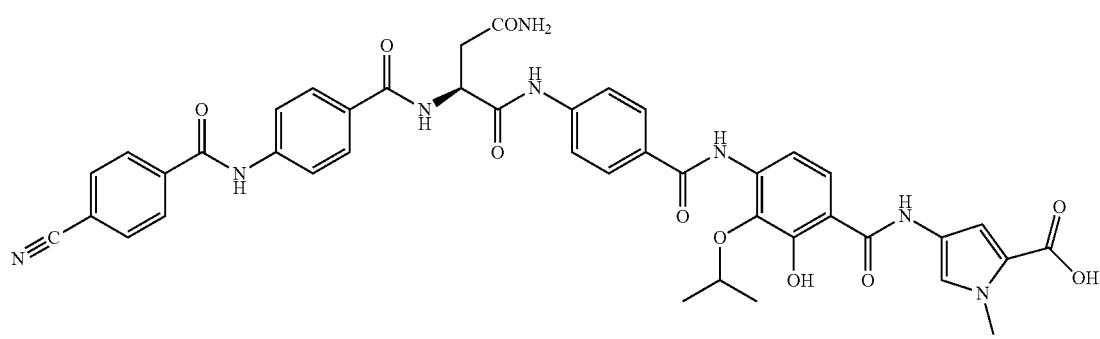

88

(S)-4-((4-(4-(4-amino-2-(4-(4-cyanobenzamido)benzamido)-4-oxobutanamido)benzamido)-2-hydroxy-3-isopropoxybenzamido)methyl)benzoic acid

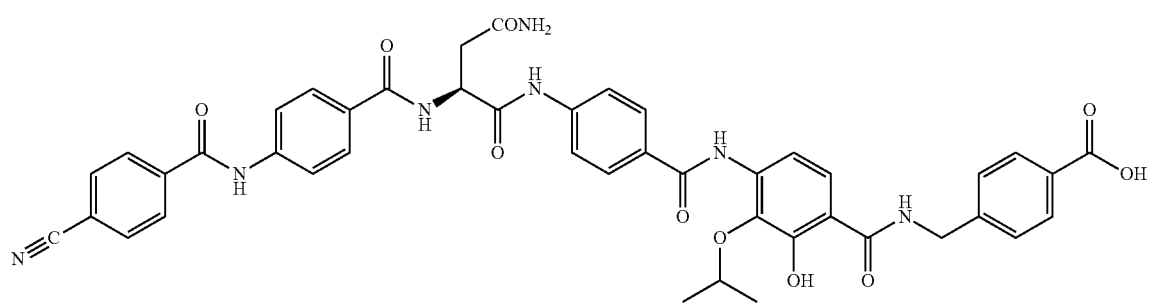

89

Compound 89 was synthesized according to the general procedures (section 4.3b) using intermediate 85 (30.0 mg, 29.1 μmol, 1.0 eq.) and 4-(aminomethyl)benzoic acid (13.2 mg, 87.3 μmol, 3.0 eq.) yielding a white solid (3.42 mg, 4.2 μmol, 14%).

$^1$H-NMR (700 MHz, DMSO): δ (ppm)=13.20 (br s, 1H), 10.70 (s, 1H), 10.47 (s, 1H), 9.53 (br s, 1H), 9.30 (s, 1H), 8.69 (d, J=7.3 Hz, 1H), 8.15-8.02 (m, 4H), 7.96-7.87 (m, 8H), 7.81 (d, J=8.6 Hz, 2H), 7.68 (d, J=9.0 Hz, 1H), 7.62 (d, J=8.8 Hz, 1H), 7.44 (d, J=8.1 Hz, 2H), 7.40 (d, J=2.5 Hz, 1H), 6.99 (d, J=2.4 Hz, 1H), 4.92 (pseudo q, J=7.1 Hz, 1H), 4.60-4.52 (m, 3H), 2.69 (d, J=7.1 Hz, 2H), 1.24 (d, J=6.1 Hz, 6H).

$^{13}$C-NMR (176 MHz, DMSO): δ (ppm)=171.3, 170.7, 169.8, 167.2, 165.7, 164.4, 164.1, 142.5, 141.6, 138.7, 136.5, 136.1, 132.5, 129.5, 129.1, 128.6, 128.4, 128.3, 128.2, 127.2, 121.7, 119.5, 118.9, 118.3, 114.0, 74.5, 51.6, 42.2, 36.8, 22.4.

HRMS (ESI+): m/z for $C_{44}H_{39}N_7O_{10}$ [M+H]+: calculated: 826.2831, found: 826.2852.

(S)-3-(4-(4-(4-amino-2-(4-(4-cyanobenzamido)benzamido)-4-oxobutanamido)benzamido)-2-hydroxy-3-isopropoxybenzamido)benzoic acid Compound 90 was synthesized according to the general procedures (section 4.3b) using intermediate 85 (30.0 mg, 29.1 μmol, 1.0 eq.) and m-aminobenzoic acid (12.0 mg, 87.3 μmol, 3.0 eq.) yielding a white solid (3.90 mg, 4.8 μmol, 17%).

$^1$H-NMR (700 MHz, DMSO): δ (ppm)=13.04 (br s, 1H), 12.51 (br s, 1H), 10.70 (s, 1H), 10.46 (s, 1H), 9.36 (s, 1H), 8.67 (d, J=7.3 Hz, 1H), 8.33 (t, J=2.0 Hz, 1H), 8.14-8.03 (m, 4H), 7.99-7.80 (m, 11H), 7.73 (d, J=7.7 Hz, 1H), 7.68 (pseudo br s, 1H), 7.51 (t, J=7.9 Hz, 1H), 7.40 (s, 1H), 6.99 (s, 1H), 4.92 (pseudo q, J=7.1 Hz, 1H), 4.58 (pseudo br s, 1H), 2.71-2.68 (m, 2H), 1.26 (d, J=6.1 Hz, 6H).

$^{13}$C-NMR (176 MHz, DMSO): δ (ppm)=171.3, 170.7, 168.5, 167.1, 165.8, 164.4, 164.1, 142.5, 141.6, 138.7, 136.3, 132.5, 131.3, 129.1, 129.0, 128.6, 128.3, 128.2, 122.6, 122.2, 119.5, 118.9, 118.3, 114.0, 54.9, 51.6, 36.8, 22.4.

HRMS (ESI+): m/z for $C_{43}H_{37}N_7O_{10}$ [M+H]+: calculated: 812.2675, found: 812.2683.

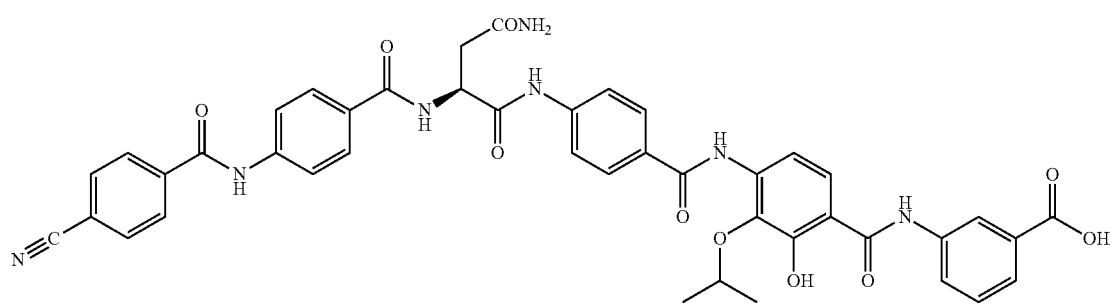

90

(S)-2-(4-(4-cyanobenzamido)benzamido)-N1-(4-((3-hydroxy-2-isopropoxy-4-(piperidin-4-ylcarbamoyl)phenyl)carbamoyl)phenyl)succinamide

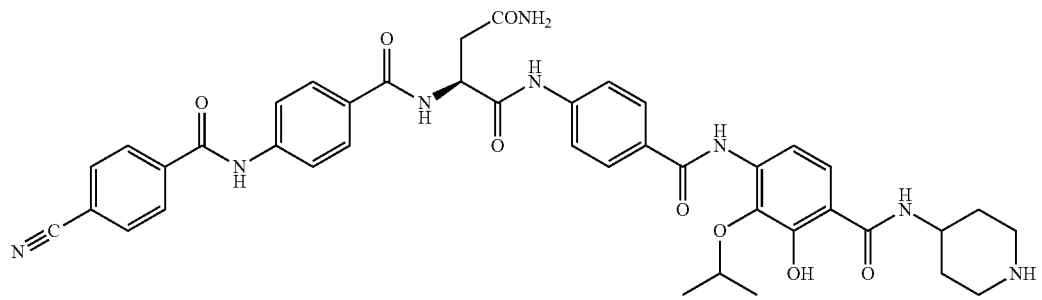

91

Compound 91 was synthesized according to the general procedures (section 4.3b) using intermediate 85 (30.0 mg, 29.1 μmol, 1.0 eq.) and tert-butyl 4-aminopiperidine-1-carboxylate (29.1 mg, 146 μmol, 5.0 eq.) yielding a white solid (6.17 mg, 8.0 μmol, 27%).

$^1$H-NMR (500 MHz, DMSO): δ (ppm)=10.71 (s, 1H), 10.47 (s, 1H), 9.24 (s, 1H), 8.69 (d, J=7.2 Hz, 1H), 8.15-8.03 (m, 4H), 7.95-7.87 (m, 6H), 7.83-7.79 (m, 2H), 7.65-7.63 (m, 2H), 7.40 (d, J=2.4 Hz, 1H), 6.99 (d, J=2.4 Hz, 1H), 4.92 (pseudo q, J=7.1 Hz, 1H), 4.57 (hept, J=6.3 Hz, 1H), 4.05-3.96 (m, 1H), 3.20-3.15 (m, 2H), 2.81 (t, J=11.9 Hz, 2H), 2.69 (d, J=7.1 Hz, 2H), 1.92-1.86 (m, 2H), 1.68-1.57 (m, 2H), 1.22 (d, J=6.1 Hz, 6H).

$^{13}$C-NMR (126 MHz, DMSO): δ (ppm)=171.3, 170.7, 169.0, 165.8, 164.4, 164.0, 142.4, 141.6, 138.7, 136.2, 136.1, 133.1, 132.5, 132.3, 129.1, 128.6, 128.5, 128.3, 128.1, 122.0, 119.5, 118.9, 118.3, 114.0, 74.0, 51.6, 45.4, 43.5, 36.8, 30.1, 22.4.

HRMS (ESI+): m/z for $C_{41}H_{42}N_8O_8$ [M+H]$^+$: calculated: 775.3198, found: 775.3209.

(S)-4-(4-(4-(4-amino-2-(4-(4-cyanobenzamido)benzamido)-4-oxobutanamido)benzamido)-2-hydroxy-3-isopropoxybenzamido)benzenesulfonic acid

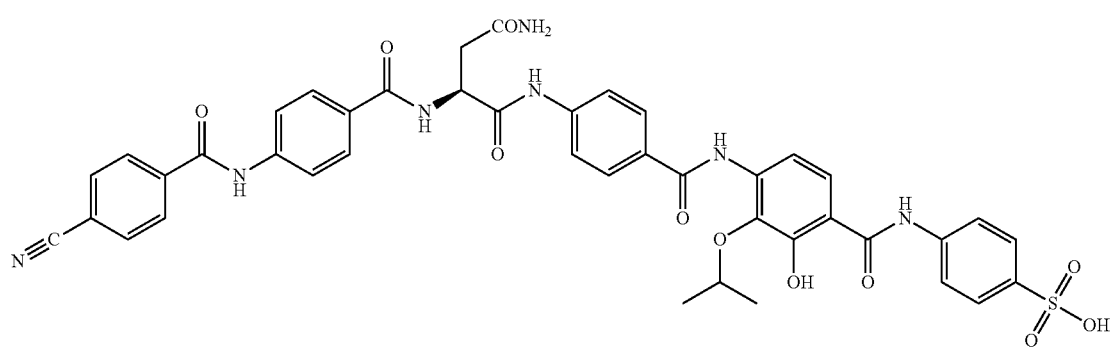

92

Compound 92 was synthesized according to the general procedures (section 4.3b) using intermediate 85 (30.0 mg, 29.1 μmol, 1.0 eq.) and sulfanilic acid (15.1 mg, 87.3 μmol, 3.0 eq.) yielding a white solid (3.53 mg, 4.2 μmol, 14%).

$^1$H-NMR (700 MHz, DMSO): δ (ppm)=10.70 (s, 1H), 10.44 (s, 1H), 9.10 (br s, 1H), 8.67 (d, J=7.3 Hz, 1H), 8.15-8.03 (m, 4H), 7.95-7.80 (m, 9H), 7.67-7.59 (m, 3H), 7.53 (d, J=8.2 Hz, 2H), 7.39 (d, J=2.4 Hz, 1H), 6.98 (d, J=2.4 Hz, 1H), 4.93 (q, J=7.2 Hz, 1H), 4.80 (pseudo br s, 1H), 2.72-2.66 (m, 2H), 1.23 (d, J=6.1 Hz, 6H).

$^{13}$C-NMR (176 MHz, DMSO): δ (ppm)=171.3, 170.7, 165.7, 164.4, 142.2, 141.6, 138.7, 132.5, 129.2, 128.6, 128.3, 127.9, 126.1, 119.5, 119.0, 118.3, 114.0, 51.6, 36.8, 22.5.

HRMS (ESI+): m/z for $C_{42}H_{37}N_7O_{11}S$ [M+H]+: calculated: 848.2345, found: 848.2363.

(S)-2-(4-(4-cyanobenzamido)benzamido)-N1-(4-((3-hydroxy-2-isopropoxy-4-(((R)-3-oxoisoxazolidin-4-yl)carbamoyl)phenyl)carbamoyl)phenyl)succinamide

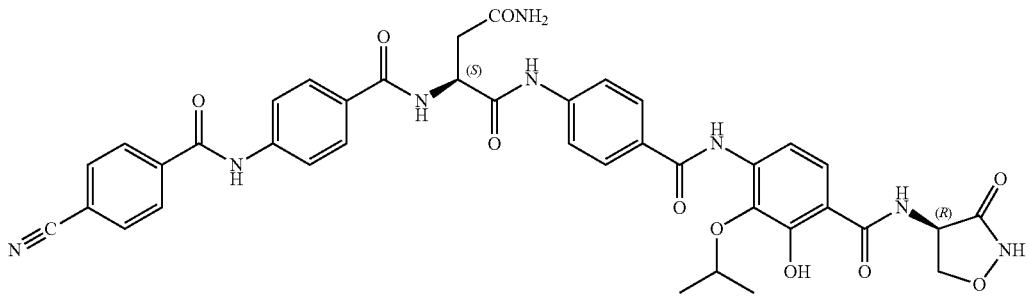

93

Compound 93 was synthesized according to the general procedures (section 4.3b) using intermediate 85 (30.0 mg, 29.1 μmol, 1.0 eq.) and (R)-(+)-cycloserine (14.9 mg, 146 μmol, 5.0 eq.) yielding a white solid still containing some allyl-protected compound (2.46 mg, 3.2 μmol, 11%).

$^1$H-NMR (700 MHz, DMSO): δ (ppm)=13.71 (s, 1H), 10.70 (s, 1H), 10.45 (s, 1H), 9.27 (s, 1H), 8.67 (d, J=7.3 Hz, 1H), 8.14-8.03 (m, 4H), 7.95-7.87 (m, 6H), 7.82-7.80 (m, 2H), 7.63-7.58 (m, 2H), 7.39 (d, J=2.4 Hz, 1H), 6.99 (d, J=2.4 Hz, 1H), 4.92 (pseudo q, J=7.1 Hz, 1H), 4.54 (hept, J=6.2 Hz, 1H), 2.71-2.66 (m, 2H), 1.24 (d, J=6.2 Hz, 6H).

$^{13}$C-NMR (176 MHz, DMSO): δ (ppm)=172.6, 171.3, 170.7, 169.7, 165.8, 164.5, 164.1, 155.2, 142.5, 141.6, 138.7, 136.6, 135.9, 132.5, 131.6, 129.1, 128.6, 128.3, 128.2, 122.2, 119.5, 118.9, 118.3, 114.0, 111.3, 110.8, 74.5, 51.6, 36.8, 22.4.

HRMS (ESI+): m/z for $C_{39}H_{36}N_8O_{10}$ [M+H]+: calculated: 777.2627, found: 777.2623.

(S)-2-(4-(4-cyanobenzamido)benzamido)-N1-(4-((3-hydroxy-2-isopropoxy-4-(pyridin-4-ylcarbamoyl)phenyl)carbamoyl)phenyl)succinamide

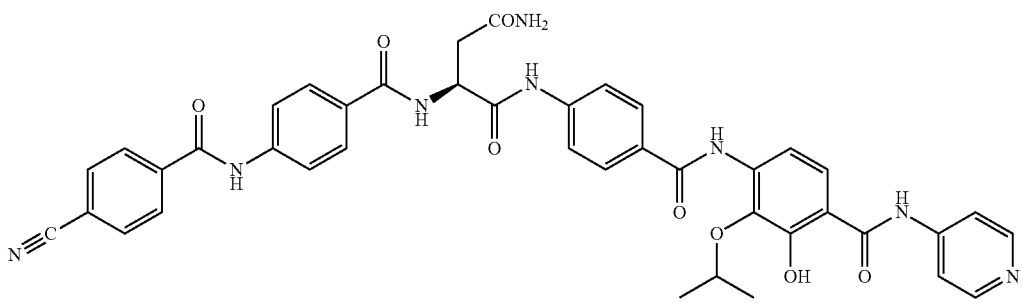

94

Compound 94 was synthesized according to the general procedure (section 4.3b) using intermediate 85 (30.0 mg, 29.1 μmol, 1.0 eq.) and 4-aminopyridine (13.7 mg, 146 μmol, 5.0 eq.) yielding a white solid (10.39 mg, 13.5 μmol, 46%).

$^1$H-NMR (500 MHz, DMSO): δ (ppm)=13.98 (s, 1H), 10.71 (s, 1H), 10.45 (s, 1H), 9.09 (s, 1H), 8.67 (d, J=7.3 Hz, 1H), 8.42-8.38 (m, 2H), 8.15-8.01 (m, 6H), 7.95-7.86 (m, 6H), 7.81 (d, J=8.9 Hz, 2H), 7.58 (d, J=8.8 Hz, 1H), 7.40 (d, J=2.4 Hz, 1H), 7.34 (d, J=8.8 Hz, 1H), 6.99 (d, J=2.4 Hz, 1H), 4.92 (pseudo q, J=7.2 Hz, 1H), 4.81 (hept, J=6.2 Hz, 1H), 2.69 (d, J=7.1 Hz, 2H), 1.22 (d, J=6.2 Hz, 6H).

$^{13}$C-NMR (126 MHz, DMSO): δ (ppm)=171.3, 170.7, 168.3, 165.7, 164.4, 163.6, 156.9, 150.1, 146.5, 144.9, 142.2, 141.6, 138.7, 137.2, 135.6, 132.5, 129.1, 128.9, 128.6, 128.3, 127.9, 123.5, 119.5, 119.0, 118.3, 114.2, 114.0, 108.8, 72.2, 51.6, 36.8, 22.5.

HRMS (ESI+): m/z for $C_{41}H_{36}N_8O_8$ [M+H]+: calculated: 769.2729, found: 769.2722.

5 Synthesis 4
5.1 Retrosynthetic Disconnection fragmets

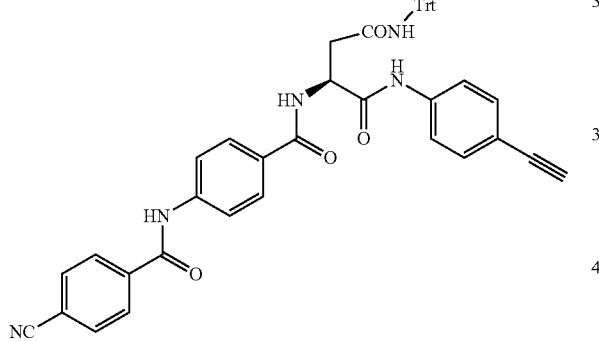

A3

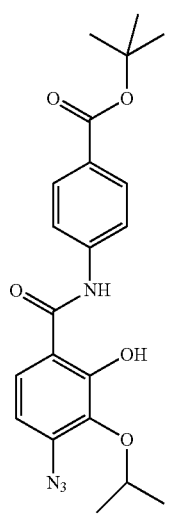

B4

5.2 Building Blocks Synthesis
a. Fragment A3:

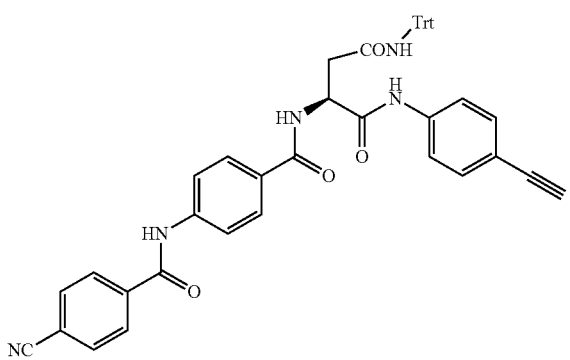

Synthesis:

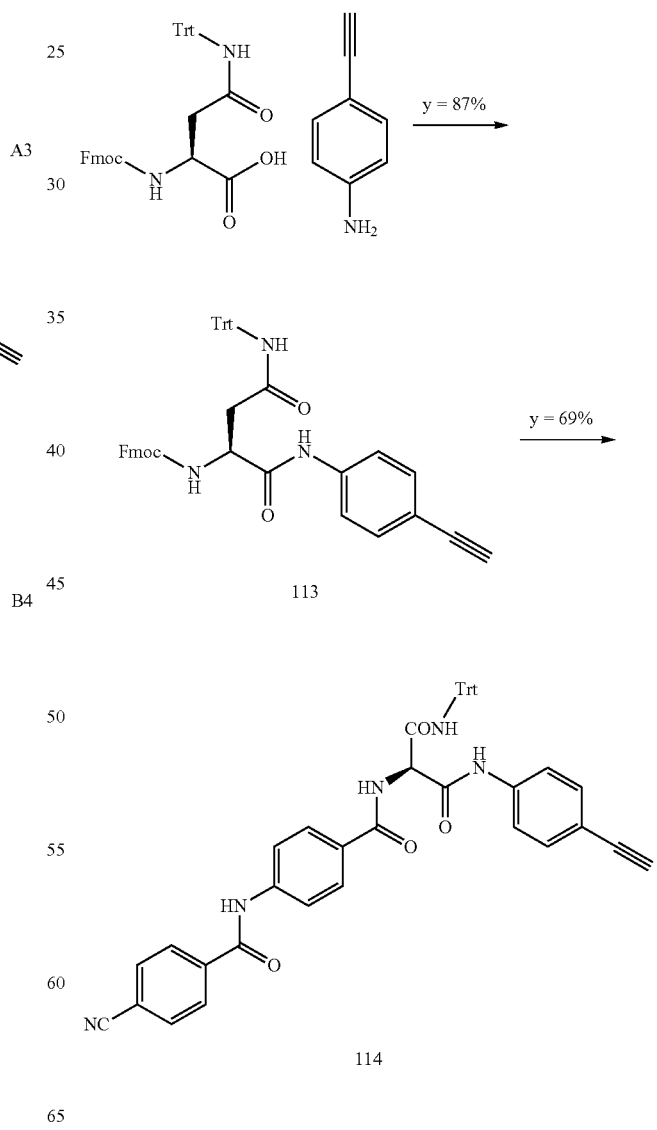

(9H-fluoren-9-yl)methyl(1-((4-ethynylphenyl)amino)-1,4-dioxo-4-(tritylamino)butan-2-yl)carbamate

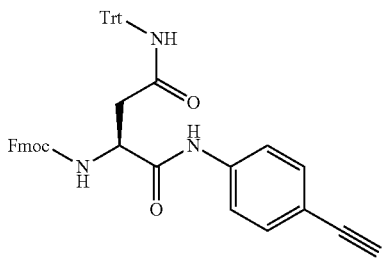

POCl$_3$ (40 µL, 0.43 mmol) was added at 0° C. to a stirred solution of Fmoc-Asn(Trt)-OH (254 mg, 0.43 mmol), triethylamine (60 µL, 0.43 mmol) and 4-ethynylaniline (25 mg, 0.215 mmol) in DCM (4 mL) under nitrogen. The reaction was stirred at 0 C for 2 hours. NaHCO$_3$ (5 mL) saturated solution and EtOAc (20 mL) were added, the organic phase washed again with NaHCO3 (5 mL) and brine (20 mL), dried over sodium sulphate and reduced under vacuum to give a yellow oil which was chromatographed on silica gel with a solution Hexane/EtOAc 7:3 to give 131 mg of a white solid (0.19 mmol; y=87%).

$^1$H NMR (500 MHz, DMSO) δ 10.27 (s, 1H), 8.61 (s, 1H), 7.90 (d, J=7.5 Hz, 2H), 7.78 (d, J=8.0 Hz, 1H), 7.74 (dd, J=7.3, 4.3 Hz, 2H), 7.65 (d, J=8.7 Hz, 2H), 7.46-7.38 (m, 3H), 7.37-7.25 (m, 2H), 7.25-7.12 (m, 15H), 4.44 (td, J=9.0, 5.3 Hz, 1H), 4.36 (dd, J=10.4, 7.0 Hz, 1H), 4.29 (dd, J=10.4, 7.0 Hz, 1H), 4.23 (t, J=6.9 Hz, 1H), 4.09 (s, 1H), 2.75 (dd, J=14.5, 9.8 Hz, 1H), 2.61 (dd, J=14.5, 5.0 Hz, 1H).

$^{13}$C NMR (126 MHz, DMSO) δ 170.5, 168.5, 155.8, 144.7, 143.8, 140.7, 139.5, 132.3, 128.6, 127.7, 127.4, 127.1, 126.3, 125.3, 125.2, 120.1, 119.1, 116.2, 83.6, 79.9, 69.4, 65.8, 52.8, 46.7, 38.4.

HRMS (ESI) calculated for C$_{46}$H$_{36}$N$_3$O$_4$ (M−H) 694.2711, found 694.2690.

(S)-2-(4-(4-cyanobenzamido)benzamido)-N1-(4-ethynylphenyl)-N4-tritylsuccinamide

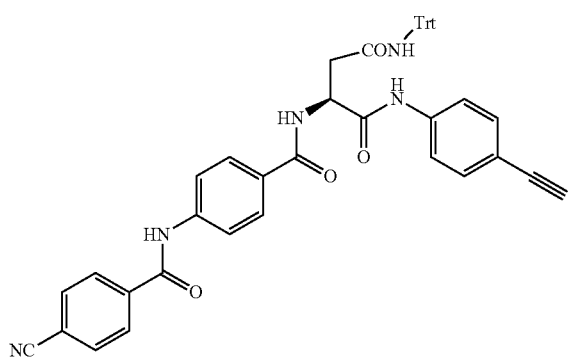

To a solution of 4-(4-cyanobenzamido) benzoic acid (15.5 mg, 0.058 mmol) and HBTU (27 mg, 0.77 mmol) in dry DMF (0.4 mL) DIPEA (30 µL, 0.174 mmol) was added. The mixture was stirred for 15 minutes before being added to a solution of 2-amino-N1-(4-ethynylphenyl)-N4-tritylsuccinamide (34 mg, 0.07 mmol) in dry DMF (0.6 mL), which was obtained cleaving the Fmoc protecting group from (9H-fluoren-9-yl)methyl (1-((4-ethynylphenyl)amino)-1,4-dioxo-4-(tritylamino)butan-2-yl)carbamate using standard conditions as already described herein (a 20% solution of diethylamine in CH$_3$CN).

The solution was stirred for 3 hours, diluted with brine (5 mL) and water (5 mL) and extracted with ethyl acetate (3×5 mL). The combined organic extracts were washed with 1N HCl (5 mL), saturated aqueous NaHCO$_3$ solution (5 mL) and brine (5 mL). After drying over anhydrous Na$_2$SO$_4$, the solvent was removed by distillation at reduced pressure and the residue was subjected to flash chromatography with a gradient MeOH 0-5% in DCM to afford 29 mg of desired product as a pale yellow solid (0.04 mmol, y=69%).

$^1$H NMR (500 MHz, CDCl$_3$) δ 9.41 (s, 1H), 8.75 (s, 1H), 8.07 (s, 1H), 7.92 (d, J=8.0 Hz, 2H), 7.65 (d, J=8.1 Hz, 4H), 7.59 (d, J=7.9 Hz, 2H), 7.42 (s, 1H), 7.37 (s, 4H), 7.25-7.13 (m, 15H), 5.05-4.94 (m, 1H), 3.19 (d, J=12.3 Hz, 1H), 3.05 (s, 1H), 2.70 (dd, J=15.3, 6.7 Hz, 1H).

$^{13}$C NMR (126 MHz, CDCl$_3$) δ 170.9, 169.1, 167.0, 164.3, 143.9, 141.1, 138.2, 138.0, 132.8, 132.4, 128.7, 128.6, 128.3, 128.0, 127.2, 120.0, 119.6, 117.9, 117.8, 115.3, 83.3, 77.0, 71.0, 51.1, 37.9.

HRMS (ESI) calculated for C$_{46}$H$_{34}$N$_5$O$_4$ (M−H) 720.2616, found 720.2618.

b. Fragment B4:

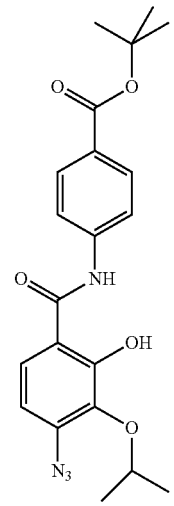 [SMILES: CC(C)Oc1c(N=[N+]=[N-])ccc(C(=O)Nc2ccc(C(=O)OC(C)(C)C)cc2)c1O]

Synthesis:

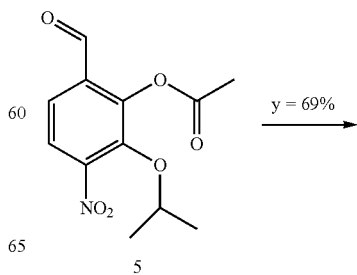

187

-continued

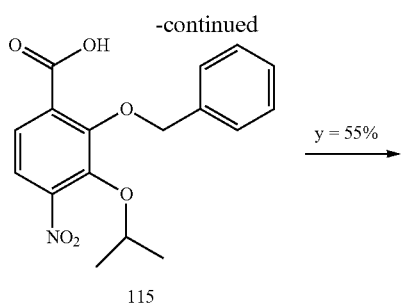

115 y = 55%

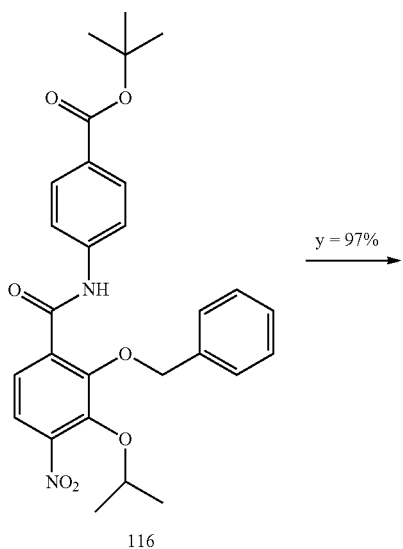

188

2-(benzyloxy)-3-isopropoxy-4-nitrobenzoic acid

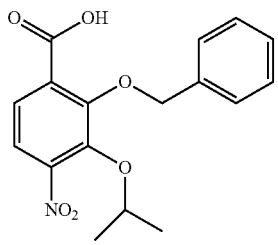 [SMILES: CC(C)Oc1c([N+](=O)[O-])ccc(C(=O)O)c1OCc1ccccc1]

6-formyl-2-isopropoxy-3-nitrophenyl acetate (2.0 g; 7.49 mmol) was dissolved in THF (38 mL) and water (19 mL), then LiOH (1.42 g; 74.9 mmol) dissolved in water (19 mL) was added at 0 C, reaction stirred overnight. In the morning, the pH was adjusted to 1, solvent partially reduced under vacuum and aqueous phase extracted with $CHCl_3$ (150 mL) three times, combined organic phases dried over sodium sulphate and reduced under vacuum to give a yellow oil, which was used in the next step without further purification. Residue was dissolved in DMF (18 mL), $K_2CO_3$ (2.07 g; 14.98 mmol) followed by benzyl bromide (1.34 mL; 11.24 mmol) were added, reaction stirred 24 h at r.t. Reaction diluted with water (200 mL) and EA (200 mL), aqueous phase extracted with EA (150 mL). Combined organic phases washed with brine (300 mL), dried over sodium sulphate and reduced under vacuum to give a crude material, which was dissolved with 2-Methyl-2-butene (8.35 mL; 78.65 mmol) in t-BuOH (45 mL). Then a solution of $NaClO_2$ 80% (1.02 g; 8.99 mmol) in Monosodium phosphate monohydrate solution 1 N (8.4 mL) was added dropwise to the solution. Reaction stirred for 1 h, then quenched by adding a solution of $Na_2SO_3$. Mixture partially reduced under vacuum, diluted with EA (200 mL) and HCl 1 N (200 mL), aqueous phase extracted again with EA (100 mL), organic phases reunited washed with brine (250 mL) and dried over sodium sulphate. Solvent reduced under vacuum, crude chromatographed on silica gel with a gradient 0-10% MeOH in DCM to afford 1.7 g of the desired compound (5.14 mmol, y=69%).

$^1$H NMR (500 MHz, $CDCl_3$) δ 7.85 (d, J=8.7 Hz, 1H), 7.57 (d, J=8.7 Hz, 1H), 7.46-7.37 (m, 5H), 4.74-4.67 (m, 1H), 1.34 (d, J=6.2 Hz, 6H).

$^{13}$C NMR (126 MHz, $CDCl_3$) δ 165.7, 153.0, 149.0, 144.8, 134.4, 129.4, 129.1, 128.9, 127.6, 126.6, 119.7, 78.7, 77.3, 22.3.

HRMS (ESI) calculated for $C_{17}H_{17}NNaO_6$ (M+Na) 354.0948, found 354.0950.

189
tert-butyl 4-(2-(benzyloxy)-3-isopropoxy-4-nitrobenzamido)benzoate

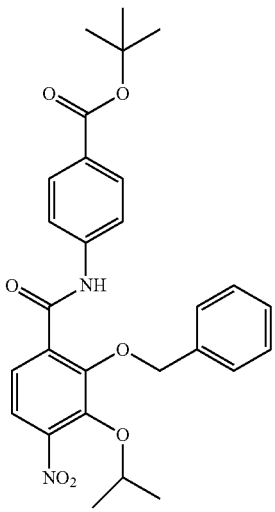 [SMILES: CC(C)Oc1c([N+](=O)[O-])ccc(C(=O)Nc2ccc(C(=O)OC(C)(C)C)cc2)c1OCc1ccccc1]

POCl$_3$ (0.031 mL; 0.33 mmol) was added at 0° C. to a stirred solution of tert-butyl 4-(2-(benzyloxy)-3-isopropoxy-4-nitrobenzamido)benzoate (110 mg; 0.33 mmol), TEA (0.077 mL; 0.55 mmol) and tert-butyl 4-aminobenzoate (53 mg; 0.27 mmol) in DCM (4.5 mL) under nitrogen. Reaction stirred 2.5 h, then quenched with NaHCO$_3$ saturated solution, solvent partially reduced under vacuum, then diluted with EtOAc (20 mL) and NaHCO$_3$ saturated solution (20 mL), organic phase then washed with HCl 1 N and brine, dried over sodium sulphate and reduced under vacuum to give around 200 mg of crude material which was chromatographed on silica gel with a gradient 5-30% EtOAc in PetEt to give 75 mg of a yellow oil (0.15 mmol; y=55%).

$^1$H NMR (500 MHz, CDCl$_3$) δ 9.94 (s, 1H), 8.09 (d, J=8.8 Hz, 1H), 7.89-7.85 (m, 2H), 7.66 (d, J=8.8 Hz, 1H), 7.47-7.36 (m, 5H), 7.28-7.23 (m, 2H), 4.73 (hept, J=6.2 Hz, 1H), 1.60 (s, 9H), 1.41 (d, J=6.2 Hz, 6H).

$^{13}$C NMR (126 MHz, CDCl$_3$) δ 165.3, 160.9, 151.8, 148.1, 144.5, 141.1, 134.5, 130.6, 130.4, 129.6, 129.2, 129.2, 127.8, 126.3, 119.9, 119.1, 81.0, 78.7, 77.7, 28.2, 22.4.

HRMS (ESI) calculated for C28H31N2O7 (M+H) 507.2126, found 507.2120.

190
tert-butyl 4-(4-amino-2-hydroxy-3-isopropoxybenzamido)benzoate

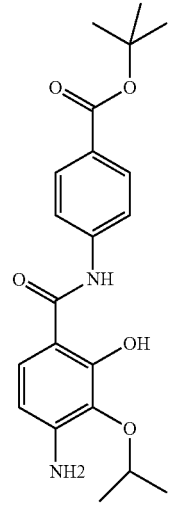 [SMILES: CC(C)Oc1c(N)ccc(C(=O)Nc2ccc(C(=O)OC(C)(C)C)cc2)c1O]

tert-butyl 4-(2-(benzyloxy)-3-isopropoxy-4-nitrobenzamido)benzoate (1.22 g; 2.41 mmol) was dissolved in MeOH (35 mL). The solution was purged with N$_2$, then Pd/C (240 mg) was added and solution purged with H$_2$. The reaction was stirred under an H$_2$ atmosphere for 2 h, afterwards the mixture was filtered over a pad of celite and solvent removed under reduced pressure. The crude thus obtained was chromatographed on silica gel with gradient 0-20% MeOH in DCM to give 906 mg of desired product (2.37 mmol; y=97%).

$^1$H NMR (500 MHz, DMSO) δ 12.57 (s, 1H), 10.15 (s, 1H), 7.92-7.84 (m, 2H), 7.83-7.78 (m, 2H), 7.59 (d, J=8.9 Hz, 1H), 6.26 (d, J=8.8 Hz, 1H), 5.66 (s, 2H), 4.46 (dt, J=12.3, 6.1 Hz, 1H), 1.55 (s, 9H), 1.22 (d, J=6.2 Hz, 6H).

$^{13}$C NMR (126 MHz, DMSO) δ 169.9, 165.1, 156.2, 148.7, 143.1, 130.3, 130.0, 126.6, 124.2, 120.7, 105.8, 103.9, 80.8, 73.2, 28.3, 22.7.

HRMS (ESI) calculated for C21H27N2O5 (M+H) 387.1914, found 387.1902.

tert-butyl 4-(4-azido-2-hydroxy-3-isopropoxybenzamido)benzoate

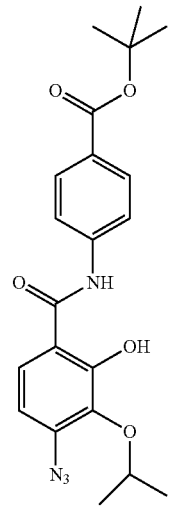 [SMILES: CC(C)Oc1c(N=[N+]=[N-])ccc(C(=O)Nc2ccc(C(=O)OC(C)(C)C)cc2)c1O]

Tert-butyl 4-(4-amino-2-hydroxy-3-isopropoxybenzamido)benzoate (40 mg, 0.10 mmol) was dissolved in acetonitrile (2 mL) and the reaction mixture was cooled to 0° C., then terbutylnitrite (18.5 μL, 0.15 mmol) and trimethylsilylazide (20.4 μL, 0.15 mmol) were subsequently added dropwise and the reaction mixture was allowed to stir at room temperature for 2 hours. After evaporation of the volatiles, the crude mixture was subjected to purification by flash column chromatography using petroleum ether/ethyl acetate 8:2 as an eluent to obtain 30 mg of a pale yellow orange solid (0.072 mmol, y=70%).

¹H NMR (500 MHz, CDCl₃) δ 10.49 (s, 1H), 8.56 (s, 1H), 8.02 (d, J=8.7 Hz, 2H), 7.68 (d, J=8.8 Hz, 2H), 7.49 (d, J=8.8 Hz, 1H), 6.65 (d, J=8.8 Hz, 1H), 4.76 (hept, 6.1 Hz, 1H), 1.61 (s, 9H), 1.37 (d, J=6.2 Hz, 6H).

¹³C NMR (126 MHz, CDCl₃) δ 166.1, 165.2, 154.0, 140.9, 138.0, 137.9, 130.7, 128.2, 122.6, 119.6, 113.1, 110.9, 81.0, 76.0, 28.2, 22.2

HRMS (ESI) calculated for $C_{21}H_{23}N_4O_5$ (M−H) 411.1674, found 411.1662.

5.3 Assembling a. General Scheme benzoate (5 mg, 0.012 mmol) were dissolved in 300 μL DMSO/THF mixture (2:1) and then sodium ascorbate (1.4 mg, 0.0072 mmol) previously dissolved in 10 μL of water was added followed by Tris(benzyltriazolylmethyl)amine (TBTA) (2.5 mg, 0.0048 mmol) previously dissolved in DMSO (10 μL). Finally; copper sulfate (0.2 mg, 0.0012 mmol) was added as a solid and the reaction mixture was allowed to stir at room temperature for 2 hours. After extraction with ethyl acetate (3×1 mL), the organic layer was washed with NH₄Cl saturated solution, water and brine, dried over sodium sulfate and evaporated under reduced pressure to obtain 14 mg (0.012 mmol, y=q.) of a yellow oil. The residue was used in the next step without further purification. Part of the residue (10 mg, 0.0088 mmol) was dissolved in DCM (250 μL), then TFA (50 μL) and TIPS (10 μL) were subsequently added and the reaction mixture was allowed to stir at room temperature for 3 hours. After evaporation of the volatiles, the crude residue was purified by preparative HPLC using water (10 mM NH₄HCO₃)/acetonitrile to afford the pure compound as a white solid (4 mg, 0.0048 mmol, 55%).

fragment A3
+
fragment B4
→

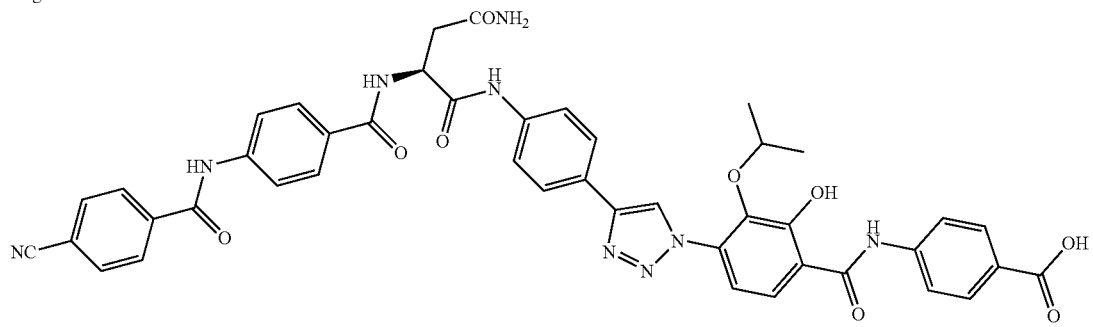

119 b. Procedure:

4-(4-(4-(4-(4-amino-2-(4-(4-cyanobenzamido)benzamido)-4-oxobutanamido)phenyl)-1H-1,2,3-triazol-1-yl)-2-hydroxy-3-isopropoxybenzamido)benzoic acid (CG178)

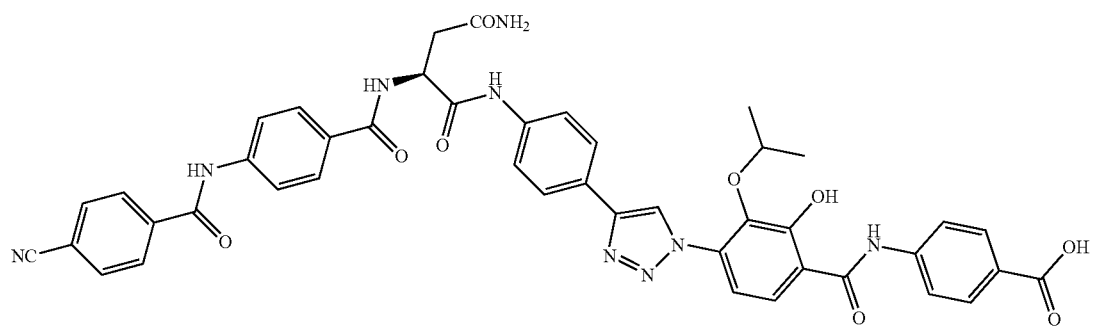

119

(S)-2-(4-(4-cyanobenzamido)benzamido)-N1-(4-ethynylphenyl)-N4-tritylsuccinamide (9 mg, 0.012 mmol) and tert-butyl 4-(4-azido-2-hydroxy-3-isopropoxybenzamido)

¹H NMR (700 MHz, DMSO) δ 15.18 (s, 1H), 10.74 (s, 1H), 10.31 (s, 1H), 8.80 (d, J=5.7 Hz, 1H), 8.69 (s, 1H), 8.14 (d, J=8.4 Hz, 2H), 8.04 (d, J=8.3 Hz, 2H), 7.95 (d, J=8.7 Hz, 2H), 7.89 (d, J=8.7 Hz, 2H), 7.87 (d, J=8.6 Hz, 2H), 7.79 (d, J=8.1 Hz, 2H), 7.74 (d, J=8.6 Hz, 2H), 7.61 (d, J=8.5 Hz, 1H), 7.59 (d, J=8.3 Hz, 2H), 7.47 (s, 1H), 6.97 (s, 1H), 6.34 (d, J=8.5 Hz, 1H), 4.92 (dd, J=13.8, 7.7 Hz, 1H), 4.83 (hept, J=6.1 Hz, 1H), 2.74-2.65 (m, 2H), 0.93 (d, J=6.0 Hz, 6H).

$^{13}$C NMR (176 MHz, DMSO) δ 171.4, 170.2, 169.8, 166.7, 166.3, 165.7, 164.4, 145.1, 141.5, 141.1, 138.7, 132.5, 129.7, 129.2, 128.6, 128.3, 126.4, 125.9, 125.6, 123.9, 122.5, 119.7, 119.5, 119.4, 118.3, 117.7, 103.1, 70.8, 51.7, 40.0, 37.0, 22.2.

HRMS (ESI) calculated for $C_{44}H_{36}N_9O_9$ (M–H) 834.2641, found 834.2661.

6. Synthesis of Further Derivatives

Compounds bearing variations of the moiety Q can be synthesized following the general schemes of SYNTHESIS 4 (used e.g. for the synthesis of compound 119) employing experimental procedures reported in the literature.

Triazole Substituted Derivatives:

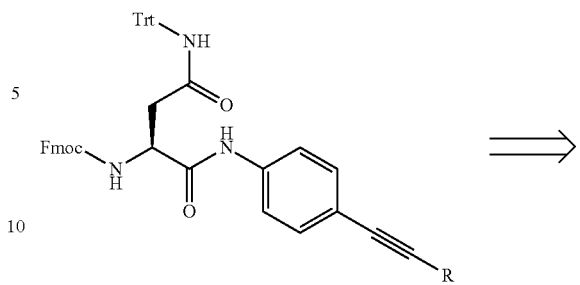

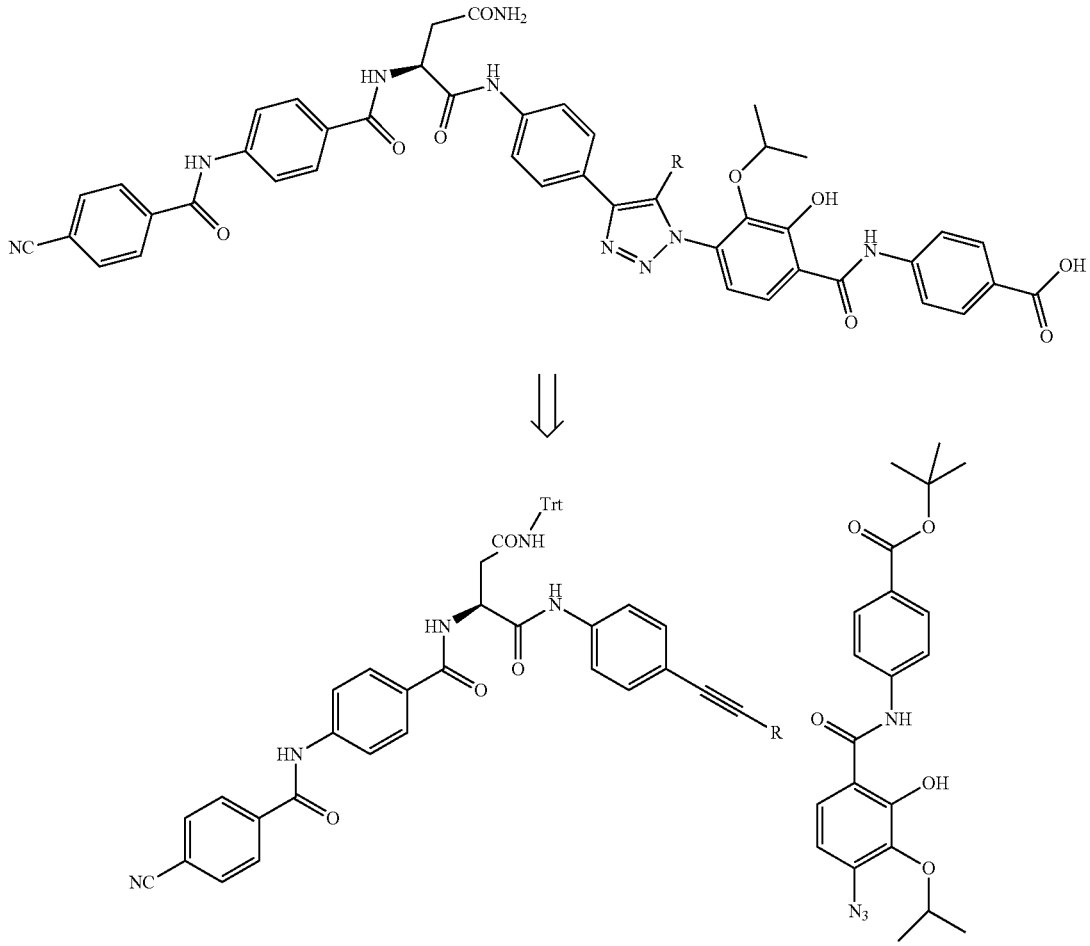

Therein, R may e.g. be an alkyl, $CF_3$, or an aryl moiety.

The coupling step of the 1,3-dipolar cycloaddition can be done following one of the experimental procedures reported in Chemical & Pharmaceutical Bulletin, 32(11), 4402-9; 1984 and Advanced Synthesis & Catalysis, 355(14-15), 2982-2991; 2013.

The fragment bearing the alkynyl moiety can be synthesized following the procedures reported in Organic Letters, 19(8), 1962-1965; 2017 and Chemical Communications (Cambridge, United Kingdom), 49(42), 4842-4844; 2013.

-continued

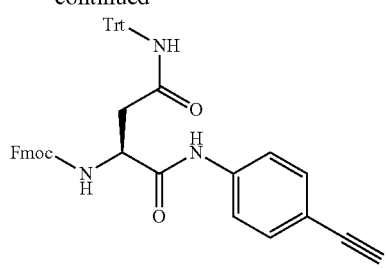

The regioisomeric products of the cycloaddition reaction can be obtained following the procedure described in Organic Letters, 9(26), 5337-5339: 2007, Chemical Communications (Cambridge, United Kingdom), 49(49), 5589-5591; 2013 and Journal of Organic Chemistry, 71(22) 8680-8683; 2006.

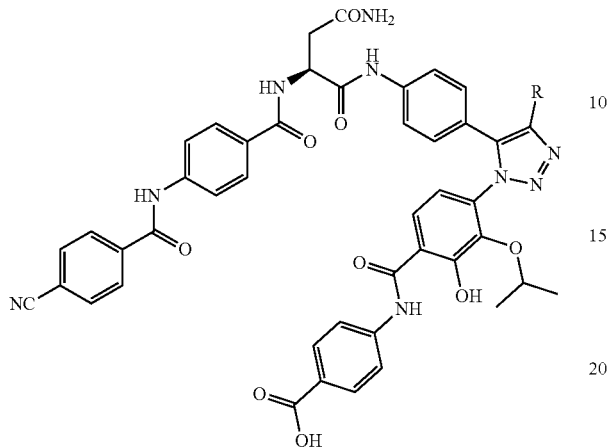

Triazole derivatives bearing modifications at different aromatic rings:

Following the general approach, any fragment C described herein can be converted into the corresponding "azido derivative", thus enabling the possibility to obtain derivatives of the general formula depicted below:

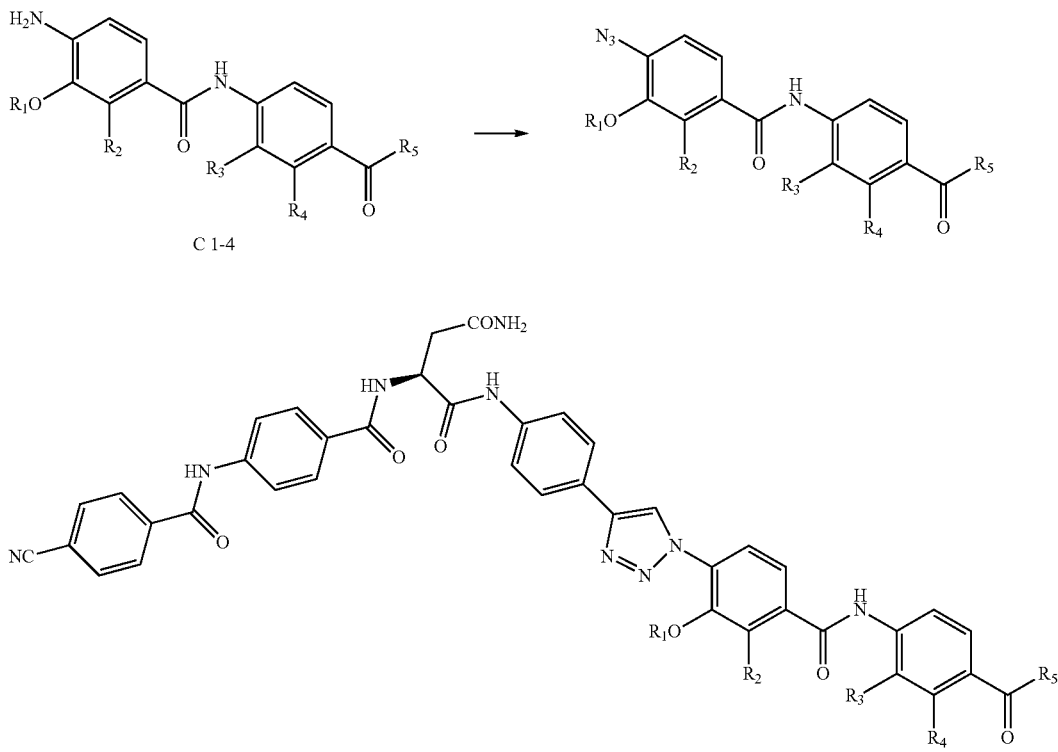

2,3-Dihydroisoxazole Derivatives

For the synthesis of such derivatives, analog retrosynthetic disconnection to the one described above can be used, particularly as follow:

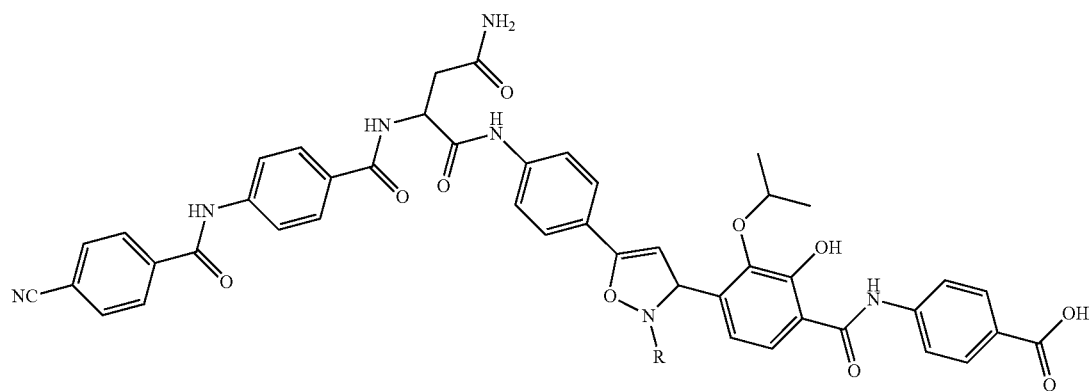
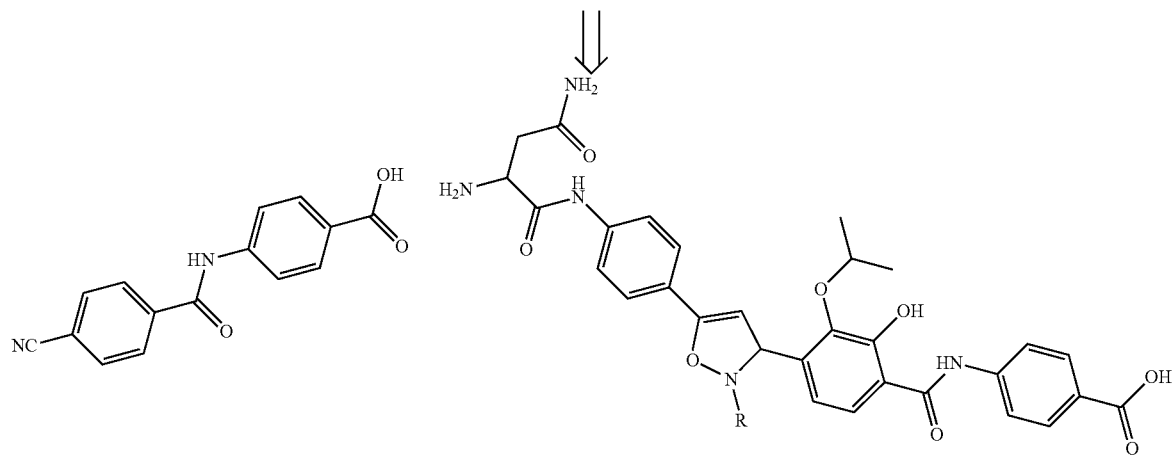
The key intermediate bearing the dihydroisoxazole moiety can be synthesized starting from the two fragments depicted below with the experimental procedure reported in Adv. Synth. Catal. 2016, 358, 1859-1863.
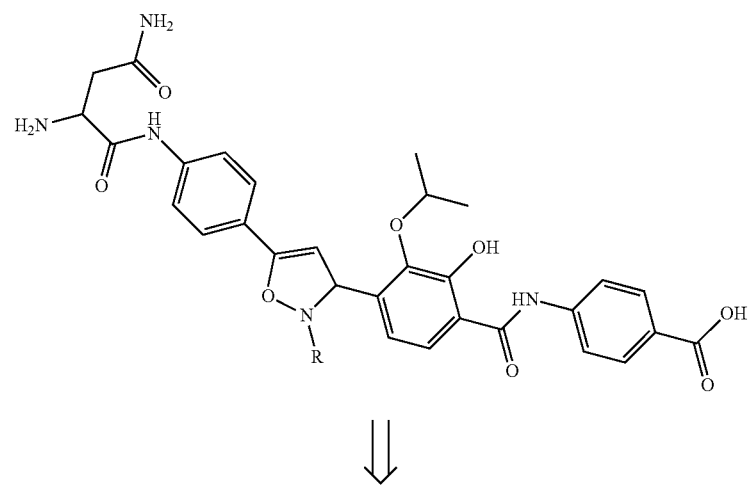

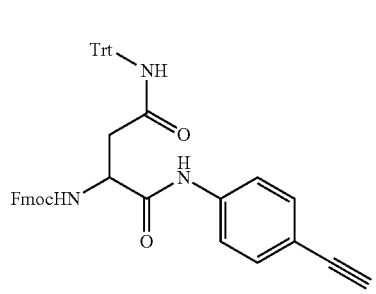
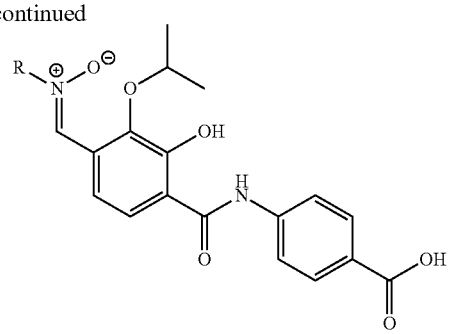

The nitrone intermediate may be prepared from the corresponding aldehyde with one of the procedures reported in J. Chem. Soc., Perkin Trans. 1, 1980, 244-248, Org. Lett., 2007, 9, 473-476, J. Org. Chem., 2009, 74, 6365-6367 and J. Org. Chem. 2017, 82, 4631-4639.

(S,E)-4-(4-(4-(4-Amino-2-(4-(3-(4-cyanophenyl)-2-methylacrylamido)benzamido)-4-oxobutanamido)benzamido)-2-hydroxy-3-isopropoxybenzamido)-2-hydroxy-3-isopropoxybenzoic acid (124)

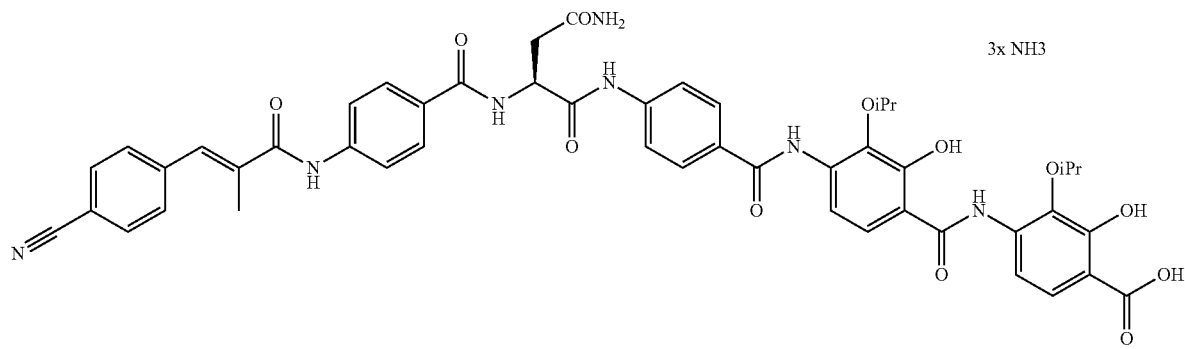

Chemical Formula: $C_{49}H_{47}N_7O_{12}$
Exact Mass: 925, 3283

Compound 124 was synthesized starting from amine 60 (20 mg; 0.023 mmol) and carboxylic acid 35 (13 mg; 0.069 mmol) using the same experimental procedure employed for the synthesis of compound 61.

Desired compound purified by preparative RP-HPLC using condition B to obtain 6.6 mg of desired product (0.0071 mmol, y=22%).

$^1$H NMR (700 MHz, DMSO) δ 11.26 (s, 1H), 10.91 (s, 1H), 10.44 (s, 1H), 10.26 (s, 1H), 9.60 (s, 1H), 8.64 (d, J=7.2 Hz, 1H), 7.97 (d, J=8.7 Hz, 2H), 7.95 (d, J=6.3 Hz, 1H), 7.91 (dd, J=11.4, 8.6 Hz, 4H), 7.83 (d, J=8.7 Hz, 2H), 7.80 (dd, J=8.8, 1.9 Hz, 3H), 7.67 (d, J=8.3 Hz, 2H), 7.53 (d, J=8.8 Hz, 1H), 7.51 (d, J=8.8 Hz, 1H), 7.40 (s, 1H), 7.37 (s, 1H), 6.99 (s, 1H), 4.92 (dd, J=14.0, 7.1 Hz, 1H), 4.69 (dt, J=12.3, 6.1 Hz, 1H), 4.31 (dt, J=12.2, 6.1 Hz, 1H), 2.69 (d, J=7.5 Hz, 2H), 2.13 (d, J=0.8 Hz, 3H), 1.27 (t, J=6.2 Hz, 12H).

$^{13}$C NMR (176 MHz, DMSO) δ 172.0, 171.3, 170.7, 168.1, 165.8, 164.3, 163.6, 162.3, 155.0, 150.4, 142.4, 142.0, 140.6, 138.4, 136.3, 135.8, 134.0, 132.4, 131.7, 130.1, 128.6, 128.4, 128.3, 125.0, 124.8, 119.2, 118.8, 116.4, 115.4, 110.3, 110.1, 75.7, 74.1, 51.6, 36.8, 22.0, 21.9, 14.6.

HRMS (ESI) calculated for C49H48N7O12 (M+H$^+$) 926.3355, found 926.3337.

(S)-4-(4-(4-(4-amino-2-(4-(4-azidobenzamido)benzamido)-4-oxobutanamido)benzamido)-2-hydroxy-3-isopropoxybenzamido)benzoic acid (120)

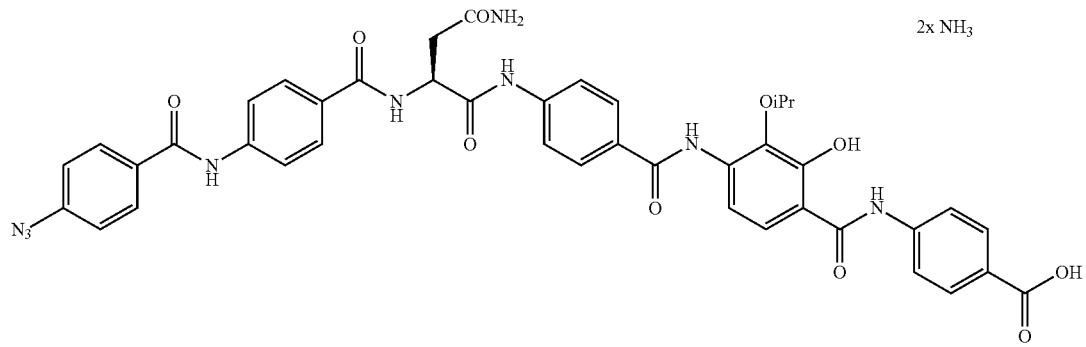

AR378

2x NH₃

Chemical Formula: $C_{42}H_{37}N_9O_{10}$
Exact Mass: 827.2663

Amine 26 (25 mg, 0.032 mmol) coupled with 4-azidobenzoic acid using coupling conditions A followed by final deprotection.

Desired compound purified by preparative HPLC condition B, to obtain 0.8 mg of desired product as a white solid (0.001 mmol, y=3%).

$^1$H NMR (700 MHz, DMSO) δ 12.61 (br, 1H), 12.29 (br, 1H), 10.46 (s, 1H), 10.45 (s, 1H), 9.19 (br, 1H), 8.65 (d, J=7.3 Hz, 1H), 8.07-8.03 (m, 2H), 7.94-7.86 (m, 9H), 7.81 (d, J=8.7 Hz, 5H), 7.40 (s, 1H), 7.30-7.27 (m, 2H), 6.98 (s, 1H), 4.92 (dd, J=14.1, 7.2 Hz, 1H), 4.70 (br, 1H), 2.69 (d, J=7.4 Hz, 2H), 1.24 (d, J=5.9 Hz, 6H).

$^{13}$C NMR (176 MHz, DMSO) δ 171.3, 170.7, 167.0, 165.8, 164.7, 143.0, 142.0, 131.0, 130.3, 129.7, 128.7, 128.3, 119.4, 119.0, 119.0, 51.6, 36.8, 22.4.

HRMS (ESI) calculated for C42H38N9O10 (M+H) 828.2736, found 828.2727.

(S)-4-(4-(4-(4-amino-2-(4-(5-cyanothiophene-2-carboxamido)benzamido)-4-oxobutanamido)benzamido)-2-hydroxy-3-isopropoxybenzamido)-2-hydroxy-3-isopropoxybenzoic acid (121)

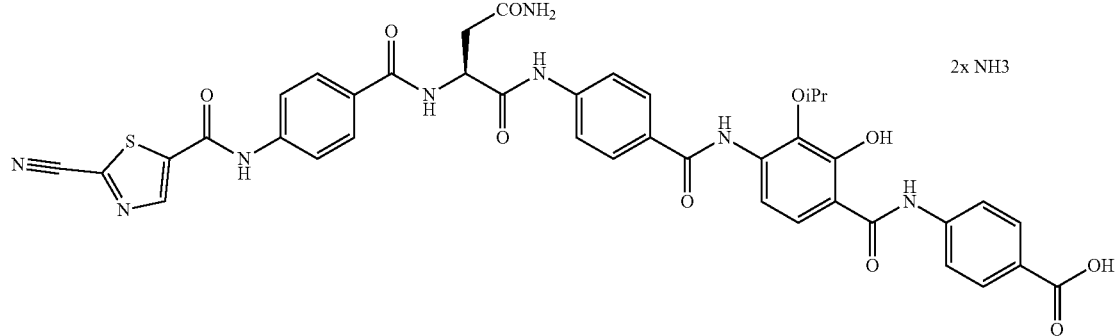

AR396

2x NH3

Chemical Formula: $C_{40}H_{34}N_8O_{10}S$
Exact Mass: 818.2119

Amine 26 (25 mg, 0.032 mmol) coupled with 2-cyanothiazole-5-carboxylic acid using coupling conditions A followed by final deprotection.

Desired compound purified by preparative HPLC condition B, to obtain 7 mg of desired product as a white solid (0.0086 mmol, y=26%).

$^1$H NMR (700 MHz, DMSO) δ 12.30 (br, 1H), 10.97 (s, 1H), 10.46 (s, 1H), 9.34 (br, 1H), 8.91 (s, 1H), 8.70 (d, J=7.3 Hz, 1H), 7.94 (t, J=9.2 Hz, 6H), 7.87-7.76 (m, 7H), 7.63 (br, 1H), 7.40 (s, 1H), 6.99 (s, 1H), 4.92 (dd, J=14.1, 7.2 Hz, 1H), 4.60 (br, 1H), 2.69 (d, J=7.8 Hz, 2H), 1.25 (d, J=6.1 Hz, 6H).

$^{13}$C NMR (176 MHz, DMSO) δ 171.2, 170.7, 168.3, 166.9, 165.7, 164.1, 157.3, 145.2, 142.4, 141.9, 140.6, 138.9, 136.5, 130.2, 129.7, 128.5, 128.2, 122.9, 120.3, 119.7, 118.9, 112.9, 51.6, 36.7, 22.3.

HRMS (ESI) calculated for C40H35N8O10S (M+H) 819.2191, found 819.2191.

(S,E)-4-(4-(4-(4-amino-2-(4-(3-(4-cyanophenyl)-2-methylacrylamido)benzamido)-4-oxobutanamido)benzamido)-2-hydroxy-3-isobutoxybenzamido)benzoic acid (125)

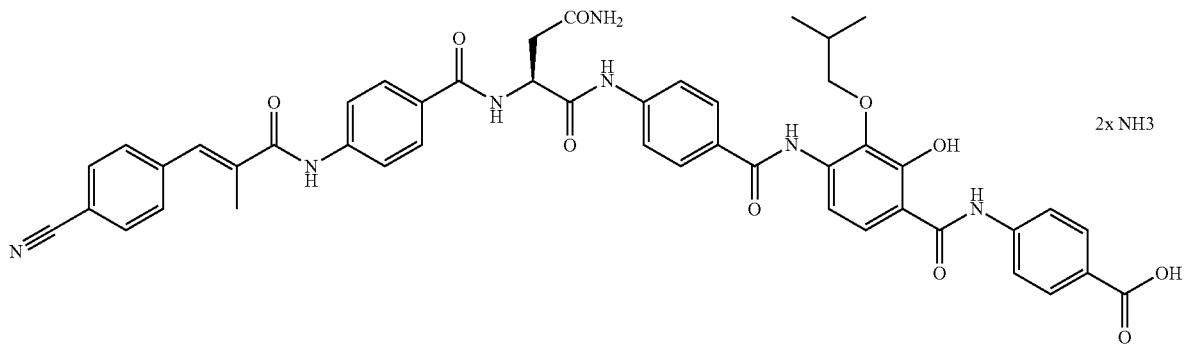

AR397

Chemical Formula: C$_{47}$H$_{43}$N$_7$O$_{10}$
Exact Mass: 865.3071

Amine 64 (25 mg, 0.032 mmol) was coupled with carboxylic acid 35 (21 mg; 0.12 mmol) using the same experimental procedure employed for the synthesis of compound 65. The final compound was purified by preparative RP-HPLC (gradient 10-70% CH$_3$CN in water 10 mM NH$_4$HCO$_3$ in 40 min) to afford 5.5 mg of desired product (0.0064 mmol; y=18%).

$^1$H NMR (700 MHz, DMSO) δ 12.73 (br, 1H), 12.27 (br, 1H), 10.63 (br, 1H), 10.44 (s, 1H), 10.26 (s, 1H), 9.40 (s, 1H), 8.63 (d, J=7.3 Hz, 1H), 7.96 (dd, J=8.7, 3.2 Hz, 4H), 7.91 (dd, J=13.1, 8.6 Hz, 4H), 7.84 (dd, J=18.2, 8.8 Hz, 5H), 7.79 (d, J=8.8 Hz, 2H), 7.67 (d, J=8.3 Hz, 2H), 7.59 (d, J=7.6 Hz, 1H), 7.39 (s, 1H), 7.37 (s, 1H), 6.99 (s, 1H), 4.91 (dd, J=14.0, 7.2 Hz, 1H), 3.82 (d, J=6.4 Hz, 2H), 2.73-2.65 (m, 2H), 2.13 (d, J=1.3 Hz, 3H), 2.01 (m, 1H) 0.95 (d, J=6.7 Hz, 6H).

$^{13}$C NMR (176 MHz, DMSO) δ 171.3, 170.7, 168.4, 168.1, 166.9, 165.8, 164.4, 142.4, 142.0, 140.6, 138.5, 136.2, 135.8, 132.4, 131.7, 130.2, 130.1, 128.6, 128.3, 128.3, 126.2, 122.9, 120.6, 119.2, 118.7, 112.8, 110.3, 78.6, 51.6, 36.7, 28.6, 19.1, 14.6.

HRMS (ESI) calculated for C47H44N7O10 (M+H) 866.3144, found 866.3141.

(S)-4-(4-(4-(4-amino-2-(4-(4-cyanobenzamido)benzamido)-4-oxobutanamido)benzamido)-2-hydroxy-3-isobutoxybenzamido)benzoic acid (126)

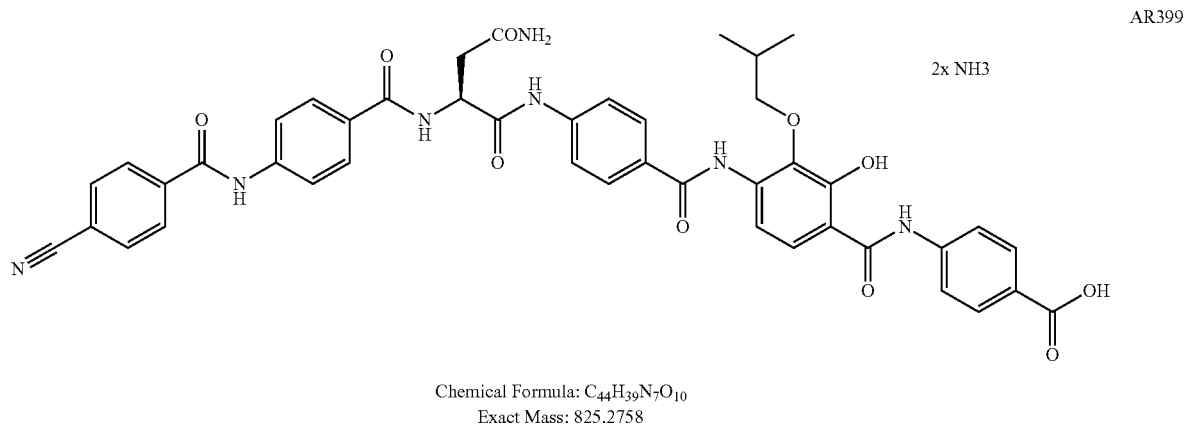 [SMILES: CC(C)COc1c(NC(=O)c2ccc(NC(=O)[C@H](CC(N)=O)NC(=O)c3ccc(NC(=O)c4ccc(C#N)cc4)cc3)cc2)ccc(C(=O)Nc2ccc(C(=O)O)cc2)c1O]

Chemical Formula: C$_{44}$H$_{39}$N$_7$O$_{10}$
Exact Mass: 825.2758

Amine 64 (30 mg; 0.038 mmol) was coupled with 4-Cyanobenzoic acid (18 mg; 0.12 mmol) using the same experimental procedure employed for the synthesis of compound 65.

The final compound was purified by preparative RP-HPLC (gradient 10-70% CH$_3$CN in water 10 mM NH$_4$HCO$_3$ in 40 min) to afford 8.5 mg of desired product (0.010 mmol; y=27%).

$^1$H NMR (700 MHz, DMSO) δ 12.27 (br, 1H), 10.70 (s, 1H), 10.44 (s, 1H), 9.34 (br, 1H), 8.67 (d, J=7.0 Hz, 1H), 8.17-8.10 (m, 2H), 8.08-8.01 (m, 2H), 7.99-7.87 (m, 8H), 7.84 (d, J=7.5 Hz, 2H), 7.82-7.75 (m, 3H), 7.51 (br, 1H), 7.40 (s, 1H), 6.99 (s, 1H), 4.91 (dd, J=12.7, 6.1 Hz, 1H), 3.83 (d, J=5.9 Hz, 2H), 2.69 (d, J=6.5 Hz, 2H), 2.00 (m, 1H), 0.95 (dd, J=6.6, 2.0 Hz, 6H).

$^{13}$C NMR (176 MHz, DMSO) δ 171.3, 170.7, 168.2, 166.9, 165.8, 164.5, 164.3, 141.6, 138.7, 132.5, 130.2, 129.1, 128.6, 128.3, 123.0, 120.3, 119.5, 118.7, 118.3, 114.0, 51.6, 36.8, 28.6, 19.1.

HRMS (ESI) calculated for C44H40N7O10 (M+H) 826.2831, found 826.2828.

Methyl 4-((4-cyanophenyl)ethynyl)benzoate palladium(II) dichloride (15 mg, 0.022 mmol), copper iodide (4.2 mg, 0.022 mmol) and triphenylphosphine (5.7 mg, 0.022 mmol) were mixed together under a N$_2$ atmosphere in THF (1.7 mL), subsequently TEA (1.7 mL) was added. The reaction was stirred for 5 hours and then diluted with EtOAc (20 mL) and water (20 mL). The watery phase was extracted with EtOAc (2×5 mL). The combined organic phases were washed with HCl 1 N, NaHCO$_3$ saturated solution and brine, dried over sodium sulphate and reduced under vacuum. The crude residue was purified on silica gel with a gradient 2-20% EtOAc in Pet.Et. to give 440 mg of desired product (0.440 mmol, y=q.).

$^1$H NMR (500 MHz, DMSO) δ 8.04-7.99 (m, 2H), 7.95-7.91 (m, 2H), 7.81-7.77 (m, 2H), 7.77-7.72 (m, 2H), 3.88 (s, 3H).

$^{13}$C NMR (126 MHz, DMSO) δ 165.5, 132.7, 132.3, 132.0, 129.9, 129.5, 126.5, 126.1, 118.4, 111.5, 92.1, 90.6, 52.4.

HRMS (ESI) calculated for C17H12NO2 (M+H) 262.0863, found 262.0861.

Methyl 4-(5-(4-cyanophenyl)-1H-1,2,3-triazol-4-yl)benzoate

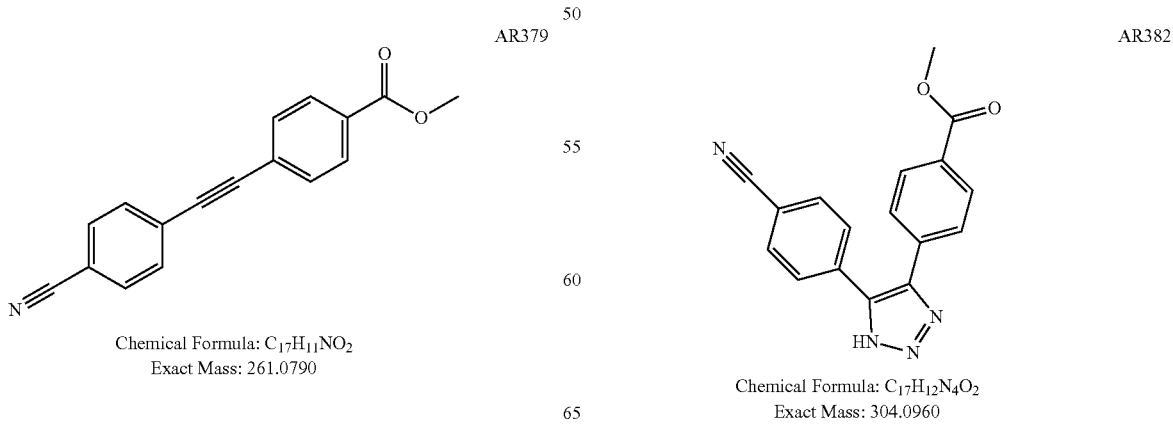

4-Iodobenzonitrile (100 mg, 0.437 mmol), methyl 4-ethynylbenzoate (77 mg, 0.481 mmol), Bis(triphenylphosphine)

Alkyne AR379 (31 mg, 0.119 mmol) and NaN₃ were mixed in DMF (1.2 mL), the reaction mixture was heated to 100° C. for 1 hour using a MW reactor. The reaction was diluted with EtOAc (12 mL) and brine (12 mL) and the layers were separated, the watery phase was extracted twice with EtOAc (5 mL). The combined organic phases were dried over sodium sulphate and reduced under vacuum. The residue thus obtained was chromatographed on silica gel with a gradient 5-40% EtOAc in Pet.Et to give 21 mg of desired product (0.069 mmol, y=58%).

¹H NMR (500 MHz, MeOD/THF-d8 3:1) δ 8.11-8.04 (m, 2H), 7.82-7.76 (m, 2H), 7.76-7.70 (m, 2H), 7.68-7.62 (m, 2H), 3.93 (s, 3H).

¹³C NMR (126 MHz, MeOD/THF-d8 3:1) δ 167.7, 133.9, 131.7, 131.2, 130.1, 129.6, 119.5, 113.4, 52.9.

HRMS (ESI) calculated for C17H13N4O2 (M+H) 305.1033, found 305.1033.

4-((4-Cyanophenyl)ethynyl)benzoic acid

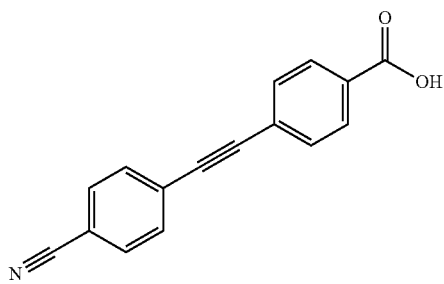

AR384

Chemical Formula: $C_{17}H_{11}NO_2$
Exact Mass: 261.0790

Alkyne AR379 (150 mg, 0.574 mmol) was dissolved in THF (2.9 mL) and water (1.4 mL), the solution was cooled to 0° C. and a solution of LiOH (137 mg, 5.74 mmol) in water (1.5 mL) was added. The reaction was stirred overnight at r.t., the pH was adjusted to 2, the precipitate thus formed was extracted with EtOAc (3×20 mL). The organic phases reunited were dried over sodium sulphate and reduced under vacuum to give 143 mg of desired product (0.578 mmol, y=q.).

¹H NMR (700 MHz, DMSO) δ 13.21 (s, 1H), 8.04-7.95 (m, 2H), 7.95-7.89 (m, 2H), 7.84-7.75 (m, 2H), 7.75-7.69 (m, 2H).

¹³C NMR (176 MHz, DMSO) δ 166.6, 132.7, 132.3, 131.8, 131.2, 129.6, 126.6, 125.7, 118.4, 111.4, 92.3, 90.3.

HRMS (ESI) calculated for C16H10NO2 (M+H) 248.0706, found 248.0707.

4-(5-(4-cyanophenyl)-1H-1,2,3-triazol-4-yl)benzoic acid

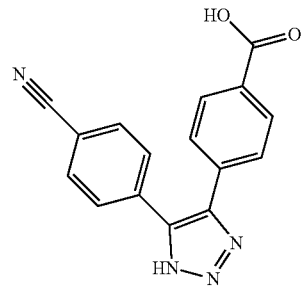

AR385

Chemical Formula: $C_{17}H_{12}N_4O_2$
Exact Mass: 304.0960

Triazole AR382 (163 mg, 0.536 mmol) was dissolved in THF (2.7 mL) and water (1.2 mL), the solution was cooled to 0° C. and a solution of LiOH (128 mg, 5.36 mmol) in water (1.5 mL) was added. The reaction was stirred overnight at r.t., the pH was adjusted to 2, the precipitate thus formed was extracted with EtOAc (3×20 mL). The organic phases reunited were dried over sodium sulphate and reduced under vacuum to give 143 mg of desired product (0.493 mmol, y=92%).

¹H NMR (500 MHz, DMSO) δ 15.65 (br, 1H), 13.10 (br, 1H), 8.00 (d, J=8.3 Hz, 2H), 7.90 (d, J=8.2 Hz, 2H), 7.72-7.65 (m, 2H), 7.66-7.55 (m, 2H).

¹³C NMR (126 MHz, DMSO) δ 166.9, 142.6, 132.8, 130.8, 129.9, 128.5, 128.2, 124.9, 118.6, 111.0.

HRMS (ESI) calculated for C16H11N4O2 (M+H) 291.0877, found 291.0879.

(S)-4-(4-(4-(4-amino-2-(3'-cyano-[1,1'-biphenyl]-3-carboxamido)-4-oxobutanamido)benzamido)-2-hydroxy-3-isopropoxybenzamido)benzoic acid (127)

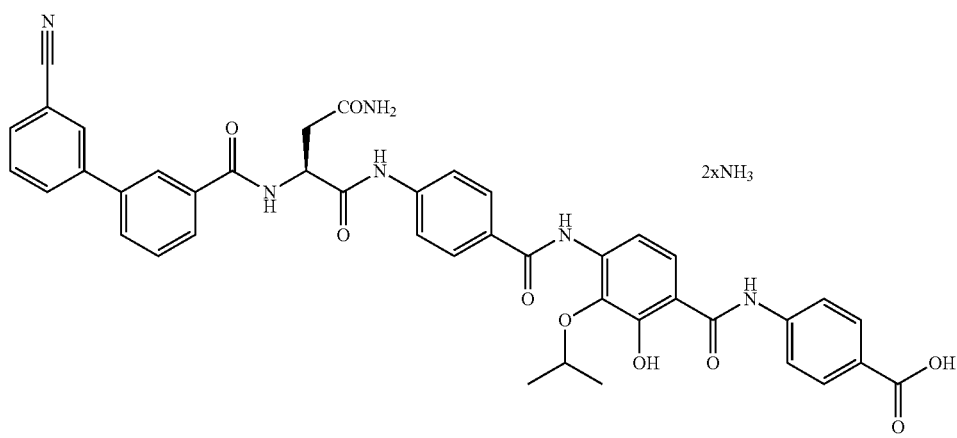

GT4_185 A

Chemical Formula: $C_{42}H_{36}N_6O_9$
Exact Mass: 768.2544

3'-cyano-[1,1'-biphenyl]-3-carboxylic acid was activated to the corresponding pentafluorophenyl ester as reported in DOI: 10.1002/ange.201705387.

The activated ester was dissolved in DMF (0.1 mL) and added at 0° C. to a stirred solution of crude amine (0.02 mmol) and DiPEA (18 μL; 0.10 mmol). Reaction stirred three hours at r.t. then diluted with EtOAc and a solution of ice cold HCl, organic phase washed with brine and evaporated under vacuum. Residue purified by preparative HPLC with a gradient 10-95% $CH_3CN$ in water 10 mM $NH_4HCO_3$ in 40 min. to give 0.9 mg of desired product (0.0011 mmol; y=5%).

$^1$H NMR (700 MHz, DMSO) δ 12.55 (br, 1H), 10.47 (s, 2H), 9.08 (br, 1H), 8.91 (d, J=7.4 Hz, 1H), 8.30-8.21 (m, 2H), 8.15-8.08 (m, 1H), 7.95 (dd, J=7.7, 1.7 Hz, 2H), 7.92-7.85 (m, 5H), 7.81 (dd, J=14.1, 8.7 Hz, 4H), 7.72 (t, J=7.8 Hz, 1H), 7.63 (t, J=7.8 Hz, 1H), 7.60 (br, 1H), 7.41 (s, 1H), 7.33 (br, 1H), 6.99 (s, 1H), 4.99 (dd, J=13.8, 7.6 Hz, 1H), 4.83 (br, 2H), 2.72 (ddd, J=23.7, 15.4, 7.1 Hz, 2H), 1.22 (d, J=6.2 Hz, 6H).

$^{13}$C NMR (176 MHz, DMSO) δ 171.2, 170.5, 167.8, 167.1, 166.0, 163.6, 142.2, 140.7, 138.0, 137.1, 134.7, 131.7, 131.4, 130.4, 130.3, 130.3, 129.9, 129.2, 127.9, 127.7, 125.9, 123.4, 119.0, 118.8, 112.2, 51.6, 36.9, 22.5.

HRMS (ESI) calculated for $C_{42}H_{37}N_6O_9$ (M+H$^+$) 769.2617, found 769.2610.

(S)-4-(4-(4-(4-Amino-2-(4-((4-cyanophenyl)ethynyl) benzamido)-4-oxobutanamido)benzamido)-2-hydroxy-3-isopropoxybenzamido)benzoic acid (128)

GT4_185 B

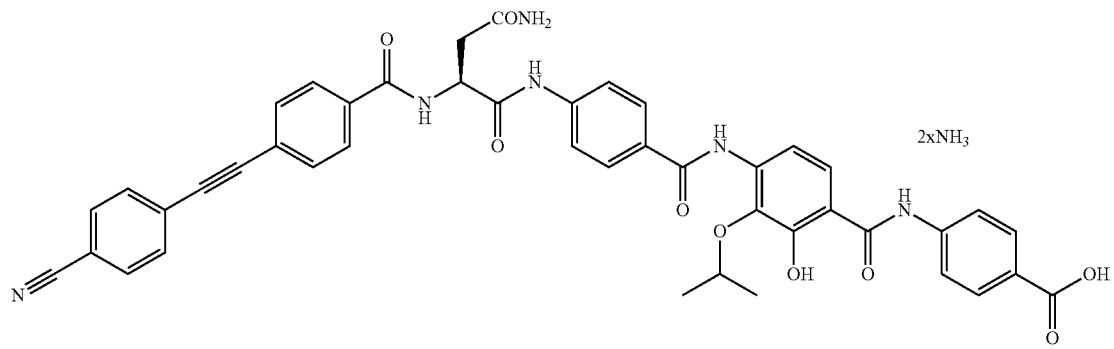

Chemical Formula: $C_{44}H_{36}N_6O_9$
Exact Mass: 792.2544

4-((4-Cyanophenyl)ethynyl)benzoic acid was activated to the corresponding pentafluorophenyl ester as reported in DOI: 10.1002/ange.201705387.

Activated ester (18.0 mg; 0.04 mmol) was dissolved in DMF (0.1 mL) and added at 0° C. to a stirred solution of crude amine (0.02 mmol) and DiPEA (18 μL; 0.10 mmol). Reaction stirred three hours at r.t. then diluted with EA and a solution of ice cold HCl, organic phase washed with brine and evaporated under vacuum. Residue purified by preparative HPLC with a gradient 10-95% $CH_3CN$ in water 10 mM $NH_4HCO_3$ in 40 min. to give 3.2 mg of desired product (0.0039 mmol; y=19%).

$^1$H NMR (700 MHz, DMSO) δ 10.46 (s, 1H), 9.18 (br, 1H), 8.88 (d, J=7.2 Hz, 1H), 7.98 (d, J=8.3 Hz, 2H), 7.92 (dd, J=15.0, 7.6 Hz, 6H), 7.85-7.76 (m, 6H), 7.73 (d, J=8.3 Hz, 2H), 7.68 (br, 1H), 7.45 (br, 1H), 7.39 (s, 1H), 6.99 (s, 1H), 4.94 (dd, J=14.0, 7.3 Hz, 1H), 4.73 (br, 1H), 2.73-2.67 (m, 2H), 1.23 (d, J=6.1 Hz, 6H).

$^{13}$C NMR (176 MHz, DMSO) δ 171.2, 170.5, 168.0, 167.0, 165.5, 163.8, 142.2, 134.3, 132.7, 132.3, 131.6, 130.3, 128.0, 126.8, 124.3, 123.2, 119.0, 118.4, 111.3, 92.6, 89.8, 51.7, 36.7, 22.5.

HRMS (ESI) calculated for $C_{44}H_{37}N_6O_9$ (M+H$^+$) 793.2617, found 793.2608.

(S)-4-(4-(4-(4-amino-2-(4-(5-(4-cyanophenyl)-1H-1,2,3-triazol-4-yl)benzamido)-4-oxobutanamido)benzamido)-2-hydroxy-3-isopropoxybenzamido)benzoic acid (129)

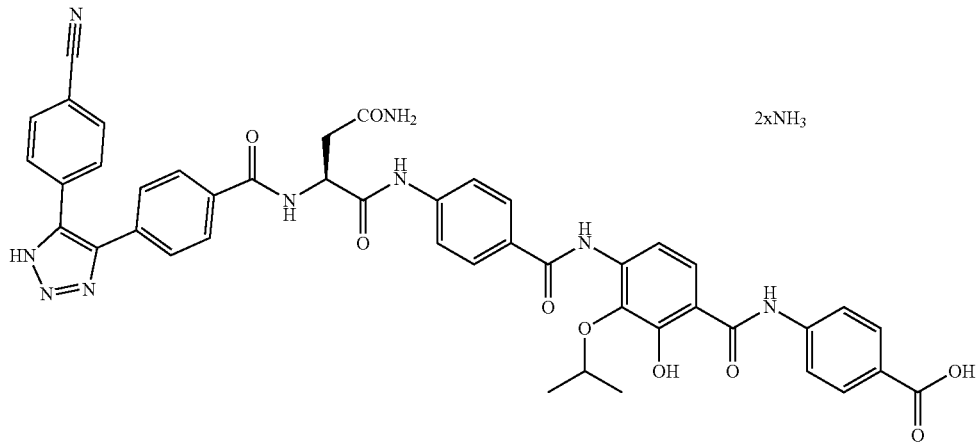

Chemical Formula: C<sub>44</sub>H<sub>37</sub>N<sub>9</sub>O<sub>9</sub>
Exact Mass: 835.2714

The carboxylic acid coupling partner AR385 was activated to the corresponding pentafluorophenyl ester as reported in DOI: 10.1002/ange.201705387.

Activated ester (18.4 mg; 0.04 mmol) was dissolved in DMF (0.1 mL) and added at 0° C. to a stirred solution of crude amine (0.02 mmol) and DiPEA (18 µL; 0.10 mmol). Reaction stirred three hours at r.t. then diluted with EA and a solution of ice cold HCl, organic phase washed with brine and evaporated under vacuum. Residue purified by preparative HPLC with a gradient 10-95% CH$_3$CN in water 10 mM NH$_4$HCO$_3$ in 40 min. to give 5.3 mg of desired product (0.0063 mmol; y=32%).

$^1$H NMR (700 MHz, DMSO) δ 15.34 (s, 1H), 10.45 (s, 1H), 8.87 (s, 1H), 8.70 (d, J=7.1 Hz, 1H), 7.86-7.80 (m, 6H), 7.77 (dd, J=16.7, 8.2 Hz, 3H), 7.66 (dd, J=23.4, 8.3 Hz, 4H), 7.57 (d, J=8.1 Hz, 2H), 7.53-7.50 (m, 2H), 7.45 (d, J=8.7 Hz, 1H), 7.42 (s, 1H), 7.08 (d, J=8.7 Hz, 1H), 6.98 (s, 1H), 5.01 (dt, J=12.3, 6.1 Hz, 1H), 4.93 (dd, J=14.1, 7.1 Hz, 1H), 2.69 (d, J=7.0 Hz, 2H), 1.20 (d, J=6.1 Hz, 6H).

$^{13}$C NMR (176 MHz, DMSO) δ 171.3, 170.7, 170.3, 167.9, 166.9, 166.3, 165.3, 163.1, 142.0, 141.7, 141.3, 141.0, 140.1, 139.6, 138.9, 137.6, 134.0, 132.0, 130.8, 130.6, 129.7, 129.5, 127.6, 127.5, 127.3, 127.0, 126.0, 126.9, 126.4, 126.0, 124.2, 123.7, 119.5, 119.1, 117.6, 116.0, 106.8, 100.7, 70.4, 51.7, 36.9, 22.7.

HRMS (ESI) calculated for C$_{44}$H$_{38}$N$_9$O$_9$ (M+H$^+$) 836.2787, found 836.2807.

Ethyl (Z)-3-(4-cyanophenyl)-2-methylacrylate

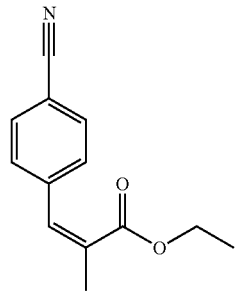

Chemical Formula: C$_{13}$H$_{13}$NO$_2$
Exact Mass: 215.09

Ethyl 2-(diethoxyphosphoryl)propanoate (100 mg, 0.29 mmol) and 18-crown-6 1 N solution in THF (1.5 mL) were dissolved in THF (3.0 mL) and cooled to −78° C., then KHMDS 0.7 M solution in toluene (0.5 mL, 0.34 mmol) was added. The reaction was stirred at this temperature for 30 min., then a solution of 4-formylbenzonitrile (42 mg, 0.32 mmol) in THF (0.5 mL) was added to it, stirring was prolonged for 2 h at −78° C. The reaction was quenched by addition of HCl 1N and diluted with EtOAc, the organic phase was washed with HCl 1N, NaHCO$_3$ sat. sol. and brine, dried over sodium sulphate and reduced under vacuum. The crude product (130 mg) was used in the next step without further purification.

(Z)-3-(4-Cyanophenyl)-2-methylacrylic acid

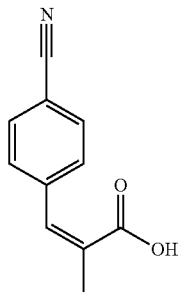

Chemical Formula: C₁₁H₉NO₂
Exact Mass: 187.06

Crude ethyl (Z)-3-(4-cyanophenyl)-2-methylacrylate (100 mg) was dissolved in THF (2.5 mL), MeOH (0.5 mL) and water (1.3 mL), the solution was cooled to 0° C. and a solution of LiOH (61 mg, 2.56 mmol) in water (1.3 mL) was added dropwise. The reaction was stirred overnight and then the pH was adjusted to 1 adding HCl 1 N. The reaction was diluted with EtOAc and HCl 1 N, the organic phase was washed with brine, dried over sodium sulphate and reduced under vacuum. The crude residue was purified on silica gel with a gradient 0-5% MeOH in DCM, both phases containing 0.1% AcOH, to obtain 23 mg (0.23 mmol, y=78% over two steps).

$^1$H NMR (500 MHz, DMSO) δ 12.95 (br, 1H), 7.83-7.75 (m, 2H), 7.47 (d, J=8.2 Hz, 2H), 6.70 (d, J=1.2 Hz, 1H), 2.05 (d, J=1.6 Hz, 3H).

$^{13}$C NMR (126 MHz, DMSO) δ 170.7, 141.5, 134.6, 132.5, 130.3, 129.2, 119.3, 110.2, 21.9.

HRMS (ESI) calculated for C11H8NO2 (M−H) 186.0560, found 186.0562.

(S,Z)-4-(4-(4-(4-amino-2-(4-(3-(4-cyanophenyl)-2-methylacrylamido)benzamido)-4-oxobutanamido)benzamido)-2-hydroxy-3-isopropoxybenzamido)benzoic acid (122)

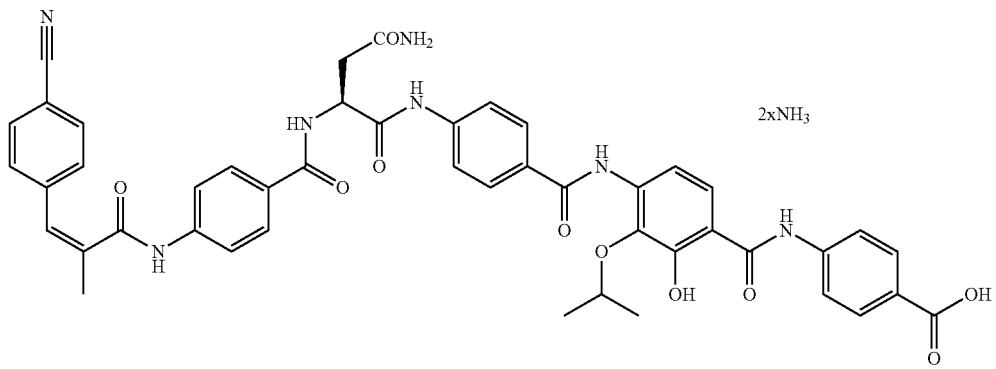

GT4_239

Chemical Formula: C₄₆H₄₁N₇O₁₀
Exact Mass: 851.2915

Amine 26 (25 mg, 0.032 mmol) was coupled with (Z)-3-(4-cyanophenyl)-2-methylacrylic acid using coupling conditions A followed by final deprotection.

Desired compound purified by preparative HPLC condition B, to obtain 3.5 mg of desired product as a white solid (0.004 mmol, y=13%).

$^1$H NMR (700 MHz, DMSO) δ 12.49 (br, 1H), 10.44 (s, 1H), 10.42 (s, 1H), 9.10 (br, 1H), 8.62 (d, J=7.3 Hz, 1H), 7.92-7.84 (m, 6H), 7.80 (d, J=8.7 Hz, 4H), 7.75 (d, J=8.4 Hz, 2H), 7.65 (d, J=8.7 Hz, 2H), 7.61 (br, 1H), 7.47 (d, J=8.4 Hz, 2H), 7.39 (s, 1H), 6.98 (br, 1H), 6.62 (s, 1H), 4.91 (dd, J=13.9, 7.3 Hz, 1H), 4.81 (br, 1H), 2.72-2.62 (m, 2H), 2.15 (d, J=1.3 Hz, 3H), 1.22 (d, J=6.1 Hz, 6H).

$^{13}$C NMR (176 MHz, DMSO) δ 171.3, 170.6, 168.8, 167.7, 167.1, 165.7, 163.6, 142.2, 141.5, 140.5, 139.2, 138.0, 132.3, 130.3, 130.0, 129.0, 128.4, 127.9, 126.6, 124.9, 123.3, 119.0, 118.8, 118.7, 109.7, 51.6, 36.8, 30.4, 22.5.

HRMS (ESI) calculated for C46H40N7O10 (M−H) 850.2842, found 850.2836.

4-(4-(4-((2S,3R)-4-amino-2-(4-((E)-3-(4-cyanophenyl)-2-methylacrylamido)benzamido)-3-methoxy-4-oxobutanamido)benzamido)-2-hydroxy-3-isopropoxybenzamido)benzoic acid (123)

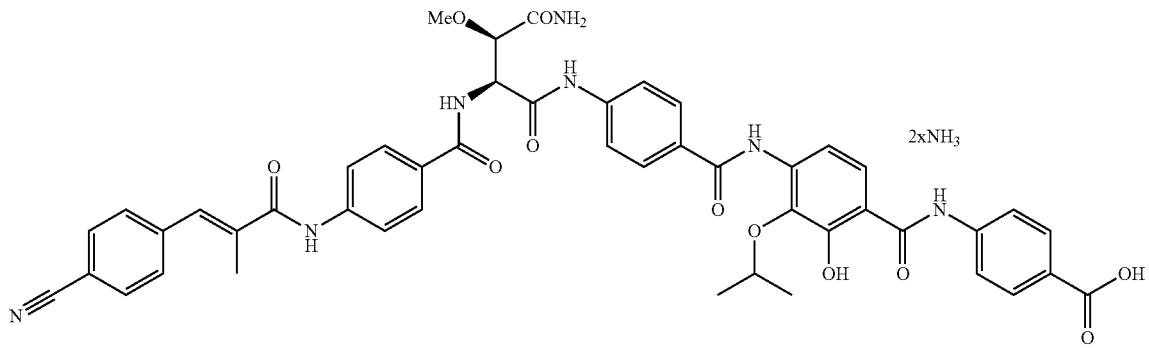

Chemical Formula: $C_{47}H_{43}N_7O_{11}$
Exact Mass: 881.30

Amine 108 (12 mg, 0.015 mmol) was coupled to (E)-3-(4-cyanophenyl)-2-methylacrylic acid using coupling conditions A followed by final deprotection.

Purification by preparative HPLC using condition B afforded 0.9 mg of desired compound (0.00102 mmol, y=7%).

$^1$H NMR (700 MHz, DMSO) δ 12.78 (br, 1H), 12.30 (br, 1H), 10.57 (s, 1H), 10.28 (s, 1H), 9.35 (br, 1H), 8.42 (d, J=8.1 Hz, 1H), 7.98-7.93 (m, 4H), 7.91 (d, J=8.3 Hz, 2H), 7.88-7.76 (m, 9H), 7.67 (d, J=8.3 Hz, 3H), 7.54 (s, 1H), 7.48 (s, 1H), 7.37 (s, 1H), 4.91 (t, J=8.1 Hz, 1H), 4.59 (br, 1H), 4.09 (d, J=8.1 Hz, 1H), 3.31 (s, 3H), 2.13 (d, J=1.0 Hz, 3H), 1.26 (d, J=6.1 Hz, 6H).

$^{13}$C NMR (176 MHz, DMSO) δ 170.9, 168.7, 168.4, 168.1, 166.9, 165.5, 164.1, 146.4, 142.2, 140.6, 139.2, 136.4, 135.8, 132.4, 132.0, 131.8, 130.2, 130.1, 129.9, 128.6, 128.3, 128.3, 128.2, 124.9, 122.9, 120.5, 119.3, 119.0, 118.8, 118.1, 110.3, 108.8, 80.0, 57.7, 40.0, 30.4, 22.3.

HRMS (ESI) calculated for C47H42N7O11 (M−H) 880.2948, found 880.2949.

Synthesis of Tetrazole Derivative 124:

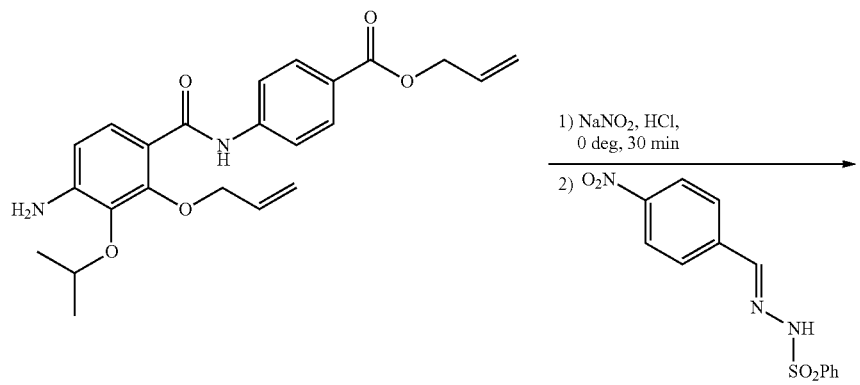

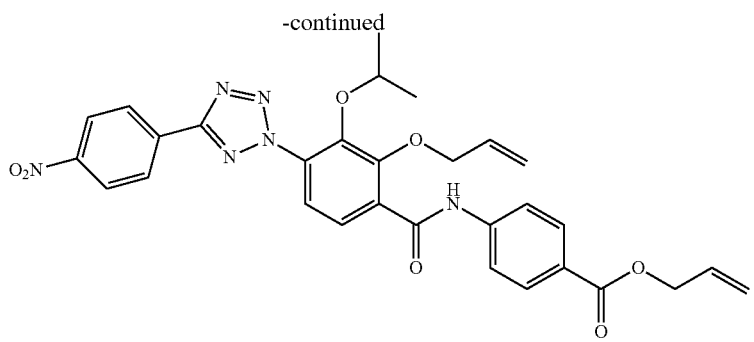

Chemical Formula: C<sub>30</sub>H<sub>28</sub>N<sub>6</sub>O<sub>7</sub>
Exact Mass: 584.2019
Molecular Weight: 584.5890

The amine (50 mg, 0.122 mmol, 1 equiv) was dissolved in ethanol (1.5 Ml) and then 300 μl of conc. Hydrochloric acid were added. The mixture was cooled to 0 degrees. In parallel, a solution of sodium nitrite (8.4 mg, 0.122 mmol, 1 equiv) in water (450 μl) was prepared and cooled to zero degrees. The amine solution was then added dropwise into the sodium nitrite solution and the reaction mixture was allowed to stir at zero degrees for half an hour.

The diazonium salt was then added dropwise to a −10 degrees cooled solution of (E)-N'-(4-nitrobenzylidene)benzenesulfonohydrazide (37.25 mg, 0.122 mmol, 1 equiv) in pyridine (1 Ml). the reaction mixture was then stir two hours at this temperature and then two more hours at room temperature. The reaction completion was checked by TLC and LCMS. The reaction mixture was then diluted in water and extracted 3 times with DCM. The combined organic layers were washed with 1 N HCl solution and dried over sodium sulfate. After filtration, the volatiles were removed under reduced pressure and the crude material was purified on flash chromatography using petroleum ether/ethyl acetate 8/2 as eluent. The pure compound was obtained with 45% yield (m=32 mg).

$^1$H NMR (500 MHz, CDCl$_3$) δ 10.29 (s, 1H), 8.51-8.45 (m, 2H), 8.45-8.39 (m, 2H), 8.23 (d, J=8.7 Hz, 1H), 8.10 (d, J=8.6 Hz, 2H), 7.80 (t, J=9.6 Hz, 2H), 7.67 (dd, J=8.7, 2.6 Hz, 1H), 6.18 (ddt, J=16.5, 10.4, 6.1 Hz, 1H), 6.06 (ddt, J=17.1, 10.5, 5.6 Hz, 1H), 5.54 (dd, J=17.1, 1.2 Hz, 1H), 5.50-5.39 (m, 2H), 5.31 (dd, J=10.4, 1.3 Hz, 1H), 4.88 (d, J=6.0 Hz, 2H), 4.84 (dt, J=5.6, 1.3 Hz, 1H), 4.47 (dt, J=12.3, 6.1 Hz, 1H), 3.91 (d, J=5.1 Hz, 1H), 1.18 (d, J=6.1 Hz, 6H).

$^{13}$C NMR (126 MHz, CDCl$_3$) δ 165.7, 163.4, 161.5, 151.59, 149.2, 145.5, 142.1, 135.0, 132.8, 132.3, 131.8, 131.4, 131.0, 129.2, 128.0, 126.8, 126.0, 124.4, 121.8, 120.9, 119.4, 118.3, 77.9, 75.7, 65.6, 22.2.

HRMS (ESI) calculated for C$_{30}$H$_{29}$N$_6$O$_7$ (M+H) 585.2092, found 585.2093.

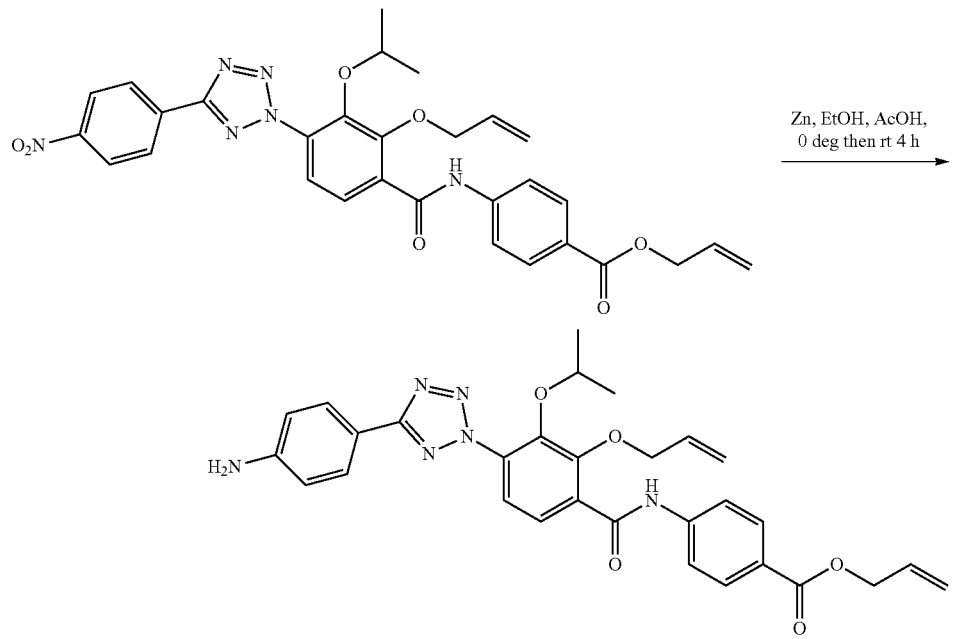

Chemical Formula: C<sub>30</sub>H<sub>30</sub>N<sub>6</sub>O<sub>5</sub>
Exact Mass: 554.2278
Molecular Weight: 554.6070

The tetrazole (22.3 mg, 0.038 mmol, 1 equiv) was dissolved in ethanol (750 μL) and acetic acid (100 μL) under inert atmosphere. The solution was cooled to zero degrees and Zinc (24 mg, 0.38 mmol, 10 equiv) was added portionwise and then the reaction mixture was allowed to stir for 1 hour at room temperature until completion of the reaction checked by TLC and LCMS. The reaction mixture was then filtered over a pad of celite and evaporated under reduced pressure. The crude material was purified by flash chromatography using petroleum ether/ethyl acetate 5/5. The pure compound was obtained with a yield of 76% (16.1 mg).

$^1$H NMR (700 MHz, MeOD) δ 8.09-8.05 (m, 2H), 7.96-7.90 (m, 2H), 7.86 (d, J=8.7 Hz, 2H), 7.71 (d, J=8.3 Hz, 1H), 7.60 (d, J=8.4 Hz, 1H), 6.85-6.78 (m, 2H), 6.09 (dtd, J=21.5, 10.7, 5.6 Hz, 2H), 5.46-5.39 (m, 2H), 5.34-5.24 (m, 2H), 1.14 (d, J=6.1 Hz, 6H).

$^{13}$C NMR (176 MHz, MeOD) δ 167.2, 167.00, 166.0, 134.2, 133.8, 131.7, 129.2, 127.0, 125.4, 123.0, 120.7, 119.5, 118.4, 116.4, 115.8, 78.5, 76.4, 66.6, 22.3. (contains some acetic acid)

HRMS (ESI) calculated for $C_{30}H_{31}N_6O_5$ (M+H) 555.2350, found 555.2350.

0.058 mmol, 2 equiv) were subsequently added dropwise. The reaction mixture was allowed to stir at this temperature for 2 hours it was diluted in ethyl acetate and washed with a saturated NaHCO$_3$ solution and brine. After drying the organic layer with sodium sulfate the volatiles were evaporated under reduced pressure. The crude material was purified by flash chromatography using petroleum ether/ethyl acetate 6/4. The pure compound was obtained with a yield of 59% (19.4 mg).

$^1$H NMR (700 MHz, CDCl$_3$) δ 10.34 (s, 1H), 9.02 (s, 1H), 8.27-8.20 (m, 3H), 8.11 (d, J=8.5 Hz, 2H), 7.81 (d, J=8.6 Hz, 2H), 7.78 (d, J=6.7 Hz, 2H), 7.70 (d, J=8.6 Hz, 1H), 7.65-7.55 (m, 4H), 7.44-7.37 (m, 2H), 7.35-7.28 (m, 2H), 7.28-7.23 (m, 10H), 7.23-7.15 (m, 5H), 6.94 (s, 1H), 6.53 (s, 1H), 6.20 (ddd, J=16.5, 11.2, 6.0 Hz, 1H), 6.07 (ddd, J=22.6, 10.9, 5.6 Hz, 1H), 5.56 (d, J=17.1 Hz, 1H), 5.51-5.40 (m, 2H), 4.90 (d, J=5.9 Hz, 2H), 4.85 (d, J=5.6 Hz, 2H), 4.71 (s, 1H), 4.55-4.38 (m, 4H), 4.23 (s, 1H), 3.23 (bs, 1H), 2.73 (bs, 1H), 1.21 (d, J=6.0 Hz, 6H).

$^{13}$C NMR (176 MHz, CDCl$_3$) δ 170.7, 169.0, 165.7, 164.8, 161.7, 156.3, 151.7, 145.3, 144.0, 143.6, 143.6, 142.2, 141.3, 139.6, 135.3, 132.3, 131.9, 131.0, 129.7,

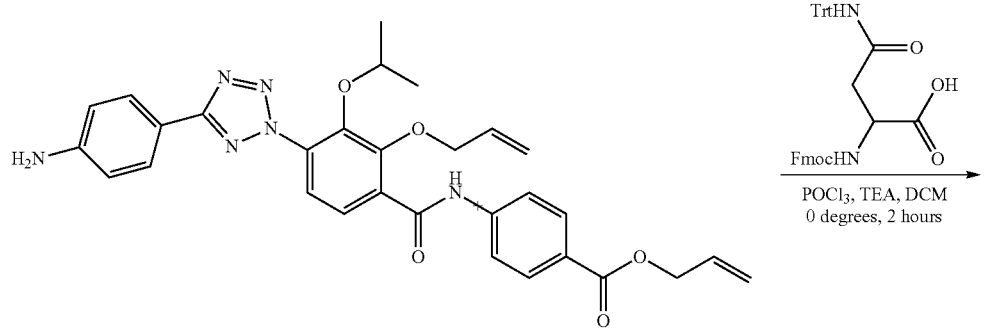

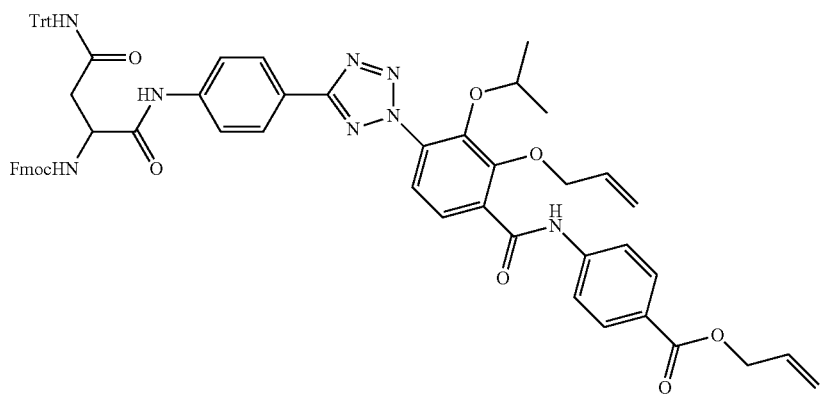

Chemical Formula: $C_{68}H_{60}N_8O_9$
Exact Mass: 1132.4483
Molecular Weight: 1133.2750

The amine (16.1 mg, 0.029 mmol, 1 equiv), the protected amino-acid (34.6 mg, 0.058 mmol, 2 equiv) were dissolved in dichloromethane (600 μL) under inert atmosphere. The reaction mixture was cooled to 0 degrees and then triethylamine (8 μL, 0.058 mmol, 2 equiv) and POCl3 (5.5 μL, 128.6, 128.1, 127.8, 127.8, 127.3, 127.1, 126.7, 125.9, 125.0, 122.8, 121.8, 120.7, 120.2, 120.1, 119.4, 118.2, 77.9, 75.7, 71.1, 67.3, 65.5, 47.1, 29.7, 22.2.

HRMS (ESI) calculated for $C_{68}H_{61}N_8O_9$ (M+H) 1133.4556, found 1133.4549.

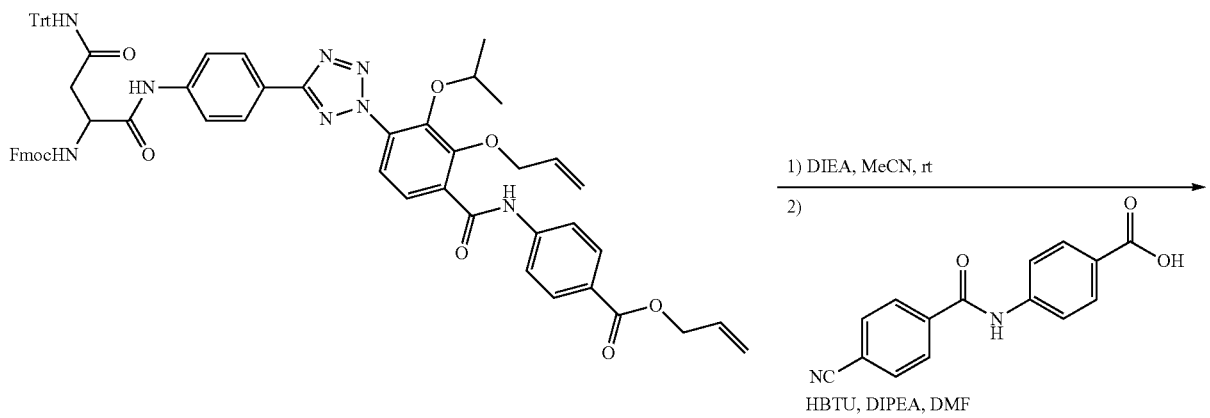

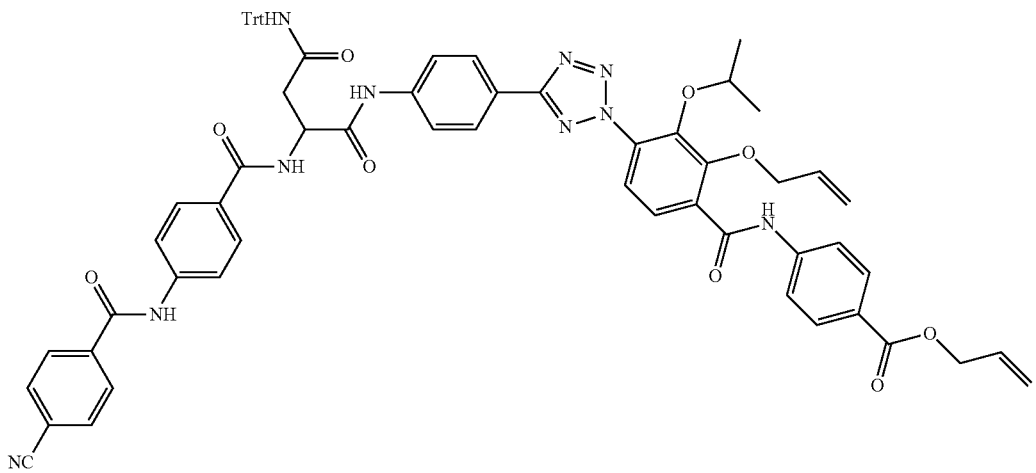

Chemical Formula: $C_{68}H_{58}N_{10}O_9$
Exact Mass: 1158.4388
Molecular Weight: 1159.2730 the Fmoc protected amine (6.5 mg, 0.006 mmol, 1 equiv) was deprotected using diethylamine (45.9 µL) in MeCN (137 µL). The reaction mixture was allowed to stir at room temperature for 2 hours then the volatiles were evaporated under vacuum. The crude material was used in the next step without further purification.

The acid (1.3 mg, 0.005 mmol, 1 equiv), and HBTU (2.3 mg, 0.006 mmol, 1.2 equiv) were dissolved in dry DMF (20.7 µL) under inert atmosphere. DIPEA (3 µL, 0.018 mmol, 3 equiv) was then added and the reaction mixture was allowed to stir for 15 min at rt. Then a solution of the amine (5.5 mg, 0.006 mg, 1.2 equiv) in dry DMF (21.2 µL) was added and the reaction mixture was allowed to stir at rt for 2 hours. Then it was diluted with brine solution and water and extracted 3 times with ethyl acetate. The combined organic layers were washed with HCl 1N, saturated NaHCO₃ and brine. After drying over sodium sulfate and filtration, the volatiles were removed under reduced pressure. The crude material was purified by flash chromatography using petroleum ether/ethyl acetate 4/6 as eluent. The pure compound was obtained with a yield of 87% (6.1 mg)

$^1$H NMR (700 MHz, CDCl₃) δ 10.33 (s, 1H), 9.55 (s, 1H), 8.28-8.17 (m, 3H), 8.10 (d, J=8.7 Hz, 2H), 8.09-7.95 (m, 3H), 7.87-7.76 (m, 4H), 7.74 (s, 2H), 7.68 (d, J=8.6 Hz, 1H), 7.62 (d, J=8.0 Hz, 2H), 7.38-7.15 (m, 15H), 6.19 (ddt, J=16.5, 10.4, 6.0 Hz, 1H), 6.07 (ddt, J=17.1, 10.5, 5.7 Hz, 1H), 5.55 (dd, J=17.1, 1.2 Hz, 1H), 5.50-5.38 (m, 2H), 5.09 (s, 1H), 4.89 (d, J=5.9 Hz, 1H), 4.84 (dt, J=5.6, 1.3 Hz, 1H), 4.41 (dt, J=12.3, 6.1 Hz, 1H), 3.40-3.27 (m, 1H), 2.82-2.68 (m, 1H), 1.19 (d, J=6.1 Hz, 6H).

$^{13}$C NMR (176 MHz, CDCl₃) δ 171.3, 169.2, 166.9, 165.7, 164.8, 163.9, 161.7, 151.6, 145.3, 144.0, 143.2, 142.14, 140.9, 139.9, 138.3, 135.3, 132.7, 132.3, 131.9, 131.0, 129.1, 128.7, 128.6, 128.1, 127.9, 127.3, 126.7, 125.9, 122.7, 121.8, 120.7, 120.2, 119.8, 119.4, 118.2, 117.7, 115.8, 77.9, 75.6, 71.2, 65.5, 51.1, 37.7, 29.7, 22.2.

HRMS (ESI) calculated for $C_{68}H_{59}N_{10}O_9$ (M+H) 1159.4461, found 1159.4471.

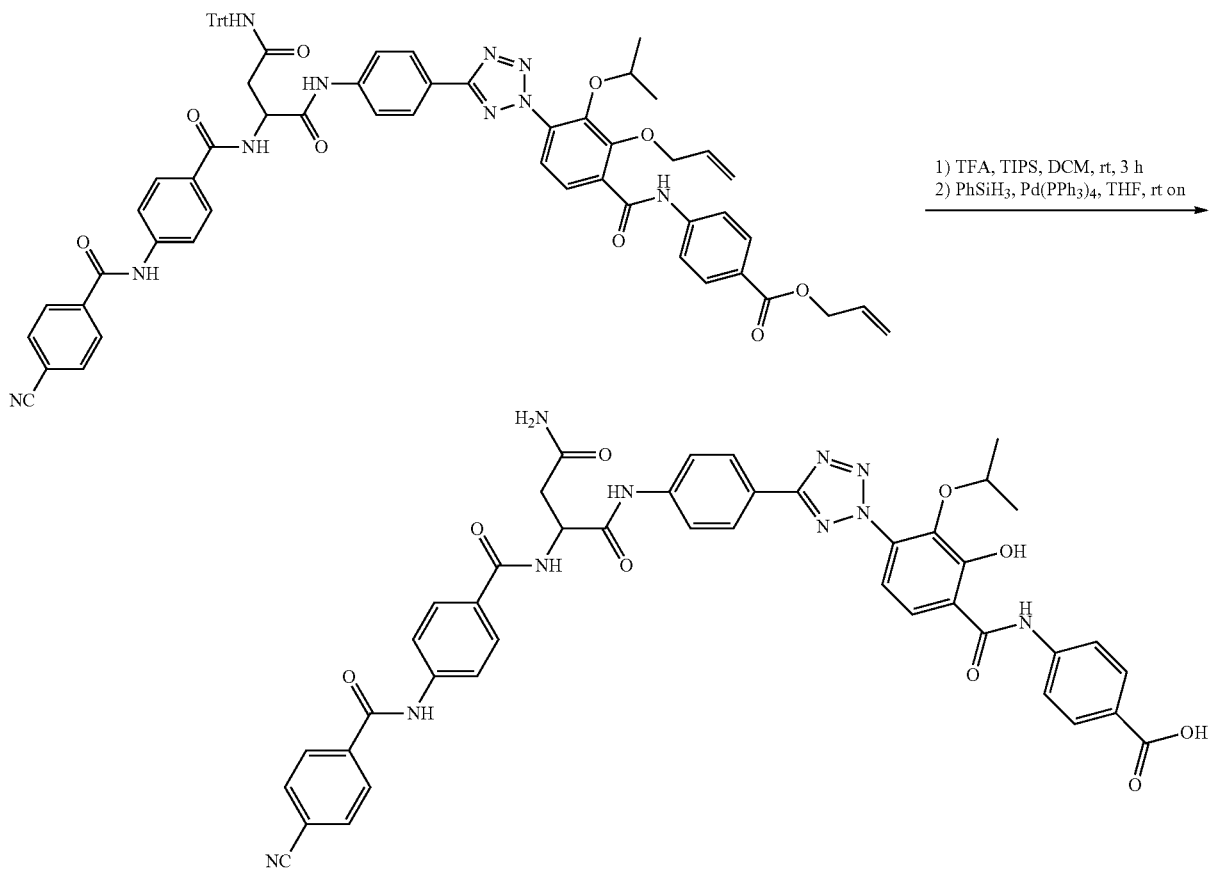

Chemical Formula: C₄₃H₃₆N₁₀O₉
Exact Mass: 836.2667
Molecular Weight: 836.8220

In order to remove the Trityl group, the compound (11.1 mg, 0.01 mmol, 1 equiv) was dissolved in dry DCM (285 µL) and then TFA (57.5 µL) and TIPS (11.3 µL) were subsequently added. The reaction mixture was allowed to stir at room temperature for 3 hours and then the volatiles were removed by evaporation under reduced pressure. The crude material was used without further purification in the next step.

In order to remove the different allyl protecting group, the crude compound (8.9 mg, 0.0097 mmol, 1 equiv) was dissolved in dry THF (1.2 Ml) under argon. Then phenyl-silane and the palladium were subsequently added and the reaction mixture was allowed to stir at room temperature for 2 hours. The solvent was evaporated and diluted in THF, water and ethyl acetate, then few drops of acetic acid were added. The mixture was extracted with ethyl acetate 3 times and the combined organic layers were dried over sodium sulfate and the volatiles were evaporated under reduced pressure.

The crude material was subjected to purification by preparative HPLC using water (with 10 mM of NH4HCO3) acetonitrile (gradient from 10 to 95% of acetonitrile).

The collected fractions were lyophilized to afford the pure final compound as a white solid (2.3 mg) with a yield over two steps of 28.4%.

$^1$H NMR (700 MHz, DMSO) δ 15.13 (s, 1H), 10.74 (s, 1H), 10.49 (s, 1H), 8.83 (d, J=7.0 Hz, 1H), 8.13 (d, J=8.4 Hz, 2H), 8.07 (d, J=8.7 Hz, 2H), 8.04 (d, J=8.4 Hz, 2H), 7.95 (d, J=8.8 Hz, 2H), 7.89 (d, J=8.7 Hz, 2H), 7.86 (d, J=8.7 Hz, 2H), 7.81 (d, J=8.4 Hz, 2H), 7.62 (d, J=8.5 Hz, 1H), 7.61 (d, J=8.5 Hz, 2H), 7.48 (s, 1H), 6.98 (s, 1H), 6.23 (d, J=8.5 Hz, 1H), 5.04 (dt, J=12.3, 6.2 Hz, 1H), 4.93 (dd, J=13.9, 7.5 Hz, 1H), 2.75-2.66 (m, 2H), 0.97 (d, J=6.2 Hz, 6H).

$^{13}$C NMR (176 MHz, DMSO) δ 171.4, 170.6, 169.9, 166.6, 166.1, 165.7, 164.5, 163.1, 144.0, 141.6, 141.0, 138.8, 132.5, 132.2, 129.7, 129.2, 128.7, 128.3, 127.0, 124.2, 123.5, 121.8, 120.7, 119.7, 119.5, 118.3, 117.8, 114.0, 104.0, 70.5, 51.8, 48.6, 40.4, 36.9, 22.4.

HRMS (ESI) calculated for C₄₃H₃₇N₁₀O₉ (M+H) 837.2739, found 837.2739.

7. Biological Activities

Cystobactamid derivatives synthesized were tested against relevant Gram negative and positive bacteria of clinical interest. Experimental procedures used for the biological characterization of the compounds are the same as previously described in WO 2016/082934.

Bioactivity Testing

Bacterial strains used in susceptibility assays (minimum inhibitory concentration, MIC) were either part of our internal strain collection or purchased from the German Collection of Microorganisms and Cell Cultures (*Deutsche Sammlung von Mikroorganismen und Zellkulturen*, DSMZ) and the American Type Culture Collection (ATCC). The susceptible *E. coli* strain (WT) and fluoroquinolone-resistant mutants *E. coli* WT-3 and WT-III were kindly provided by Prof Dr. P. Heisig, Pharmaceutical Biology and Microbiology, University of Hamburg, Germany. The efflux-deficient strain *P. aeruginosa* ΔmexAB was kindly provided by Prof Dr. S. Häußler, Institute for Molecular Bacteriology, TWINCORE, Hannover, Germany. All compounds were prepared as DMSO stocks and MIC values were determined in standard microbroth dilution assays in 96-well MTPs as described in Baumann et al., Angew Chem Int Ed Engl. 2014; 53(52):14605-9. In brief, overnight cultures of bacteria were diluted in either tryptic soy broth (TSB: 1.7% peptone casein, 0.3% peptone soymeal, 0.25% glucose, 0.5% NaCl, 0.25% $K_2HPO_4$; pH 7.3; *S. pneumoniae* and *E. faecalis*) or cation-adjusted Müller-Hinton Broth (BBL™, BD; all other bacteria) and adjusted to $10^4$-$10^6$ cfu/mL. Bacteria were grown in the presence of the derivatives in serial dilution for approx. 16 h at 30-37° C. MIC values were determined and were defined as the antibiotic concentration at which no visual growth of bacteria was observed.

The target activity on *E. coli* gyrase was assessed as described in Baumann et al., Angew Chem Int Ed Engl. 2014; 53(52):14605-9 using a commercial supercoiling (sc) assay kit from Inspiralis according to the manufacturer's instructions. The samples were separated on 0.8% (w/v) agarose gels and relaxed and supercoiled plasmid was visualized by ethidium bromide staining. Half-inhibitory concentrations ($IC_{50}$) were calculated after image analysis and quantification (ImageJ) based on sigmoidal curve fitting (OriginPro).

TABLE 1a

Antibacterial activities (MIC µg/mL) of cystobactamids derivatives herein described in comparison with two natural cystobactamids (cys861-2 and cys919-2) on a small panel of pathogens.

| MIC [µg/ml] | *E. coli* ΔtolC | *E. coli* WT DSM-1116 | *P. aeruginosa* ΔmexAB | *P. aeruginosa* WT PA14 | *S. aureus* Newman | Ec gyrase sc $IC_{50}$ [µM] |
|---|---|---|---|---|---|---|
| Cys861-2 | 0.125 | 0.125 | 0.5 | 2 | 0.5 | 0.22 |
| Cys919-2 | 0.25 | 0.5 | 4 | >64 | 0.25 | 0.67 |
| CP | ≤0.003 | 0.006 | 0.013 | 0.05 | 0.4 | 0.40 |
| 69 | 0.06 | >64 | 1 | >64 | >64 | n.d. |
| 36 | 0.06 | 16 | >64 | >64 | 64 | n.d. |
| 28 | 0.06 | 0.13 | 1 | >64 | 0.5 | 0.11 |
| 53 | 0.06 | 0.25 | 0.25 | 1 | 0.25 | n.d. |
| 40 | 32 | 2 | 4 | >64 | >64 | n.d. |
| 39 | 0.5 | 0.5 | 2 | >64 | 2 | n.d. |
| 44 | 0.06 | 0.5 | 0.25 | 2 | 0.25 | 0.08 |
| 38 | 0.5 | >64 | 2 | >64 | >64 | n.d. |
| 41 | 0.25 | >64 | 0.5 | >64 | >64 | n.d. |
| 42 | 2 | 32 | 4 | >64 | >64 | n.d. |
| 48 | >64 | >64 | >64 | >64 | >64 | n.d. |
| 49 | 0.01-0.06 | 2 | 2-4 | >64 (32) | >64 | n.d. |
| 54 | 4 | >64 | >64 | >64 | >64 | n.d. |
| 37 | 8 | 16 | >64 | >64 | >64 | 16 |
| 65 | >64 (2) | >64 | >64 | >64 | 1 | n.d. |
| 78 | ≤0.03 | 32 (1) | >64 | >64 | 64 | n.d. |
| 43 | 2 | >64 (8) | >64 (16) | >64 | >64 | n.d. |
| 47 | >64 | 2 (0.5) | >64 | >64 | >64 | n.d. |
| 46 | 0.03 | 0.5 | 4 | >64 | 64 | n.d. |
| 45 | ≤0.03 | 0.5 | >64 (64) | >64 | 16-32 | n.d. |
| 62 | ≤0.03 | 0.25 | 1 | >64 (2) | ≤0.03 | n.d. |
| 61 | 0.125-0.25 | 0.5 | 1-2 | >64 | 0.05 | n.d. |
| 50 | 0.03 | 0.5 | 2 | >64 (8) | 64 | n.d. |
| 51 | ≤0.03 | 0.25 | 0.5 | 8 | 2 | n.d. |
| 52 | 0.03 | 0.5 | 0.5 | 4 | 2 | n.d. |
| 55 | <0.03 | 1 | 2 | >64 | >64 | n.d. |
| 56 | <0.03 | 2 | >64 (4) | >64 | >64 | n.d. |
| 57 | <0.03 | <0.03 | 1 | >64 | 1 | n.d. |
| 58 | <0.03 | 0.125 | 0.25 | 1 | 0.06 | n.d. |
| 87 | <0.03 | >64 | >64 | >64 | >64 | n.d. |
| 88 | <0.03 | 0.5 | 8 | >64 | 64 | n.d. |
| 89 | 0.25 | >64 | >64 | >64 | >64 | n.d. |
| 90 | 0.03 | 0.5 | >64 | >64 | 2 | n.d. |
| 91 | >64 | >64 | >64 | >64 | >64 | n.d. |
| 92 | 0.25 | >64 | >64 | >64 | >64 | n.d. |
| 93 | 0.5 | >64 | >64 | >64 | >64 | n.d. |
| 94 | 0.03 | >64 | >64 | >64 | >64 | n.d. |
| 109 | <0.03 | <0.03 | <0.03 | 0.5 | <0.03 | 0.4 |
| 119 | <0.03 | 0.06 | 2 | 8 | <0.03 | 1.5 | n.d.: not determined; CP: ciprofloxacin; Cys861-2: cystobactamid 861-2 (=cystobactamide F; see WO 2015/003816); Cys919-2: cystobactamid 919-2 (see WO 2016/082934).

TABLE 1b

Antibacterial activities (MIC µg/mL) of further cystobactamids derivatives herein described on a small panel of pathogens.

| MIC [µg/ml] | E. coli ΔtolC | E. coli WT DSM-1116 | P. aeruginosa ΔmexAB | P. aeruginosa WT PA14 | S. aureus Newman | Ec gyrase sc IC$_{50}$ [µM] |
|---|---|---|---|---|---|---|
| 124 | <0.03 | 0.125 | 0.25 | 1 | 0.06 | 0.2 |
| 120 | nd | nd | nd | nd | nd | |
| 121 | <0.03 | 0.06 | 1 | >64 | 4 | nd |
| 125 | 0.06 | 0.5 | >64 | >64 | 0.06 | nd |
| 126 | <0.03 | 0.25 | >64 | >64 | 0.25 | nd |
| 128 | 0.06 | 0.06* | 0.5* | >64 | <0.03 | nd |
| 122 | 0.25 | 1 | >64 | >64 | 8 | nd |
| 123 | 0.5 | 1 | 2 | 8 | 4 | nd |
| 124 | 0.125 | 0.5 | 1 | >64 | 0.06 | nd |

*value could not be determined unambiguously and might be higher than assigned

TABLE 2a

Antibacterial activities (MIC µg/mL) of selected cystobactamids derivatives on a large panel of pathogens.

| MIC [µg/ml] | Cys861-2 | Cys919-2 | CP | 28 | 44 | 53 | 49 | 62 | 61 |
|---|---|---|---|---|---|---|---|---|---|
| E. faecalis ATCC-29212 | 1 | 0.1 | 0.8 | 2 | 0.5 | 0.5 | nd | nd | nd |
| S. aureus ATCC-29213 | 0.25 | 0.1 | 0.1 | 0.5 | 0.5 | 0.5 | >64 | 0.025 | 0.05 |
| S. epidermidis DSM-28765 | 0.5 | 0.25 | 0.2 | 1 | 0.06 | 0.25 | nd | nd | nd |
| S. pneumoniae DSM-20566 | 0.06 | 0.13 | 0.8 | 0.25 | 0.13 | 2 | nd | nd | nd |
| A. baumannii DSM-30008 | 0.5 | 8 | 0.8 | 0.25 | 1 | 0.25 | 32 | 0.5 | 1 |
| E. coli WT | 0.13 | 0.5 | 0.013 | 0.06 | 0.25 | 0.13 | 2 | 0.125-0.25 | 0.5 |
| E. coli WT-3 [gyrA(S83L, D87G)] | 0.5 | 64 | 0.8 | 0.25 | 0.13 | 0.06 | | | |
| E. coli WT-III [marRΔ74bp] | 0.5 | >64 | 0.1 | 0.06 | 0.25 | 0.06 | | | |
| E. aerogenes DSM-30053 | >64 | >64 | 0.01 | >64 | 1 | 1 | >64 | >64 | >64 |
| E. cloacae DSM-30054 | 64 | >64 | 0.2 | 0.25 | 0.25 | >64 | nd | nd | nd |
| P. aeruginosa DSM-24600 | 1 | 64 | 3.2 | >64 | >64 | >64 | nd | nd | nd |
| P. aeruginosa DSM-46316 | 2 | 64 | 0.1 | >64 | 2 | 2 | nd | nd | nd |
| K. pneumoniae DSM-30104 | >64 | >64 | 0.02 | >64 | 0.5 | >64 | >64 | >64 | >64 |
| C. freundii DSM-30039 | 0.06 | 1 | 0.003 | 0.06 | <0.03 | 0.13 | 2 | 0.125 | 0.5 |
| S. marcescens DSM-30121 | 64 | >64 | 0.1 | >64 | >64 | 64 | >64 | >64 | >64 |
| P. vulgaris DSM-2140 | 0.25 | 4 | 0.013 | 0.13 | 0.25 | 0.13 | 4 | 0.25 | 0.5 |
| P. mirabilis DSM-2140 | >64 | >64 | 0.03 | >64 | 64 | 2 | nd | nd | nd |

TABLE 2b

Antibacterial activities (MIC µg/mL) of selected cystobactamids derivatives on a larger panel of pathogens in comparison with Cys 861-2, Albicidin (Alb) and ciprofloxacin (CIP).

| MIC [µg/mL] | Cys 861-2 | Alb | CIP | 44 | 109 |
|---|---|---|---|---|---|
| E. faecalis | 1 | 4 | 0.64 | 0.5 | 0.125 |
| S. epidermidis | 0.5 | 0.5 | 0.3 | <0.03 | <0.03 |
| A. baumannii | 1 | >64 | 0.32 | 1 | 1 |
| E. coli WT | 0.06 | 0.06 | 0.005 | 0.25* | 2 |
| E. coli WT-3 [gyrA(S83L, D87G)] | 0.5 | 0.06 | 0.64 | 0.25 | 0.25 |
| E. aerogenes | >64 | >64 | 0.08 | 0.06* | 2 |
| E. cloacae | >64 | >64 | 0.16 | 0.25* | >64 |

TABLE 2b-continued

Antibacterial activities (MIC µg/mL) of selected cystobactamids derivatives on a larger panel of pathogens in comparison with Cys 861-2, Albicidin (Alb) and ciprofloxacin (CIP).

| MIC [µg/mL] | Cys 861-2 | Alb | CIP | 44 | 109 |
|---|---|---|---|---|---|
| P. aeruginosa ESBL 1 | 4 | 16 | 6.4 | 4* | 2 |
| P. aeruginosa ESBL 2 | 2 | 16 | 0.16 | 4 | 1 |
| K. pneumoniae | >64 | >64 | 0.02 | 0.5* | 8 |
| C. freundii | 0.125 | <0.03 | 0.003 | <0.03 | <0.03 |
| S. marcescens | >64 | >64 | 0.32 | >64 | >64 |
| P. vulgaris | 0.25 | <0.03 | 0.005 | 0.25 | 0.125 |
| P. mirabilis | 32 | >64 | 0.04 | >64 | 4 |

The invention claimed is:

1. A compound of formula (Ib):

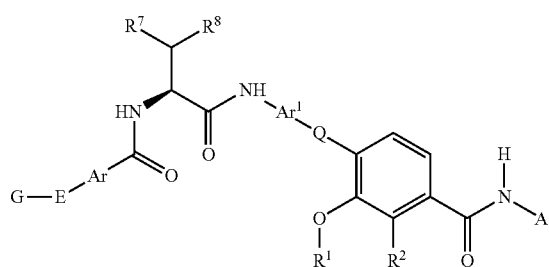

(Ib)

wherein $R^1$ is a hydrogen atom or a group of formula —$C_{1-6}$ alkyl;

$R^2$ is a hydrogen atom, an OH group or a group of formula —O—$C_{1-6}$ alkyl;

A is an alkynyl, a cycloalkyl, heterocycloalkyl, alkylcycloalkyl, heteroalkylcycloalkyl, aryl, heteroaryl, aralkyl or heteroaralkyl group, all of which may optionally be substituted;

Q is a group of formula —C(=O)—NH—, wherein the NH-group is bound to the phenyl group carrying $R^2$;

Ar is a phenylene group or a naphthylene group or a heteroarylene group containing 5 or 6 to 10 ring atoms selected from O, S, N and C or a $C_{3-7}$ cycloalkyl group or a heterocycloalkyl group containing from 3 to 7 ring atoms selected from C, O, S and N or a $C_{2-4}$ alkynyl group; all of which groups may optionally be substituted;

$Ar^1$ is a phenylene group or a naphthylene group or a heteroarylene group containing 5 or 6 to 10 ring atoms selected from O, S, N and C or a $C_{3-7}$ cycloalkyl group or a heterocycloalkyl group containing from 3 to 7 ring atoms selected from C, O, S and N or a $C_{2-4}$ alkynyl group; all of which groups may optionally be substituted;

E is a bond or a group of formula —C≡C— or a heteroarylene group containing 5 ring atoms selected from O, S, N and C or a group of formula -L-C(=O)—NH—*, —C(=O)—NH—$(CH_2)_m$—*, —$SO_2$—NH—$(CH_2)_m$—*, -L-$SO_2$—NH—* or —N=N—, wherein * denotes the point of attachment to group Ar and wherein L is a bond or a —NH—, a $C_{1-6}$ alkylene or a heteroalkylene group containing from 1 to 6 carbon atoms and 1, 2 or 3 heteroatoms selected from O, S and N, and wherein m is an integer of from 1 to 4;

G is a phenyl group or a heteroaryl group containing 5 or 6 to 10 ring atoms selected from O, S, N and C or a heterocycloalkyl group containing 5 or 6 ring atoms selected from O, S, N and C; all of which groups may be unsubstituted or substituted by 1, 2, 3, 4 or 5 groups $R^6$;

the groups $R^6$ are independently from each other selected from a halogen atom, $NO_2$, $N_3$, OH, $NH_2$, SH, CN or an alkyl, alkenyl, alkynyl, heteroalkyl, cycloalkyl, heterocycloalkyl, alkylcycloalkyl, heteroalkylcycloalkyl, aryl, heteroaryl, aralkyl or heteroaralkyl group, all of which groups may optionally be substituted; or two groups $R^6$ are linked together via an alkylene, alkenylene or heteroalkylene group, all of which may optionally be substituted;

$R^7$ is a hydrogen atom; and $R^8$ is a group of formula —C(=O)—$NH_2$;

or a pharmaceutically acceptable salt, solvate or hydrate or a pharmaceutically acceptable formulation thereof.

2. A compound according to claim 1, wherein Ar is a phenylene group or a pyridylene group (especially wherein Ar is an unsubstituted phenylene group).

3. A compound according to claim 1 having the following formula (II):

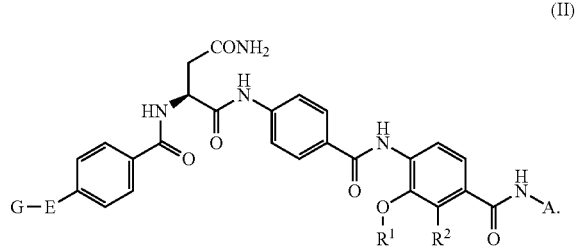

(II)

4. A compound according to claim 1, wherein $R^1$ is a $C_{1-4}$ alkyl group and wherein $R^2$ is an OH group.

5. A compound according to claim 1, wherein A is an optionally substituted phenyl group; an optionally substituted heteroaryl group containing 5 or 6 ring atoms selected from O, S, N and C; an optionally substituted cycloalkyl group containing from 3 to 7 ring atoms; or an optionally substituted heterocycloalkyl group containing from 3 to 7 ring atoms selected from O, S, N and C; or an optionally substituted acetylenyl group; or wherein A is a group of formula —$CH_2$-A' or —NH-A', wherein A' is an optionally substituted phenyl group; an optionally substituted heteroaryl group containing 5 or 6 ring atoms selected from O, S, N and C; an optionally substituted cycloalkyl group containing from 3 to 7 ring atoms; or an optionally substituted heterocycloalkyl group containing from 3 to 7 ring atoms selected from O, S, N and C; or an optionally substituted acetylenyl group.

6. A compound according to claim 1, wherein A is a group of the following formula:

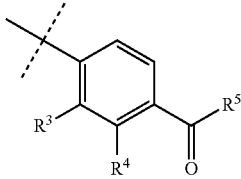

wherein R³ is a hydrogen atom, a halogen atom, an OH group, a $C_{1-6}$ alkyl group or a group of formula —O—$C_{1-6}$ alkyl; R⁴ is a hydrogen atom, a halogen atom, an OH group, a $C_{1-6}$ alkyl group or a group of formula —O—$C_{1-6}$ alkyl; and R⁵ is an OH group or a NH₂ group; especially preferably, R³ is a hydrogen atom or a group of formula —O—$C_{1-4}$ alkyl, R⁴ is a hydrogen atom or an OH group and R⁵ is an OH group.

7. A compound according to claim 1, wherein E is selected from the following groups: —C(=O)—NH—*, —O—CH(CH₃)—C(=O)—NH—*, —S—CH(CH₃)—C(=O)—NH—*, —CH₂—C(=O)—NH—*, —CH₂—CH₂—C(=O)—NH—*, —C(=O)—NH—CH₂—*, —C(=O)—NH—CH₂—CH₂—*, —SO₂—NH—* or —N=N—, wherein * denotes the point of attachment to group Ar.

8. A compound according to claim 1, wherein E is a group of formula: —C(=O)—NH—*, wherein * denotes the point of attachment to group Ar.

9. A compound according to claim 1, wherein G is an optionally substituted phenyl group or an optionally substituted heteroaryl group containing 5 or 6 ring atoms selected from C, N, O and S.

10. A compound according to claim 1, wherein G is a phenyl group which is unsubstituted or substituted by 1, 2 or 3 groups R⁶.

11. A compound according to claim 1, wherein G is substituted by a —CN group.

12. A compound according to claim 1, wherein G is a group of the following formula:

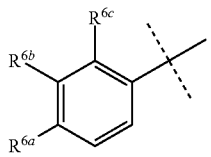

wherein $R^{6a}$ a is —H, —NO₂, —F, —NHAc, —N₃, —NMe₂, —CN, —OH, —NH₂, —CF₃, —NHCONH₂ or —SO₂Me; $R^{6b}$ is —H, —NO₂, —OMe, —Cl, —Br, —NH₂, —O—CH(CH₃)₂, —F or —Me; and $R^{6'}$ is —H, —F, —NO₂, —NH₂, —OH or -Me; or wherein $R^{6c}$ is —H and $R^{6a}$ and $R^{6b}$ together form a group of the formula —CH₂—O—C(=O)—.

13. A compound according to claim 1, wherein G-E together are selected from the following groups:

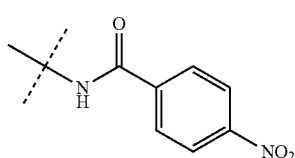

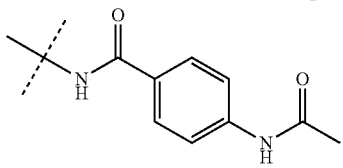

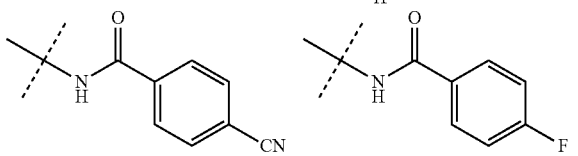

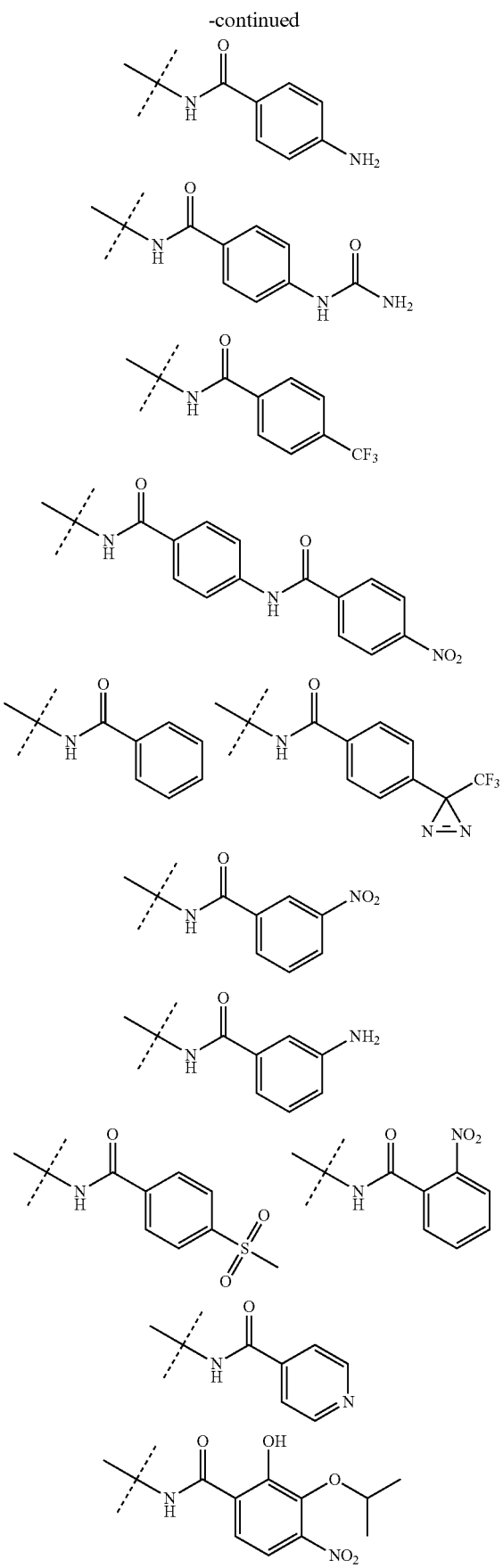

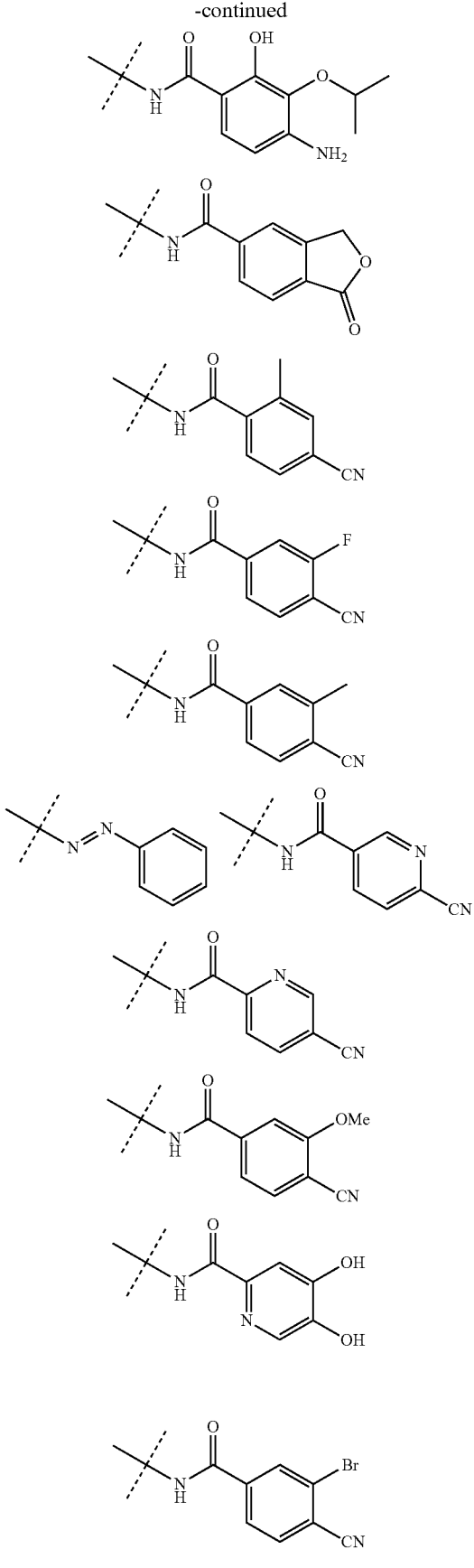
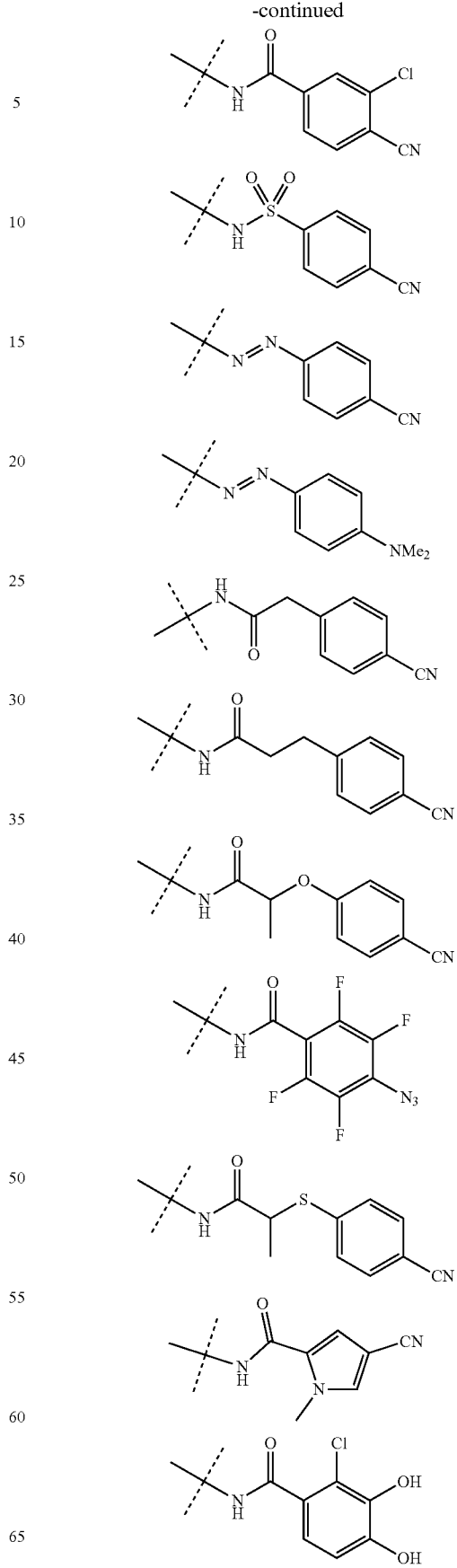

235

-continued

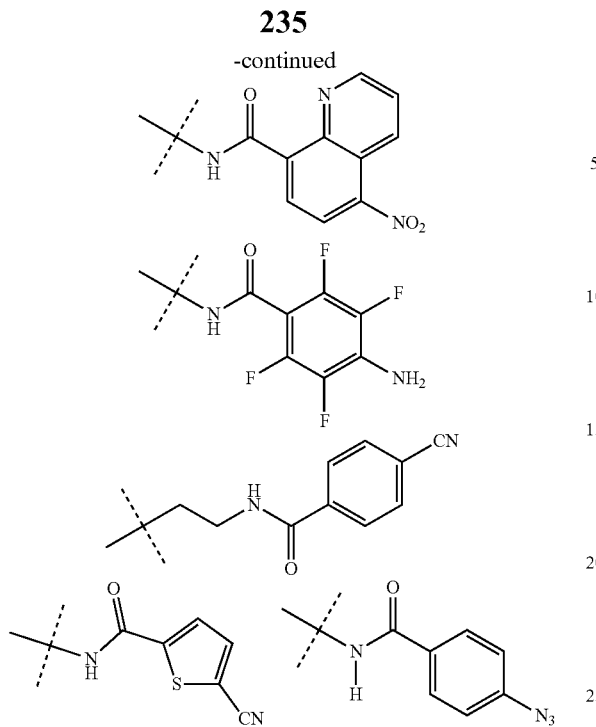

236

-continued

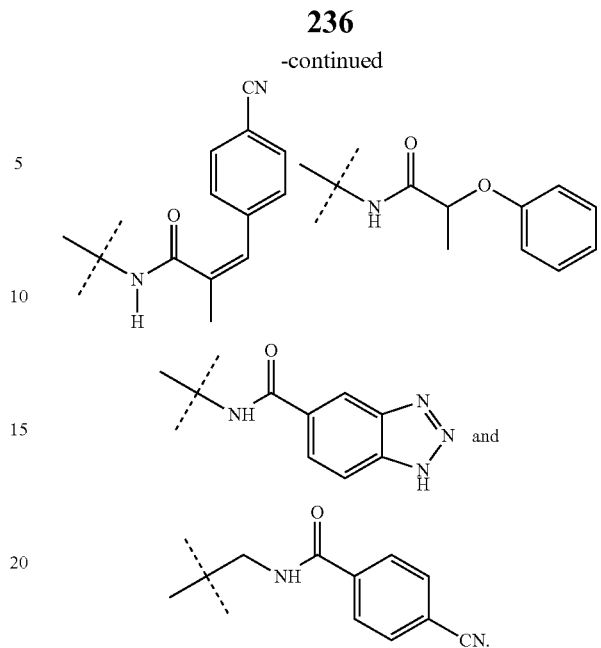

14. A compound according to claim 1 of formula (III):

(III)

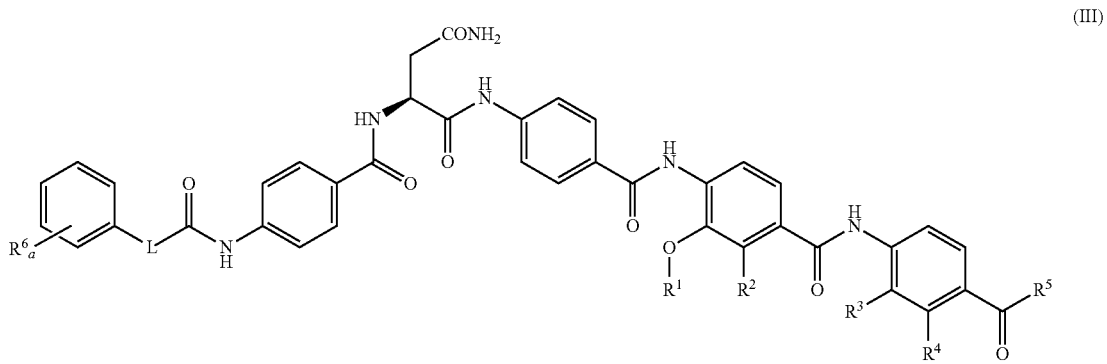

wherein
$R^1$ is a hydrogen atom or a group of formula —$C_{1-6}$ alkyl;
$R^2$ is a hydrogen atom, an OH group or a group of formula —O—$C_{1-6}$ alkyl;
$R^3$ is a hydrogen atom, a halogen atom, an OH group, a $C_{1-6}$ alkyl group or a group of formula —O—$C_{1-6}$ alkyl;
$R^4$ is a hydrogen atom, a halogen atom, an OH group, a $C_{1-6}$ alkyl group or a group of formula —O—$C_{1-6}$ alkyl;
$R^5$ is an OH group or a $NH_2$ group;
the groups $R^6$ are independently from each other selected from —F, —$NO_2$, —OH, —O—$C_{1-6}$ alkyl, —$NH_2$, —CN, —Me, —$CF_3$, NHAc, —NHCONH$_2$ and —SO$_2$Me; or wherein two groups $R^6$ together form a group of the formula —$CH_2$—O—C(=O)—,
a is 0, 1, 2 or 3; and
L is a bond or a —NH—, a $C_{1-6}$ alkylene or a heteroalkylene group containing from 1 to 6 carbon atoms and 1, 2 or 3 heteroatoms selected from O, S and N;
or a pharmaceutically acceptable salt, solvate or hydrate or a pharmaceutically acceptable formulation thereof.

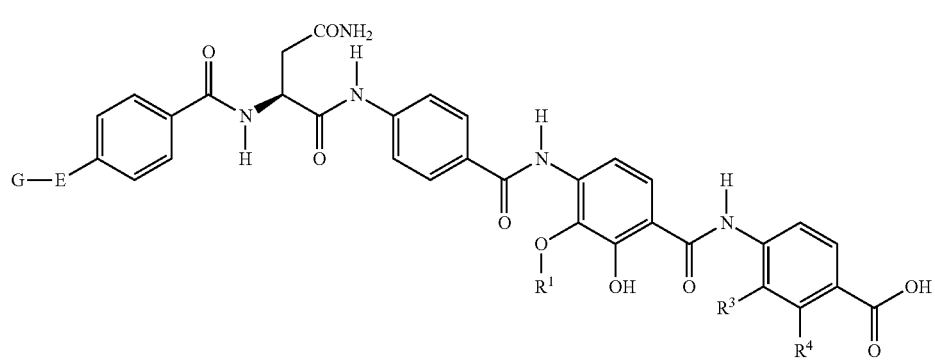

(IV)

wherein
R¹ is a $C_{1-4}$ alkyl group;
R³ is hydrogen or a —O—$C_{1-4}$ alkyl group;
R⁴ is hydrogen or an OH group; and
G and E are defined as in any one of the preceding claims;
or a pharmaceutically acceptable salt, solvate or hydrate
or a pharmaceutically acceptable formulation thereof.

16. A compound of claim 15, wherein G-E are selected from the following groups:

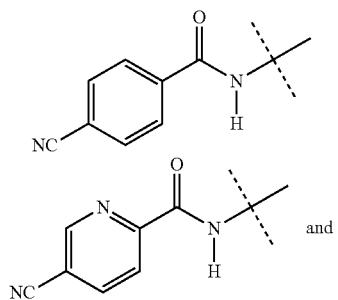 and

-continued

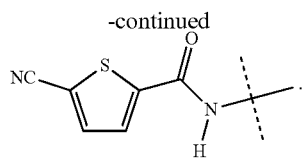

17. A compound according to claim 1, wherein Ar¹ is an optionally substituted 1,4 phenylene group.

18. Pharmaceutical composition comprising a compound according to claim 1 and optionally one or more carrier substances and/or one or more adjuvants.

19. A method of treating a subject suffering from or susceptible to a bacterial infection, comprising administering a compound of claim 1 to the subject.

* * * * *